US008975032B2

(12) United States Patent
Nozoe

(10) Patent No.: US 8,975,032 B2
(45) Date of Patent: Mar. 10, 2015

(54) TEST KIT FOR PLASMA OR SERUM ANTIBODY TITER AGAINST PERIODONTAL DISEASE-CAUSING BACTERIA

(75) Inventor: Mikio Nozoe, Takatsuki (JP)

(73) Assignee: Sunstar Inc., Osaka (JP)

( * ) Notice: Subject to any disclaimer, the term of this patent is extended or adjusted under 35 U.S.C. 154(b) by 0 days.

(21) Appl. No.: 13/994,005

(22) PCT Filed: Oct. 18, 2011

(86) PCT No.: PCT/JP2011/073942

§ 371 (c)(1), (2), (4) Date: Aug. 7, 2013

(87) PCT Pub. No.: WO2012/081306

PCT Pub. Date: Jun. 21, 2012

(65) Prior Publication Data

US 2013/0316371 A1 Nov. 28, 2013

(30) Foreign Application Priority Data

Dec. 15, 2010 (JP) ................................ 2010-279268

(51) Int. Cl.
*G01N 33/68* (2006.01)
*G01N 33/569* (2006.01)
*C07K 14/195* (2006.01)
*G01N 33/543* (2006.01)

(52) U.S. Cl.
CPC .......... *G01N 33/6893* (2013.01); *C07K 14/195* (2013.01); *G01N 33/54366* (2013.01); *G01N 33/56955* (2013.01); *G01N 33/6854* (2013.01); *G01N 2800/18* (2013.01); *Y10S 435/81* (2013.01)
USPC ............ 435/7.1; 435/7.2; 435/7.32; 435/7.9; 435/810; 530/300; 530/350

(58) Field of Classification Search
CPC ................ G01N 33/56955; G01N 2333/7056; G01N 33/0031; G01N 33/0075; G01N 33/5091; G01N 33/5306; G01N 33/531; G01N 33/56911; G01N 33/6893
See application file for complete search history.

(56) References Cited

U.S. PATENT DOCUMENTS 6,160,087 A 12/2000 Ogawa
7,416,852 B2 * 8/2008 Progulske-Fox et al. .... 435/7.32

FOREIGN PATENT DOCUMENTS

| | | |
|---|---|---|
| JP | 2-135096 | 5/1990 |
| JP | 2000-83676 | 3/2000 |
| JP | 2001-526035 | 12/2001 |
| JP | 2003-192616 | 7/2003 |
| JP | 2009-544279 | 12/2009 |
| WO | 99/29870 | 6/1999 |
| WO | 2005/019249 | 3/2005 |
| WO | 2005/112992 | 12/2005 |
| WO | 2006/032104 | 3/2006 |
| WO | 2008-000028 | 1/2008 |
| WO | 2010/075441 | 7/2010 |

OTHER PUBLICATIONS

Extended European Search Report dated Apr. 22, 2014 in corresponding European Application No. 11 84 8325.

International Search Report issued Jan. 17, 2012 in International (PCT) Application No. PCT/JP2011/73942.

M. Tani et al., "Studies on Antigenic Proteins of *Porphyromonas gingivalis* and *Actinobacillus actinomycetemcomitans* by Western Blotting Assay Using Purified IgGs from Patients with Periodontitis", Journal of the Japanese Society of Periodontology, vol. 34, No. 1, pp. 194-203, 1992.

M. Nozoe et al., "Kecchu IgG Kotaika Sokutei ni Mochiiru *Porphyromonas gingivalis* Kogen Tanpakushitsu no Senbatsu to Gosei", The Japanese Society of Periodontology Gakujutsu Taikai Program Oyobi Koen Shorokushu, vol. 54*th* Shunki, p. 103, Apr. 8, 2011.

A. Hisaeda et al., "Supportive Periodontal Therapy-ki no Shishubyo Saihatsu no Yochi ni Okeru Kessei IgG Kotaika no Yuyosei", The Japanese Society of Periodontology Gakujutsu Taikai Program Oyobi Koen Shorokushu, vol. 50*th* Shunki, p. 104, Apr. 30, 2007.

Y. Soga et al., "A Study on the Relationships Between the Severity of Periodontitis and Serum IgG Antibody Titer Against *Porphyromonas gingivalis* Among Patients with Hematologic Malignancies", Nihon Shika Hozongaku Zasshi, vol. 49, No. 6, pp. 731-738, Dec. 31, 2006.

International Preliminary Report on Patentability and Written Opinion issued Jun. 18, 2013 in corresponding International Application No. PCT/JP2011/073942 (with English translation).

* cited by examiner

*Primary Examiner* — Padma V Baskar
(74) *Attorney, Agent, or Firm* — Wenderoth, Lind & Ponack, L.L.P.

(57) ABSTRACT

The object of the present invention is to provide: a test kit for an antibody titer or an antibody against a periodontal disease-causing bacterium in a blood sample, which enables the testing on a periodontal disease in patients having a wide scope of immunotypes with high accuracy and can be treated by an automated device at a high speed; a periodontal disease-causing bacterium antigen protein which can be suitably used in the kit; a method for testing an antibody titer or the presence of an antibody in a blood sample using the kit; and a kit for typing strains of Porphyromonas gingivalis. The present invention discloses: a test kit comprising a set of polypeptides respectively having the acid sequences represented by SEQ ID NOs: 1, 3, 9, 15, 19, 31, 41, 43, 63, 65 and 67; a modified polypeptide having the amino acid sequence represented by SEQ ID NO: 67; and a method for determining an antibody titer or the presence of an antibody against a periodontal disease-causing bacterium in a blood sample separated from a human body, comprising bringing the blood sample into contact with the above-mentioned set of polypeptides.

4 Claims, 21 Drawing Sheets

A
F S
250
150
100
75
50
37
25
20
15
NAI
TOM
KOB
F: P. g. bacterium strain FDC381
S: P. g. bacterium strain SU63
B
No.7350
No.6921
No.6870
C
No.7107
No.7523
No.6980

(FDC381)

Lane A: antigen purified from healthy subject sera
Lane B: antigen purified from patient sera 1
Lane C: antigen purified from patient sera 2

Lane A: antigen purified from healthy subject sera
Lane B: antigen purified from patient sera 1
Lane C: antigen purified from patient sera 2

(SU63)

Lane A: antigen purified from healthy subject sera
Lane B: antigen purified from patient sera 1
Lane C: antigen purified from patient sera 2

Lane A: antigen purified from healthy subject sera
Lane B: antigen purified from patient sera 1
Lane C: antigen purified from patient sera 2

Fig.6

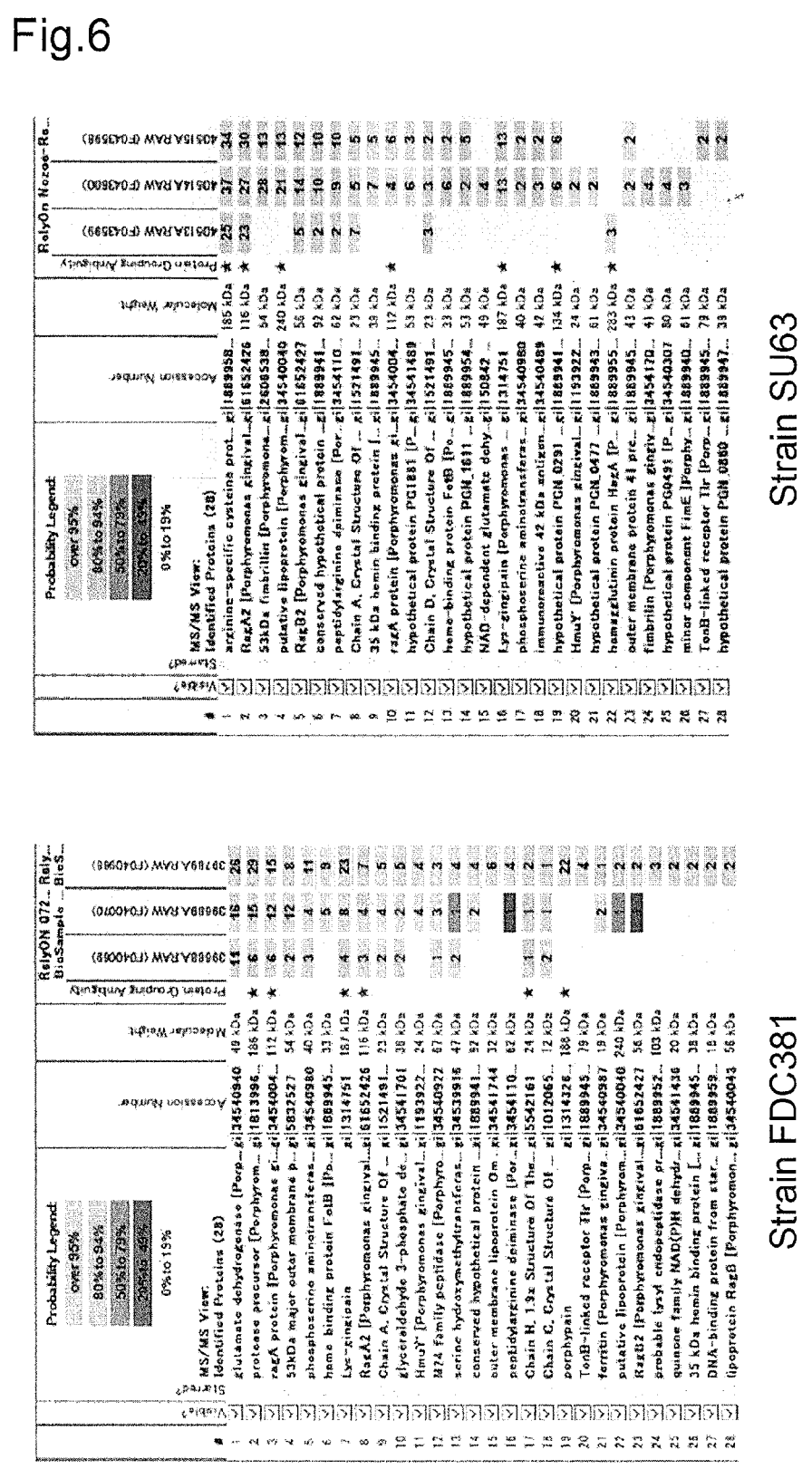

Probability Legend:
over 95%
80% to 94%
50% to 79%
20% to 49%
0% to 19%

| # | Visible? | Starred? | MS/MS View: Identified Proteins (28) | Accession Number | Molecular Weight | Protein Grouping Ambiguity | RelyON 072... BioSample ... 39688A.RAW (F040069) | 39689A.RAW (F040070) | Rely... BioS... 39789A.RAW (F040098) |
|---|---|---|---|---|---|---|---|---|---|
| 1 | ✓ | | glutamate dehydrogenase [Porp... | gi\|34540940 | 49 kDa | | 11 | 16 | 26 |
| 2 | ✓ | | protease precursor [Porphyrom... | gi\|1813996... | 186 kDa | ★ | 6 | 15 | 29 |
| 3 | ✓ | | ragA protein [Porphyromonas gi... | gi\|3454004... | 112 kDa | ★ | 6 | 12 | 15 |
| 4 | ✓ | | 53kDa major outer membrane p... | gi\|5832527 | 54 kDa | | 2 | 12 | 8 |
| 5 | ✓ | | phosphoserine aminotransferas... | gi\|34540980 | 40 kDa | | 3 | 4 | 11 |
| 6 | ✓ | | heme binding protein FetB [Po... | gi\|1889945... | 33 kDa | | | 5 | 9 |
| 7 | ✓ | | Lys-gingipain | gi\|1314751 | 187 kDa | ★ | 4 | 8 | 23 |
| 8 | ✓ | | RagA2 [Porphyromonas gingival... | gi\|61652426 | 116 kDa | ★ | 3 | 4 | 7 |
| 9 | ✓ | | Chain A, Crystal Structure Of ... | gi\|1521491... | 23 kDa | | 2 | 4 | 5 |
| 10 | ✓ | | glyceraldehyde 3-phosphate de... | gi\|34541701 | 38 kDa | | 2 | 2 | 5 |
| 11 | ✓ | | HmuY' [Porphyromonas gingival... | gi\|1193922... | 24 kDa | | | 4 | 4 |
| 12 | ✓ | | M24 family peptidase [Porphyro... | gi\|34540922 | 67 kDa | | 1 | 3 | 3 |
| 13 | ✓ | | serine hydroxymethyltransferas... | gi\|34539916 | 47 kDa | | 2 | 1 | 4 |
| 14 | ✓ | | conserved hypothetical protein ... | gi\|1889941... | 92 kDa | | | 2 | 4 |
| 15 | ✓ | | outer membrane lipoprotein Om... | gi\|34541744 | 32 kDa | | | | 6 |
| 16 | ✓ | | peptidylarginine deiminase [Por... | gi\|3454110... | 62 kDa | | | 1 | 4 |
| 17 | ✓ | | Chain H, 1.9a Structure Of The... | gi\|5542161 | 24 kDa | ★ | 1 | 1 | 2 |
| 18 | ✓ | | Chain C, Crystal Structure Of ... | gi\|1012065... | 12 kDa | | 2 | 1 | 1 |
| 19 | ✓ | | porphypain | gi\|1314326... | 186 kDa | ★ | | | 22 |
| 20 | ✓ | | TonB-linked receptor Tlr [Porp... | gi\|1889945... | 79 kDa | | | | 4 |
| 21 | ✓ | | ferritin [Porphyromonas gingiva... | gi\|34540987 | 19 kDa | | | 2 | 1 |
| 22 | ✓ | | putative lipoprotein [Porphyrom... | gi\|34540040 | 240 kDa | | | 1 | 2 |
| 23 | ✓ | | RagB2 [Porphyromonas gingival... | gi\|61652427 | 56 kDa | | | 1 | 2 |
| 24 | ✓ | | probable lysyl endopeptidase pr... | gi\|1889952... | 103 kDa | | | | 3 |
| 25 | ✓ | | quinone family NAD(P)H dehydr... | gi\|34541436 | 20 kDa | | | | 2 |
| 26 | ✓ | | 35 kDa hemin binding protein [... | gi\|1889945... | 38 kDa | | | | 2 |
| 27 | ✓ | | DNA-binding protein from star... | gi\|1889959... | 18 kDa | | | | 2 |
| 28 | ✓ | | lipoprotein RagB [Porphyromon... | gi\|34540043 | 56 kDa | | | | 2 |

Strain FDC381

Probability Legend:
over 95%
80% to 94%
50% to 79%
20% to 49%
0% to 19%

| # | Visible? | Starred? | MS/MS View: Identified Proteins (28) | Accession Number | Molecular Weight | Protein Grouping Ambiguity | RelyOn Nozoe-Re... 40513A.RAW (F043599) | 40514A.RAW (F043600) | 40515A.RAW (F043598) |
|---|---|---|---|---|---|---|---|---|---|
| 1 | ✓ | | arginine-specific cysteine prot... | gi\|1889958... | 185 kDa | ★ | 25 | 37 | 34 |
| 2 | ✓ | | RagA2 [Porphyromonas gingival... | gi\|61652426 | 116 kDa | ★ | 23 | 27 | 30 |
| 3 | ✓ | | 53kDa fimbrillin [Porphyromona... | gi\|2608538... | 54 kDa | | | 28 | 13 |
| 4 | ✓ | | putative lipoprotein [Porphyrom... | gi\|34540040 | 240 kDa | ★ | | 21 | 13 |
| 5 | ✓ | | RagB2 [Porphyromonas gingival... | gi\|61652427 | 56 kDa | | 5 | 14 | 12 |
| 6 | ✓ | | conserved hypothetical protein ... | gi\|1889941... | 92 kDa | | 2 | 10 | 10 |
| 7 | ✓ | | peptidylarginine deiminase [Por... | gi\|3454110... | 62 kDa | | 2 | 9 | 10 |
| 8 | ✓ | | Chain A, Crystal Structure Of ... | gi\|1521491... | 23 kDa | | 7 | 5 | 5 |
| 9 | ✓ | | 35 kDa hemin binding protein [... | gi\|1889945... | 38 kDa | | | 7 | 5 |
| 10 | ✓ | | ragA protein [Porphyromonas gi... | gi\|3454004... | 112 kDa | ★ | | 4 | 6 |
| 11 | ✓ | | hypothetical protein PG1881 [P... | gi\|34541489 | 53 kDa | | | 6 | 3 |
| 12 | ✓ | | Chain D, Crystal Structure Of ... | gi\|1521491... | 23 kDa | | 3 | 3 | 2 |
| 13 | ✓ | | heme-binding protein FetB [Po... | gi\|1889945... | 33 kDa | | | 6 | 2 |
| 14 | ✓ | | hypothetical protein PGN_1611 ... | gi\|1889954... | 53 kDa | | | 2 | 5 |
| 15 | ✓ | | NAD-dependent glutamate dehy... | gi\|150842 ... | 49 kDa | | | 4 | |
| 16 | ✓ | | Lys-gingipain [Porphyromonas ... | gi\|1314751 | 187 kDa | ★ | | 13 | 13 |
| 17 | ✓ | | phosphoserine aminotransferas... | gi\|34540980 | 40 kDa | | | 2 | 2 |
| 18 | ✓ | | immunoreactive 42 kDa antigen... | gi\|34540489 | 42 kDa | | | 3 | 2 |
| 19 | ✓ | | hypothetical protein PGN_0291 ... | gi\|1889941... | 134 kDa | ★ | | 6 | 6 |
| 20 | ✓ | | HmuY' [Porphyromonas gingival... | gi\|1193922... | 24 kDa | | | 2 | |
| 21 | ✓ | | hypothetical protein PGN_0477 ... | gi\|1889943... | 61 kDa | | | 2 | |
| 22 | ✓ | | hemagglutinin protein HagA [P... | gi\|1889955... | 283 kDa | ★ | 3 | | |
| 23 | ✓ | | outer membrane protein 41 pre... | gi\|1889945... | 43 kDa | | | 2 | 2 |
| 24 | ✓ | | fimbrilin [Porphyromonas gingiv... | gi\|3454170... | 41 kDa | | | 4 | |
| 25 | ✓ | | hypothetical protein PG0491 [P... | gi\|34540307 | 80 kDa | | | 4 | |
| 26 | ✓ | | minor component FimE [Porphy... | gi\|1889940... | 61 kDa | | | 3 | |
| 27 | ✓ | | TonB-linked receptor Tlr [Porp... | gi\|1889945... | 79 kDa | | | | 2 |
| 28 | ✓ | | hypothetical protein PGN_0860 ... | gi\|1889947... | 38 kDa | | | | 2 |

Strain SU63

Fig.7

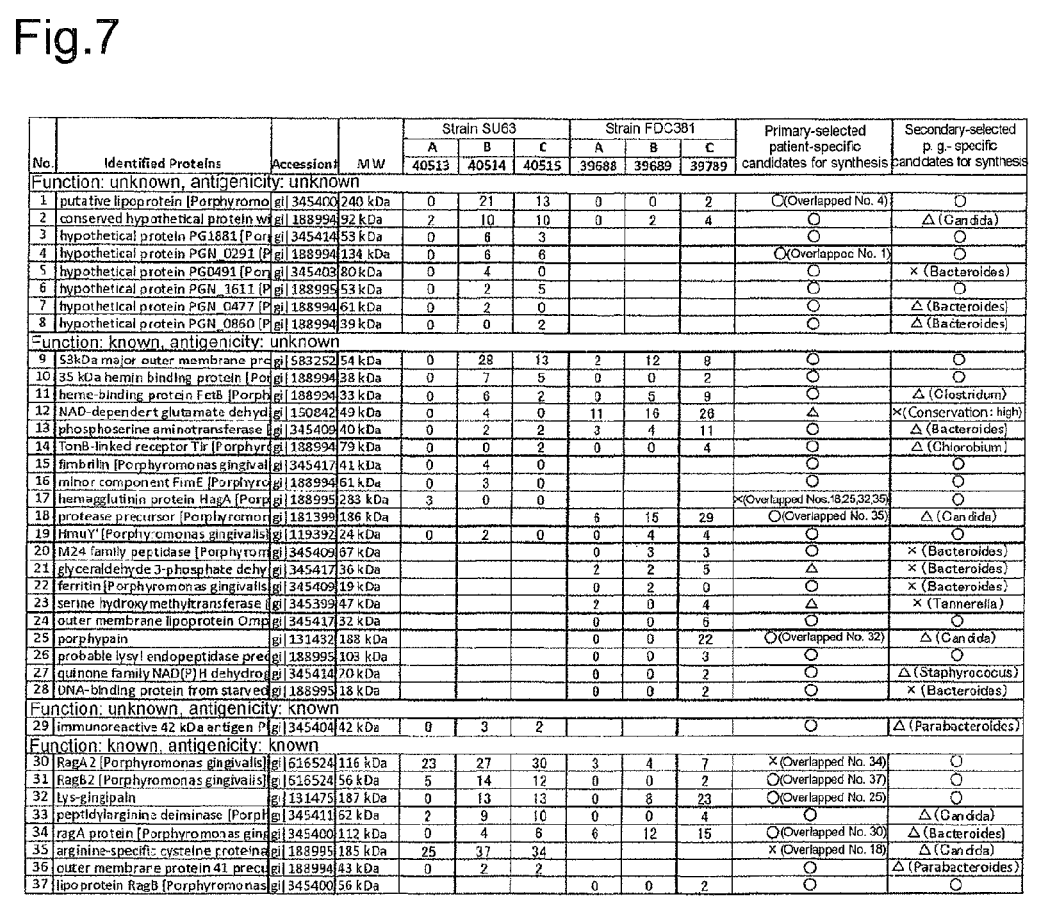

| No. | Identified Proteins | Accession# | MW | Strain SU63 | | | Strain FDC381 | | | Primary-selected patient-specific candidates for synthesis | Secondary-selected p. g.- specific candidates for synthesis |
|---|---|---|---|---|---|---|---|---|---|---|---|
| | | | | A | B | C | A | B | C | | |
| | | | | 40513 | 40514 | 40515 | 39688 | 39689 | 39789 | | |
| Function: unknown, antigenicity: unknown | | | | | | | | | | | |
| 1 | putative lipoprotein [Porphyromo | gi\|345400 | 240 kDa | 0 | 21 | 13 | 0 | 0 | 2 | ○(Overlapped No. 4) | ○ |
| 2 | conserved hypothetical protein wi | gi\|188994 | 92 kDa | 2 | 10 | 10 | 0 | 2 | 4 | ○ | △ (Candida) |
| 3 | hypothetical protein PG1881 [Por | gi\|345414 | 53 kDa | 0 | 6 | 3 | | | | ○ | ○ |
| 4 | hypothetical protein PGN_0291 [P | gi\|188994 | 134 kDa | 0 | 6 | 6 | | | | ○(Overlapped No. 1) | ○ |
| 5 | hypothetical protein PG0491 [Por | gi\|345403 | 80 kDa | 0 | 4 | 0 | | | | ○ | × (Bacteroides) |
| 6 | hypothetical protein PGN_1611 [P | gi\|188995 | 53 kDa | 0 | 2 | 5 | | | | ○ | ○ |
| 7 | hypothetical protein PGN_0477 [P | gi\|188994 | 61 kDa | 0 | 2 | 0 | | | | ○ | △ (Bacteroides) |
| 8 | hypothetical protein PGN_0860 [P | gi\|188994 | 39 kDa | 0 | 0 | 2 | | | | ○ | △ (Bacteroides) |
| Function: known, antigenicity: unknown | | | | | | | | | | | |
| 9 | 53kDa major outer membrane pro | gi\|583252 | 54 kDa | 0 | 28 | 13 | 2 | 12 | 8 | ○ | ○ |
| 10 | 35 kDa hemin binding protein [Por | gi\|188994 | 38 kDa | 0 | 7 | 5 | 0 | 0 | 2 | ○ | ○ |
| 11 | heme-binding protein FetB [Porph | gi\|188994 | 33 kDa | 0 | 6 | 2 | 0 | 5 | 9 | ○ | △ (Clostridum) |
| 12 | NAD-dependent glutamate dehyd | gi\|150842 | 49 kDa | 0 | 4 | 0 | 11 | 16 | 26 | △ | ×(Conservation: high) |
| 13 | phosphoserine aminotransferase [ | gi\|345409 | 40 kDa | 0 | 2 | 2 | 3 | 4 | 11 | ○ | △ (Bacteroides) |
| 14 | TonB-linked receptor Tlr [Porphyro | gi\|188994 | 79 kDa | 0 | 0 | 2 | 0 | 0 | 4 | ○ | △ (Chlorobium) |
| 15 | fimbrilin [Porphyromonas gingival | gi\|345417 | 41 kDa | 0 | 4 | 0 | | | | ○ | ○ |
| 16 | minor component FimE [Porphyro | gi\|188994 | 61 kDa | 0 | 3 | 0 | | | | ○ | ○ |
| 17 | hemagglutinin protein HagA [Porp | gi\|188995 | 283 kDa | 3 | 0 | 0 | | | | ×(Overlapped Nos.18,25,32,35) | ○ |
| 18 | protease precursor [Porphyromon | gi\|181399 | 186 kDa | | | | 6 | 15 | 29 | ○(Overlapped No. 35) | △ (Candida) |
| 19 | HmuY' [Porphyromonas gingivalis | gi\|119392 | 24 kDa | 0 | 2 | 0 | 0 | 4 | 4 | ○ | ○ |
| 20 | M24 family peptidase [Porphyrom | gi\|345409 | 67 kDa | | | | 0 | 3 | 3 | ○ | × (Bacteroides) |
| 21 | glyceraldehyde 3-phosphate dehy | gi\|345417 | 36 kDa | | | | 2 | 2 | 5 | △ | × (Bacteroides) |
| 22 | ferritin [Porphyromonas gingivalis | gi\|345409 | 19 kDa | | | | 0 | 2 | 0 | ○ | × (Bacteroides) |
| 23 | serine hydroxymethyltransferase [ | gi\|345399 | 47 kDa | | | | 2 | 0 | 4 | △ | × (Tannerella) |
| 24 | outer membrane lipoprotein Omp | gi\|345417 | 32 kDa | | | | 0 | 0 | 6 | ○ | ○ |
| 25 | porphypain | gi\|131432 | 188 kDa | | | | 0 | 0 | 22 | ○(Overlapped No. 32) | △ (Candida) |
| 26 | probable lysyl endopeptidase pred | gi\|188995 | 103 kDa | | | | 0 | 0 | 3 | ○ | ○ |
| 27 | quinone family NAD(P)H dehydrog | gi\|345414 | 70 kDa | | | | 0 | 0 | 2 | ○ | △ (Staphyrococus) |
| 28 | DNA-binding protein from starved | gi\|188995 | 18 kDa | | | | 0 | 0 | 2 | ○ | × (Bacteroides) |
| Function: unknown, antigenicity: known | | | | | | | | | | | |
| 29 | immunoreactive 42 kDa antigen P | gi\|345404 | 42 kDa | 0 | 3 | 2 | | | | ○ | △ (Parabacteroides) |
| Function: known, antigenicity: known | | | | | | | | | | | |
| 30 | RagA2 [Porphyromonas gingivalis] | gi\|616524 | 116 kDa | 23 | 27 | 30 | 3 | 4 | 7 | × (Overlapped No. 34) | ○ |
| 31 | RagB2 [Porphyromonas gingivalis] | gi\|616524 | 56 kDa | 5 | 14 | 12 | 0 | 0 | 2 | ○(Overlapped No. 37) | ○ |
| 32 | Lys-gingipain | gi\|131475 | 187 kDa | 0 | 13 | 13 | 0 | 8 | 23 | ○(Overlapped No. 25) | ○ |
| 33 | peptidylarginine deiminase [Porph | gi\|345411 | 62 kDa | 2 | 9 | 10 | 0 | 0 | 4 | ○ | △ (Candida) |
| 34 | ragA protein [Porphyromonas ging | gi\|345400 | 112 kDa | 0 | 4 | 6 | 6 | 12 | 15 | ○(Overlapped No. 30) | △ (Bacteroides) |
| 35 | arginine-specific cysteine proteina | gi\|188995 | 185 kDa | 25 | 37 | 34 | | | | × (Overlapped No. 18) | △ (Candida) |
| 36 | outer membrane protein 41 precu | gi\|188994 | 43 kDa | 0 | 2 | 2 | | | | ○ | △ (Parabacteroides) |
| 37 | lipoprotein RagB [Porphyromonas | gi\|345400 | 56 kDa | | | | 0 | 0 | 2 | ○ | ○ |

Fig.8
Layout
| | A | B | C | D |
|---|---|---|---|---|
| 1 | 2 | 11 | 21 | 32 |
| 2 | 3 | 12 | 22 | 34 |
| 3 | 4 | 13 | 23 | 35 |
| 4 | 6 | 14 | 24 | 36 |
| 5 | 7 | 15 | 26 | 37 |
| 6 | 8 | 16 | 27 | |
| 7 | 9 | 19 | 28 | |
| 8 | 10 | 20 | 29 | |
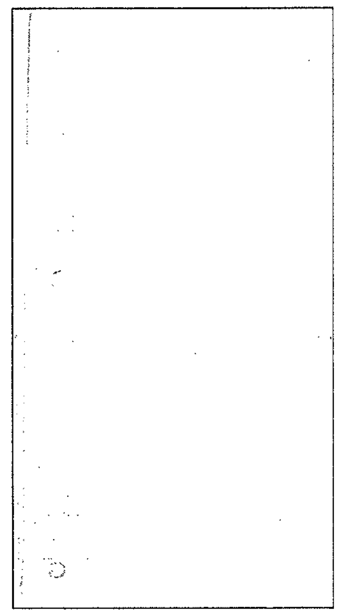
Healthy subject serum pool
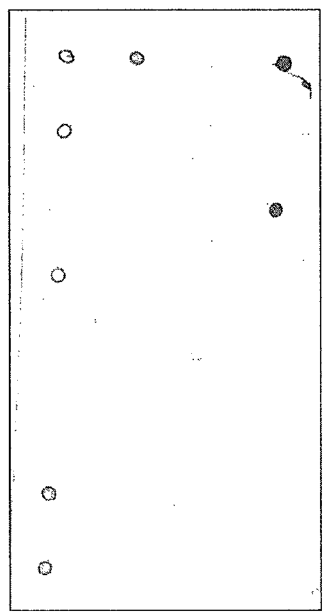
Patient serum pool 1
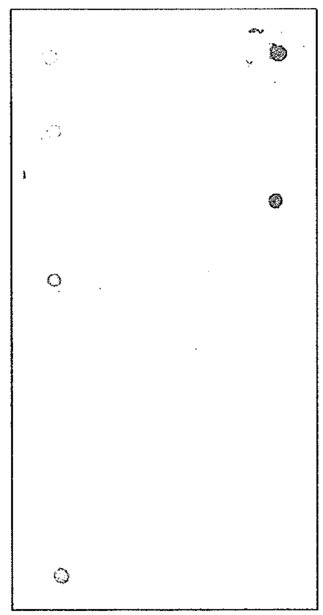
Patient serum pool 2

Fig.9

| Antigen No. | Healthy subject serum pool | Patient serum pool 1 | Patient serum pool 2 |
|---|---|---|---|
| 2 | 258581 | 10299784 | 4544221 |
| 3 | 0 | 7938453 | 3591925 |
| 4 | 0 | 533560 | 1030417 |
| 6 | 2586477 | 8030066 | 8508309 |
| 7 | 0 | 0 | 0 |
| 8 | 0 | 0 | 0 |
| 9 | noize | 12972685 | 0 |
| 10 | 7803423 | 12163942 | 13135284 |
| 11 | 0 | 11823066 | 4149132 |
| 12 | 0 | 0 | noize |
| 13 | 0 | 133558 | noize |
| 14 | 0 | 0 | noize |
| 15 | 0 | 0 | noize |
| 16 | 0 | 0 | 0 |
| 19 | 0 | 3750092 | noize |
| 20 | noize | noize | noize |
| 21 | 0 | 331257 | noize |
| 22 | 0 | 416198 | noize |
| 23 | 0 | noize | noize |
| 24 | 0 | 3308269 | 6252161 |
| 26 | 431110 | 2392354 | 1561578 |
| 27 | 0 | 0 | 0 |
| 28 | noize | noize | noize |
| 29 | 120564 | 0 | noize |
| 32 | 2539358 | 20813860 | 21344255 |
| 34 | 0 | 57190 | noize |
| 35 | 3778184 | 16754505 | 15833022 |
| 36 | noize | noize | noize |
| 37 | noize | noize | noize |
| Blank 1 | 6471 | 40767 | 231273 |
| Blank 2 | 214 | 2544 | 568794 |
| Blank 3 | 118823 | 56711 | 803725 |

(Note) Antigens having signal values equal to or lower than blank 3 were treated as noises

Fig.11

| Antigen protein No. | Healthy subject sera TOM | NAI | KOB | Healthy subject reference |
|---|---|---|---|---|
| 2 | 1598447 | n.d. | 2085186 | 2085186 |
| 3 | n.d. | n.d. | n.d. | 0 |
| 4 | n.d. | n.d. | n.d. | 0 |
| 6 | 5738276 | 6763839 | 7678131 | 7678131 |
| 9 | n.d. | n.d. | n.d. | 0 |
| 10 | 4314709 | n.d. | 10899925 | 10899925 |
| 11 | n.d. | n.d. | n.d. | 0 |
| 13 | n.d. | n.d. | n.d. | 0 |
| 19 | n.d. | n.d. | n.d. | 0 |
| 21 | n.d. | n.d. | n.d. | 0 |
| 22 | n.d. | n.d. | n.d. | 0 |
| 24 | n.d. | n.d. | n.d. | 0 |
| 26 | 867630 | n.d. | 70695 | 867630 |
| 28 | n.d. | n.d. | n.d. | 0 |
| 32 | 2060812 | n.d. | 2503064 | 2503064 |
| 35 | 1207265 | 2214521 | 4781758 | 4781758 |

Fig.12

| Antigen protein No. | Patient sera 6809 | 6816 | 6823 | 6896 | 6918 | 6921 | 6923 | 6926 | 6975 | 6980 | 6991 | 7056 |
|---|---|---|---|---|---|---|---|---|---|---|---|---|
| 2 | 5803638 | 34058 | 1831604 | 11420150 | 8725092 | 21783541 | 4819959 | 1122471 | 7637207 | 3846670 | 6366756 | 13327426 |
| 3 | 4213786 | 1052796 | 2673715 | 1786686 | 2667842 | 1717493 | n.d. | 4076342 | n.d. | 3063362 | 755382 | n.d. |
| 4 | n.d. | n.d. | 4275779 | 774743 | n.d. | 260566 | n.d. | 445621 | 484018 | n.d. | 1468594 | n.d. |
| 6 | 982269 | n.d. | 3339197 | 5638192 | 9315389 | 13563288 | 2638447 | n.d. | 8730205 | 1660360 | 5769628 | 12045846 |
| 9 | 2138181 | 530806 | n.d. | n.d. | 8130699 | 19108792 | 2475879 | 18839709 | n.d. | n.d. | 4945931 | n.d. |
| 10 | 3011852 | 3196144 | 51497 | 4567676 | 5466625 | 12568914 | 8659082 | 3539280 | 7551358 | 4304725 | 1185998 | 10191477 |
| 11 | n.d. | 1698642 | n.d. | 1784310 | n.d. | 15880529 | n.d. | n.d. | n.d. | 4819952 | 631311 | n.d. |
| 13 | n.d. | n.d. | n.d. | n.d. | n.d. | n.d. | n.d. | n.d. | n.d. | n.d. | n.d. | n.d. |
| 19 | n.d. | 2835786 | n.d. | n.d. | 843581 | n.d. | 1992580 | n.d. | n.d. | 1057635 | n.d. | n.d. |
| 21 | n.d. | n.d. | n.d. | n.d. | n.d. | n.d. | n.d. | n.d. | n.d. | n.d. | n.d. | n.d. |
| 22 | n.d. | n.d. | n.d. | n.d. | n.d. | n.d. | n.d. | n.d. | n.d. | n.d. | n.d. | n.d. |
| 24 | n.d. | n.d. | n.d. | 956146 | 400189 | n.d. | 623094 | n.d. | n.d. | n.d. | n.d. | 1214323 |
| 26 | n.d. | 3100160 | n.d. | 781088 | 1811202 | n.d. | n.d. | 2124685 | 7148056 | 689655 | 1040848 | 2654894 |
| 28 | n.d. | n.d. | n.d. | n.d. | n.d. | n.d. | n.d. | n.d. | n.d. | n.d. | n.d. | n.d. |
| 32 | 10050844 | 31073871 | 15677565 | 24806162 | 27580055 | 37993686 | 21951328 | 13493555 | 24471576 | 33808621 | 18913419 | 18459270 |
| 35 | 16400320 | 30769150 | 22164743 | 26989140 | 32034025 | 39202988 | 28512158 | 25685815 | 27395794 | 34695924 | 24907585 | 19496370 |

| Antigen protein No. | Patient sera 7107 | 7125 | 7350 | 7395 | 7457 | 7492 | 7495 | 7500 | 7523 | 7524 | 7835 |
|---|---|---|---|---|---|---|---|---|---|---|---|
| 2 | 7135308 | 6492410 | 8247603 | 3679263 | 3307117 | 5189959 | 6648274 | 10273473 | n.d. | 2760055 | 7201491 |
| 3 | 1156814 | 5296326 | 9692008 | n.d. | 1984077 | n.d. | 527102 | n.d. | 3708897 | 2113402 | n.d. |
| 4 | 136479 | 2753433 | 2796850 | n.d. | n.d. | n.d. | n.d. | n.d. | 4009799 | n.d. | n.d. |
| 6 | 13004770 | 4107684 | 5643361 | 9015055 | 3946328 | 1826855.8 | 2965608 | 5731338 | 3647004 | n.d. | 5566052 |
| 9 | n.d. | n.d. | n.d. | n.d. | n.d. | n.d. | 9834044 | 1950829 | n.d. | 16886309 | n.d. |
| 10 | 12724626 | 8993618 | 8154442 | 6181998 | 10541814 | 335299.48 | 8538616 | 12731218 | 5609949 | 17302265 | 8010635 |
| 11 | 5872259 | 3720359 | 28845908 | n.d. | n.d. | n.d. | n.d. | 2628677 | n.d. | n.d. | n.d. |
| 13 | n.d. | n.d. | n.d. | n.d. | n.d. | n.d. | n.d. | n.d. | n.d. | n.d. | n.d. |
| 19 | 1432198 | 2206455 | 4725876 | n.d. | n.d. | n.d. | n.d. | n.d. | n.d. | 7109750 | n.d. |
| 21 | n.d. | n.d. | n.d. | n.d. | n.d. | n.d. | n.d. | n.d. | n.d. | n.d. | n.d. |
| 22 | n.d. | n.d. | n.d. | n.d. | n.d. | n.d. | n.d. | n.d. | n.d. | 1074568 | n.d. |
| 24 | 9692976 | 4159059 | 4521232 | n.d. | n.d. | n.d. | 2919715 | 1769221 | n.d. | 2666362 | n.d. |
| 26 | 372510 | −36479 | 1222952 | n.d. | 1963418 | n.d. | 2505485 | 1727201 | 1356828 | 3635711 | n.d. |
| 28 | n.d. | n.d. | n.d. | n.d. | n.d. | n.d. | n.d. | n.d. | n.d. | n.d. | n.d. |
| 32 | 24188732 | 25021544 | 35044983 | 6232588 | 28278169 | 26049378 | 22508836 | 9803250 | 20720662 | 25697472 | 10567896 |
| 35 | 33620714 | 29575885 | 37979539 | 11704948 | 31550088 | 25661283 | 22786143 | 13741482 | 22551414 | 26216464 | 16145927 |

Fig.13

| | | Antigen protein No. | | | | | | | | | | | | | | | |
|---|---|---|---|---|---|---|---|---|---|---|---|---|---|---|---|---|---|
| | | 2 | 3 | 4 | 6 | 9 | 10 | 11 | 13 | 19 | 21 | 22 | 24 | 26 | 28 | 32 | 35 |
| Patients | 6809 | ○ | ○ | | | ○ | | | | | | | | | | ○ | ○ |
| | 6816 | | ○ | | | ○ | | ○ | | | | | | ○ | | ○ | ○ |
| | 6823 | | ○ | ○ | | | | | | | | | | | | ○ | ○ |
| | 6896 | ○ | ○ | ○ | | | | ○ | | | | | ○ | | | ○ | ○ |
| | 6918 | ○ | ○ | | ○ | ○ | | | | ○ | | | ○ | ○ | | ○ | ○ |
| | 6921 | ○ | ○ | ○ | ○ | ○ | ○ | ○ | | | | | | | | ○ | ○ |
| | 6923 | ○ | | | | ○ | | | | ○ | | | ○ | | | ○ | ○ |
| | 6926 | | ○ | ○ | | ○ | | | | | | | | ○ | | ○ | ○ |
| | 6975 | ○ | | ○ | ○ | | | | | | | | | ○ | | ○ | ○ |
| | 6980 | ○ | ○ | | | | | ○ | | ○ | | | | | | ○ | ○ |
| | 6991 | ○ | ○ | ○ | | ○ | | ○ | | | | | | ○ | | ○ | ○ |
| | 7056 | ○ | | | ○ | | | | | | | | ○ | ○ | | ○ | ○ |
| | 7107 | ○ | ○ | ○ | ○ | | ○ | ○ | | ○ | | | ○ | | | ○ | ○ |
| | 7125 | ○ | ○ | ○ | | | | ○ | | ○ | | | ○ | | | ○ | ○ |
| | 7350 | ○ | ○ | ○ | | | | ○ | | ○ | | | ○ | ○ | | ○ | ○ |
| | 7395 | ○ | | | ○ | | | | | | | | | | | ○ | ○ |
| | 7457 | ○ | ○ | | | | | | | | | | | ○ | | ○ | ○ |
| | 7492 | ○ | | | | | | | | | | | | | | ○ | ○ |
| | 7495 | ○ | ○ | | | ○ | | | | | | | ○ | ○ | | ○ | ○ |
| | 7500 | ○ | | | | ○ | ○ | ○ | | | | | ○ | ○ | | ○ | ○ |
| | 7523 | | ○ | ○ | | | | | | | | | | ○ | | ○ | ○ |
| | 7524 | ○ | ○ | | | ○ | ○ | | | ○ | | ○ | ○ | ○ | | ○ | ○ |
| | 7835 | ○ | | | | | | | | | | | | | | ○ | ○ |

Fig.16

| | Serum No. | Antigen No. | | | | | | | | | | | | | | | |
|---|---|---|---|---|---|---|---|---|---|---|---|---|---|---|---|---|---|
| | | 2 | 3 | 4 | 6 | 9 | 10 | 11 | 13 | 19 | 21 | 22 | 24 | 26 | 28 | 32A | 35A |
| Healthy subject serum group | H1 | 5654109 | 0 | 0 | 1381433 | 0 | 4515749 | 0 | 0 | 0 | 117043 | 0 | 0 | 189483 | 0 | 6397032 | 11798073 |
| | H2 | 7208773 | 0 | 0 | 744716 | 0 | 2644644 | 0 | 0 | 0 | 0 | 0 | 0 | 572129 | 0 | 8191840 | 8490813 |
| | H3 | 0 | 0 | 0 | 478138 | 0 | 417326 | 0 | 0 | 0 | 0 | 0 | 0 | 358337 | 0 | 1347285 | 1244723 |
| | H4 | 2389618 | 0 | 0 | 1236766 | 0 | 3617334 | 0 | 0 | 0 | 0 | 0 | 0 | 0 | 0 | 1476959 | 2239358 |
| | H5 | 885872 | 0 | 0 | 996337 | 0 | 1843154 | 0 | 0 | 0 | 0 | 0 | 0 | 0 | 0 | 4601450 | 5098186 |
| | H6 | 3177760 | 0 | 0 | 1906100 | 0 | 1956331 | 0 | 0 | 0 | 0 | 0 | 0 | 0 | 0 | 1919412 | 1734553 |
| | H7 | 0 | 0 | 0 | 334140 | 0 | 0 | 0 | 0 | 0 | 0 | 0 | 0 | 0 | 0 | 0 | 0 |
| | H8 | 188496 | 0 | 0 | 505527 | 0 | 1566083 | 0 | 0 | 0 | 0 | 0 | 0 | 440992 | 67383 | 259018 | 265806 |
| | H9 | 1391316 | 0 | | 14444905 | 0 | 17585332 | 0 | 0 | 0 | 0 | 0 | 0 | 1063896 | 0 | 5076288 | 7148812 |
| | H10 | 8325690 | 0 | | 1742290 | 0 | 5214255 | 0 | 0 | 155293 | 0 | 0 | 0 | 807559 | 0 | 4951639 | 8324489 |
| Patient serum group | P1 | 2100735 | 492763 | 129941 | 1874985 | 13946742 | 2939217 | 1023 | 0 | 910676 | 30133 | 0 | 236165 | 444335 | 0 | 20473257 | 23790516 |
| | P2 | 520878 | 421042 | 0 | 858542 | 0 | 805653 | 0 | 0 | 0 | 0 | 0 | 303320 | 260758 | 0 | 4248022 | 20782596 |
| | P3 | 0 | 0 | 0 | 41654 | 0 | 0 | 0 | 0 | 0 | 0 | 0 | 0 | 0 | 0 | 730462 | 646517 |
| | P4 | 0 | 0 | 0 | 1655204 | 0 | 0 | 0 | 0 | 0 | 0 | 132241 | 0 | 0 | 0 | 774381 | 1141623 |
| | P5 | 0 | 0 | 0 | 125371 | 0 | 0 | 0 | 0 | 0 | 0 | 0 | 402299 | 0 | 0 | 8556587 | 12433742 |
| | P6 | 0 | 0 | 0 | 760653 | 116173 | 0 | 0 | 0 | 54753 | 0 | 0 | 0 | 0 | 0 | 2632130 | 5102330 |
| | P7 | 6324287 | 0 | 0 | 5727508 | 0 | 8301958 | 369154 | 0 | 0 | 0 | 0 | 418574 | 727651 | 0 | 8654785 | 16150790 |
| | P8 | 3047617 | 0 | 0 | 5501148 | 5756030 | 6049493 | 7015822 | 0 | 19070325 | 0 | 0 | 825206 | 0 | 0 | 23401904 | 24713418 |
| | P9 | 4149839 | 0 | 0 | 304774 | 0 | 7270566 | 0 | 0 | 1592 | 0 | 0 | 0 | 0 | 0 | 9146531 | 11542814 |
| | P10 | 1462739 | 252940 | | 865484 | 0 | 2918847 | 0 | 0 | 0 | 0 | 0 | 0 | 0 | 0 | 11480440 | 13529758 |
| | P11 | 3270706 | 0 | 0 | 1882807 | 0 | 4084577 | 69175 | 0 | 227608 | 0 | 0 | 230281 | 266678 | 0 | 12921785 | 16177136 |
| | P12 | 644249 | 0 | 0 | 417911 | 0 | 2494042 | 0 | 0 | 0 | 0 | 0 | 0 | 0 | 0 | 10550115 | 13825087 |
| | P13 | 264425 | 257478 | 4712 | 575860 | 0 | 2795891 | 340783 | 0 | 0 | 0 | 0 | 1336425 | 1122389 | 0 | 9244550 | 13546232 |
| | P14 | 3835136 | 0 | 0 | 1776591 | 0 | 5934493 | 0 | 0 | 0 | 0 | 0 | 0 | 0 | 0 | 5772340 | 5713361 |
| | P15 | 1417 | 0 | 0 | 227025 | 0 | 238700 | 39426 | 0 | 0 | 0 | 0 | 284636 | 356886 | 0 | 4905648 | 8373424 |
| | P16 | 337451 | 0 | 301375 | 1123415 | 0 | 682491 | 660068 | 0 | 0 | 0 | 0 | 0 | 0 | 0 | 7655953 | 11996144 |
| | P17 | 19456228 | 224392 | 0 | 10971464 | 0 | 20892789 | 832291 | 0 | 0 | 0 | 0 | 473064 | 1235810 | 0 | 14333172 | 19856112 |
| | P18 | 9926484 | 1293374 | 241915 | 8109836 | 1193607 | 12625957 | 1912661 | 0 | 13017556 | 0 | 0 | 349732 | 374868 | 0 | 18439438 | 27460913 |
| | P19 | 7159271 | 0 | 0 | 803503 | 53955 | 8134039 | 0 | 0 | 0 | 0 | 0 | 0 | 745666 | 0 | 1869678 | 3228540 |
| | P20 | 4413581 | 0 | | 1481315 | 0 | 2330308 | 0 | 0 | 0 | 0 | 0 | 0 | 0 | 0 | 3404305 | 3420444 |

Fig.17

| | Serum No. | Antigen No. | | | | | | | | | | | | | | | |
|---|---|---|---|---|---|---|---|---|---|---|---|---|---|---|---|---|---|
| | | 2 | 3 | 4 | 6 | 9 | 10 | 11 | 13 | 19 | 21 | 22 | 24 | 26 | 28 | 32A | 35A |
| Healthy subject serum group | H1 | ○ | | | ○ | | ○ | | | | ○ | | | ○ | | ○ | ○ |
| | H2 | ○ | | | ○ | | ○ | | | | | | | ○ | | ○ | ○ |
| | H3 | | | | ○ | | ○ | | | | | | | ○ | | ○ | ○ |
| | H4 | ○ | | | ○ | | ○ | | | | | | | | | ○ | ○ |
| | H5 | ○ | | | ○ | | ○ | | | | | | | | | ○ | ○ |
| | H6 | ○ | | | ○ | | ○ | | | | | | | | | ○ | ○ |
| | H7 | | | | ○ | | | | | | | | | | | | |
| | H8 | ○ | | | ○ | | ○ | | | | | | | ○ | ○ | ○ | ○ |
| | H9 | ○ | | — | ○ | | ○ | | | | | | | ○ | | ○ | ○ |
| | H10 | ○ | | — | ○ | | ○ | | | ○ | | | | ○ | | ○ | ○ |
| Patient serum group | P1 | ○ | ○ | ○ | ○ | ○ | ○ | ○ | | ○ | ○ | | ○ | ○ | | ○ | ○ |
| | P2 | ○ | ○ | | ○ | | ○ | | | | | | ○ | ○ | | ○ | ○ |
| | P3 | | | | ○ | | | | | | | | | | | ○ | ○ |
| | P4 | | | | ○ | | | | | | | ○ | | | | ○ | ○ |
| | P5 | | | | ○ | | | | | | | | ○ | | | ○ | ○ |
| | P6 | | | | ○ | ○ | | | | ○ | | | | | | ○ | ○ |
| | P7 | ○ | | | ○ | | ○ | ○ | | | | | ○ | ○ | | ○ | ○ |
| | P8 | ○ | | | ○ | ○ | ○ | ○ | | ○ | | | ○ | | | ○ | ○ |
| | P9 | ○ | | | ○ | | ○ | | | ○ | | | | | | ○ | ○ |
| | P10 | ○ | ○ | — | ○ | | ○ | | | | | | | | | ○ | ○ |
| | P11 | ○ | | | ○ | | ○ | ○ | | ○ | | | ○ | ○ | | ○ | ○ |
| | P12 | ○ | | | ○ | | ○ | | | | | | | | | ○ | ○ |
| | P13 | ○ | ○ | ○ | ○ | | ○ | ○ | | | | | ○ | ○ | | ○ | ○ |
| | P14 | ○ | | | ○ | | ○ | | | | | | | | | ○ | ○ |
| | P15 | ○ | | | ○ | | ○ | ○ | | | | | ○ | ○ | | ○ | ○ |
| | P16 | ○ | | ○ | ○ | | ○ | ○ | | | | | | | | ○ | ○ |
| | P17 | ○ | ○ | | ○ | | ○ | ○ | | | | | ○ | ○ | | ○ | ○ |
| | P18 | ○ | ○ | ○ | ○ | ○ | ○ | ○ | | ○ | | | ○ | ○ | | ○ | ○ |
| | P19 | ○ | | | ○ | ○ | ○ | | | | | | | ○ | | ○ | ○ |
| | P20 | ○ | | — | ○ | | ○ | | | | | | | | | ○ | ○ |

Fig.18

| Antigen No. | Signal average value | | Signal/Noise ratio | |
|---|---|---|---|---|
| | Healthy subject G (Noise) | Patient G (Signal) | | |
| 2 | 2922163 | 3345752 | 1.14 | |
| 3 | 0 | 147099 | Noise: 0 | ☆ |
| 4 | 0 | 37664 | Noise: 0 | ☆ |
| 6 | 2377035 | 2254253 | 0.95 | |
| 9 | 0 | 1053325 | Noise: 0 | ☆ |
| 10 | 3936021 | 4424951 | 1.12 | |
| 11 | 0 | 562020 | Noise: 0 | ☆ |
| 13 | 0 | 0 | Noise: 0 | |
| 19 | 15529 | 1664125 | 107.16 | ☆ |
| 21 | 11704 | 1507 | 0.13 | |
| 22 | 0 | 6612 | Noise: 0 | |
| 24 | 0 | 242985 | Noise: 0 | ☆ |
| 26 | 343240 | 276752 | 0.81 | |
| 28 | 6738 | 0 | 0.00 | |
| 32A | 3422092 | 8959774 | 2.62 | ☆ |
| 35A | 4634482 | 12671575 | 2.73 | ☆ |

| Antigen No. | 2 | 3 | 4 | 6 | 9 | 10 | 11 | 13 |
|---|---|---|---|---|---|---|---|---|
| AUC | 0.490 | 0.650 | 0.611 | 0.495 | 0.625 | 0.530 | 0.725 | 0.500 |

| Antigen No. | 19 | 21 | 22 | 24 | 26 | 28 | 32A | 35A |
|---|---|---|---|---|---|---|---|---|
| AUC | 0.605 | 0.473 | 0.525 | 0.750 | 0.430 | 0.450 | 0.780 | 0.815 |

Fig.21

| No. | Strains | Healthy subject serum group | | | | | | | | | | Patient serum group | | | | | | | | | | | | | | | | | | | |
|---|---|---|---|---|---|---|---|---|---|---|---|---|---|---|---|---|---|---|---|---|---|---|---|---|---|---|---|---|---|---|---|
| | | 1 | 2 | 3 | 4 | 5 | 6 | 7 | 8 | 9 | 10 | 1 | 2 | 3 | 4 | 5 | 6 | 7 | 8 | 9 | 10 | 11 | 12 | 13 | 14 | 15 | 16 | 17 | 18 | 19 | 20 |
| 15 | FDC381 | | | | | | | | | | | | | | | | | | | | | | | | | | | | | ○ | |
| | SU63 | | | | | | | | | | | | | | | | | | | | | | | | | | | | | ○ | |
| 16 | FDC381 | | | | | | | | | | | | | | | | ○ | | | | | | | ○ | | | | | | | |
| | SU63 | | | | | | | | | | | ○ | | | | ○ | | ○ | ○ | | ○ | ○ | ○ | | | ○ | | ○ | ○ | ○ | |
| 34 | FDC381 | | | | | | | | | | | | | | | | | | | | | | | | | | | | | | |
| | SU63 | | | | | | | | | | | | | | | | | ○ | | | | | | | | | | | | | |
| 37 | FDC381 | | | | | | | | | | | | | | | | | | | | | | | ○ | | | | | | | |
| | SU63 | | ○ | | | | | | | | | | | | | | | | ○ | | ○ | | | | | ○ | | ○ | ○ | | |

SEQUENCE LISTING

```
<160> NUMBER OF SEQ ID NOS: 172

<210> SEQ ID NO 1
<211> LENGTH: 820
<212> TYPE: PRT
<213> ORGANISM: Porphyromonas  gingivalis

<400> SEQUENCE: 1

Lys Lys Lys Asn Phe Leu Leu Leu Gly Ile Phe Val Ala Leu Leu Thr
1               5                   10                  15
```

```
Phe Ile Gly Ser Met Gln Ala Gln Gln Ala Lys Asp Tyr Phe Asn Phe
            20                  25                  30

Asp Glu Arg Gly Glu Ala Tyr Phe Ser Phe Lys Val Pro Asp Arg Ala
        35                  40                  45

Val Leu Gln Glu Leu Ala Leu Ile Met Ser Ile Asp Glu Phe Asp Pro
    50                  55                  60

Val Thr Asn Glu Ala Ile Ala Tyr Ala Ser Glu Glu Glu Phe Glu Ala
65                  70                  75                  80

Phe Leu Arg Tyr Gly Leu Lys Pro Thr Phe Leu Thr Pro Pro Ser Met
                85                  90                  95

Gln Arg Ala Val Glu Met Phe Asp Tyr Arg Ser Gly Glu Lys Tyr Glu
            100                 105                 110

Trp Asn Ala Tyr Pro Thr Tyr Glu Ala Tyr Ile Ser Met Met Glu Glu
        115                 120                 125

Phe Gln Thr Lys Tyr Pro Ser Leu Cys Thr Thr Ser Val Ile Gly Lys
    130                 135                 140

Ser Val Lys Asp Arg Lys Leu Met Ile Cys Lys Leu Thr Ser Ser Ala
145                 150                 155                 160

Asn Thr Gly Lys Lys Pro Arg Val Leu Tyr Thr Ser Thr Met His Gly
                165                 170                 175

Asp Glu Thr Thr Gly Tyr Val Val Leu Leu Arg Leu Ile Asp His Leu
            180                 185                 190

Leu Ser Asn Tyr Glu Ser Asp Pro Arg Ile Lys Asn Ile Leu Asp Lys
        195                 200                 205

Thr Glu Val Trp Ile Cys Pro Leu Thr Asn Pro Asp Gly Ala Tyr Arg
    210                 215                 220

Ala Gly Asn His Thr Val Gln Gly Ala Thr Arg Tyr Asn Ala Asn Asn
225                 230                 235                 240

Val Asp Leu Asn Arg Asn Phe Lys Asp Asp Val Ala Gly Asp His Pro
                245                 250                 255

Asp Gly Lys Pro Trp Gln Pro Glu Ala Thr Ala Phe Met Asp Leu Glu
            260                 265                 270

Gly Asn Thr Ser Phe Val Leu Gly Ala Asn Ile His Gly Gly Thr Glu
        275                 280                 285

Val Val Asn Tyr Pro Trp Asp Asn Lys Lys Glu Arg His Ala Asp Asp
    290                 295                 300

Glu Trp Tyr Lys Leu Ile Ser Arg Asn Tyr Ala Ala Ala Cys Gln Ser
305                 310                 315                 320

Ile Ser Ala Ser Tyr Met Thr Ser Glu Thr Asn Ser Gly Ile Ile Asn
                325                 330                 335

Gly Ser Asp Trp Tyr Val Ile Arg Gly Ser Arg Gln Asp Asn Ala Asn
            340                 345                 350

Tyr Phe His Arg Leu Arg Glu Ile Thr Leu Glu Ile Ser Asn Thr Lys
        355                 360                 365

Leu Val Pro Ala Ser Gln Leu Pro Lys Tyr Trp Asn Leu Asn Lys Glu
    370                 375                 380

Ser Leu Leu Ala Leu Ile Glu Glu Ser Leu Tyr Gly Ile His Gly Thr
385                 390                 395                 400

Val Thr Ser Ala Ala Asn Gly Gln Pro Leu Lys Cys Gln Ile Leu Ile
                405                 410                 415

Glu Asn His Asp Lys Arg Asn Ser Asp Val Tyr Ser Asp Ala Thr Thr
            420                 425                 430
```

```
Gly Tyr Tyr Val Arg Pro Ile Lys Ala Gly Thr Tyr Thr Val Lys Tyr
        435                 440                 445

Lys Ala Glu Gly Tyr Pro Glu Ala Thr Arg Thr Ile Thr Ile Lys Asp
    450                 455                 460

Lys Glu Thr Val Ile Met Asp Ile Ala Leu Gly Asn Ser Val Pro Leu
465                 470                 475                 480

Pro Val Pro Asp Phe Thr Ala Ser Pro Met Thr Ile Ser Val Gly Glu
                485                 490                 495

Ser Val Gln Phe Gln Asp Gln Thr Thr Asn Asn Pro Thr Asn Trp Glu
            500                 505                 510

Trp Thr Phe Glu Gly Gly Gln Pro Ala Met Ser Thr Glu Gln Asn Pro
        515                 520                 525

Leu Val Ser Tyr Ser His Pro Gly Gln Tyr Asp Val Thr Leu Lys Val
    530                 535                 540

Trp Asn Ala Ser Gly Ser Asn Thr Ile Thr Lys Glu Lys Phe Ile Thr
545                 550                 555                 560

Val Asn Ala Val Met Pro Val Ala Glu Phe Val Gly Thr Pro Thr Glu
                565                 570                 575

Ile Glu Glu Gly Gln Thr Val Ser Phe Gln Asn Gln Ser Thr Asn Ala
            580                 585                 590

Thr Asn Tyr Val Trp Ile Phe Asp Gly Gly Thr Pro Ala Thr Ser Glu
        595                 600                 605

Asp Glu Asn Pro Thr Val Leu Tyr Ser Lys Ala Gly Gln Tyr Asp Val
    610                 615                 620

Thr Leu Lys Ala Ile Ser Ala Ser Gly Glu Thr Val Lys Thr Lys Glu
625                 630                 635                 640

Lys Tyr Ile Thr Val Lys Lys Ala Pro Val Pro Ala Pro Val Ala Asp
                645                 650                 655

Phe Glu Gly Thr Pro Arg Lys Val Lys Lys Gly Glu Thr Val Thr Phe
            660                 665                 670

Lys Asp Leu Ser Thr Asn Asn Pro Thr Ser Trp Leu Trp Val Phe Glu
        675                 680                 685

Gly Gly Ser Pro Ala Thr Ser Thr Glu Gln Asn Pro Val Val Thr Tyr
    690                 695                 700

Asn Glu Thr Gly Lys Tyr Asp Val Gln Leu Thr Ala Thr Asn Glu Gly
705                 710                 715                 720

Gly Ser Asn Val Lys Lys Ala Glu Asp Tyr Ile Glu Val Ile Leu Asp
                725                 730                 735

Asp Ser Val Glu Asp Ile Val Ala Gln Thr Gly Ile Val Ile Arg Pro
            740                 745                 750

Gln Asn Gly Thr Lys Gln Ile Leu Ile Glu Ala Asn Ala Ala Ile Lys
        755                 760                 765

Ala Ile Val Leu Tyr Asp Ile Asn Gly Arg Val Val Leu Lys Thr Thr
    770                 775                 780

Pro Asn Gln Leu Arg Ser Thr Val Asp Leu Ser Ile Leu Pro Glu Gly
785                 790                 795                 800

Ile Tyr Thr Ile Asn Ile Lys Thr Glu Lys Ser Ala Arg Thr Glu Lys
                805                 810                 815

Ile His Ile Gly
            820

<210> SEQ ID NO 2
<211> LENGTH: 2463
<212> TYPE: DNA
```

<213> ORGANISM: Porphyromonas gingivalis

<400> SEQUENCE: 2

```
aagaaaaaga atttttttgct tcttggcatt ttcgttgctt tgctgacttt catcggcagc    60
atgcaggcac aacaggccaa agattatttc aactttgacg aacggggcga ggcctacttc   120
tcattcaaag tgcctgatag ggccgttcta caagagctgg ctctgatcat gtccatcgac   180
gagtttgacc ccgtaaccaa tgaagccatt gcctatgcca gcgaagagga gttcgaggca   240
ttcctgcgct atgggctcaa gcctacattc ttgactcctc catccatgca gcgcgctgtc   300
gagatgttcg actaccgctc aggagaaaaa tacgaatgga atgcttaccc cacctatgaa   360
gcctatatca gcatgatgga agagttccaa acaaagtatc catcactttg tactacttcc   420
gtcattggca agtccgtaaa ggatcgtaaa ctgatgattt gcaagctgac gtcctctgcc   480
aatacaggga aaaagcctcg cgtgctctat acttctacga tgcacggaga cgaaacgacc   540
ggatatgtgg tactgctccg actcatagac catctgctgt cgaactacga atccgatccg   600
aggattaaga acattctgga taaaacggaa gtatggatct gccctttgac caatccggac   660
ggagcataca gagccggaaa ccacaccgta caaggagcta ctcgctacaa tgccaacaat   720
gtcgatttga accgtaactt caaggatgat gtagccggtg atcaccccga tggaaaacct   780
tggcagccgg aggcaactgc attcatggat ttggaaggaa acacctcttt cgtgctcggt   840
gccaatatac atggaggaac agaggtggtg aactatccat gggataataa aaaagaaaga   900
catgcagacg atgagtggta caaactgatc agtcgcaact acgcagccgc ttgtcagagt   960
atttccgcca gctacatgac ctccgaaacc aattcgggaa tcatcaacgg ttcagactgg  1020
tatgtaattc gcggaagtcg tcaggacaat gcaaattatt tccatcgtct gcgagaaatt  1080
acccttgaaa tcagcaacac gaagttggtg ccggcctctc aacttccaaa gtattggaat  1140
ctgaacaaag aatctctgct tgctctgatc gaagaatcct tatacggcat ccatggtaca  1200
gtgacttccg ctgcgaacgg acagcctctc aaatgccaga tcttgataga aaaccatgac  1260
aagcgcaact ccgatgttta ctccgatgct accacaggct actacgtacg tcctatcaaa  1320
gccggcactt atacggtgaa atacaaagcc gagggttatc ctgaggcaac tcgtaccatt  1380
acgatcaagg acaaagaaac cgtcatcatg gacattgcat tgggcaactc ggttcctctg  1440
cctgtacccg atttcacagc ttctcctatg accatctcag taggcgaaag cgtccaattc  1500
caagatcaaa cgacaaataa ccccacgaat tgggagtgga cgttcgaagg cggacagcct  1560
gccatgagta cagagcagaa tccgctcgta tcctatagtc atcccggtca gtacgacgtt  1620
acgctcaaag tgtggaatgc aagtggttcc aacacgatta cgaaagaaaa attcatcact  1680
gtcaatgccg ttatgcctgt agctgaattc gtcggtaccc cgacggaaat agaagagggc  1740
cagacggtat ctttccaaaa ccaatccacc aatgccacca actacgtatg gatattcgat  1800
ggcggcactc ccgctaccag tgaagacgaa aacccgactg tgctttacag caaagccggc  1860
caatacgatg tcacgctcaa ggcgatcagt gcttccggtg aaacggtgaa gacgaaagaa  1920
aaatacatca ctgtcaagaa agctccggtc cctgctccgg tagccgactt cgaaggaaca  1980
cctcgaaaag taaagaaagg cgagacagtt actttcaaag acttgtctac gaacaatccg  2040
acttcatggc tttgggtgtt cgaaggcggc tctcctgcca ccagcacgga gcaaaacccg  2100
gtggtcacct acaatgaaac aggcaagtac gatgtccagc tgactgccac caacgagggc  2160
ggaagcaatg tgaagaaagc agaagactac attgaggtta tcctcgatga cagtgtcgag  2220
gacatagtgg cacagacggg tatcgtcatt cgtccgcaaa acggaacgaa gcagatcctc  2280
```

```
atagaagcca acgctgctat caaagcgatc gttctctatg acatcaatgg acgggtcgta   2340

ctcaaaacta ctccgaatca gctccgctcg accgtagatc tttccatcct gcccgaagga   2400

atctacacca tcaatatcaa aacggaaaaa tccgctcgca cggaaaagat ccatatcggg   2460

taa                                                                  2463


<210> SEQ ID NO 3
<211> LENGTH: 479
<212> TYPE: PRT
<213> ORGANISM: Porphyromonas  gingivalis

<400> SEQUENCE: 3

Leu Thr Lys Leu Lys Thr Leu Leu Leu Gly Cys Ser Leu Ala Cys Ile
1               5                   10                  15

Gly Phe Ser Cys Ser Asn His Pro Val Leu Thr Asn Ala Asp Asp Val
            20                  25                  30

Glu Gln Pro Leu Asp Ser Gly Tyr Ile Thr Leu Asp Leu Arg Ser Asn
        35                  40                  45

Leu His Leu Ser Arg Lys Gly Gly Thr His Asp Pro Leu Gln Ser Val
    50                  55                  60

Arg Arg Ile Thr Phe Leu Phe Phe His Glu Thr Asp Ser Lys Leu Leu
65                  70                  75                  80

Leu Ser Arg Thr Val Glu Pro Thr Ser Asp Leu Ser Phe Asp Leu Lys
                85                  90                  95

Ile Pro Lys Gln Asn Tyr Arg Leu Ala Val Leu Val Asn Ser Gly Ser
            100                 105                 110

Ser Tyr Ala Ala Ile Ile Pro Glu Ile Leu Leu Pro Thr Thr Ala Ile
        115                 120                 125

Gln Ala Thr Ser Gln Thr Leu Phe Glu Ser Phe Ala Ala Tyr Glu Thr
    130                 135                 140

Gly Asn Ile Thr Ser Glu Ser Glu His Ser Val Thr Met Ala Asn Asp
145                 150                 155                 160

Gln Gly Leu Ile Lys Leu Leu Ser Thr Gln Ile Val Asp Lys Lys Ser
                165                 170                 175

Gln Leu Ser Glu Ala Ser Arg Leu Ser Val Asn Val Glu Pro Cys Leu
            180                 185                 190

Ala Arg Val Leu Val Val Gly Lys Pro Thr Ile Ser Gly Gly Glu Tyr
        195                 200                 205

Thr Gly Asp Val Ser Cys Tyr Val Ile Asp Val Val Pro Gln Arg Ile
    210                 215                 220

Tyr Pro Leu Arg His Leu Ala Lys Leu Ser Ser Gly Thr Asn Glu Ala
225                 230                 235                 240

Tyr Gly Asp Asn Ser Pro Leu Ala Asp Arg Tyr Ala Ser Ser Trp Ala
                245                 250                 255

Glu Glu Ser Ile Ala Ala Gly Val Ala Tyr Asn Asn Val Tyr Gly Tyr
            260                 265                 270

Val Lys Ala Asp Met Phe Asp Asn Pro Val Ala Ala Thr Lys Met Gln
        275                 280                 285

Glu Lys Lys Thr Asp Phe Asn Leu Asn Gln Val Ala Ile Tyr Thr Lys
    290                 295                 300

Glu Ser Thr Val Asn Pro Lys Asn Tyr Phe Thr Ala Tyr Val Pro Arg
305                 310                 315                 320

Val Val Leu Arg Ala Lys Tyr Val Pro His Gly Ile Pro Gly Val Lys
                325                 330                 335
```

```
Pro Asp Glu Gly Trp Ile Glu Phe Gln Gly Arg Lys Met Ser Leu Glu
            340                 345                 350

Gln Phe Lys Lys Tyr Val Asp Asn Pro Val Ser Ala Gly Met Ala Leu
        355                 360                 365

Ala Asp Ser Ile Lys Lys Ala Lys Ala Asp Asn Ser Leu Val Tyr Thr
    370                 375                 380

Gly Gly Phe Val Ser His Gly Ile Gln Phe Tyr Tyr Lys Ser Gln Asn
385                 390                 395                 400

Tyr Tyr Ala Ile Pro Ile Arg His Phe Asp Asp Glu Lys Ala Pro Asn
                405                 410                 415

Lys Asp Ser Tyr Gly Arg Phe Gly Leu Val Arg Asn Asn Glu Tyr Ile
            420                 425                 430

Leu Ser Val Lys Ser Ile Thr Gly Ala Gly Ser Pro Ile Val Pro Pro
        435                 440                 445

Val Ser Thr Thr Glu Ala Ile Glu Lys Glu Gly Tyr Leu Pro Ala Ser
    450                 455                 460

Ile Ala Val Asn Gln Thr Thr Ala His Glu Gln Asp Val Asp Leu
465                 470                 475


<210> SEQ ID NO 4
<211> LENGTH: 1440
<212> TYPE: DNA
<213> ORGANISM: Porphyromonas gingivalis

<400> SEQUENCE: 4

cttacgaaac taaaaacact gctacttggc tgctctttgg cttgtattgg attttcttgc      60

tccaatcatc cggtactgac gaatgccgat gatgttgaac aaccattgga ttcgggttat     120

atcacccttg atcttagatc caacctacac ctctccagaa agggtggtac acatgatcca     180

cttcagtctg ttcgtcgcat taccttcttg ttctttcatg agactgattc aaaactgctg     240

ctaagtcgaa ccgttgaacc gacaagtgac ctctccttcg atctcaaaat accgaaacag     300

aactatcgtc tggccgtgtt ggtcaatagt ggaagttcct atgcagcgat tattccggaa     360

atactattac ctacaacagc cattcaagct acgagtcaga cgctttttga gtcattcgct     420

gcatatgaga ccggtaatat tacatccgag tcggaacatt ccgttaccat ggccaacgat     480

caggggttga tcaaattgct gtctactcag atcgtagaca aaaagagcca gctttccgag     540

gcatcacggt tgtccgtaaa cgtggaaccg tgtctggcac gtgtattggt cgtagggaaa     600

ccgacaatat cgggcggaga gtacacaggc gatgtttcct gctatgtcat tgatgtagta     660

ccacaaagga tataccccctt gcgccatttg gccaaactct ccagtggcac taatgaagcc     720

tatggagaca attcgcctct tgctgaccgt tatgcctcaa gttgggcaga ggaatcgata     780

gccgccggtg tagcatacaa caacgtctat gggtatgtca aggcagacat gtttgacaat     840

cctgtggcag caaccaagat gcaggagaaa aagacggact tcaatctgaa ccaagtagcg     900

atctatacaa aagaatcgac cgtaaatcct aaaaactact ttacggctta tgtgccgaga     960

gtagtcttgc gtgcaaaata cgttcctcat ggcatccccg gcgtgaagcc ggatgaaggc    1020

tggatcgaat ttcagggtag aaagatgagt ctggagcagt tcaaaaaata cgtagacaat    1080

ccggtttctg ccggtatggc tctggccgac agcatcaaga aggcgaaagc tgacaattca    1140

ttggtctata caggtggatt cgtcagtcat ggaatacagt tctattacaa atcgcagaat    1200

tattatgcca tccctattcg ccatttcgat gatgaaaaag ctcctaacaa agattcctac    1260

gggcgtttcg gcctcgtacg aaacaatgag tatatcctct cggtaaagtc cattacagga    1320
```

```
gccggttcac cgattgttcc gcctgtttcg accaccgaag caatcgaaaa ggagggctat   1380

ttacctgctt ctattgcagt caatcagaca acagctcacg agcaggacgt ggatctgtag   1440


<210> SEQ ID NO 5
<211> LENGTH: 1140
<212> TYPE: PRT
<213> ORGANISM: Porphyromonas  gingivalis

<400> SEQUENCE: 5

Met Lys Arg Tyr Thr Ile Ile Leu Ala Val Phe Leu Leu Phe Cys Thr
1               5                   10                  15

Val Phe Thr Phe Gln Ile Lys Ala Arg Pro Tyr Glu Arg Phe Ala Asp
            20                  25                  30

Val Glu Lys Pro Trp Ile Gln Lys His Ser Met Asp Ser Lys Leu Val
        35                  40                  45

Pro Ala Asn Lys Gly Asn Leu Ile Gln Ala Glu Ile Val Tyr Gln Ser
    50                  55                  60

Val Ser Glu His Ser Asp Leu Val Ile Ser Pro Val Asn Glu Ile Arg
65                  70                  75                  80

Pro Ala Asn Arg Phe Pro Ser His Arg Lys Ser Phe Phe Ala Glu Asn
                85                  90                  95

Leu Arg Ala Ser Pro Pro Val Val Pro Val Ala Val Asp Lys Tyr Ala
            100                 105                 110

Val Pro Val Ala Asn Pro Met Asp Pro Glu Asn Pro Asn Ala Trp Asp
        115                 120                 125

Val Thr Leu Lys Ile Thr Thr Lys Ala Val Thr Val Pro Val Asp Val
    130                 135                 140

Val Met Val Ile Asp Gln Ser Ser Ser Met Gly Gly Gln Asn Ile Ala
145                 150                 155                 160

Arg Leu Lys Ser Ala Ile Ala Ser Gly Gln Arg Phe Val Lys Lys Met
                165                 170                 175

Leu Pro Lys Gly Thr Ala Thr Glu Gly Val Arg Ile Ala Leu Val Ser
            180                 185                 190

Tyr Asp His Glu Pro His Arg Leu Ser Asp Phe Thr Lys Asp Thr Ala
        195                 200                 205

Phe Leu Cys Gln Lys Ile Arg Ala Leu Thr Pro Ile Trp Gly Thr His
    210                 215                 220

Thr Gln Gly Gly Leu Lys Met Ala Arg Asn Ile Met Ala Thr Ser Thr
225                 230                 235                 240

Ala Val Asp Lys His Ile Ile Leu Met Ser Asp Gly Leu Ala Thr Glu
                245                 250                 255

Gln Tyr Pro Val Lys Asn Val Thr Thr Ala Asp Phe Ile Gly Lys Thr
            260                 265                 270

Gly Asn Ala Asn Asp Pro Ile Asp Leu Val Ile Gln Gly Ala Ile Asn
        275                 280                 285

Phe Pro Thr Asn Tyr Val Ser Asn Asn Pro Ser Thr Pro Leu Thr Pro
    290                 295                 300

Asn Tyr Pro Thr His Ser Ser Lys Val Gly Arg Arg Asn Leu Pro Glu
305                 310                 315                 320

Ser Lys Phe Asp Tyr Ser Asn Leu Ser Ala Arg Ile Thr Phe Asp Gly
                325                 330                 335

Val Ala Gly Ala Leu Val Tyr Glu Pro Arg Phe Pro His Pro Tyr Tyr
            340                 345                 350
```

```
Tyr Tyr Phe Pro Cys Asn Ala Ala Ile Asn Glu Ala Gln Phe Ala Lys
        355                 360                 365

Asn Ser Gly Tyr Thr Ile His Thr Ile Gly Tyr Asp Leu Gly Asp Phe
    370                 375                 380

Ala Leu Ala Asn Asn Ser Leu Lys Leu Thr Ala Thr Asp Glu Asn His
385                 390                 395                 400

Phe Phe Thr Ala Thr Pro Ala Asn Leu Ala Ala Ala Phe Asp Asn Ile
                405                 410                 415

Ala Gln Thr Ile Asn Ile Gly Ile Gln Arg Gly Glu Val Thr Asp Phe
            420                 425                 430

Val Ala Pro Gly Phe Ile Val Lys Asn Leu Thr Gln Ser Gly Asp Val
        435                 440                 445

Thr His Leu Leu Asn Val Ser Asn Gly Thr Val His Tyr Asp Val Ser
    450                 455                 460

Thr Lys Lys Leu Thr Trp Thr Thr Gly Thr Ile Leu Ser Ser Ser Glu
465                 470                 475                 480

Ala Thr Ile Thr Tyr Arg Ile Tyr Ala Asp Leu Asp Tyr Ile Gln Asn
                485                 490                 495

Asn Asp Ile Pro Val Asn Thr Thr Ser Ala Ile Gly Pro Asp Leu Gly
            500                 505                 510

Gly Phe Asp Thr Asn Thr Glu Ala Lys Leu Thr Tyr Thr Asn Ser Asn
        515                 520                 525

Gly Glu Pro Asn Gln Gln Leu Ile Phe Pro Arg Pro Thr Val Lys Leu
    530                 535                 540

Gly Tyr Gly Val Ile Lys Arg His Tyr Val Leu Val Asn Lys Asp Gly
545                 550                 555                 560

Gln Pro Ile Gln Ala Asn Gly Thr Val Val Ser Ser Leu Ser Glu Ala
                565                 570                 575

His Val Leu Gln Ser Gln Asp Phe Phe Leu Pro Ser Gly Gly Gly His
            580                 585                 590

Ile Val Pro Lys Trp Ile Lys Leu Asp Lys Thr Thr Glu Ala Leu Gln
        595                 600                 605

Tyr Tyr Ser Val Pro Pro Thr Asn Thr Val Ile Thr Thr Ala Asp Gly
    610                 615                 620

Lys Arg Tyr Arg Phe Val Glu Val Pro Gly Ser Thr Pro Asn Pro Gly
625                 630                 635                 640

Gln Ile Gly Ile Ser Trp Lys Lys Pro Ala Gly Asn Ala Tyr Phe Ala
                645                 650                 655

Tyr Lys Leu Leu Asn Tyr Trp Met Gly Gly Thr Thr Asp Gln Gln Ser
            660                 665                 670

Glu Trp Asp Val Thr Ser Asn Trp Thr Gly Ala Gln Val Pro Leu Thr
        675                 680                 685

Gly Glu Asp Val Glu Phe Ala Thr Thr Glu Asn Phe Gly Ser Pro Ala
    690                 695                 700

Val Ala Asp Leu His Val Pro Thr Thr Asn Pro Lys Ile Ile Gly Asn
705                 710                 715                 720

Leu Ile Asn Asn Ser Asp Lys Asp Leu Val Val Thr Thr Ser Ser Gln
                725                 730                 735

Leu Thr Ile Asn Gly Val Val Glu Asp Asn Asn Pro Asn Val Gly Thr
            740                 745                 750

Ile Val Val Lys Ser Ser Lys Asp Asn Pro Thr Gly Thr Leu Leu Phe
        755                 760                 765

Ala Asn Pro Gly Tyr Asn Gln Asn Val Gly Gly Thr Val Glu Phe Tyr
```

```
    770                 775                 780

Asn Gln Gly Tyr Asp Cys Ala Asp Cys Gly Met Tyr Arg Arg Ser Trp
785                 790                 795                 800

Gln Tyr Phe Gly Ile Pro Val Asn Glu Ser Gly Phe Pro Ile Asn Asp
                805                 810                 815

Val Gly Gly Asn Glu Thr Val Asn Gln Trp Val Glu Pro Phe Asn Gly
            820                 825                 830

Asp Lys Trp Arg Pro Ala Pro Tyr Ala Pro Asp Thr Glu Leu Gln Lys
        835                 840                 845

Phe Lys Gly Tyr Gln Ile Thr Asn Asp Val Gln Ala Gln Pro Thr Gly
    850                 855                 860

Val Tyr Ser Phe Lys Gly Met Ile Cys Val Cys Asp Ala Phe Leu Asn
865                 870                 875                 880

Leu Thr Arg Thr Ser Gly Val Asn Tyr Ser Gly Ala Asn Leu Ile Gly
                885                 890                 895

Asn Ser Tyr Thr Gly Ala Ile Asp Ile Lys Gln Gly Ile Val Phe Pro
            900                 905                 910

Pro Glu Val Glu Gln Thr Val Tyr Leu Phe Asn Thr Gly Thr Arg Asp
        915                 920                 925

Gln Trp Arg Lys Leu Asn Gly Ser Thr Val Ser Gly Tyr Arg Ala Gly
    930                 935                 940

Gln Tyr Leu Ser Val Pro Lys Asn Thr Ala Gly Gln Asp Asn Leu Pro
945                 950                 955                 960

Asp Arg Ile Pro Ser Met His Ser Phe Leu Val Lys Met Gln Asn Gly
                965                 970                 975

Ala Ser Cys Thr Leu Gln Ile Leu Tyr Asp Lys Leu Leu Lys Asn Thr
            980                 985                 990

Thr Val Asn Asn Gly Asn Gly Thr  Gln Ile Thr Trp Arg  Ser Gly Asn
        995                 1000                1005

Ser Gly  Ser Ala Asn Met Pro  Ser Leu Val Met Asp  Val Leu Gly
    1010                1015                1020

Asn Glu  Ser Ala Asp Arg Leu  Trp Ile Phe Thr Asp  Gly Gly Leu
    1025                1030                1035

Ser Phe  Gly Phe Asp Asn Gly  Trp Asp Gly Arg Lys  Leu Thr Glu
    1040                1045                1050

Lys Gly  Leu Ser Gln Leu Tyr  Ala Met Ser Asp Ile  Gly Asn Asp
    1055                1060                1065

Lys Phe  Gln Val Ala Gly Val  Pro Glu Leu Asn Asn  Leu Leu Ile
    1070                1075                1080

Gly Phe  Asp Ala Asp Lys Asp  Gly Gln Tyr Thr Leu  Glu Phe Ala
    1085                1090                1095

Leu Ser  Asp His Phe Ala Lys  Gly Ala Val Tyr Leu  His Asp Leu
    1100                1105                1110

Gln Ser  Gly Ala Lys His Arg  Ile Thr Asn Ser Thr  Ser Tyr Ser
    1115                1120                1125

Phe Asp  Ala Lys Arg Gly Asp  Ser Gly Ala Arg Phe
    1130                1135                1140
```

<210> SEQ ID NO 6
<211> LENGTH: 3423
<212> TYPE: DNA
<213> ORGANISM: Porphyromonas gingivalis

<400> SEQUENCE: 6

```
atgaaacgat atacaataat tcttgcagtt tttcttttat tctgcacggt atttaccttt     60
caaataaaag ctcgccctta tgaaagattt gcagatgtag agaagccttg gattcagaaa    120
cattcaatgg attctaaatt ggtgcctgca aataagggta acttaattca agctgaaatt    180
gtataccaat ctgtttctga acatagtgac ttagttattt cacctgtgaa cgaaataagg    240
cctgcaaatc gtttcccttc gcataggaag tcttttttg cagaaaatct acgggcatct    300
ccccccgtag ttcccgttgc cgtcgacaag tatgcggtac cggttgccaa tccaatggat    360
cctgaaaatc ccaatgcctg ggatgtgacg ctaaaaatca ctactaaagc ggtaacagta    420
cctgtcgatg tggtgatggt tatcgaccag tcttcgtcaa tgggagggca aaacattgcc    480
agattaaagt ctgccattgc atcgggacag cgttttgtga aaaaaatgtt gcctaagggg    540
acggctacag aaggggtgcg tatcgctctt gtgagttatg accatgagcc tcatcgctta    600
tctgatttta ccaaagacac tgcttttctc tgtcaaaaaa tccgggcttt gactcctatt    660
tggggaacac atacccaggg gggggcttaaa atggcgagaa acattatggc cacttctact    720
gctgtggata agcatatcat attgatgtct gacgggttag cgacggagca gtatcctgtt    780
aaaaatgtaa ctactgcaga cttcattggc aaaactggaa atgcgaatga tcccattgat    840
ttggttatac aaggagcaat taatttccct acaaattatg tttccaacaa tccatctaca    900
cctcttaccc caaattatcc aactcattct tctaaagttg gacggagaaa tctgccggaa    960
tccaaattcg attatagtaa tctgagtgca aggattactt ttgatggtgt tgctggcgca   1020
ttggtctatg aaccgaggtt tcctcatccc tattattatt atttcccttg taacgctgct   1080
atcaatgagg ctcagtttgc gaaaaactct ggttatacaa tccatactat tggctatgac   1140
ctgggagatt ttgccttggc caacaattcg ttgaaactaa ccgctacaga cgagaatcac   1200
ttctttacgg cgacaccggc caatttagct gcagcgtttg ataatattgc ccaaactatt   1260
aatataggta tacagagggg ggaggtgacg gactttgtag ctcctggttt catcgttaaa   1320
aatctgacgc aatcgggaga tgttactcat ttgctaaatg tttcaaatgg aacggtgcac   1380
tatgatgtct ctactaaaaa actgacatgg actactggta ctatcctgag ctcatcagaa   1440
gctaccataa cttatcgtat ttatgccgat ttggattata tacagaacaa tgatattccg   1500
gtaaatacta cttctgctat cggcccggat cttggtggat tcgataccaa taccgaggca   1560
aaattgacct ataccaattc caatggcgaa ccgaatcagc agttaatttt cccacgtccg   1620
acggttaagt taggttatgg tgttattaag cggcactatg tattggtaaa taaagacggt   1680
caacccatac aggcaaatgg aacagttgtc agttccctaa gcgaggctca tgttctacag   1740
tcacaagatt tctttttgcc ctcaggtgga ggtcatattg ttcccaaatg gataaagttg   1800
gacaaaacga ccgaagcatt acagtactat tccgtaccgc cgactaacac ggtcatcact   1860
actgccgatg gtaaacgtta tcgttttgtc gaagtcccag gctccacgcc gaatccgggc   1920
caaatcggta tcagttggaa aaaaccggca ggaaacgctt acttcgctta caagctcctc   1980
aattattgga tgggaggaac aacagaccaa cagagtgaat gggatgtgac gtccaattgg   2040
acaggagccc aagtaccgct cacaggagaa gatgtagagt ttgcaacgac agaaaatttc   2100
ggttctccgg cggtagccga tttgcatgtc ccgacaacca accccaaaat tatcggtaac   2160
cttatcaata attccgacaa ggatttagtt gttaccacaa gcagtcaatt gacgatcaac   2220
ggcgtggttg aggataacaa tccgaatgtc ggtacgatcg tcgtgaagtc gtcgaaagac   2280
aatcctacgg ggacattgct tttgccaat ccgggctata atcaaaatgt agggggggacc   2340
gtcgagtttt acaatcaggg atatgattgt gccgattgtg gtatgtatcg caggagctgg   2400
```

```
cagtatttcg gtatccctgt caatgaatca ggttttccaa ttaatgatgt gggcggaaac   2460

gagaccgtca accaatgggt tgagcctttc aatggcgata agtggcggcc agcaccttat   2520

gcacctgata cagagcttca aaaattcaag ggctaccaga tcacgaatga cgtgcaggca   2580

cagcctacgg gagtttacag cttcaagggt atgatttgtg tgtgcgatgc cttcctgaat   2640

ctgacacgca cgtccggtgt caactactcg ggcgccaact tgatcggcaa ctcatacact   2700

ggagccatcg acatcaagca gggtattgtc ttcccgccgg aagtcgagca gacggtgtat   2760

ctgttcaaca cgggaacacg cgaccagtgg cgtaagctta atggaagcac ggtttcaggc   2820

tatcgagccg gtcagtacct ctctgtacct aagaatacag cgggtcagga caatcttccg   2880

gatcgtattc catcgatgca ttccttcttg gtgaagatgc agaacggagc gtcttgtacg   2940

ttgcagatct tgtacgataa gctgctcaag aacacgactg taaacaacgg taatggtacg   3000

cagatcacat ggcgatccgg caactccgga tcggcgaata tgccgtcact tgtgatggat   3060

gttcttggta acgagtcggc cgaccgtttg tggatcttta ccgatggggg tctttctttc   3120

ggattcgaca acggctggga tggtcgcaag ctgactgaaa aaggtttgtc acaactttat   3180

gcgatgtctg acatcggtaa tgataaattc caggttgcag ggttccggga gttgaataac   3240

ctgctgatcg gcttcgatgc ggataaggat ggtcaataca cgttggagtt tgctctttcg   3300

gatcattttg cgaaaggggc tgtttacctg cacgatcttc agtcaggagc caaacaccgt   3360

attacgaatt ctacgtcgta ttcattcgat gccaagcggg gagattccgg ggctcgtttc   3420

taa                                                                 3423
```

<210> SEQ ID NO 7
<211> LENGTH: 711
<212> TYPE: PRT
<213> ORGANISM: Porphyromonas gingivalis

<400> SEQUENCE: 7

```
Gln Met Lys Leu Lys Ser Ile Leu Leu Gly Ala Ala Leu Leu Leu Gly
1               5                   10                  15

Ala Ser Gly Val Ala Lys Ala Asp Lys Gly Met Trp Leu Leu Asn Glu
            20                  25                  30

Leu Asn Gln Glu Asn Leu Asp Arg Met Arg Glu Leu Gly Phe Thr Leu
        35                  40                  45

Pro Leu Asp Ser Leu Tyr Ser Phe Asp Lys Pro Ser Ile Ala Asn Ala
    50                  55                  60

Val Val Ile Phe Gly Gly Gly Cys Thr Gly Ile Thr Val Ser Asp Gln
65                  70                  75                  80

Gly Leu Ile Phe Thr Asn His His Cys Gly Tyr Gly Ala Ile Gln Ser
                85                  90                  95

Gln Ser Thr Val Asp His Asp Tyr Leu Arg Asp Gly Phe Val Ser Arg
            100                 105                 110

Thr Met Gly Glu Glu Leu Pro Ile Pro Gly Leu Ser Val Lys Tyr Leu
        115                 120                 125

Arg Lys Ile Val Lys Val Thr Asp Lys Val Glu Gly Gln Leu Lys Gly
    130                 135                 140

Ile Thr Asp Glu Met Glu Arg Leu Arg Lys Ala Gln Glu Val Cys Gln
145                 150                 155                 160

Glu Leu Ala Lys Lys Glu Asn Ala Asp Glu Asn Gln Leu Cys Ile Val
                165                 170                 175

Glu Pro Phe Tyr Ser Asn Asn Glu Tyr Phe Leu Ile Val Tyr Asp Val
```

```
            180                 185                 190

Phe Lys Asp Val Arg Met Val Phe Ala Pro Pro Ser Ser Val Gly Lys
        195                 200                 205

Phe Gly Gly Asp Thr Asp Asn Trp Met Trp Pro Arg His Thr Gly Asp
    210                 215                 220

Phe Ser Val Phe Arg Val Tyr Ala Gly Ala Asp Asn Arg Pro Ala Glu
225                 230                 235                 240

Tyr Ser Lys Asp Asn Lys Pro Tyr Lys Pro Val Tyr Phe Ala Ala Val
                245                 250                 255

Ser Met Gln Gly Tyr Lys Ala Asp Asp Tyr Ala Met Thr Ile Gly Phe
            260                 265                 270

Pro Gly Ser Thr Asp Arg Tyr Leu Thr Ser Trp Gly Val Glu Asp Arg
        275                 280                 285

Ile Glu Asn Glu Asn Asn Pro Arg Ile Glu Val Arg Gly Ile Lys Gln
    290                 295                 300

Gly Ile Trp Lys Glu Ala Met Ser Ala Asp Gln Ala Thr Arg Ile Lys
305                 310                 315                 320

Tyr Ala Ser Lys Tyr Ala Gln Ser Ala Asn Tyr Trp Lys Asn Ser Ile
                325                 330                 335

Gly Met Asn Arg Gly Leu Ala Arg Leu Asp Val Ile Gly Arg Lys Arg
            340                 345                 350

Ala Glu Glu Arg Ala Phe Ala Asp Trp Ile Arg Lys Asn Gly Lys Ser
        355                 360                 365

Ala Val Tyr Gly Asp Val Leu Ser Ser Leu Glu Lys Ala Tyr Lys Glu
    370                 375                 380

Gly Ala Lys Ala Asn Arg Glu Met Thr Tyr Leu Ser Glu Thr Leu Phe
385                 390                 395                 400

Gly Gly Thr Glu Val Val Arg Phe Ala Gln Phe Ala Asn Ala Leu Ala
                405                 410                 415

Thr Asn Pro Asp Ala His Ala Gly Ile Leu Lys Ser Leu Asp Asp Lys
            420                 425                 430

Tyr Lys Asp Tyr Leu Pro Ser Leu Asp Arg Lys Val Leu Pro Ala Met
        435                 440                 445

Leu Asp Ile Val Arg Arg Arg Ile Pro Ala Asp Lys Leu Pro Asp Ile
    450                 455                 460

Phe Lys Asn Val Ile Asp Lys Lys Phe Lys Gly Asp Thr Lys Lys Tyr
465                 470                 475                 480

Ala Asp Phe Val Phe Asp Lys Ser Val Val Pro Tyr Ser Asp Lys Phe
                485                 490                 495

His Ala Met Leu Lys Ser Met Asp Lys Glu Lys Phe Ala Lys Ala Ile
            500                 505                 510

Glu Lys Asp Pro Ala Val Glu Leu Ser Lys Ser Val Ile Ala Ala Ala
        515                 520                 525

Arg Ala Ile Gln Ala Asp Ala Met Ala Asn Ala Tyr Ala Ile Glu Lys
    530                 535                 540

Gly Lys Arg Leu Phe Phe Ala Gly Leu Arg Glu Met Tyr Pro Gly Arg
545                 550                 555                 560

Ala Leu Pro Ser Asp Ala Asn Phe Thr Met Arg Met Ser Tyr Gly Ser
                565                 570                 575

Ile Lys Gly Tyr Glu Pro Gln Asp Gly Ala Trp Tyr Asn Tyr His Thr
            580                 585                 590

Thr Gly Lys Gly Val Leu Glu Lys Gln Asp Pro Lys Ser Asp Glu Phe
        595                 600                 605
```

```
Ala Val Gln Glu Asn Ile Leu Asp Leu Phe Arg Thr Lys Asn Tyr Gly
    610                 615                 620

Arg Tyr Ala Glu Asn Gly Gln Leu His Ile Ala Phe Leu Ser Asn Asn
625                 630                 635                 640

Asp Ile Thr Gly Gly Asn Ser Gly Ser Pro Val Phe Asp Lys Asn Gly
                645                 650                 655

Arg Leu Ile Gly Leu Ala Phe Asp Gly Asn Trp Glu Ala Met Ser Gly
            660                 665                 670

Asp Ile Glu Phe Glu Pro Asp Leu Gln Arg Thr Ile Ser Val Asp Ile
        675                 680                 685

Arg Tyr Val Leu Phe Met Ile Asp Lys Trp Gly Gln Cys Pro Arg Leu
    690                 695                 700

Ile Gln Glu Leu Lys Leu Ile
705                 710


<210> SEQ ID NO 8
<211> LENGTH: 2136
<212> TYPE: DNA
<213> ORGANISM: Porphyromonas gingivalis

<400> SEQUENCE: 8

caaatgaaat taaaaagtat tcttctcgga gcagccctgc tgttgggtgc ttcaggggta      60

gccaaagccg acaaaggcat gtggctcctc aacgaactca atcaggagaa tctggatcga     120

atgcgtgagc tcggctttac gctcccgttg gattcgctct acagtttcga caagccgtcc     180

attgccaatg ccgtggttat cttcggtggc ggatgtaccg gtatcacagt gtccgatcag     240

ggcctgatct ttaccaacca ccactgcgga tacggtgcta tccagagcca aagcacggtg     300

gatcacgact atctgcgcga tggtttcgtt tctcgcacga tgggtgagga gcttccgatt     360

ccgggtcttt ccgtgaagta tctgcgcaag atcgtgaagg taacggacaa ggtagaagga     420

cagctcaagg gtatcactga cgagatggag cgtctgcgca aagctcagga ggtatgccaa     480

gaactggcca aaaaagaaaa tgcagacgag aaccaactct gcatcgtaga gcctttctat     540

tccaacaacg aatacttcct catcgtctac gatgtattca aggacgttcg tatggtattt     600

gctcctccca gctctgtagg taagttcgga ggcgatacgg acaactggat gtggccgcgt     660

cacacgggcg acttcagcgt attccgcgtg tatgccggtg ccgacaaccg gccggccgaa     720

tacagcaagg acaataaacc ctataagccc gtttacttcg ctgccgtatc catgcaaggc     780

tacaaggctg acgactatgc catgaccatc ggtttcccgg gcagtacgga tcgctacctc     840

acttcttggg gtgtggaaga tcgtatcgaa aacgagaaca atcctcgtat cgaagttcgc     900

ggtatcaagc aaggcatctg gaaggaagcc atgagcgcag atcaggctac ccgtatcaaa     960

tatgccagca agtatgctca gagtgctaac tattggaaga attcgatcgg tatgaaccgc    1020

ggtctcgctc gtcttgacgt gataggtcgt aagcgtgccg aggaaagagc attcgcagac    1080

tggatccgta agaacggcaa gagtgctgtc tatggcgatg tattgtcttc tctcgaaaag    1140

gcttataagg aaggagccaa ggccaaccgt gagatgactt atttgagcga gacgctcttc    1200

ggtggtaccg aggtggttcg ttttgcacag tttgccaacg cattggctac aaatcctgat    1260

gctcatgccg gtatcctcaa atcgcttgac gacaagtaca aagactacct cccctcgctc    1320

gaccgtaagg tgctgcccgc catgctcgat attgtacgcc ggcgtatccc tgccgacaag    1380

ctccccgata tattcaagaa tgtaatcgac aagaaattca aaggcgacac gaagaagtat    1440

gcagacttcg tattcgacaa gagtgtggtt ccttatagcg acaagttcca tgccatgctc    1500
```

```
aagtccatgg acaaggaaaa gtttgccaag gctatcgaga aagatccggc agtagagctt   1560

tccaagagcg taatagctgc tgctcgcgct attcaggccg atgcgatggc caatgcctat   1620

gccattgaga agggcaagcg tcttttcttt gccggtttgc gtgagatgta ccccggacgt   1680

gctctgccga gcgatgccaa cttcaccatg cgtatgagct acggctccat caagggatat   1740

gaaccgcagg acggtgcctg gtacaactat catacgacag gcaagggcgt attggagaag   1800

caggatccta agagcgatga gtttgccgta caggagaata tcctcgacct cttccgcacc   1860

aaaaactatg gtcgctatgc cgagaacggt cagctccata tcgctttcct atcgaacaac   1920

gacatcacgg gcggtaactc cggtagcccc gtattcgata agaacggccg tctgatcggt   1980

cttgctttcg atggcaactg ggaagctatg agtggtgaca tcgagttcga acccgatctg   2040

cagcgcacaa tcagcgtgga catccgctac gttctcttca tgattgacaa atggggtcag   2100

tgcccccgtc tcatccaaga gctgaagttg atctaa                             2136
```

```
<210> SEQ ID NO 9
<211> LENGTH: 483
<212> TYPE: PRT
<213> ORGANISM: Porphyromonas  gingivalis

<400> SEQUENCE: 9

Lys Arg Lys Pro Leu Phe Ser Ala Leu Val Ile Leu Ser Gly Phe Phe
1               5                   10                  15

Gly Ser Val His Pro Ala Ser Ala Gln Lys Val Pro Ala Pro Val Asp
            20                  25                  30

Gly Glu Arg Ile Ile Met Glu Leu Ser Glu Ala Asp Val Glu Cys Thr
        35                  40                  45

Ile Lys Ile Glu Ala Glu Asp Gly Tyr Ala Asn Asp Ile Trp Ala Asp
    50                  55                  60

Leu Asn Gly Asn Gly Lys Tyr Asp Ser Gly Glu Arg Leu Asp Ser Gly
65                  70                  75                  80

Glu Phe Arg Asp Val Glu Phe Arg Gln Thr Lys Ala Ile Val Tyr Gly
                85                  90                  95

Lys Met Ala Lys Phe Leu Phe Arg Gly Ser Ser Ala Gly Asp Tyr Gly
            100                 105                 110

Ala Thr Phe Ile Asp Ile Ser Asn Cys Thr Gly Leu Thr Ala Phe Asp
        115                 120                 125

Cys Phe Ala Asn Leu Leu Thr Glu Leu Asp Leu Ser Lys Ala Asn Gly
    130                 135                 140

Leu Thr Phe Val Asn Cys Gly Lys Asn Gln Leu Thr Lys Leu Asp Leu
145                 150                 155                 160

Pro Ala Asn Ala Asp Ile Glu Thr Leu Asn Cys Ser Lys Asn Lys Ile
                165                 170                 175

Thr Ser Leu Asn Leu Ser Thr Tyr Thr Lys Leu Lys Glu Leu Tyr Val
            180                 185                 190

Gly Asp Asn Gly Leu Thr Ala Leu Asp Leu Ser Ala Asn Thr Leu Leu
        195                 200                 205

Glu Glu Leu Val Tyr Ser Asn Asn Glu Val Thr Thr Ile Asn Leu Ser
    210                 215                 220

Ala Asn Thr Asn Leu Lys Ser Leu Tyr Cys Ile Asn Asn Lys Met Thr
225                 230                 235                 240

Gly Leu Asp Val Ala Ala Asn Lys Glu Leu Lys Ile Leu His Cys Asn
                245                 250                 255
```

```
Asn Asn Gln Leu Thr Ala Leu Asn Leu Ser Ala Asn Thr Lys Leu Thr
            260                 265                 270

Thr Leu Ser Phe Phe Asn Asn Glu Leu Thr Asn Ile Asp Leu Ser Asp
        275                 280                 285

Asn Thr Ala Leu Glu Trp Leu Phe Cys Asn Gly Asn Lys Leu Thr Lys
    290                 295                 300

Leu Asp Val Ser Ala Asn Ala Asn Leu Ile Ala Leu Gln Cys Ser Asn
305                 310                 315                 320

Asn Gln Leu Thr Ala Leu Asp Leu Ser Lys Thr Pro Lys Leu Thr Thr
                325                 330                 335

Leu Asn Cys Tyr Ser Asn Arg Ile Lys Asp Thr Ala Met Arg Ala Leu
            340                 345                 350

Ile Glu Ser Leu Pro Thr Ile Thr Glu Gly Glu Gly Arg Phe Val Pro
        355                 360                 365

Tyr Asn Asp Asp Glu Gly Gly Glu Glu Glu Asn Val Cys Thr Thr Glu
    370                 375                 380

His Val Glu Met Ala Lys Ala Lys Asn Trp Lys Val Leu Thr Ser Trp
385                 390                 395                 400

Gly Glu Pro Phe Pro Gly Ile Thr Ala Leu Ile Ser Ile Glu Gly Glu
                405                 410                 415

Ser Glu Tyr Ser Val Tyr Ala Gln Asp Gly Ile Leu Tyr Leu Ser Gly
            420                 425                 430

Met Glu Gln Gly Leu Pro Val Gln Val Tyr Thr Val Gly Gly Ser Met
        435                 440                 445

Met Tyr Ser Ser Val Ala Ser Gly Ser Ala Met Glu Ile Gln Leu Pro
    450                 455                 460

Arg Gly Ala Ala Tyr Val Val Arg Ile Gly Ser His Ala Ile Lys Thr
465                 470                 475                 480

Ala Met Pro
```

<210> SEQ ID NO 10
<211> LENGTH: 1452
<212> TYPE: DNA
<213> ORGANISM: Porphyromonas gingivalis

<400> SEQUENCE: 10

```
aaaagaaaac cgctattctc agcccttgta atcctttccg gcttcttcgg atcggttcac      60

ccggcctcag cacagaaagt tcctgcaccc gtcgatggcg agcgcattat catggagcta     120

agtgaagccg atgtggagtg tacaatcaaa atagaagccg aggatggcta tgccaacgac     180

atttgggcag acctcaacgg aaacggcaag tacgattcgg gggagaggct cgattcaggt     240

gagtttcgtg atgttgagtt cagacaaaca aaggccatcg tctatggcaa aatggccaaa     300

ttcttgttta gaggttcttc tgcaggggac tatggtgcta cctttataga tattagcaat     360

tgtaccggcc tgactgcttt cgactgcttt gccaatctgc tgacagaact cgatctgtcc     420

aaagcaaacg gtctgacttt tgtaaactgc ggcaaaaacc agctgaccaa gcttgacctg     480

cccgcaaatg cggacattga gacgctgaac tgctccaaaa acaagataac gagtctcaac     540

ctatcgacct ataccaagct gaaagagctt tatgtgggcg acaacgggct gacagccttg     600

gatctctccg ccaatacgct cctcgaagag ctggtgtatt ctaacaacga ggtgactacg     660

ataaacctgt ctgccaatac gaacttgaaa agcctgtatt gcataaacaa taagatgacc     720

ggactcgatg tcgcagccaa caaagagctg aaaatactcc actgcaacaa caatcagctg     780

accgccctca atctctcggc caataccaag ctgacgactc taagcttctt caacaacgag     840
```

```
ctgacaaata tcgatctctc cgacaacacg gctttggagt ggcttttctg caacggcaat    900

aagctgacga agttagatgt atctgccaac gccaatctga tagcactgca atgcagcaac    960

aaccagctga ctgctctgga tctgtcaaaa acgccgaaac tgacaacgtt gaattgctac   1020

tccaaccgga tcaaagatac cgccatgcgt gcattgatcg aaagcctgcc tacgatcact   1080

gaaggagaag gcaggttcgt tccttacaac gacgatgaag gaggagaaga ggagaacgtg   1140

tgtacaaccg aacacgtgga aatggccaag gccaagaatt ggaaggtact tacctcgtgg   1200

ggagagcctt tccccggaat aacggctttg atttccatcg aaggtgagag cgaatattcc   1260

gtatatgctc aagatggcat cctctacctc tccggtatgg agcagggctt gcccgttcag   1320

gtatataccg tgggaggaag catgatgtac tcatctgtcg cttccggatc agccatggaa   1380

atacagctcc cgagaggtgc agcctatgta gtacgtatcg gcagccatgc gatcaaaacc   1440

gcgatgccgt aa                                                       1452
```

```
<210> SEQ ID NO 11
<211> LENGTH: 553
<212> TYPE: PRT
<213> ORGANISM: Porphyromonas  gingivalis

<400> SEQUENCE: 11

Arg Ile Lys Pro Ser Leu Lys Thr Met Lys Lys Ile Ser Ala Tyr Val
1               5                   10                  15

Ile Gly Ala Ala Leu Ser Val Ala Ser Gly Val Pro Ser Val Tyr Ala
            20                  25                  30

Gln Gly Glu Ala Asp Ala Ile Arg Tyr Ser Arg Thr Glu Leu Gly Gly
        35                  40                  45

Ser Ala Arg Phe Arg Ser Met Ala Gly Ala Phe Gly Ala Leu Gly Gly
    50                  55                  60

Asp Phe Ser Ala Ile Gly Gln Asn Pro Ala Gly Leu Gly Ile Phe Arg
65                  70                  75                  80

Ser Ser Glu Val Ser Ala Thr Ile Asp Phe Ser Ser Ile Ser Asn Gln
                85                  90                  95

Ala Ala Trp Gln Gly Ser Ser Glu Thr Phe Asn Lys Asn Lys Leu Leu
            100                 105                 110

Phe Thr Gly Ile Gly Tyr Val Gly Ser Trp Gly Lys Ala Asn Glu Asp
        115                 120                 125

Val Ser Val Asn Phe Gly Leu Gly Ala Lys Arg Val Leu Asp Tyr Glu
    130                 135                 140

Arg Ser Phe Arg Ile Ala Gly Gly Glu Gln Lys Phe Ser Val Ala Asp
145                 150                 155                 160

Tyr Val Ala Ala Gln Thr Pro Gly Lys Ala Asn Pro Ser His Phe Asn
                165                 170                 175

Tyr Asn Gly Leu Glu Ser Ser Trp Leu Thr Asp Leu Gly Tyr Asn Ala
            180                 185                 190

Gly Trp Ile Ala Gln Leu Pro Gly Gly Tyr Gly Phe Glu Ser Ile Phe
        195                 200                 205

Lys Tyr Lys Gln Asn Gly Glu Tyr Gln Ile Phe Gly Pro Ser Ser Thr
    210                 215                 220

Ala Phe Asp Leu Lys Glu Thr Gly His Val Trp Asn Tyr Asp Phe Gly
225                 230                 235                 240

Leu Gly Ile Asn Ile Gln Asp Thr Trp Tyr Leu Gly Ala Ser Met Thr
                245                 250                 255
```

```
Tyr Ser Asp Leu Gln Phe Asp Thr Asn Thr Phe Tyr Gln Glu Asn Phe
            260                 265                 270

Ser Phe Asn Asn Gly Ala Ile Asn Asp Tyr Leu Lys Leu Glu Asn Thr
        275                 280                 285

Leu Ser Thr Ser Gly Ser Gly Leu Asn Ile Gly Ile Gly Ala Ile Tyr
    290                 295                 300

Arg Pro Ala Asp Ala Val Arg Ile Gly Leu Ser Tyr Tyr Thr Pro Thr
305                 310                 315                 320

Trp Tyr Trp Met Lys Ser Tyr Tyr Arg Ala Tyr Gly Ser Ser Tyr Tyr
                325                 330                 335

Ser Gln Gly Val Asp Ser Asn Gly Gln Pro Leu Pro Glu Asn Leu Tyr
            340                 345                 350

Phe Met Ser Ser Gln Thr Pro Glu Ser Tyr Asn Thr Tyr Gln Met Ser
        355                 360                 365

Ser Pro Gly Arg Phe Val Ala Ser Leu Ala Val Val Ala Gly Lys Ile
    370                 375                 380

Gly Leu Leu Ser Met Asp Tyr Glu Leu Glu Ser Tyr Gly Gln Ile Lys
385                 390                 395                 400

Leu Lys Asp Glu Asn Gly Thr Ala Tyr Val Asp Asn Lys Phe Ile Ser
                405                 410                 415

Glu Asp Phe Gly Ser Arg His Thr Ile Arg Leu Gly Gly Glu Leu Arg
            420                 425                 430

Pro Ile Ser Arg Leu Ser Leu Arg Ala Gly Tyr Ser His Thr Ser Asn
        435                 440                 445

Pro Ile Lys Asn Glu Lys Leu Lys Ala Phe Asp Gly Ser Ala Gln Val
    450                 455                 460

Thr Val Phe Pro Met Gly Ala Met Pro His Tyr Glu Leu Pro Gly Asn
465                 470                 475                 480

Ser Tyr Thr Val Thr Gly Gly Leu Gly Tyr Arg Phe Thr Arg Asn Leu
                485                 490                 495

Ser Gly Asp Leu Ala Val Ile Tyr Arg Asn Glu Lys Ser Tyr Tyr Tyr
            500                 505                 510

Thr Phe Gly Arg Met Val Ser Asp Asp Pro Asn Pro Ala Asn Val Leu
        515                 520                 525

Glu Val Glu Ser Pro Ala Pro Ala Lys Leu Thr Arg Ser Asn Phe Arg
    530                 535                 540

Leu Ala Met Thr Met Ser Tyr Arg Phe
545                 550
```

<210> SEQ ID NO 12
<211> LENGTH: 1662
<212> TYPE: DNA
<213> ORGANISM: Porphyromonas gingivalis

<400> SEQUENCE: 12

```
aggatcaagc cctctctgaa aacgatgaaa aagatatcag catatgttat tggtgcggca      60

ctttcggttg cttccggcgt gccgtcagtt tatgctcaag gcgaagccga tgctattcgt     120

tacagtcgca cagagcttgg aggttcggct cgtttccgtt ccatggcagg tgctttcggt     180

gctttgggcg gtgacttttc tgctatagga cagaatccgg ccggcctggg catttttcgc     240

tcttcggaag tctcggctac cattgatttc tcttccatat ccaatcaggc agcttggcag     300

ggatcaagtg agaccttcaa taaaaacaaa ttgcttttca cgggtatcgg ttatgtcgga     360

tcatggggca aagccaatga agatgtaagc gtcaatttcg ggctgggggc gaagcgagtg     420
```

```
ctggactacg agcgatcgtt tcggatagcc ggaggtgagc agaagttttc cgtggcggac    480

tatgtggcag ctcagactcc cggcaaagcc aatccgtctc atttcaatta taatggattg    540

gagagcagtt ggcttacgga cttagggtat aatgccggtt ggatagctca gcttcccggc    600

gggtatggtt ttgagtccat attcaagtat aaacagaatg gtgagtacca gatcttcggg    660

ccttcctcca cggctttcga cctgaaagag acggggcacg tatggaacta tgactttggc    720

ttgggcatta acatccaaga cacatggtat ttgggtgcga gcatgactta tagcgatctg    780

caatttgaca cgaacacttt ctatcaggag aatttttctt tcaacaatgg tgctatcaat    840

gactacctga aactcgaaaa tactctctct acatcaggaa gcggactgaa tatcggtatc    900

ggagccatct atcgtccggc tgatgctgtt cggataggtt tgtcctacta tacgcctaca    960

tggtactgga tgaagagtta ctatagggct tatggctctt cttattattc ccaaggggta   1020

gactccaatg gtcagccgct tccggagaat ctctacttca tgagtagcca gactcccgaa   1080

tcgtataata cttatcaaat gagtagtccg ggacgatttg tggctagttt ggcagtcgtt   1140

gctggcaaaa tcggccttct cagtatggat tatgaattgg aatcttacgg ccagatcaaa   1200

ttaaaggatg agaacggtac ggcctacgtt gataataagt tcatttcaga ggattttggt   1260

tcacgccaca ccatccgttt gggaggagaa ctgcgtccca tatcgcgtct gagtctgcgt   1320

gccgggtatt cacacacttc caatcccatt aaaaatgaaa aattgaaagc tttcgacggc   1380

tcggcacagg tgaccgtctt ccctatgggg gctatgcctc attacgaact tccgggcaat   1440

tcctataccg tgacaggagg cttgggttac cgtttcacgc gtaatctttc gggcgatttg   1500

gctgtgatct atcgtaatga gaagagttac tactatactt ttggccgaat ggtatcggac   1560

gacccgaatc cggccaatgt gttggaagtg gaatctcctg caccggcaaa actcactcgc   1620

tctaacttca gattagcaat gacaatgtcg tatcgcttct ga                      1662


<210> SEQ ID NO 13
<211> LENGTH: 348
<212> TYPE: PRT
<213> ORGANISM: Porphyromonas  gingivalis

<400> SEQUENCE: 13

Lys Val Lys His Leu Leu Ala Ala Ser Leu Met Met Leu Gly Thr Gly
1               5                   10                  15

Asn Ile Cys Ala Gln Lys Ser Ala Asn Ser Ile Phe Asn Ala Ile Lys
            20                  25                  30

Glu Arg Val Ser Leu Ser Gly Tyr Ala Gln Ala Gly Phe Ser Ser Leu
        35                  40                  45

Trp Leu Pro Thr Ala Ser Ser Glu Lys Glu Asn Tyr Asn Thr Phe Asp
    50                  55                  60

Val Lys Arg Ile Thr Leu Arg Ala Asn Val Ala Ile Thr Asp Lys Trp
65                  70                  75                  80

Ser Val Thr Phe Ile Pro Asp Phe Ala Lys Arg Tyr Thr Asn Leu Glu
                85                  90                  95

Leu Tyr Thr Ser Phe Arg Thr Cys Ser Gly Phe Gly Ile Arg Leu Gly
            100                 105                 110

Gln Phe Lys Thr Ala Phe Ser Ile Glu Asn Gln Leu Ser Pro Thr Thr
        115                 120                 125

Ile Glu Thr Ile Ser Cys Gly Ser Met Ala Thr Asn Phe Leu Ala Ala
    130                 135                 140

Gly Asn Gly Ser Asp Pro Leu Met Gly Ala Gln Ser Gly Arg Asp Val
145                 150                 155                 160
```

```
Gly Leu Glu Ile Tyr Gly Asp Leu Phe Asn Asp Ile Leu Gly Tyr Arg
                165                 170                 175

Leu Gly Val Leu Asn Gly Gln Gly Ile Asn Thr Leu Asp Gly Ser Lys
            180                 185                 190

His Lys Thr Leu Glu Gly Ser Leu Thr Leu Arg Pro Ile Glu Cys Leu
        195                 200                 205

Ser Phe Thr Gly Ser Phe Met Ser Gly Lys Thr Ala Ala Leu Asn Asp
    210                 215                 220

Ala Pro Ile Lys Ile Asn Ser Lys Gln Ile Met Ala Gly Asp Leu Tyr
225                 230                 235                 240

Asp Arg Ser Arg Trp Ser Val Gly Gly Met Phe Arg Ser Lys Tyr Leu
                245                 250                 255

Asp Leu Arg Ser Glu Tyr Leu Glu Gly Lys Asp Asp Asp Met Ile Ser
            260                 265                 270

Lys Gly Phe Tyr Val Thr Gly Val Gly Arg Leu Phe Lys Asn Leu Asp
        275                 280                 285

Ile Ile Gly Ser Tyr Asp Phe Met Asp Leu Tyr Glu Arg Gln Gln Val
    290                 295                 300

His Asn Ile Thr Ala Gly Leu Gln Tyr Trp Phe Phe Pro Lys Cys Arg
305                 310                 315                 320

Leu Gln Ala Gln Tyr Val Leu Ser Asn Pro Lys Gly Glu Tyr Asn Asn
                325                 330                 335

Thr His Ala Leu Leu Thr Gln Val Gln Val Ala Phe
            340                 345
```

<210> SEQ ID NO 14
<211> LENGTH: 1047
<212> TYPE: DNA
<213> ORGANISM: Porphyromonas gingivalis

<400> SEQUENCE: 14

```
aaagtaaaac atctattagc tgcatccttg atgatgctag gaacagggaa tatttgcgcc      60

caaaagtccg caaacagtat tttcaatgca atcaaagaac gggttagcct cagtggttat     120

gcgcaagcag ggttttcctc cttgtggctc cctacggcga gttccgaaaa ggagaactac     180

aacacattcg atgtaaagcg tatcaccctt cgtgccaatg tcgccatcac ggacaaatgg     240

tctgtaacct tcattcctga ttttgcaaaa agatacacca atttagaact atacacttcc     300

ttccgcactt gttctggttt tggaatacga ttgggacagt tcaagacagc attttcgatc     360

gaaaaccaac tgtctccaac taccatcgaa actatttcat gcggatcgat ggccaccaac     420

ttcctcgcag caggaaatgg ctccgatcct ctgatggggg ctcagagtgg ccgcgacgta     480

ggcttggaaa tctacggtga tctcttcaat gatatactgg gctatcgtct cggagtgctc     540

aacggccaag gcataaatac actcgatggc agcaaacaca aaactttaga agggagtctt     600

acacttcgtc ccatcgagtg tctatccttt accggtagtt tcatgagtgg caagaccgct     660

gccctgaatg atgctcccat caaaatcaat agcaaacaga ttatggccgg agatttatac     720

gacagatccc gctggagtgt aggaggtatg ttccgttcca aatacttgga tctgcgtagt     780

gaatacctcg aaggcaaaga cgatgacatg attagtaagg gcttttacgt cacaggggta     840

ggacgattgt tcaaaaacct cgatatcatc ggatcatatg acttcatgga tttgtacgaa     900

aggcaacaag ttcataatat taccgccggc cttcagtact ggttcttccc aaagtgtcgt     960

ttgcaggcac agtatgtatt gagcaatccg aaaggcgagt acaacaacac acacgctctg    1020
```

```
ctaacacagg tgcaggtagc attctga                                   1047


<210> SEQ ID NO 15
<211> LENGTH: 498
<212> TYPE: PRT
<213> ORGANISM: Porphyromonas  gingivalis

<400> SEQUENCE: 15

Met Lys Leu Asn Lys Met Phe Leu Val Gly Ala Leu Leu Ser Leu Gly
1               5                   10                  15

Phe Ala Ser Cys Ser Lys Glu Gly Asn Gly Pro Ala Pro Asp Ser Ser
            20                  25                  30

Ser Thr Ala Asp Thr His Met Ser Val Ser Met Ser Leu Pro Gln His
        35                  40                  45

Asn Arg Ala Gly Asp Asn Asp Tyr Asn Pro Ile Gly Glu Tyr Gly Gly
    50                  55                  60

Val Asp Lys Ile Asn Asp Leu Thr Val Tyr Val Val Gly Asp Gly Lys
65                  70                  75                  80

Ile Asp Val Arg Lys Leu Ser Thr Ala Asp Leu Gln Val Asn Gln Gly
                85                  90                  95

Ala Ser Thr Thr Ser Ile Val Thr Ala Pro Phe Gln Val Lys Ser Gly
            100                 105                 110

Glu Lys Thr Val Tyr Ala Ile Val Asn Ile Thr Pro Lys Val Glu Ala
        115                 120                 125

Ala Leu Asn Ala Ala Thr Asn Ala Ala Asp Leu Lys Val Ala Tyr Glu
    130                 135                 140

Ala Ala Tyr Ala Ala Phe Ser Asp Ala Gly Ser Glu Ile Ala Thr Leu
145                 150                 155                 160

Val Asn Ser Gln Asp Gln Met Ile Met Ser Gly Lys Pro Val Val Gln
                165                 170                 175

Thr Ile Leu Ala Asn Val Ser Ala Ala Asn Ala Ser Val Gln Asn Lys
            180                 185                 190

Val Pro Ile Ile Val Lys Arg Ala Ala Ile Arg Ala Ser Met Thr Ile
        195                 200                 205

Thr Gln Gln Pro Val Asn Gly Ala Tyr Glu Ile Lys Ala Leu Arg Pro
    210                 215                 220

Gly Asn Val Glu Val Gly Ile Ala Thr Val Ser Asp Leu Lys Trp Ala
225                 230                 235                 240

Val Ala Gln Tyr Glu Lys Lys Tyr Tyr Leu Gln Gln Lys Asp Asp Ala
                245                 250                 255

Leu Ser Pro Ala Ala Ser Phe Val Pro Ala Ser Thr Asn Asp Tyr Asn
            260                 265                 270

Gly Ala Asn Gly Ala Met Lys Tyr Tyr Asp Tyr Ser Gln Leu Ala Asn
        275                 280                 285

Arg Ile Thr Val His Gln Leu Asn Gly Ala Tyr Ser Ala Ala Asp Val
    290                 295                 300

Pro Asn Ala Pro Tyr Lys Tyr Val Ser Gly Thr Thr His Ala Asp Asn
305                 310                 315                 320

Asp Tyr Arg Lys Gly Asn Thr Thr Tyr Ile Leu Val Lys Gly Lys Leu
                325                 330                 335

Lys Pro Val Ala Thr Met Trp Ala Asp Gly Glu Gln Ala Thr Tyr Gln
            340                 345                 350

Glu Gly Gly Asp Leu Phe Leu Gly Leu Val Thr Gly Lys Phe Tyr Ala
        355                 360                 365
```

```
Asn Glu Ala Asn Ala Asn Ala Ala Asn Pro Ala Ser Gly Gly Ala Gly
    370                 375                 380

Asn Pro Arg Val Val Thr Tyr Lys Ala Ala Ala Val Tyr Tyr Tyr Ala
385                 390                 395                 400

Trp Leu Asn Pro Asn Thr Leu Asp Pro Thr Thr Trp Thr Met Ser Pro
                405                 410                 415

Ala Arg Arg Asn Asn Ile Tyr Asn Val Asn Ile Ser Lys Phe Arg Asn
            420                 425                 430

Ile Gly Leu Ser Gly Asn Pro Phe Val Pro Thr Asp Pro Asp Pro Asn
        435                 440                 445

Asn Pro Asp Thr Pro Asp Asn Pro Asp Thr Pro Asp Pro Glu Asp Pro
    450                 455                 460

Asp Thr Pro Asn Pro Glu Glu Pro Leu Pro Val Gln Lys Thr Tyr Met
465                 470                 475                 480

Val Val Asp Val Thr Val Thr Pro Trp Thr Leu His Asn Tyr Asp Ile
                485                 490                 495

Glu Phe


<210> SEQ ID NO 16
<211> LENGTH: 1497
<212> TYPE: DNA
<213> ORGANISM: Porphyromonas gingivalis

<400> SEQUENCE: 16

atgaagttaa acaaaatgtt tttggtcgga gcattgctct cattgggctt tgcttcttgt      60

agtaaagagg gcaatgggcc tgctcccgat agctcttcta cagcagacac tcacatgtct     120

gtttctatgt cgttaccgca gcacaatcgt gctggtgaca acgactacaa tcccataggt     180

gagtatggtg gtgtagacaa aatcaacgac ttgactgttt atgttgtcgg tgatggcaag     240

attgatgtga gaaaactttc tacagctgat ctgcaagtta atcagggagc ctctactact     300

tctattgtga cagctccttt ccaggtaaag agtggtgaaa agactgtcta tgccattgtc     360

aatatcactc ctaaggtaga ggcagctctt aatgcagcga ccaatgctgc tgacctaaag     420

gttgcatatg aagcagctta cgctgccttt tctgatgccg gcagtgagat tgctacgttg     480

gtaaatagcc aggatcagat gattatgtct ggtaagcctg tggtgcagac tattttggct     540

aatgtgagtg ctgccaatgc ttctgtgcag aataaggttc ccataatcgt taaacgtgct     600

gcaatacgtg catcaatgac tattactcag cagcccgtga atggtgctta tgaaatcaag     660

gcgcttcgtc cgggtaatgt agaggttggc atcgctacgg tttctgatct gaagtgggct     720

gtagctcagt acgaaaagaa gtactacctc cagcagaaag acgatgctct ctctccagct     780

gcttctttcg tacctgcaag taccaacgac tacaatggtg ctaatggtgc catgaagtac     840

tatgactact cccagttggc caatagaatc actgttcacc agctgaatgg tgcttattct     900

gccgcagatg tacccaatgc gccttataag tatgtttctg ggactactca tgctgacaat     960

gattacagaa aaggtaatac gacttatatc ctcgtaaagg gtaagctgaa gcctgtcgct    1020

accatgtggg ctgatggaga gcaagctaca tatcaagagg gtggcgacct cttcttgggg    1080

cttgtgaccg gtaagttcta tgcaaatgaa gccaatgcaa acgctgctaa ccctgcttct    1140

ggcggtgccg gtaaccctcg agtagtgacg tacaaagctg cagctgttta ttactatgct    1200

tggttgaatc cgaacacgtt ggatcctacg acatggacta tgtctcctgc acgtcgtaac    1260

aatatctaca acgtgaatat ctctaagttc cgcaacatcg gtctttctgg taatccattc    1320

gttcctacgg atcctgatcc gaacaacccg gatactcctg ataatcctga tactccggac    1380
```

```
cccgaagatc ctgatactcc caatcctgaa gagccgctgc cggttcagaa gacatacatg   1440

gttgtggacg tgacagtgac accttggacg ttgcataact atgatatcga attctaa      1497


<210> SEQ ID NO 17
<211> LENGTH: 343
<212> TYPE: PRT
<213> ORGANISM: Porphyromonas  gingivalis

<400> SEQUENCE: 17

Lys Arg Leu Leu Leu Ser Ala Ala Ile Leu Ser Ser Met Ala Leu Phe
1               5                   10                  15

Asn Val Asn Ala Gln Glu Leu Lys Thr Ser Ala Asp Met Lys Gly Ser
            20                  25                  30

Phe Lys Lys Asn Val Val Leu Glu Val Phe Thr Ala Glu Trp Cys Gly
        35                  40                  45

Tyr Cys Pro Gly Gly Lys Glu Arg Ile Ala Lys Ala Ile Glu Met Leu
    50                  55                  60

Asp Asp Glu Tyr Lys Glu Arg Val Phe Gln Thr Phe Val His Tyr Asn
65                  70                  75                  80

Asp Gly Ile Ser Lys Lys Trp Pro Arg Val Gly Gln Leu Phe Ile Ala
                85                  90                  95

Leu Asp Gln Thr Leu Gly Ile Pro Gly Phe Pro Thr Phe Ser Val Cys
            100                 105                 110

Arg Met Glu Lys Lys Gly Glu Asn Leu Ser Ile Gly Ala Pro Ile Ala
        115                 120                 125

Ile Lys Asn Lys Ile Met Lys Gly Phe Gly Asp Gly Thr Ala Pro Ala
    130                 135                 140

Glu Val Asn Leu Lys Leu Thr Lys Gly Ala Thr Pro Glu Asp Val Cys
145                 150                 155                 160

Thr Ala Thr Phe Thr Gly Lys Val Asp Ala Asp Leu Ile Gly Lys Pro
                165                 170                 175

Leu Met Leu Thr Ala Tyr Val Leu Lys Asn Asn Met Lys Pro Ile Asn
            180                 185                 190

Pro Gln Asn Gly Ala Gly Asp Gly Tyr Leu His Gln His Thr Val Leu
        195                 200                 205

Met Ile Leu Ser Thr Asp Val Lys Gly Asp Ala Leu Asn Ile Ala Ala
    210                 215                 220

Asp Gly Ser Phe Thr Ile Lys Lys Glu Phe Lys Leu Asp Gly Phe Glu
225                 230                 235                 240

Ile Lys Asp Thr Asp Val Leu Ala Phe Val His His Pro Met Ser Asn
                245                 250                 255

Ala Glu Asn His Ser Ile Ile Asn Ala Gly Gln Glu Ser Leu Asp Lys
            260                 265                 270

Ala Glu Pro Thr Ala Thr Glu Gln Ile Val Ala Thr Pro Ser Val Lys
        275                 280                 285

Ala Tyr Val Gln Asn Gly Lys Ile Val Val Glu Glu Glu Tyr Ser Lys
    290                 295                 300

Met Glu Val Phe Asn Ala Thr Gly Gln Leu Val Lys Asn Glu Ser Leu
305                 310                 315                 320

Val Pro Gly Val Tyr Val Val Arg Ile Thr Ala Asn Gly Val Met Tyr
                325                 330                 335

Phe Leu Lys Val Leu Val Pro
            340
```

<210> SEQ ID NO 18
<211> LENGTH: 1032
<212> TYPE: DNA
<213> ORGANISM: Porphyromonas gingivalis

<400> SEQUENCE: 18

```
aaaagattat tactctctgc tgctatccta agtagtatgg ctttgtttaa tgtcaatgca     60

caagagttga aaacctctgc tgacatgaaa ggttctttta agaagaatgt ggtattggag    120

gtatttactg ccgaatggtg cggttactgt ccaggtggaa aagagcgcat tgcaaaagca    180

attgaaatgt tggatgatga atataaggag cgtgtttttc agacatttgt tcattataat    240

gatgggatct caaaaaaatg gcctcgtgtt ggccaacttt tcattgcatt ggatcaaaca    300

ttgggcattc cgggttttcc gactttttca gtttgccgta tggagaaaaa aggtgaaaat    360

ctttcaatag gtgctccaat agcaattaaa aataagatta tgaaaggttt tggtgatggt    420

acagcccctg cagaggtaaa ccttaaattg accaaaggtg caacaccgga agatgtatgt    480

acagctacat ttactggtaa agtcgatgct gacctcatag ggaaacctct tatgttgact    540

gcatatgtat tgaaaaacaa tatgaagcct attaatccgc aaaatggagc tggggatgga    600

tatctccacc aacatactgt gttaatgatt ctctccacag atgtaaaagg agacgcttta    660

aatattgcag ccgatggaag ttttaccatc aagaaagaat ttaagttgga tggctttgaa    720

attaaagata cagatgttct tgctttcgta caccatccaa tgtccaatgc ggaaaaccat    780

tctattatca atgccgggca agaaagcctt gataaagcag agcctacagc tacagaacaa    840

attgttgcta ccccctctgt caaagcatat gttcagaatg gcaaaattgt tgtagaggaa    900

gagtattcca agatggaagt attcaatgca actggtcaac ttgtcaaaaa tgaatccctt    960

gtccccggtg tctatgttgt ccgtataacg gcaaacggtg taatgtattt ccttaaagtc   1020

ttagttcctt ga                                                       1032
```

<210> SEQ ID NO 19
<211> LENGTH: 292
<212> TYPE: PRT
<213> ORGANISM: Porphyromonas gingivalis

<400> SEQUENCE: 19

```
Lys Lys Leu Ile Leu Ala Thr Leu Gly Leu Met Ala Ile Ala Met Leu
1               5                   10                  15

Ser Cys Ser Ser Asn Asn Lys Asp Leu Glu Asn Lys Gly Glu Ala Thr
            20                  25                  30

Leu Leu Val Thr Phe Gly Ser Ser Tyr Lys Ala Pro Arg Glu Thr Tyr
        35                  40                  45

Ala Lys Ile Glu Lys Thr Phe Ala Ala Ala Tyr Pro Asp Gln Arg Ile
    50                  55                  60

Ser Trp Thr Tyr Thr Ser Ser Ile Ile Arg Lys Lys Leu Ala Gln Gln
65                  70                  75                  80

Gly Ile Tyr Ile Asp Ala Pro Asp Glu Ala Leu Glu Lys Leu Ala Arg
                85                  90                  95

Leu Gly Tyr Lys Lys Ile Asn Val Gln Ser Leu His Val Ile Pro Gly
            100                 105                 110

Arg Glu Tyr Asp Glu Met Ile Asp Phe Val Asn Lys Phe Lys Ala Ala
        115                 120                 125

His Ser Asp Ile Thr Val Lys Val Gly Ala Pro Leu Phe Asp Thr Asp
    130                 135                 140
```

```
Glu Asp Met Arg Glu Val Ala Glu Ile Leu His Lys Arg Phe Gln Gln
145                 150                 155                 160

Thr Ile Glu Lys Gly Glu Ala Ile Val Phe Met Gly His Gly Thr Glu
                165                 170                 175

His Ala Ala Asn Asp Arg Tyr Ala Arg Ile Asn Lys Ile Met Lys Asn
            180                 185                 190

Tyr Ser Lys Phe Met Ile Val Gly Thr Val Glu Ser Asp Pro Ser Ile
        195                 200                 205

Asn Asp Val Ile Ala Glu Leu Lys Glu Thr Gly Ala Thr Ala Val Thr
    210                 215                 220

Met Met Pro Leu Met Ser Val Ala Gly Asp His Ala Thr Asn Asp Met
225                 230                 235                 240

Ala Gly Asp Glu Asp Asp Ser Trp Lys Thr Leu Leu Thr Asn Ala Gly
                245                 250                 255

Tyr Thr Val Ser Ile Asp Lys Leu Asp Asn Gly Asn Phe Ser Ala Leu
            260                 265                 270

Gly Asp Ile Glu Glu Ile Arg Asn Ile Trp Leu Lys His Met Lys Ala
        275                 280                 285

Thr Ser Ala Arg
    290


<210> SEQ ID NO 20
<211> LENGTH: 879
<212> TYPE: DNA
<213> ORGANISM: Porphyromonas gingivalis

<400> SEQUENCE: 20

aaaaaactga ttttagcgac tttgggactt atggccattg ccatgctctc atgttcaagc      60

aacaacaagg atttggagaa caaaggggag gctactcttt tggtaacgtt tggtagctcc     120

tataaagctc cacgcgaaac ctatgcgaag attgagaaga cttttgccgc agcttatccc     180

gatcaaagga taagctggac atacacgtct tctattatcc gaaagaaact ggctcagcag     240

ggtatttata tcgatgctcc ggatgaggct ttggagaaat tggctcgtct gggttataag     300

aagatcaatg tacagagtct tcatgtgatt cccggccgag aatatgatga gatgatcgac     360

tttgtcaata agtttaaggc agcacatagt gatattactg tgaaggtagg ggctccgctt     420

ttcgataccg atgaagatat gcgcgaggtg gcagagatct tgcacaagcg ttttcagcaa     480

acgatagaga aaggtgaagc tattgtattc atgggacacg gcaccgagca tgctgccaat     540

gacaggtatg cccgtatcaa taagatcatg aagaactata gcaagttcat gatcgtcgga     600

accgtcgagt ccgatccctc tatcaatgat gttattgccg aactgaaaga aaccggtgcc     660

acggccgtaa caatgatgcc gctgatgagt gtggcaggcg accatgctac gaatgatatg     720

gccggagatg aggacgatag ctggaagacg ttgctgacca atgccggcta cacagtttct     780

atagacaagc tggacaatgg caatttctca gctcttggag atatagaaga gatccggaat     840

atctggctca agcatatgaa agccacctct gctcgctaa                            879


<210> SEQ ID NO 21
<211> LENGTH: 444
<212> TYPE: PRT
<213> ORGANISM: Porphyromonas gingivalis

<400> SEQUENCE: 21

Lys Asn Gln Glu Ile Met Thr Met Leu Glu Ala Lys His Pro Gly Glu
1               5                   10                  15
```

-continued

```
Ser Glu Phe Leu Gln Ala Val Lys Glu Val Leu Leu Ser Val Glu Glu
            20                  25                  30

Val Tyr Asn Gln His Pro Glu Phe Glu Lys Asn Gly Ile Ile Glu Arg
        35                  40                  45

Ile Val Glu Pro Asp Arg Val Phe Thr Phe Arg Val Pro Trp Val Asp
    50                  55                  60

Asp Gln Gly Lys Val Gln Val Asn Ile Gly Tyr Arg Val Gln Phe Asn
65                  70                  75                  80

Asn Ala Ile Gly Pro Tyr Lys Gly Gly Ile Arg Phe His Pro Ser Val
                85                  90                  95

Asn Leu Ser Ile Leu Lys Phe Leu Gly Phe Glu Gln Met Phe Lys Asn
            100                 105                 110

Ala Leu Thr Thr Leu Pro Met Gly Gly Gly Lys Gly Gly Ala Asp Phe
        115                 120                 125

Ser Pro Lys Gly Lys Ser Glu Ala Glu Ile Met Arg Phe Cys Gln Ser
    130                 135                 140

Phe Met Thr Glu Leu Trp Arg Asn Ile Gly Pro Asp Thr Asp Ile Pro
145                 150                 155                 160

Ala Gly Asp Ile Gly Val Gly Gly Arg Glu Val Gly Tyr Met Phe Gly
                165                 170                 175

Met Tyr Lys Lys Leu Ala Arg Glu His Thr Gly Thr Leu Thr Gly Lys
            180                 185                 190

Gly Phe Glu Phe Gly Gly Ser Arg Leu Arg Pro Glu Ser Thr Gly Phe
        195                 200                 205

Gly Ala Val Tyr Phe Val Gln Asn Met Cys Lys Gln Asn Gly Val Asp
    210                 215                 220

Tyr Lys Gly Lys Thr Leu Ala Ile Ser Gly Phe Gly Asn Val Ala Trp
225                 230                 235                 240

Gly Val Ala Gln Lys Ala Thr Glu Leu Gly Ile Lys Val Val Thr Ile
                245                 250                 255

Ser Gly Pro Asp Gly Tyr Val Tyr Asp Pro Asp Gly Ile Asn Thr Pro
            260                 265                 270

Glu Lys Phe Arg Cys Met Leu Asp Leu Arg Asp Ser Gly Asn Asp Val
        275                 280                 285

Val Ser Asp Tyr Val Lys Arg Phe Pro Asn Ala Gln Phe Phe Pro Gly
    290                 295                 300

Lys Lys Pro Trp Glu Gln Lys Val Asp Phe Ala Met Pro Cys Ala Thr
305                 310                 315                 320

Gln Asn Glu Met Asn Leu Glu Asp Ala Lys Thr Leu His Lys Asn Gly
                325                 330                 335

Val Thr Leu Val Ala Glu Thr Ser Asn Met Gly Cys Thr Ala Glu Ala
            340                 345                 350

Ser Glu Tyr Tyr Val Ala Asn Lys Met Leu Phe Ala Pro Gly Lys Ala
        355                 360                 365

Val Asn Ala Gly Gly Val Ser Cys Ser Gly Leu Glu Met Thr Gln Asn
    370                 375                 380

Ala Met His Leu Val Trp Thr Asn Glu Glu Val Asp Lys Trp Leu His
385                 390                 395                 400

Gln Ile Met Gln Asp Ile His Glu Gln Cys Val Thr Tyr Gly Lys Asp
                405                 410                 415

Gly Asn Tyr Ile Asp Tyr Val Lys Gly Ala Asn Ile Ala Gly Phe Met
            420                 425                 430

Lys Val Ala Lys Ala Met Val Ala Gln Gly Val Cys
```

435 440

<210> SEQ ID NO 22
<211> LENGTH: 1335
<212> TYPE: DNA
<213> ORGANISM: Porphyromonas gingivalis

<400> SEQUENCE: 22
aagaaccaag aaattatgac aatgctggag gctaagcacc ccggcgaaag cgaattcctc 60
caagcagtga aggaagttct tctctctgta gaagaagtgt acaaccaaca tcccgagttc 120
gaaaagaacg gtatcatcga gcgtatcgta gagccggatc gtgtattcac attccgtgta 180
ccctgggtag atgaccaagg taaggtacag gtaaacatcg gctaccgcgt tcagttcaac 240
aatgccatcg gtccgtacaa gggcggtatc cgtttccatc cttcagtgaa cctctctatc 300
ctgaagttcc tcggtttcga acagatgttc aagaatgcac tcactactct ccccatgggt 360
ggtggtaaag gtggtgccga cttctctccc aagggtaaga gcgaagccga aatcatgcgt 420
ttctgccaga gcttcatgac cgaattgtgg cgcaacatcg gccctgacac cgacattcct 480
gccggtgaca tcggcgtagg cggtcgcgaa gtaggttata tgttcggtat gtacaagaag 540
ctcgctcgcg agcacacagg tacgcttacc ggcaagggat tcgagttcgg cggttctcgt 600
ctgcgtcccg aatctaccgg tttcggtgct gtttacttcg tacagaacat gtgtaagcaa 660
aacggtgtag actacaaggg caaaactctt gctatctccg gattcggtaa cgttgcttgg 720
ggtgtggctc agaaagctac cgagttgggc attaaggttg ttacgatctc cggtcctgac 780
ggctatgttt acgaccccga cggtatcaac acaccggaga aattccgatg catgcttgac 840
ctccgtgaca gcggtaacga cgtagtatca gactatgtga agagattccc caatgctcag 900
ttcttccccg gcaagaagcc ttgggagcaa aaggtagact tcgctatgcc ttgcgctacg 960
cagaacgaga tgaacctcga agatgccaag acgttgcaca agaatggtgt tactcttgta 1020
gctgaaactt ctaacatggg ttgtacggcc gaagccagcg aatactatgt agcaaacaag 1080
atgctcttcg ctccgggtaa ggctgttaat gcaggtggtg tttcttgctc aggtctcgaa 1140
atgacgcaga acgctatgca cctcgtttgg acgaatgaag aagtggacaa gtggctgcac 1200
cagatcatgc aagacatcca cgagcagtgc gttacatacg gtaaagacgg caactacatc 1260
gactatgtga agggtgccaa tatcgccggc ttcatgaagg ttgccaaggc tatggtagct 1320
cagggcgttt gctaa 1335

<210> SEQ ID NO 23
<211> LENGTH: 359
<212> TYPE: PRT
<213> ORGANISM: Porphyromonas gingivalis

<400> SEQUENCE: 23

Lys Lys His Asn Phe Thr Ala Gly Pro Cys Ile Leu Asn Asp Leu Val
1 5 10 15

Leu Lys Asp Ala Ala Ser Ala Cys Leu Asn Phe Ala Gly Thr Gly Leu
20 25 30

Ser Val Leu Glu Val Ser His Arg Asp Lys Glu Phe Asp Ala Val Met
35 40 45

Leu Glu Ala Arg Asn Leu Phe Lys Glu Leu Leu Asp Val Pro Glu Gly
50 55 60

Tyr Glu Val Leu Phe Leu Gly Gly Gly Ala Ser Leu Gln Phe Tyr Gln
65 70 75 80

```
Val Pro Leu Asn Leu Leu Lys Lys Lys Ala Ala Phe Ile Asn Thr Gly
                85                  90                  95

Thr Trp Ala Thr Asn Ala Ile Lys Gln Ala Lys Ile Met Thr Gln Val
            100                 105                 110

Tyr Gly Gly Glu Val Glu Val Leu Ala Ser Ser Glu Asp Lys Asn Phe
        115                 120                 125

Ser Tyr Ile Pro Lys Asp Phe Val Ile Pro Glu Asp Val Asp Tyr Phe
    130                 135                 140

His Phe Thr Thr Asn Asn Thr Ile Tyr Gly Thr Glu Ile Arg Lys Asp
145                 150                 155                 160

Phe Asp Thr Lys Thr Arg Leu Val Ala Asp Met Ser Ser Asp Ile Phe
                165                 170                 175

Ser Arg Pro Ile Asp Val Ser Lys Tyr Asp Leu Ile Tyr Gly Gly Ala
            180                 185                 190

Gln Lys Asn Ile Gly Pro Ala Gly Ala Thr Phe Val Leu Val Lys Thr
        195                 200                 205

Asp Val Leu Gly Gln Val Asp Arg Pro Leu Pro Asp Met Leu Asn Tyr
    210                 215                 220

Gln Ile His Ile Lys Lys Asp Ser Met Phe Asn Thr Pro Pro Val Phe
225                 230                 235                 240

Pro Val Tyr Val Ala Leu Gln Thr Met Lys Trp Tyr Lys Glu Leu Gly
                245                 250                 255

Gly Val Lys Val Leu Glu Lys Met Asn Leu Asp Lys Ala Ala Leu Ile
            260                 265                 270

Tyr Asp Ala Ile Asp Ser Ser Lys Ile Phe Arg Gly Thr Val Asn Pro
        275                 280                 285

Glu Asp Arg Ser Ile Met Asn Ala Cys Phe Val Met Lys Asp Glu Tyr
    290                 295                 300

Lys Glu Leu Glu Lys Glu Phe Ala Thr Phe Ala Ala Ser Arg Gly Met
305                 310                 315                 320

Val Gly Ile Lys Gly His Arg Ser Val Gly Gly Phe Arg Ala Ser Leu
                325                 330                 335

Tyr Asn Ala Leu Pro Ile Glu Ser Val Gln Ser Leu Val Ser Val Met
            340                 345                 350

Lys Glu Phe Glu Ala Lys His
        355


<210> SEQ ID NO 24
<211> LENGTH: 1080
<212> TYPE: DNA
<213> ORGANISM: Porphyromonas  gingivalis

<400> SEQUENCE: 24

aagaagcaca atttcaccgc aggaccctgt atcctcaatg acttagtttt gaaagatgct      60

gcatcagcat gtctcaattt tgcaggaacg ggtctttctg ttcttgaagt ttctcaccgc     120

gacaaagagt tcgatgctgt aatgctcgaa gctcgcaatc tcttcaaaga acttcttgat     180

gtgcccgaag gctatgaagt acttttcctc ggtggtggcg ccagcctcca attctaccaa     240

gtaccgctga acctgctaaa gaagaaagca gcctttatca acaccggtac atgggcaacc     300

aacgccatca agcaggccaa gatcatgacg caggtatatg gtggagaagt agaggttttg     360

gcttcatctg aagacaagaa cttctcatac atccccaagg atttcgttat tcctgaggac     420

gtagattatt tccacttcac gacaaacaac acgatctacg gtactgaaat tcgtaaggac     480

ttcgacacga agactcgcct tgtagcagac atgtcttccg acattttctc tcgtccgata     540
```

```
gacgtttcca agtatgacct catctacggt ggtgctcaga agaacatcgg tccggccgga    600

gctactttcg tattggtaaa aacggatgtg ctcggacaag tagatcgtcc tctacccgat    660

atgctgaact atcagatcca catcaagaaa gactctatgt tcaacactcc tcccgtattc    720

cccgtttatg tagcactcca gacgatgaag tggtacaaag aactcggcgg tgtgaaggtg    780

ttggaaaaga tgaatctgga caaggcagcc cttatctacg atgccatcga cagcagcaag    840

atcttccgcg gcacggttaa tcctgaagac cgctctatca tgaacgcttg cttcgtgatg    900

aaggatgagt acaaagaact ggagaaagag ttcgctacgt ttgcagcttc acgcggcatg    960

gtaggtatca agggacaccg ctctgtaggc ggtttccgcg cttctctcta caacgcattg   1020

cctatcgaaa gcgtacaatc tttggttagc gtaatgaagg aattcgaagc taagcactaa   1080


<210> SEQ ID NO 25
<211> LENGTH: 705
<212> TYPE: PRT
<213> ORGANISM: Porphyromonas  gingivalis

<400> SEQUENCE: 25

Lys Lys Phe Phe Phe Ala Leu Leu Ser Ile Gly Ile Ser Ala Gln Ala
1               5                   10                  15

Phe Ala Lys Thr Asp Asn Val Pro Thr Asp Ser Leu Arg Val His Asn
            20                  25                  30

Leu Gln Thr Val Thr Val Tyr Ser Thr Arg Thr Ala Val Pro Leu Lys
        35                  40                  45

Lys Ile Pro Ala Lys Met Glu Leu Ile Ser Ser Arg Asn Ile Lys Gln
    50                  55                  60

Ser Gly Phe Asn Asn Met Thr Asp Ile Leu Lys Thr Gln Ser Ser Leu
65                  70                  75                  80

Asp Val Ile Gln Tyr Pro Gly Phe Ser Ser Asn Ile Gly Ile Arg Gly
                85                  90                  95

Phe Lys Pro Ser Gly Lys Tyr Val Thr Val Leu Val Asn Gly Ile Pro
            100                 105                 110

Ala Gly Thr Asp Asn Ile Ser Thr Leu Asn Thr Ser Asn Ile Glu Gln
        115                 120                 125

Ile Glu Ile Leu Lys Gly Pro Phe Ser Ser Ile Tyr Gly Thr Asn Ala
    130                 135                 140

Met Gly Gly Val Val Asn Ile Ile Thr His Lys Ser Lys Asp Lys Ile
145                 150                 155                 160

His Gly Asn Val Ser Leu Phe Gly Gly Ser Tyr Gln Thr Met Ala Gly
                165                 170                 175

Ser Phe Asn Leu Gly Gly Arg Phe Glu Asp Ile Phe Ser Phe Asp Leu
            180                 185                 190

Ser Leu Gly Leu Asp Lys Gln Asn Lys Asp Tyr Lys Thr Gly Ser Asn
        195                 200                 205

Asn Phe Leu Ser Leu Ser Lys Leu Glu Glu Ala Ile Val Asp Val Asn
    210                 215                 220

Ala Thr Lys Asn Lys Lys Met Lys Gly Ser Asp Tyr Thr Val Ala Thr
225                 230                 235                 240

Gly Arg Leu Arg Phe Gly Ile Asp Phe Thr Pro Glu Trp Ser Leu Asn
                245                 250                 255

Leu Tyr Gln Asn Val Phe Leu Gly Asp Ala Ile Pro Val Gly Gly Ser
            260                 265                 270

Ile Trp Gly Val Tyr Gly Glu Ser Lys Lys Asn Leu Asn Arg Ser Ser
```

```
        275                 280                 285

Thr Ser Phe Glu Leu Leu Gly Lys His Gly Cys His Thr Leu Gln Phe
    290                 295                 300

Ser Pro Tyr Phe Asn Ile Glu Lys Ser Glu Asn Tyr Asn Asn Ala Asp
305                 310                 315                 320

Pro Thr Gly Phe Ile Asn Tyr Lys Ser Asp Tyr Tyr Thr Tyr Gly Ala
                325                 330                 335

Leu Leu Gln Asp Lys Ile Ser Phe Gly Gly Gln Asn Ile Val Leu Gly
            340                 345                 350

Val Asp Ser Arg Asn Met Thr Met Glu Ser Glu Arg Phe Glu Gln Ala
        355                 360                 365

Gly Val Asn Thr Lys Pro Tyr Asn Pro Gly Tyr Ala Thr Asn Asn Ile
    370                 375                 380

Gly Leu Phe Gly Gln Ala Asn Phe Tyr Leu Leu Asn Asp Ala Leu Ser
385                 390                 395                 400

Ile Ser Ala Gly Ala Arg Ala Asp Phe Met Phe Phe Asp Leu Lys Ala
                405                 410                 415

Asn Glu Tyr Leu Asn Asn Glu Ala Lys Gln Glu Thr His Asn Val Ile
            420                 425                 430

Asn Pro Asn Val Gly Ile Lys Tyr Glu Phe Val Lys Gly Leu Thr Ala
        435                 440                 445

His Gly Thr Phe Gly Ser Ala Phe Ser Ala Pro Asp Ala Phe Gln Lys
    450                 455                 460

Ala Gly Gln Tyr Val Gly Pro Phe Gly Thr Thr Ile Gly Asn Pro Asp
465                 470                 475                 480

Leu Lys Pro Glu Lys Ser Met Thr Trp Asp Phe Gly Ile Gly Tyr Ser
                485                 490                 495

Asn Ala Arg Cys Gly Ile Gln Ala Asp Val Thr Tyr Phe His Thr Asp
            500                 505                 510

His Lys Asp Leu Ile Leu Ser Ser Pro Asp Tyr Ala Asn Asn Ile Thr
        515                 520                 525

Thr Tyr Ile Asn Ala Asp Lys Ala Arg Met Ser Gly Ile Glu Ala Leu
    530                 535                 540

Leu Ser Tyr Asp Phe Gly Ser Leu Phe Ala Asn Lys Phe Ser Leu Arg
545                 550                 555                 560

Ala Phe Ala Asn Ala Thr Ile Met Leu Asn Ser Glu Met Lys Lys Ser
                565                 570                 575

Gln Thr Asp Ala Pro Trp Ser Glu Met Tyr Tyr Val Arg Lys Gln Asn
            580                 585                 590

Ile Thr Phe Gly Ile Glu Tyr Arg Gly Lys Glu Gly Leu Glu Val Met
        595                 600                 605

Leu Asn Gly Arg Phe Met Gly Arg Arg Ile Glu Gln Asn Trp Tyr Ala
    610                 615                 620

Tyr Tyr Pro Glu Val Arg Pro Glu Leu Gln Gln Leu Leu Ala Ala Glu
625                 630                 635                 640

Glu Pro Glu Leu Ala Ala Gln Gly Leu Leu Arg His Pro Gln Ala Met
                645                 650                 655

Val Phe Asn Ala Ser Ala Tyr Tyr His Met Asn Lys Tyr Leu Thr Phe
            660                 665                 670

Gly Val Asn Leu Asn Asn Ile Leu Asp Glu Leu Tyr Thr Glu Lys Asp
        675                 680                 685

Gly Tyr His Met Pro Gly Arg Asn Ile Met Gly Lys Val Met Val Asn
    690                 695                 700
```

Phe
705

<210> SEQ ID NO 26
<211> LENGTH: 2118
<212> TYPE: DNA
<213> ORGANISM: Porphyromonas gingivalis

<400> SEQUENCE: 26
aaaaagtttt tcttcgcgct actatcgatt ggtatttcag cgcaggcttt tgccaagacg 60
gacaacgtcc cgacagattc gctacgagta cacaatcttc agaccgtcac ggtctattct 120
acacgcacgg ccgtacctct gaaaaagata ccggccaaga tggaactcat ctcatcgcgc 180
aacatcaagc agtccggctt taacaacatg accgacatcc tcaagacgca aagttcgctc 240
gatgtcatac aatacccggg ctttagttcg aacatcggta tccgcggttt caagccctcc 300
ggcaagtatg taaccgtatt ggtaaacggc atccctgcgg gaacggacaa tatctctacg 360
ctcaacacga gcaacatcga acaaatcgag atcctcaaag gcccgttctc ttccatctac 420
ggcaccaatg ccatgggcgg tgtggtgaac atcatcaccc acaaatccaa ggacaagatc 480
catggcaacg tttctctctt cggcggtagc taccagacca tggccggatc attcaacttg 540
ggtggccgct tcgaggatat tttctcattc gatcttagtc tgggcttgga caagcagaac 600
aaggactata agaccggatc aaacaatttc ctatccctga gcaaactgga agaagctata 660
gtagatgtaa atgctaccaa aaacaagaaa atgaagggga gcgactatac tgtagcaacg 720
ggacgtctgc gtttcggtat cgacttcacg cccgaatggt cgctgaatct gtatcaaaac 780
gtattcctcg gagatgcgat ccccgtagga ggatctatat ggggcgttta cggagaatcc 840
aaaaaaaatc tgaatcgttc ttcgacctct ttcgagctgc tcggcaaaca tggctgccac 900
acgcttcaat tctcccccta cttcaacata gagaaatcgg agaactataa caatgccgat 960
cccaccggtt tcatcaacta caaaagcgac tactacacct atggtgccct actccaggac 1020
aagatttcct ttggaggaca aaatatcgta ctcggtgtcg acagccgaaa catgacgatg 1080
gagtcagaaa gattcgagca ggcaggagtg aatacaaagc catacaaccc cggatatgcc 1140
acgaacaata tcggtttgtt cggacaggcc aatttctacc tgctgaacga tgctctatcg 1200
atatctgccg gtgcacgtgc cgacttcatg ttctttgacc tgaaagcgaa cgagtatctc 1260
aacaatgaag ccaaacagga aactcataac gtaatcaatc cgaatgtcgg aatcaaatat 1320
gagtttgtga aaggccttac agctcatggt acattcggta gtgcattcag tgctcccgat 1380
gctttccaaa aagcaggcca atacgtaggc ccgttcggca cgaccatagg caatcctgac 1440
ctgaaacccg aaaagtccat gacctgggac ttcggtatcg gatacagcaa tgcacgctgc 1500
gggatccaag ccgacgtaac ctatttccac accgaccaca aagatctgat cttgtccagc 1560
cctgactatg ctaataatat caccacatac atcaatgccg acaaggctcg tatgagcggt 1620
atcgaggccc ttttgtctta tgacttcggc agcctctttg ccaacaagtt ctctctccgc 1680
gcatttgcga atgccacgat catgctcaat tccgagatga agaaaagcca gaccgatgcc 1740
ccttggagcg aaatgtacta cgttcgcaag cagaacatca ccttcggtat cgaatatcgt 1800
ggcaaagaag gacttgaagt gatgctcaac ggtcgcttca tgggacgcag gatcgagcaa 1860
aactggtatg cttactaccc cgaagttcgc cccgaactcc agcaactgct tgcagcagaa 1920
gagcctgaat tggctgctca gggactgctc cgtcatccgc aagcaatggt gttcaatgcc 1980
tctgcttact accacatgaa caagtatctc accttcggtg tgaacttgaa caacatcttg 2040

```
gatgagcttt atacggagaa agacggctac cacatgcccg gacgtaacat catgggtaag   2100

gttatggtca acttctaa                                                  2118


<210> SEQ ID NO 27
<211> LENGTH: 387
<212> TYPE: PRT
<213> ORGANISM: Porphyromonas  gingivalis

<400> SEQUENCE: 27

Lys Lys Thr Lys Phe Phe Leu Leu Gly Leu Ala Ala Leu Ala Met Thr
1               5                   10                  15

Ala Cys Asn Lys Asp Asn Glu Ala Glu Pro Val Val Glu Thr Asn Ala
            20                  25                  30

Thr Val Ser Phe Ile Ile Lys Ser Gly Glu Ser Arg Ala Val Gly Asp
        35                  40                  45

Asp Leu Thr Asp Ala Lys Ile Thr Lys Leu Thr Ala Met Val Tyr Ala
    50                  55                  60

Gly Gln Val Gln Glu Gly Ile Lys Thr Val Glu Glu Asp Gly Gly Val
65                  70                  75                  80

Leu Lys Val Glu Gly Ile Pro Cys Lys Ser Gly Ala Asn Arg Val Leu
                85                  90                  95

Val Val Val Ala Asn His Asn Tyr Glu Leu Thr Gly Lys Ser Leu Asn
            100                 105                 110

Glu Val Glu Ala Leu Thr Thr Ser Leu Thr Ala Glu Asn Gln Asn Ala
        115                 120                 125

Lys Asn Leu Ile Met Thr Gly Lys Ser Ala Ala Phe Thr Ile Lys Pro
    130                 135                 140

Gly Ser Asn His Tyr Gly Tyr Pro Gly Gly Thr Ala Ser Asp Asn Leu
145                 150                 155                 160

Val Ser Ala Gly Thr Pro Leu Ala Val Thr Arg Val His Ala Gly Ile
                165                 170                 175

Ser Phe Ala Gly Val Glu Val Asn Met Ala Thr Gln Tyr Gln Asn Tyr
            180                 185                 190

Tyr Ser Phe Lys Pro Ala Asp Ala Lys Ile Ala Ala Leu Val Ala Lys
        195                 200                 205

Lys Asp Ser Lys Ile Phe Gly Asn Ser Leu Val Ser Asn Thr Asn Ala
    210                 215                 220

Tyr Leu Tyr Gly Val Gln Thr Pro Ala Gly Leu Tyr Thr Pro Asp Ala
225                 230                 235                 240

Ala Gly Glu Thr Tyr Glu Leu Glu Ala Ser Leu Asn Thr Asn Tyr Ala
                245                 250                 255

Val Gly Ala Gly Phe Tyr Val Leu Glu Ser Lys Tyr Asp Ala Ser Asn
            260                 265                 270

Glu Leu Arg Pro Thr Ile Leu Cys Ile Tyr Gly Lys Leu Leu Asp Lys
        275                 280                 285

Asp Gly Asn Pro Leu Thr Glu Pro Ala Leu Thr Asp Ala Ile Asn Ala
    290                 295                 300

Gly Phe Cys Asp Gly Asp Gly Thr Thr Tyr Tyr Pro Val Leu Val Asn
305                 310                 315                 320

Tyr Asp Gly Asn Gly Tyr Ile Tyr Ser Gly Ala Ile Thr Gln Gly Gln
                325                 330                 335

Asn Lys Ile Val Arg Asn Asn His Tyr Lys Ile Ser Leu Asn Ile Thr
            340                 345                 350
```

```
Gly Pro Gly Thr Asn Thr Pro Glu Asn Pro Gln Pro Val Gln Ala Asn
        355                 360                 365

Leu Asn Val Thr Cys Gln Val Thr Pro Trp Val Val Val Asn Gln Ala
    370                 375                 380

Ala Thr Trp
385
```

<210> SEQ ID NO 28
<211> LENGTH: 1164
<212> TYPE: DNA
<213> ORGANISM: Porphyromonas gingivalis

<400> SEQUENCE: 28

```
aaaaaaacaa agtttttctt gttgggactt gctgctcttg ctatgacagc ttgtaacaaa      60

gacaacgagg cagaacccgt tgtagaaact aacgctactg ttagtttcat aattaagagc     120

ggtgagagcc gcgctgtagg cgatgacctt acagatgcta agatcacaaa gctcaccgcc     180

atggtctatg caggtcaagt tcaagaaggt attaagacag tggaagagga cggcggagtc     240

cttaaagtag aaggaattcc gtgtaaatct ggagccaacc gtgtcctcgt cgttgtagcc     300

aatcacaatt atgagcttac cggtaaaagt ttgaatgagg ttgaggcctt gacgacttct     360

ttgacagctg aaaaccaaaa tgccaaaaac ttgatcatga caggtaagtc agcagctttt     420

acaatcaaac cgggctccaa ccactatggc tatcctggtg ggactgcatc cgacaacctt     480

gtttctgctg gaactcctct tgccgttact cgcgtgcatg ccggtatctc attcgcagga     540

gtagaggtaa atatggctac acagtatcaa aactactatt cttttaaacc agctgacgct     600

aaaatcgcag cccttgtcgc aaagaaagat tctaagattt tcggcaattc tttggtctca     660

aacactaatg catatttgta tggagtccaa acgcctgccg gtctttacac tccggatgct     720

gcaggagaaa catacgaatt ggaggcgtct ttgaatacga attatgctgt aggtgccggc     780

ttctatgtgc tggaaagtaa atatgatgca agcaacgagc ttcgtccgac gatcctttgt     840

atctatggaa agctgctcga taaggacggc aaccctctca cggaaccagc cttgacggat     900

gctataaatg ccggattctg cgacggagat ggcacgactt actatccggt attggtgaac     960

tatgatggca atggctacat ctattcaggt gctattaccc aaggacaaaa caaaatcgtt    1020

cgcaacaacc actacaagat ttcgctgaac atcaccggcc ccggtacgaa tactcctgaa    1080

aatcctcaac cggtacaagc caacctgaat gttacttgcc aagttacacc ttgggttgtt    1140

gttaatcagg ctgctacttg gtaa                                            1164
```

<210> SEQ ID NO 29
<211> LENGTH: 553
<212> TYPE: PRT
<213> ORGANISM: Porphyromonas gingivalis

<400> SEQUENCE: 29

```
Lys Lys Leu Leu Tyr Ile Leu Leu Leu Pro Leu Leu Ile Leu Ser Cys
1               5                   10                  15

Val Lys Glu Gln Asn Met Ser Val Pro Gly Asp Glu Ala Val Val Arg
            20                  25                  30

Phe Ser Leu Asp Gln Ser Asp Phe Ser Ser Leu Arg Ser Arg Ser Tyr
        35                  40                  45

Glu Asp Leu Ile Gln Thr Leu Glu Leu Trp Val Phe Asp Glu Gln Gly
    50                  55                  60

Leu Phe Val Glu Lys Ala Lys Glu Val Gln Tyr Asn Pro Phe Ala Asn
65                  70                  75                  80
```

```
Ser Phe Thr Ala Lys Val Ser Lys Ser Met Ser Pro Arg Ile Ile His
                85                  90                  95

Phe Ile Val Asn Tyr Thr Leu Ala Asn Glu Ala Asn Trp Val Gly His
            100                 105                 110

Asp Glu Lys Glu Met Val Pro Ser Leu Ser Val Gly Thr Gln Pro Thr
        115                 120                 125

Tyr Leu His Met Trp Ala Arg Lys Arg Tyr Glu Lys Ile Glu Gly Asn
    130                 135                 140

Asp Asn Leu Gln Thr Ile Thr Val Arg Arg Asn Met Ala Lys Phe Ser
145                 150                 155                 160

Leu Ala Met Asn Thr Ala Lys Leu Thr Glu Val Glu Tyr Ser Leu Tyr
                165                 170                 175

Asn Thr Phe Asp Lys Gly Thr Leu Ala Pro Phe Asp Pro Ser Glu Thr
            180                 185                 190

Asn Pro Asp Leu Ala Phe Lys Lys Asp Phe Val Thr Glu Pro Ala Gly
        195                 200                 205

Ala Asp Phe Asp Asn Gln Lys Gly Phe Lys Pro Val Gly Pro Glu Asn
    210                 215                 220

Phe Phe Tyr Gly Phe Glu Arg Lys Asn Ser Val Ile Ala Ala Gly Glu
225                 230                 235                 240

Gln Ile Ser Cys Leu Ile Ile Lys Gly Lys Tyr Gln Gly Ser Asn Ala
                245                 250                 255

Phe Ser Tyr Tyr Lys Ile Asp Phe Val His Gln Asp Asp Lys Thr Lys
            260                 265                 270

Arg Tyr Asp Ile Ile Arg Asn His Phe Tyr Lys Val Thr Ile Asn Asp
        275                 280                 285

Val Phe Lys Ala Gly Phe Pro Thr Ile Glu Ala Ala Leu Ser Gly Ala
    290                 295                 300

Ala Ala Asn Asn Ile Ala Leu Ser Glu Glu Leu Gln Met Tyr Pro Ser
305                 310                 315                 320

Phe Ser Asp Gly Lys Gly Lys Ile Glu Val Asp His Thr Tyr Leu Ala
                325                 330                 335

Phe Thr Asp Gly Gln Thr Thr Gly Thr Ile Lys Ala Ala Tyr Tyr Pro
            340                 345                 350

Asn Val Gly Asn Val Thr Gln Gln Asn Asn Leu Ile Thr Val Thr Tyr
        355                 360                 365

Ser Gly Asp Ala Val Thr Gly Ala Thr Asn Asn Asn Gly Thr Ile Ser
    370                 375                 380

Leu Ser Leu Ala Ala Thr Pro Gly Ser Gly Ser Cys Thr Ser Asp Ile
385                 390                 395                 400

Ile Val Gly Ala Gln Asp Asn Pro Asp Leu Lys Arg Leu Val Arg Val
                405                 410                 415

Val Val Arg Lys Pro Tyr Val Tyr Asn Pro Phe Ala Val Arg Thr Gln
            420                 425                 430

Lys Gly Ala Gly Asp Ala Phe Thr Glu Tyr Thr Ala Thr Ser Asn Ala
        435                 440                 445

Val Ser Cys Gln Val His Lys Thr Gln Asp Lys Ala Leu Asn Ile Val
    450                 455                 460

Met Asn Ile Pro Ala Asp Phe Asn Pro Ala Leu Leu Pro Thr Thr Phe
465                 470                 475                 480

Arg Ile Lys Thr Asn Asn Phe Tyr Pro Ser Gly Gly Gln Gly Leu Ile
                485                 490                 495
```

```
Phe Gly Asn Glu Ala Glu Lys Pro Phe Tyr Asp Tyr Ile Leu Thr Ala
            500                 505                 510

Ile Pro Thr Asp Arg Lys Val Glu Leu Met Phe Lys Ser Asn Lys Ser
        515                 520                 525

Ala Ser Ala Glu Thr Ile Thr Val Ser Ser Arg Ser Lys Tyr Phe His
    530                 535                 540

Thr Gln Thr Ile Thr Val Ala Asn Pro
545                 550


<210> SEQ ID NO 30
<211> LENGTH: 1662
<212> TYPE: DNA
<213> ORGANISM: Porphyromonas  gingivalis

<400> SEQUENCE: 30

aaaaaattgc tatatatact gttgctaccc ctgctaatac tttcgtgtgt caaggaacag     60

aatatgtctg ttccggggga cgaggcagta gtgcgtttta gtttggatca atccgatttc    120

agttctttgc gcagcagaag ctatgaagat ctgatacaga ctttagagct atgggttttc    180

gatgagcaag gtcttttcgt ggaaaaagcc aaagaagtgc agtacaatcc cttcgctaat    240

tcttttacgg cgaaggtttc gaaatcgatg tcgcctcgta tcattcattt cattgtgaat    300

tatacgttgg ccaacgaggc aaactgggtc ggacacgatg agaaagaaat ggtaccgtca    360

ttgtcagtcg gcacacaacc tacttactta catatgtggg ctcgaaagag atacgagaaa    420

attgagggca atgacaattt gcaaacgata acagtgcgtc gcaatatggc caaattcagc    480

ttggccatga ataccgccaa gctgacagag gtggagtact ctctttataa cacctttgac    540

aaaggcacct tggctccatt cgacccctcc gaaacgaatc cagacttagc attcaaaaaa    600

gattttgtga ccgagccggc cggagctgat tttgataatc agaaagggtt caaacctgtc    660

ggtcctgaga atttctttta tggtttcgag cgtaaaaatt cagttattgc tgcgggagaa    720

caaatctctt gcctgatcat aaaaggcaaa tatcaaggta gtaatgcctt ttcttactac    780

aagatagact ttgtccatca ggacgacaag accaagcgtt acgacatcat acgcaatcac    840

ttctataagg tgacgatcaa tgatgtattt aaagccggat ttcccacaat cgaggcggct    900

ctttcaggtg ctgctgcgaa caacatagct ctctccgagg agctgcaaat gtacccgtct    960

ttctctgacg ggaaaggtaa gatcgaagtg gatcatactt acttggcctt taccgatggg   1020

cagacaacgg gcacaatcaa agcggcttat tatccgaatg ttggcaacgt aacacagcag   1080

aacaatctga tcaccgtcac atatagcggt gatgcagtaa ccggtgctac taacaacaac   1140

ggtacgattt cgttgtcatt ggctgcaaca cccggttcag gctcatgtac gtcagacatc   1200

attgtgggag cacaagataa tcctgacctc aaacgtctgg tgcgtgtggt agtgaggaag   1260

ccctacgttt acaatccatt tgcagtccgc acacaaaagg gtgcaggaga tgcattcaca   1320

gaatacacag ccacttcgaa cgcagtctct tgtcaggtac ataagacgca ggataaagca   1380

ctgaacatcg tcatgaatat cccggccgat ttcaatccgg ctttgcttcc tactactttc   1440

cgaatcaaga cgaacaactt ttatccctcc ggtggtcagg ggcttatctt tggcaacgag   1500

gccgaaaagc ctttttacga ctatatcctg acggcaatcc cgaccgatcg caaggtggaa   1560

ctgatgttca aatcgaataa atctgcttcg gctgagacga tcacagtttc ttctcgttca   1620

aaatacttcc acacacagac gataacggtg gcgaatccgt aa                      1662


<210> SEQ ID NO 31
<211> LENGTH: 215
```

<212> TYPE: PRT
<213> ORGANISM: Porphyromonas gingivalis

<400> SEQUENCE: 31

```
Lys Lys Ile Ile Phe Ser Ala Leu Cys Ala Leu Pro Leu Ile Val Ser
1               5                   10                  15

Leu Thr Ser Cys Gly Lys Lys Lys Asp Glu Pro Asn Gln Pro Ser Thr
            20                  25                  30

Pro Glu Ala Val Thr Lys Thr Val Thr Ile Asp Ala Ser Lys Tyr Glu
        35                  40                  45

Thr Trp Gln Tyr Phe Ser Phe Ser Lys Gly Glu Val Val Asn Val Thr
    50                  55                  60

Asp Tyr Lys Asn Asp Leu Asn Trp Asp Met Ala Leu His Arg Tyr Asp
65                  70                  75                  80

Val Arg Leu Asn Cys Gly Glu Ser Gly Lys Gly Lys Gly Gly Ala Val
                85                  90                  95

Phe Ser Gly Lys Thr Glu Met Asp Gln Ala Thr Thr Val Pro Thr Asp
            100                 105                 110

Gly Tyr Thr Val Asp Val Leu Gly Arg Ile Thr Val Lys Tyr Glu Met
        115                 120                 125

Gly Pro Asp Gly His Gln Met Glu Tyr Glu Glu Gln Gly Phe Ser Glu
    130                 135                 140

Val Ile Thr Gly Lys Lys Asn Ala Gln Gly Phe Ala Ser Gly Gly Trp
145                 150                 155                 160

Leu Glu Phe Ser His Gly Pro Ala Gly Pro Thr Tyr Lys Leu Ser Lys
                165                 170                 175

Arg Val Phe Phe Val Arg Gly Ala Asp Gly Asn Ile Ala Lys Val Gln
            180                 185                 190

Phe Thr Asp Tyr Gln Asp Ala Glu Leu Lys Lys Gly Val Ile Thr Phe
        195                 200                 205

Thr Tyr Thr Tyr Pro Val Lys
    210                 215
```

<210> SEQ ID NO 32
<211> LENGTH: 648
<212> TYPE: DNA
<213> ORGANISM: Porphyromonas gingivalis

<400> SEQUENCE: 32

```
aaaaaaatca ttttctccgc actctgtgca ttgccattga ttgtgtctct aacttcttgt      60

gggaagaaga aagacgagcc gaaccaaccc tccacacccg aagcagtaac caaaaccgta     120

actatcgatg cttcgaaata cgaaacgtgg cagtatttct ctttttccaa aggtgaagtc     180

gtaaatgtta ccgactataa gaacgatttg aactgggaca tggctcttca ccgctatgac     240

gttcgtctca attgtggcga aagtggtaag ggaaaaggtg gtgccgtatt ctccggcaag     300

acagaaatgg atcaggctac taccgttccg acagacggat atactgtaga tgttctcggc     360

cgtattacag tcaagtacga aatgggacct gatggtcatc agatggaata tgaagaacag     420

ggcttcagcg aagtgattac cggcaagaag aacgcacagg gatttgcttc aggtggttgg     480

ctggaattct ctcacggtcc tgccggtccc acttacaagc tgagcaaaag agtcttcttc     540

gttcgtggtg ctgatggtaa tattgccaaa gtgcagttca ctgactatca ggatgcagaa     600

ctcaaaaaag gagtcatcac tttcacttat acatacccg ttaaataa                 648
```

<210> SEQ ID NO 33

```
<211> LENGTH: 598
<212> TYPE: PRT
<213> ORGANISM: Porphyromonas  gingivalis

<400> SEQUENCE: 33

Thr Asn Asp Ile Leu Gln Arg Leu Ala Ser Leu Arg Lys Val Met Ser
1               5                   10                  15

His Glu His Ile Asp Ala Tyr Ile Ile Pro Ser Ser Asp Ala His Leu
            20                  25                  30

Ser Glu Tyr Thr Pro Glu His Trp Lys Gly Arg Arg Trp Ile Ser Gly
        35                  40                  45

Phe Thr Gly Ser Ala Gly Thr Val Val Val Thr Ala Asn Lys Ala Gly
    50                  55                  60

Leu Trp Thr Asp Gly Arg Tyr Phe Leu Gln Ala Gly Gln Gln Leu Glu
65                  70                  75                  80

Gly Thr Ser Ile Asp Leu Tyr Lys Glu Gly Ile Pro Gly Thr Pro Ser
                85                  90                  95

Ile Glu Gln Phe Leu Ala Ala Glu Leu Lys Ala Gly Gln Thr Val Gly
            100                 105                 110

Ile Asp Gly Arg Cys Phe Pro Ala Gly Ala Ala Ser Ala Thr Glu Ser
        115                 120                 125

Ala Leu Asp Ile Tyr Gly Ile Lys Leu Arg Thr Asp Lys Asp Leu Phe
    130                 135                 140

Asp Glu Ala Trp Arg Asp Arg Pro Glu Ile Pro Arg Gly Glu Leu Phe
145                 150                 155                 160

Val Gln Pro Val Lys Tyr Ala Gly Glu Ser Val Lys Asp Lys Ile Ala
                165                 170                 175

Arg Val Asn Lys Glu Leu Ala Thr Gln Gly Ala Asn Ala Thr Ile Ile
            180                 185                 190

Thr Met Leu Asp Glu Leu Ala Trp Ile Phe Asn Leu Arg Gly Arg Asp
        195                 200                 205

Val Glu Cys Asn Pro Val Gly Val Ala Phe Gly Tyr Val Ser Ala Arg
    210                 215                 220

Glu Ser Val Leu Phe Ala Phe Pro Glu Lys Ile Thr Lys Glu Val Arg
225                 230                 235                 240

Ser Ala Met Glu Glu Gly Gly Val Lys Ile Met Pro Tyr Glu Ala Ile
                245                 250                 255

Tyr Glu Tyr Ile Pro Ala Leu Pro Ala Glu Glu Arg Leu Leu Ile Asp
            260                 265                 270

Lys Lys Arg Ile Thr Arg Ala Leu Tyr Asp Leu Ile Pro Ala Ala Cys
        275                 280                 285

Arg Lys Ile Asp Gly Val Ser Thr Ile Thr Ala Leu Lys Ala Ile Lys
    290                 295                 300

Asn Glu Gln Glu Leu Ser Gly Val Arg Ala Ala Met Val Arg Asp Gly
305                 310                 315                 320

Val Ala Leu Thr Arg Phe Phe Met Trp Leu Glu Gln Glu Trp Glu Ala
                325                 330                 335

Gly Arg Asn His Asp Glu Val Val Leu Gly Glu Lys Leu Thr Ala Phe
            340                 345                 350

Arg Thr Ala Gln Pro Leu Tyr Phe Gly Asp Ser Phe Asp Thr Ile Cys
        355                 360                 365

Gly Tyr Gln Asp His Gly Ala Ile Ile His Tyr Arg Ala Thr Pro Glu
    370                 375                 380

Ser Ala His Val Val Lys Arg Glu Gly Val Leu Leu Leu Asp Ser Gly
```

```
385                 390                 395                 400

Ala Gln Tyr His Asp Gly Thr Thr Asp Ile Thr Arg Thr Val Ala Leu
                405                 410                 415

Ser Thr Pro Ser Ala Glu Leu Lys Arg Asn Tyr Thr Leu Val Met Lys
            420                 425                 430

Gly His Ile Ala Ile Ala Thr Ala Gln Tyr Leu Glu Gly Thr Arg Gly
        435                 440                 445

Ser Gln Ile Asp Val Leu Ala Arg Lys Ala Leu Trp Asp Asn Gly Met
    450                 455                 460

Asn Tyr Ala His Gly Thr Gly His Gly Val Gly Cys Phe Leu Asn Val
465                 470                 475                 480

His Glu Gly Pro Gln Asn Ile Arg Met Asp Glu Asn Pro Thr Glu Met
                485                 490                 495

Lys Ile Gly Met Ile Thr Ser Asn Glu Pro Gly Leu Tyr Arg Ser Gly
            500                 505                 510

Lys Tyr Gly Ile Arg Ile Glu Asn Leu Val Val Thr Lys Leu Asn Val
        515                 520                 525

Glu Thr Glu Phe Gly Arg Phe Phe Gly Phe Glu Thr Leu Thr Ala Phe
    530                 535                 540

Tyr Phe Asp Asn Glu Leu Ile Glu Lys Ser Leu Leu Thr Ala Asp Glu
545                 550                 555                 560

Leu Lys Trp Tyr Asn Asp Tyr Gln Gln Trp Val Tyr Lys Thr Leu Ala
                565                 570                 575

Pro Glu Leu Thr Thr Glu Glu Arg Ala Trp Leu Lys Glu Lys Thr Gln
            580                 585                 590

Thr Ser Lys Arg Pro His
        595
```

<210> SEQ ID NO 34
<211> LENGTH: 1797
<212> TYPE: DNA
<213> ORGANISM: Porphyromonas gingivalis

<400> SEQUENCE: 34

```
acaaacgata tcttgcagcg tcttgcgtct ttgcgcaaag tcatgagtca tgagcatatc      60

gatgcttata tcatcccgag ttcggatgcc cacctaagcg aatacacacc ggaacactgg     120

aaaggtcgcc gttggatttc cggtttcacc ggatcggccg gcacagtagt ggtcacagca     180

aataaggccg gactatggac ggacggacgc tacttcctcc aagcaggcca acagctcgaa     240

ggcacttcta tcgacctcta caaagaaggc atccccggaa ctccctccat cgaacagttt     300

cttgccgccg agctgaaagc cgggcaaaca gtgggtatag atggacgttg ctttccggca     360

ggtgctgcct ctgcaaccga atcggctttg gatatatacg gcatcaaact aaggactgac     420

aaggatcttt tcgatgaagc atggcgagat cgtccagaaa tccctcgtgg agagcttttc     480

gttcagcccg tgaagtatgc aggagaaagc gtgaaagaca agatcgcacg tgtcaataaa     540

gaactggcga cacaaggtgc caatgccact attatcacca tgttggacga attggcttgg     600

atattcaatc ttcgtggtag agatgtggag tgcaaccccg taggagttgc ttttggttat     660

gtatcggctc gagaatctgt cctctttgct ttccctgaga agattactaa ggaggttcgc     720

tcagctatgg aagaaggcgg ggtcaagatt atgccctacg aagccatata tgaatatatc     780

ccagcactac ctgccgaaga aaggctgctt atcgacaaga aacgcattac acgcgcactt     840

tatgacctta taccggctgc ttgtcggaaa atagacggtg tcagcacaat tacagcgttg     900
```

```
aaagctatca agaacgagca agagctatcc ggtgttcgtg ccgctatggt acgtgatggc    960

gttgccctta cccgattctt tatgtggttg gaacaggagt gggaagccgg tcgcaaccat   1020

gacgaagtgg tattgggtga aaagctcaca gcattccgta ctgctcagcc cctctatttc   1080

ggagatagtt tcgatacgat atgcggctat caggatcatg gtgctatcat ccattaccgc   1140

gccacacccg aatccgccca cgtagtcaaa cgagaaggtg tactcctcct cgatagcgga   1200

gcacagtatc atgatggcac tacagacatc acacgtactg tcgctttgag tactccatcg   1260

gccgaactca aacggaacta tacccttgtg atgaaagggc atatcgctat tgccacggca   1320

caatatctgg agggtacgcg cggtagtcag atcgatgtat tggcacgcaa agccctttgg   1380

gacaatggaa tgaactatgc tcatggcacg ggacatggcg tcggttgctt cctcaacgtc   1440

catgaagggc cgcagaatat tcgcatggat gagaatccta ccgaaatgaa gattggaatg   1500

attacgagca atgaaccggg tctttatcgt tccggcaaat atggtatccg aatcgaaaac   1560

ctcgtagtga ccaagttgaa tgtagagact gaattcggcc gattcttcgg attcgaaacg   1620

ctgacggctt tctatttcga caacgaactc atcgaaaaaa gcttgctcac agcagatgaa   1680

ttgaagtggt acaatgacta ccagcagtgg gtgtacaaga cgcttgctcc cgaactgact   1740

accgaggaaa gagcttggct caaagagaaa actcagactt ctaagcggcc gcactag      1797
```

<210> SEQ ID NO 35
<211> LENGTH: 335
<212> TYPE: PRT
<213> ORGANISM: Porphyromonas gingivalis

<400> SEQUENCE: 35

```
Thr Lys Val Gly Ile Asn Gly Phe Gly Arg Ile Gly Arg Leu Val Phe
1               5                   10                  15

Arg Ala Ala Gln Thr Gln Asn Arg Ser Asp Ile Glu Ile Val Ala Ile
            20                  25                  30

Asn Asp Leu Ile Asp Val Glu Tyr Met Ala Tyr Met Leu Lys Tyr Asp
        35                  40                  45

Ser Val His Gly Arg Phe Asn Gly Thr Val Glu Val Lys Asp Gly Gln
    50                  55                  60

Leu Ile Val Asn Gly Lys Ala Ile Arg Val Thr Ala Glu Lys Asn Pro
65                  70                  75                  80

Ala Asp Leu Lys Trp Asp Gln Val Gly Val Glu Tyr Val Val Glu Ser
                85                  90                  95

Thr Gly Leu Phe Leu Thr Lys Glu Lys Ser Glu Ala His Leu Ala Ala
            100                 105                 110

Gly Ala Lys Tyr Val Val Met Ser Ala Pro Ser Lys Asp Asp Thr Pro
        115                 120                 125

Met Phe Val Cys Gly Val Asn Thr Asp Lys Tyr Val Lys Gly Thr Lys
    130                 135                 140

Ile Val Ser Asn Ala Ser Cys Thr Thr Asn Cys Leu Ala Pro Ile Ala
145                 150                 155                 160

Lys Val Leu Asn Asp Asn Trp Gly Met Val Gly Gly Leu Met Thr Thr
                165                 170                 175

Val His Ala Thr Thr Ala Thr Gln Lys Thr Val Asp Gly Pro Ser Ala
            180                 185                 190

Lys Asp Trp Arg Gly Gly Arg Ala Ala Gly Gly Asn Ile Ile Pro Ser
        195                 200                 205

Ser Thr Gly Ala Ala Lys Ala Val Gly Lys Val Ile Pro Glu Leu Asn
    210                 215                 220
```

```
Gly Lys Leu Thr Gly Met Ser Phe Arg Val Pro Thr Leu Asp Val Ser
225                 230                 235                 240

Val Val Asp Leu Thr Cys Gln Leu Ala Lys Pro Ala Lys Tyr Glu Asp
                245                 250                 255

Ile Cys Ala Ala Met Lys Lys Ala Ser Glu Gly Glu Leu Lys Gly Ile
            260                 265                 270

Leu Gly Tyr Thr Asp Glu Glu Val Val Ser Ser Asp Phe Ile Gly Glu
        275                 280                 285

Thr Arg Thr Ser Val Phe Asp Ala Lys Ala Gly Ile Ala Leu Thr Asp
    290                 295                 300

Thr Phe Val Lys Ile Val Ser Trp Tyr Asp Asn Glu Ile Gly Tyr Ser
305                 310                 315                 320

Asn Lys Val Leu Asp Leu Ile Ala Tyr Met Ala Lys Val Asn Ala
                325                 330                 335


<210> SEQ ID NO 36
<211> LENGTH: 1008
<212> TYPE: DNA
<213> ORGANISM: Porphyromonas  gingivalis

<400> SEQUENCE: 36

acgaaagtag gtattaacgg ctttggccgt atcggccgct tggtattccg cgcagcacaa      60

acacaaaaca gaagcgacat tgaaattgta gccatcaacg acctgatcga tgtggaatat     120

atggcgtaca tgctcaagta cgacagtgta cacggtcgtt tcaatgggac agtcgaagtc     180

aaagatggtc agctgatagt aaacgggaaa gccattcgag ttacagctga gaagaaccct     240

gccgatctga aatgggatca agtcggagtg gaatacgtag tggaatccac cggtcttttc     300

ctcacgaaag aaaaatccga agcacacctt gctgccggtg ccaagtatgt agttatgtcg     360

gctccctcta aagacgacac gcctatgttc gtatgcggag tgaatacgga taagtacgta     420

aaaggcacga agatcgtttc caacgcttct tgtaccacca actgtctggc acccattgcc     480

aaggtactga atgacaactg gggcatggta ggaggtctca tgaccacggt acatgccacc     540

acagctacgc agaagacagt ggacggcccc tctgcaaaag actggcgcgg cggtagagca     600

gcaggcggca atatcatccc ctcttccacc ggtgcagcca aagcagtagg caaggtgatc     660

cccgaactga acggcaaact gacgggtatg tcattccgtg tgccgacact ggacgtatcg     720

gtagtagacc tgacatgcca gttggcgaaa ccggctaaat acgaagatat ttgtgctgcc     780

atgaagaaag cttcggaagg cgaactcaaa ggcattttgg gctacacgga cgaagaagtg     840

gtttcctccg acttcatcgg cgaaacccgt acttccgtat tcgatgccaa ggccggtatc     900

gcacttacgg atacttttgt gaagatcgtt tcatggtacg acaacgaaat cggatactcc     960

aacaaagtac tcgatctcat cgcctacatg gctaaggtaa acgcataa                1008


<210> SEQ ID NO 37
<211> LENGTH: 159
<212> TYPE: PRT
<213> ORGANISM: Porphyromonas  gingivalis

<400> SEQUENCE: 37

Lys Ile Ser Glu Asn Val Thr Lys Ala Ile Asn Asp Gln Ile Lys Ala
1               5                   10                  15

Glu Met Trp Ser Ser Asn Leu Tyr Leu Ser Met Ser Val His Phe Ala
            20                  25                  30

Gln Val Gly Tyr Asn Gly Phe Ala His Trp Leu Lys Lys Gln Ser Leu
```

```
        35                  40                  45

Glu Glu Met Glu His Ala Tyr Asp Met Met Asp Tyr Leu Leu Lys Arg
    50                  55                  60

Gly Gly Glu Val Lys Ile Glu Ala Ile Asp Ala Val Pro Gln Lys Phe
65                  70                  75                  80

Gly Ser Val Leu Glu Val Phe Gln Gln Val Tyr Glu His Glu Cys Lys
                85                  90                  95

Val Thr Glu Met Ile Glu Ala Val Val Arg Ala Ala Ser Glu Ala Gly
            100                 105                 110

Asp Met Ala Ser Gln Asp Phe Phe Trp Lys Tyr Ile Arg Glu Gln Val
        115                 120                 125

Glu Glu Glu Ala Thr Ala Ala Glu Ile Val Glu Thr Ile Arg Leu Ser
    130                 135                 140

Gln Glu Gln Asn Leu Ile Phe Ile Asp His Gln Leu Ala Arg Arg
145                 150                 155


<210> SEQ ID NO 38
<211> LENGTH: 480
<212> TYPE: DNA
<213> ORGANISM: Porphyromonas gingivalis

<400> SEQUENCE: 38

aaaataagcg aaaacgtaac taaagcgatc aatgaccaaa tcaaggccga aatgtggtct      60

tcaaacctct atttgtccat gtctgtgcat tttgcgcagg tagggtacaa cggctttgct     120

cattggctca aaaagcagag cctcgaggaa atggaacatg cctacgatat gatggactac     180

ctcctgaagc gtggcggcga ggtgaagata gaagctatcg atgccgtgcc ccagaagttc     240

ggctctgtat tggaggtatt ccaacaggtg tacgaacacg agtgcaaagt gaccgaaatg     300

atcgaggctg tcgtaagggc tgcttccgaa gccggagata tggcatcaca ggacttcttc     360

tggaagtata tccgcgagca ggtagaagag gaagccactg ctgccgaaat cgtcgaaacg     420

atccgtctct ctcaggagca gaatctgatc ttcatcgatc atcagctcgc ccggagataa     480


<210> SEQ ID NO 39
<211> LENGTH: 425
<212> TYPE: PRT
<213> ORGANISM: Porphyromonas gingivalis

<400> SEQUENCE: 39

Lys Lys Asp Ser Val Ile Phe Asp Leu Ile Glu Lys Glu His Gln Arg
1               5                   10                  15

Gln Leu Lys Gly Ile Glu Leu Ile Ala Ser Glu Asn Phe Val Ser Glu
            20                  25                  30

Gln Val Met Gln Ala Met Gly Ser Cys Met Thr Asn Lys Tyr Ala Glu
        35                  40                  45

Gly Tyr Pro Gly Lys Arg Tyr Tyr Gly Gly Cys Glu Val Val Asp Gln
    50                  55                  60

Ser Glu Gln Ile Ala Ile Asp Arg Ile Lys Gln Leu Tyr Gly Ala Glu
65                  70                  75                  80

Trp Ala Asn Val Gln Pro His Ser Gly Ala Gln Ala Asn Met Ala Val
                85                  90                  95

Leu Leu Ala Cys Leu Glu Ala Gly Asp Thr Phe Met Gly Leu Asn Leu
            100                 105                 110

Glu His Gly Gly His Leu Ser His Gly Ser Leu Val Asn Ser Ser Gly
        115                 120                 125
```

```
Ile Leu Tyr Arg Pro Ile Gly Tyr Asn Leu Ser Glu Glu Thr Gly Met
    130                 135                 140

Val Asp Tyr Asp His Met Glu Lys Met Ala Ile Glu His Lys Pro Lys
145                 150                 155                 160

Leu Ile Ile Gly Gly Gly Ser Ala Tyr Ser Arg Glu Trp Asp Tyr Lys
                165                 170                 175

Arg Met Arg Glu Ile Ala Asp Lys Val Gly Ala Leu Leu Met Ile Asp
            180                 185                 190

Met Ala His Pro Ala Gly Leu Ile Ala Ala Gly Leu Leu Glu Asn Pro
        195                 200                 205

Val Lys Tyr Ala His Ile Val Thr Ser Thr Thr His Lys Thr Leu Arg
    210                 215                 220

Gly Pro Arg Gly Gly Ile Ile Leu Met Gly Lys Asp Phe Asp Asn Pro
225                 230                 235                 240

Trp Gly Lys Lys Thr Pro Lys Gly Glu Ile Lys Lys Met Ser Ala Leu
                245                 250                 255

Leu Asp Ser Ala Val Phe Pro Gly Val Gln Gly Gly Pro Leu Glu His
            260                 265                 270

Val Ile Ala Ala Lys Ala Val Ala Phe Gly Glu Ala Leu Asp Pro Ser
        275                 280                 285

Phe Lys Glu Tyr Gln Thr Gln Val Lys Lys Asn Ala Ala Val Leu Ala
    290                 295                 300

Gln Ala Phe Met Asp Lys Gly Tyr Lys Val Ile Ser Gly Gly Thr Asp
305                 310                 315                 320

Asn His Ser Met Leu Ile Asp Leu Arg Pro Lys Phe Pro Glu Leu Thr
                325                 330                 335

Gly Lys Val Ala Glu Lys Ala Leu Val Ala Ala Asp Ile Thr Val Asn
            340                 345                 350

Lys Asn Met Val Pro Phe Asp Ser Arg Ser Ala Phe Gln Thr Ser Gly
        355                 360                 365

Phe Arg Val Gly Thr Pro Ala Ile Thr Thr Arg Gly Val Lys Glu Asp
    370                 375                 380

Lys Met Gly Tyr Ile Val Glu Leu Ile Asp Arg Val Leu Ser Ala Pro
385                 390                 395                 400

Glu Asp Glu Ala Val Ile Ala Ser Val Arg Thr Glu Val Asn Arg Met
                405                 410                 415

Met Ala Asp Tyr Pro Leu Phe Ala Trp
            420                 425


<210> SEQ ID NO 40
<211> LENGTH: 1278
<212> TYPE: DNA
<213> ORGANISM: Porphyromonas gingivalis

<400> SEQUENCE: 40

aaaaaagaca gcgtaatttt cgatctgatc gaaaaagaac atcagcgcca gctcaaaggc      60

atcgagctga tcgcatcgga aaactttgta agcgaacaag ttatgcaggc tatgggtagc     120

tgtatgacca ataagtatgc cgaaggttat cccggcaaac gctattacgg tggttgtgaa     180

gtggtagacc aaagcgagca aatcgccatc gaccgtatca aacaactcta cggagccgaa     240

tgggccaacg tacagcctca ctccggagca caggccaata tggccgttct tctggcttgc     300

ctcgaagcag gcgatacgtt catgggactg aacctcgaac acggcggcca cctatcgcac     360

ggctcactcg tcaatagctc gggtatcctc taccgtccca tcggctacaa tctgagcgaa     420
```

```
gagacgggaa tggtggatta cgaccacatg gagaaaatgg ccatcgagca caaacccaag    480

ctgatcatcg gcggtggttc ggcctattct cgtgagtggg actacaagcg tatgcgtgag    540

atcgctgaca aggtgggtgc cttgttgatg atcgatatgg cacaccctgc cggtctgatc    600

gctgccggtc tgctggagaa ccccgtgaag tatgctcata tcgttacttc tacgactcac    660

aagacactgc gtggcccccg tggcggtatc atccttatgg gcaaggactt cgacaatcct    720

tggggcaaga aaaccccgaa gggcgagatc aagaagatga gcgcactcct cgactctgcc    780

gtattccccg gtgtacaggg tggtccgctc gagcacgtta tagctgctaa ggctgtagct    840

ttcggagaag cactggatcc ttcgttcaag gaataccaaa cgcaggtgaa aaagaatgct    900

gccgttttgg ctcaggcttt catggacaaa ggctataaag tgatttccgg tggtacggac    960

aaccacagta tgctgatcga tcttcgtccg aagttccccg aactgacagg taaagtggca   1020

gagaaagccc tcgtggcagc ggatattacc gtcaataaga acatggtacc gttcgattct   1080

cgctctgcat tccagacatc gggcttccgc gtgggtactc cggccatcac cactcgtggc   1140

gtaaaagaag ataagatggg ctatatcgtg gagttgatag accgtgtgct ctccgcaccg   1200

gaggacgaag ccgtaatagc atcggttcgt accgaagtca accggatgat ggccgattat   1260

cctctctttg cttggtaa                                                   1278
```

<210> SEQ ID NO 41
<211> LENGTH: 289
<212> TYPE: PRT
<213> ORGANISM: Porphyromonas gingivalis

<400> SEQUENCE: 41

```
Lys Lys Leu Phe Leu Ser Leu Thr Ser Leu Val Met Val Phe Ala Val
1               5                   10                  15

Ala Ser Cys Asp Ile Ile Asp Lys Asp Gln Thr Leu Leu Pro Ala Pro
            20                  25                  30

Thr Asn Val Thr Pro Asp Asn Pro Asp Asp Asn Pro Ser Glu Ile Asp
        35                  40                  45

Ile Thr Gln Thr His Thr Glu Lys Tyr Val Leu Ala Glu Glu Phe Thr
    50                  55                  60

Gly Gln Lys Cys Leu Asn Cys Pro Lys Gly His Arg Lys Leu Ala Ala
65                  70                  75                  80

Leu Lys Glu Gln Tyr Gly Lys Arg Leu Thr Val Val Gly Ile His Ala
                85                  90                  95

Gly Pro Gly Ser Leu Val Pro Pro Leu Phe Arg Thr Glu Ala Gly Asp
            100                 105                 110

Ala Tyr Tyr Ser Lys Phe Ala Asn Asn Thr Pro Leu Pro Ala Leu Met
        115                 120                 125

Val Ser Arg Lys Lys Phe Gly Ser Ser Tyr Val Tyr Asp Lys Ser Tyr
    130                 135                 140

Lys Thr Trp Asp Val Pro Ile Ala Glu Gln Met Glu Gln Lys Ala Lys
145                 150                 155                 160

Ile Asn Ile Phe Ala Val Ala Glu Tyr Thr Asp Thr Gln Lys Ile Lys
                165                 170                 175

Val Thr Val Lys Gly Lys Ile Leu Glu Gly Asn Thr Leu Pro Lys Ser
            180                 185                 190

Met Val Gln Val Tyr Leu Leu Glu Asp Lys Leu Ile Ala Pro Gln Val
        195                 200                 205

Asp Gly Asn Thr Thr Val Glu Asn Tyr Glu His Asn His Val Leu Arg
    210                 215                 220
```

```
Gly Ala Val Asn Gly Ile Trp Gly Glu Glu Phe Val Asn Leu Lys Asp
225                 230                 235                 240

Tyr Leu Tyr Thr Tyr Ala Val Glu Pro Leu Ser Gly Met Ser Phe Val
                245                 250                 255

Ala Glu Asn Tyr Ser Ile Val Ala Phe Val Tyr Asp Val Gln Thr Phe
            260                 265                 270

Glu Val Tyr Asp Val Val His Val Lys Ile Asn Pro Gln Ser Asp Gly
        275                 280                 285

Lys
```

<210> SEQ ID NO 42
<211> LENGTH: 870
<212> TYPE: DNA
<213> ORGANISM: Porphyromonas gingivalis

<400> SEQUENCE: 42

```
aaaaagctat ttctctcgct cacgagtctt gtaatggtct tcgctgttgc aagttgcgat      60

ataatcgaca aggatcaaac cctcttgccg gctccgacca atgtgacacc cgataatccg     120

gatgacaatc cttcggagat cgacattacg cagacgcaca cagaaaaata tgttttggct     180

gaagaattta ccggccaaaa atgtctcaac tgtccgaaag gtcatcgcaa actggcggct     240

ctcaaggagc aatacggtaa gagattgact gttgtcggta tacatgccgg ccctggatct     300

ctcgtgccac ctcttttccg tacagaagcc ggagacgcat attatagcaa gttcgccaat     360

aatacccctc tccctgcgct gatggtttcg cgcaaaaagt tcggctcttc ctacgtttat     420

gataagagct acaaaacgtg ggacgtgcct attgccgagc agatggagca aaaggcgaag     480

atcaatatct ttgccgtggc cgaatacacc gatacccaaa agatcaaggt gactgtaaag     540

ggtaaaatac tggaggggaa tacactcccg aagtccatgg ttcaggtgta tctgttggag     600

gataagctga tcgctccgca ggtggatggc aatacgacag tcgagaatta cgagcacaat     660

cacgtgttgc gtggagccgt taatggtatt tggggcgaag aatttgtgaa tctcaaagat     720

tatttgtata cttacgccgt tgaaccgctc tcgggtatgt ccttcgtagc cgagaattat     780

tcgattgtgg cttttgtata cgatgtgcag acgttcgaag tgtatgacgt tgtgcatgta     840

aagatcaatc cgcaatccga tggcaaataa                                       870
```

<210> SEQ ID NO 43
<211> LENGTH: 939
<212> TYPE: PRT
<213> ORGANISM: Porphyromonas gingivalis

<400> SEQUENCE: 43

```
Asn Lys Phe Tyr Lys Ser Leu Leu Gln Ser Gly Leu Ala Ala Phe Val
1               5                   10                  15

Ser Met Ala Thr Ala Leu Thr Ala Ser Ala Gln Ile Ser Phe Gly Gly
            20                  25                  30

Glu Pro Leu Ser Phe Ser Ser Arg Ser Ala Gly Thr His Ser Phe Asp
        35                  40                  45

Asp Ala Met Thr Ile Arg Leu Thr Pro Asp Phe Asn Pro Glu Asp Leu
    50                  55                  60

Ile Ala Gln Ser Arg Trp Gln Ser Gln Arg Asp Gly Arg Pro Val Arg
65                  70                  75                  80

Ile Gly Gln Val Ile Pro Val Asp Val Asp Phe Ala Ser Lys Ala Ser
                85                  90                  95
```

```
His Ile Ser Ser Ile Gly Asp Val Asp Val Tyr Arg Leu Gln Phe Lys
            100                 105                 110

Leu Glu Gly Ala Lys Ala Ile Thr Leu Tyr Tyr Asp Ala Phe Asn Ile
        115                 120                 125

Pro Glu Gly Gly Arg Leu Tyr Ile Tyr Thr Pro Asp His Glu Ile Val
    130                 135                 140

Leu Gly Ala Tyr Thr Asn Ala Thr His Arg Arg Asn Gly Ala Phe Ala
145                 150                 155                 160

Thr Glu Pro Val Pro Gly Ser Glu Leu Ile Met Asp Tyr Glu Val Ser
                165                 170                 175

Arg Gly Gly Thr Leu Pro Asp Ile Lys Ile Ser Gly Ala Gly Tyr Ile
            180                 185                 190

Phe Asp Lys Val Gly Gly Arg Pro Val Thr Asp Asn His Tyr Gly Ile
        195                 200                 205

Gly Glu Asp Asp Ser Asp Ser Asp Cys Glu Ile Asn Ile Asn Cys Pro
    210                 215                 220

Glu Gly Ala Asp Trp Gln Ala Glu Lys Asn Gly Val Val Gln Met Ile
225                 230                 235                 240

Met Val Lys Gly Gln Tyr Ile Ser Met Cys Ser Gly Asn Leu Leu Asn
                245                 250                 255

Asn Thr Lys Gly Asp Phe Thr Pro Leu Ile Ile Ser Ala Gly His Cys
            260                 265                 270

Ala Ser Ile Thr Thr Asn Phe Gly Val Thr Gln Ser Glu Leu Asp Lys
        275                 280                 285

Trp Ile Phe Thr Phe His Tyr Glu Lys Arg Gly Cys Ser Asn Gly Thr
    290                 295                 300

Leu Ala Ile Phe Arg Gly Asn Ser Ile Ile Gly Ala Ser Met Lys Ala
305                 310                 315                 320

Phe Leu Pro Ile Lys Gly Lys Ser Asp Gly Leu Leu Leu Gln Leu Asn
                325                 330                 335

Asp Glu Val Pro Leu Arg Tyr Arg Val Tyr Tyr Asn Gly Trp Asp Ser
            340                 345                 350

Thr Pro Asp Ile Pro Ser Ser Gly Ala Gly Ile His His Pro Ala Gly
        355                 360                 365

Asp Ala Met Lys Ile Ser Ile Leu Lys Lys Thr Pro Ala Leu Asn Thr
    370                 375                 380

Trp Ile Ser Ser Ser Gly Ser Gly Gly Thr Asp Asp His Phe Tyr Phe
385                 390                 395                 400

Lys Tyr Asp Gln Gly Gly Thr Glu Gly Gly Ser Ser Gly Ser Ser Leu
                405                 410                 415

Phe Asn Gln Asn Lys His Val Val Gly Thr Leu Thr Gly Gly Ala Gly
            420                 425                 430

Asn Cys Gly Gly Thr Glu Phe Tyr Gly Arg Leu Asn Ser His Trp Asn
        435                 440                 445

Glu Tyr Ala Ser Asp Gly Asn Thr Ser Arg Met Asp Ile Tyr Leu Asp
    450                 455                 460

Pro Gln Asn Asn Gly Gln Thr Thr Ile Leu Asn Gly Thr Tyr Arg Asp
465                 470                 475                 480

Gly Tyr Lys Pro Leu Pro Ser Val Pro Arg Leu Leu Leu Gln Ser Thr
                485                 490                 495

Gly Asp Gln Val Glu Leu Asn Trp Thr Ala Val Pro Ala Asp Gln Tyr
            500                 505                 510

Pro Ser Ser Tyr Gln Val Glu Tyr His Ile Phe Arg Asn Gly Lys Glu
```

-continued

```
        515                 520                 525

Ile Ala Thr Thr Lys Glu Leu Ser Tyr Ser Asp Ala Ile Asp Glu Ser
    530                 535                 540

Ile Ile Gly Ser Gly Ile Ile Arg Tyr Glu Val Ser Ala Arg Phe Ile
545                 550                 555                 560

Tyr Pro Ser Pro Leu Asp Gly Val Glu Ser Tyr Lys Asp Thr Asp Lys
                565                 570                 575

Thr Ser Ala Asp Leu Ala Ile Gly Asp Ile Gln Thr Lys Leu Lys Pro
            580                 585                 590

Asp Val Thr Pro Leu Pro Gly Gly Gly Val Ser Leu Ser Trp Lys Val
        595                 600                 605

Pro Phe Leu Ser Gln Leu Val Ser Arg Phe Gly Glu Ser Pro Asn Pro
    610                 615                 620

Val Phe Lys Thr Phe Glu Val Pro Tyr Val Ser Ala Ala Ala Ala Gln
625                 630                 635                 640

Thr Pro Asn Pro Pro Val Gly Val Val Ile Ala Asp Lys Phe Met Ala
                645                 650                 655

Gly Thr Tyr Pro Glu Lys Ala Ala Ile Ala Ala Val Tyr Val Met Pro
            660                 665                 670

Ser Ala Pro Asp Ser Thr Phe His Leu Phe Leu Lys Ser Asn Thr Asn
        675                 680                 685

Arg Arg Leu Gln Lys Val Thr Thr Pro Ser Asp Trp Gln Ala Gly Thr
    690                 695                 700

Trp Leu Arg Ile Asn Leu Asp Lys Pro Phe Pro Val Asn Asn Asp His
705                 710                 715                 720

Met Leu Phe Ala Gly Ile Arg Met Pro Asn Lys Tyr Lys Leu Asn Arg
                725                 730                 735

Ala Ile Arg Tyr Val Arg Asn Pro Asp Asn Leu Phe Ser Ile Thr Gly
            740                 745                 750

Lys Lys Ile Ser Tyr Asn Asn Gly Val Ser Phe Glu Gly Tyr Gly Ile
        755                 760                 765

Pro Ser Leu Leu Gly Tyr Met Ala Ile Lys Tyr Leu Val Val Asn Thr
    770                 775                 780

Asp Ala Pro Lys Ile Asp Met Ser Leu Val Gln Glu Pro Tyr Ala Lys
785                 790                 795                 800

Gly Thr Asn Val Ala Pro Phe Pro Glu Leu Val Gly Ile Tyr Val Tyr
                805                 810                 815

Lys Asn Gly Thr Phe Ile Gly Thr Gln Asp Pro Ser Val Thr Thr Tyr
            820                 825                 830

Ser Val Ser Asp Gly Thr Glu Ser Asp Glu Tyr Glu Ile Lys Leu Val
        835                 840                 845

Tyr Lys Gly Ser Gly Ile Ser Asn Gly Val Ala Gln Ile Glu Asn Asn
    850                 855                 860

Asn Ala Val Val Ala Tyr Pro Ser Val Val Thr Asp Arg Phe Ser Ile
865                 870                 875                 880

Lys Asn Ala His Met Val His Ala Ala Ala Leu Tyr Ser Leu Asp Gly
                885                 890                 895

Lys Gln Val Arg Ser Trp Asn Asn Leu Arg Asn Gly Val Thr Phe Ser
            900                 905                 910

Val Gln Gly Leu Thr Ala Gly Thr Tyr Met Leu Val Met Gln Thr Ala
        915                 920                 925

Asn Gly Pro Val Ser Gln Lys Ile Val Lys Gln
    930                 935
```

<210> SEQ ID NO 44
<211> LENGTH: 2820
<212> TYPE: DNA
<213> ORGANISM: Porphyromonas gingivalis

<400> SEQUENCE: 44

```
aacaaatttt acaaatcact tttgcagtca ggactggctg ccttcgtgtc gatggcaact     60
gcactgaccg cttctgcaca gatttcgttc ggaggggaac ccttgagttt ctcttcaaga    120
tccgccggaa cgcattcatt cgacgatgca atgactatcc gccttactcc ggatttcaat    180
ccggaagacc tgatcgcaca gagccgttgg caatcgcaaa gagatggccg gcccgtccgg    240
ataggacaag taataccggt ggatgtggac tttgcatcca aggcttcgca catctcttcc    300
atcggagacg tagatgtata tcgcctgcaa ttcaagttgg aaggagccaa agccattacg    360
ctttattacg atgcattcaa tattccggag ggcggacgcc tctatatcta tacccccgac    420
catgaaattg tgttgggagc atatacgaac gccactcatc gccgcaacgg agcttttgcc    480
acagagccgg taccggggag tgagcttatt atggattatg aagtgtctcg cggagggact    540
ttgcctgaca tcaagatctc cggtgcgggt tatatattcg acaaagtcgg cggacgcccc    600
gtaacggata accattacgg gatcggtgag gacgattccg attcggattg cgagatcaac    660
atcaattgtc ctgaaggtgc agactggcag gcagagaaga acggtgtggt gcaaatgatc    720
atggtaaaag gacagtatat ctcaatgtgc tcaggcaacc tgctcaataa tacgaaagga    780
gactttactc cgctgatcat ttctgccgga cactgtgctt ccataacaac caatttcggt    840
gtaacgcaat ccgagttgga taagtggatc ttcactttcc actatgaaaa aagaggatgc    900
agcaatggta cattggccat cttccgtggc aacagtatca tcggagcttc catgaaggct    960
ttcctcccga tcaaaggtaa atccgatggt ctcttgctgc aactcaacga tgaagtccct   1020
ctgcgctatc gtgtctatta caatggatgg gacagtacgc ccgatattcc ctcgagcggt   1080
gccggtattc atcatccggc cggagatgcc atgaagattt ccatcctaaa gaagactccg   1140
gctctgaata catggatctc ctccagtggt tccggaggga ctgacgatca cttctatttc   1200
aaatacgatc aaggtggtac ggaaggagga tcgtccggtt cttctctctt caatcagaat   1260
aagcacgtgg tcggcacact gaccggaggt gccggcaatt gtggcgggac ggagttctac   1320
ggcagactga acagtcattg gaacgagtat gcatccgatg gcaatacgag ccgcatggac   1380
atctatctgg atccccaaaa caatggccag acgaccatcc tcaacggaac gtatcgtgac   1440
ggttataagc ctttgccctc tgtgccccgg ctattgttgc agtctacagg cgatcaggtc   1500
gaattgaatt ggacggctgt tcctgccgat caatatccat catcttatca ggtcgaatac   1560
cacatattcc gaaatggaaa ggaaatagct acgacaaagg agttgtccta ttcggatgcc   1620
atcgacgaaa gtattatcgg tagcggtatc attcgatacg aagtaagcgc acgcttcatt   1680
tatccctcgc cgttggatgg agtggaatct tataaggata cggacaagac ttctgccgac   1740
cttgccatag gagacattca gaccaagctg aagccggacg taacacctct ccccggagga   1800
ggagtatcat taagctggaa agttcctttc ttaagccagt tggtttcccg attcggagaa   1860
agccccaatc ctgtgttcaa aacctttgaa gtgccctatg tttctgccgc agccgcacaa   1920
acccccaatc ctcccgttgg cgtagtcatt gcagacaagt ttatggccgg tacatatccc   1980
gaaaaggctg ctatcgctgc cgtttatgta atgccatccg ctccggactc tactttccac   2040
ctcttcctca agagcaacac aaacagaaga ttgcagaagg tgacaactcc ctccgattgg   2100
```

```
caggccggaa catggttgag gatcaatttg gataagccgt tcccggtgaa taatgaccat   2160

atgctttttg ccggtatcag aatgcctaat aagtacaagc tcaatcgtgc tatccgttat   2220

gtaagaaatc cggataacct tttctccatt accggtaaga agatttcata taacaacgga   2280

gtctctttcg aaggctacgg aataccctcg ctcttgggct atatggctat caaatatctg   2340

gtggtaaata ccgatgctcc gaagatcgat atgtcgcttg tacaggagcc ttatgctaag   2400

ggaacgaatg tggctccatt ccccgaattg gtcggcatat atgtctataa gaacggaaca   2460

tttatcggca cacaggatcc atccgtcaca acttattcgg tttcagacgg aacagagagc   2520

gatgaatacg aaataaaact ggtatataag ggatcgggca tttcgaatgg cgttgctcag   2580

attgagaata acaatgctgt cgttgcatat ccgtctgttg taacagatcg tttcagcatt   2640

aagaacgctc atatggttca cgctgccgcc ctctactcat tggatggcaa gcaggttcgt   2700

tcttggaaca acctccgcaa tggcgtgaca ttcagtgttc aaggacttac ggccggtact   2760

tatatgctcg ttatgcagac ggcaaacggc cctgtgagcc aaaagatcgt gaagcagtag   2820
```

<210> SEQ ID NO 45
<211> LENGTH: 172
<212> TYPE: PRT
<213> ORGANISM: Porphyromonas gingivalis

<400> SEQUENCE: 45

```
Lys Lys Thr Leu Val Ile Val Val His Pro Asp Leu Thr Lys Ser Val
1               5                   10                  15

Ile Asn Lys Ala Trp Ala Lys Ala Ile Glu Gly Ala Ala Thr Ile His
            20                  25                  30

His Leu Tyr Glu Gln Tyr Pro Asn Gly Gln Ile Asp Leu Ala His Glu
        35                  40                  45

Gln Ala Leu Leu Glu Ala His Asp Arg Ile Val Phe Gln Phe Pro Leu
    50                  55                  60

Tyr Trp Tyr Ala Ala Pro Tyr Leu Leu Lys Lys Trp Met Asp Glu Val
65                  70                  75                  80

Phe Thr Glu Gly Trp Ala Tyr Gly Ala Gly Gly Asp Lys Met Glu Gly
                85                  90                  95

Lys Glu Ile Cys Ala Ala Val Ser Cys Gly Ser Pro Lys Ser Ala Phe
            100                 105                 110

Ala Glu Gly Ala Gln Gln Cys His Thr Leu Arg Ser Tyr Leu Asn Val
        115                 120                 125

Phe Asp Gly Ile Ala Ala Phe Leu Arg Ala Arg Phe Thr Gly Tyr His
    130                 135                 140

Ala Cys Tyr Asp Ser Tyr Asn Pro Arg Leu Pro Glu Met Leu Pro Ala
145                 150                 155                 160

Asn Cys Glu Ala Tyr Leu Arg Phe Ile Lys Gly Glu
                165                 170
```

<210> SEQ ID NO 46
<211> LENGTH: 519
<212> TYPE: DNA
<213> ORGANISM: Porphyromonas gingivalis

<400> SEQUENCE: 46

```
aaaaaaacgc tcgtaatagt cgttcacccc gatttgacca aatccgttat caacaaggct     60

tgggccaaag ccatcgaagg tgcagccact atccaccatc tctacgaaca gtatccgaac    120

ggacaaatcg atctagcaca tgaacaagcc ctgctggagg ctcatgaccg catcgtcttc    180
```

```
caattccccc tctattggta tgcagctccc tatctgctga agaagtggat ggacgaggtc    240

tttactgagg gctgggccta tggtgccggt ggagacaaga tggagggtaa agaaatctgt    300

gcagcagtct cctgcggatc acccaaatca gcttttgccg aaggagcaca gcaatgccac    360

acgctgcgaa gctacttgaa tgtattcgac gggatagctg ctttcctgcg cgctcgattc    420

accggctacc atgcctgcta cgattcctac aatcctcgcc tgccggaaat gctgccggcc    480

aactgcgaag cctatctccg ctttatcaaa ggagaatga                           519
```

<210> SEQ ID NO 47
<211> LENGTH: 158
<212> TYPE: PRT
<213> ORGANISM: Porphyromonas gingivalis

<400> SEQUENCE: 47

```
Lys Lys Ile Leu Glu Val Thr Gly Leu Lys Glu Gln Gln Val Ala Pro
1               5                   10                  15

Val Val Lys Gly Leu Ser Gly Leu Leu Ala Asp Leu Gln Val Tyr Tyr
            20                  25                  30

Ser Asn Leu Arg Gly Phe His Trp Asn Ile Arg Gly Ala Glu Phe Phe
        35                  40                  45

Val Leu His Glu Gln Tyr Glu Lys Met Tyr Asp Asp Leu Ala Gly Lys
    50                  55                  60

Ile Asp Glu Val Ala Glu Arg Ile Leu Gln Leu Gly Gly Lys Pro Glu
65                  70                  75                  80

Asn Arg Phe Ser Glu Tyr Leu Lys Val Ala Glu Val Lys Glu Glu His
                85                  90                  95

Glu Leu Val Cys Ala Ala Ser Thr Leu Lys Asn Val Thr Asp Thr Leu
            100                 105                 110

Gln Ile Ile Met Ala Lys Glu Arg Ala Ile Ala Glu Val Ala Gly Glu
        115                 120                 125

Ala Gly Asp Glu Val Thr Val Asp Leu Met Ile Gly Phe Leu Ser Glu
    130                 135                 140

Gln Glu Lys Leu Val Trp Met Leu Ser Ala Tyr Ala Thr Lys
145                 150                 155
```

<210> SEQ ID NO 48
<211> LENGTH: 477
<212> TYPE: DNA
<213> ORGANISM: Porphyromonas gingivalis

<400> SEQUENCE: 48

```
aaaaagattc ttgaagtaac gggtttgaaa gagcagcaag ttgctcccgt agtgaaaggt     60

ttgtccggtt tgttggccga cctccaagtg tattactcca accttcgcgg gttccactgg    120

aatatccgtg gcgcagagtt cttcgttctg catgagcagt acgagaagat gtacgatgac    180

ctcgcaggga aaatcgacga ggtagctgag cgtatcctcc aacttggtgg caagcctgag    240

aaccgcttca gcgagtacct gaaagtagca gaagtgaagg aagagcacga actcgtttgc    300

gctgcaagta cgctgaagaa tgtgaccgat acgctgcaga tcatcatggc gaaggagcgt    360

gccatcgcag aagttgccgg tgaggcaggc gatgaggtaa cggtggattt gatgatcggt    420

ttcctctccg agcaagagaa gctcgtttgg atgctgtctg cctacgctac caagtaa       477
```

<210> SEQ ID NO 49
<211> LENGTH: 379
<212> TYPE: PRT
<213> ORGANISM: Porphyromonas gingivalis

```
<400> SEQUENCE: 49

Lys Ala Lys Ser Leu Leu Leu Ala Leu Ala Gly Leu Ala Cys Thr Phe
1               5                   10                  15

Ser Ala Thr Ala Gln Glu Ala Thr Thr Gln Asn Lys Ala Gly Met His
            20                  25                  30

Thr Ala Phe Gln Arg Asp Lys Ala Ser Asp His Trp Phe Ile Asp Ile
        35                  40                  45

Ala Gly Gly Ala Gly Met Ala Leu Ser Gly Trp Asn Asn Asp Val Asp
    50                  55                  60

Phe Val Asp Arg Leu Ser Ile Val Pro Thr Phe Gly Ile Gly Lys Trp
65                  70                  75                  80

His Glu Pro Tyr Phe Gly Thr Arg Leu Gln Phe Thr Gly Phe Asp Ile
                85                  90                  95

Tyr Gly Phe Pro Gln Gly Ser Lys Glu Arg Asn His Asn Tyr Phe Gly
            100                 105                 110

Asn Ala His Leu Asp Phe Met Phe Asp Leu Thr Asn Tyr Phe Gly Val
        115                 120                 125

Tyr Arg Pro Asn Arg Val Phe His Ile Ile Pro Trp Ala Gly Ile Gly
    130                 135                 140

Phe Gly Tyr Lys Phe His Ser Glu Asn Ala Asn Gly Glu Lys Val Gly
145                 150                 155                 160

Ser Lys Asp Asp Met Thr Gly Thr Val Asn Val Gly Leu Met Leu Lys
                165                 170                 175

Phe Arg Leu Ser Arg Val Val Asp Phe Asn Ile Glu Gly Gln Ala Phe
            180                 185                 190

Ala Gly Lys Met Asn Phe Ile Gly Thr Lys Arg Gly Lys Ala Asp Phe
        195                 200                 205

Pro Val Met Ala Thr Ala Gly Leu Thr Phe Asn Leu Gly Lys Thr Glu
    210                 215                 220

Trp Thr Glu Ile Val Pro Met Asp Tyr Ala Leu Val Asn Asp Leu Asn
225                 230                 235                 240

Asn Gln Ile Asn Ser Leu Arg Gly Gln Val Glu Glu Leu Ser Arg Arg
                245                 250                 255

Pro Val Ser Cys Pro Glu Cys Pro Glu Pro Thr Gln Pro Thr Val Thr
            260                 265                 270

Arg Val Val Val Asp Asn Val Val Tyr Phe Arg Ile Asn Ser Ala Lys
        275                 280                 285

Ile Asp Arg Asn Gln Glu Ile Asn Val Tyr Asn Thr Ala Glu Tyr Ala
    290                 295                 300

Lys Thr Asn Asn Ala Pro Ile Lys Val Val Gly Tyr Ala Asp Glu Lys
305                 310                 315                 320

Thr Gly Thr Ala Ala Tyr Asn Met Lys Leu Ser Glu Arg Arg Ala Lys
                325                 330                 335

Ala Val Ala Lys Met Leu Glu Lys Tyr Gly Val Ser Ala Asp Arg Ile
            340                 345                 350

Thr Ile Glu Trp Lys Gly Ser Ser Glu Gln Ile Tyr Glu Glu Asn Ala
        355                 360                 365

Trp Asn Arg Ile Val Val Met Thr Ala Ala Glu
    370                 375

<210> SEQ ID NO 50
<211> LENGTH: 1140
<212> TYPE: DNA
```

<213> ORGANISM: Porphyromonas gingivalis

<400> SEQUENCE: 50

```
aaagctaaat ctttattatt agcacttgcg ggtctcgcat gcacattcag tgcaacagcc     60
caagaagcta ctacacagaa caaagcaggg atgcacaccg cattccaacg tgataaggcc    120
tccgatcatt ggttcattga cattgcaggt ggagcaggta tggctctctc gggatggaat    180
aatgatgtag actttgtaga tcgtctaagt atcgttccta ctttcggtat cggtaaatgg    240
catgagcctt atttcggtac tcgtctccaa ttcacaggat tcgacatcta tggattcccg    300
caagggagca aggagcgtaa ccacaattac tttggaaacg cccaccttga cttcatgttc    360
gatctgacga actatttcgg tgtataccgt cccaatcgtg tcttccatat catcccatgg    420
gcaggtatag gatttggtta taaattccat agcgaaaacg ccaatggtga aaaagtagga    480
agtaaagatg atatgaccgg aacagttaat gtcggtttga tgctgaaatt ccgcctatca    540
agagtcgtag acttcaatat tgaaggacaa gcttttgccg gaaagatgaa ctttatcggg    600
acaaagagag gaaaagcaga cttccctgta atggctacag caggtctaac gttcaacctt    660
ggcaagacag agtggacaga aattgttcct atggactatg ctttggtcaa tgacctgaac    720
aaccaaatca actcacttcg cggtcaagtg gaagagttga gccgtcgtcc tgtttcatgc    780
cctgaatgcc ctgagcctac acagcctaca gttactcgtg tagtcgttga caatgtggtt    840
tacttccgta tcaatagtgc aaagattgat cgtaatcaag aaatcaatgt ttacaataca    900
gctgaatatg cgaagaccaa caacgcaccg atcaaggtag taggttacgc tgacgaaaaa    960
accggtactg cggcctataa catgaagctt tcagagcgtc gtgcaaaagc ggtagccaag   1020
atgcttgaaa agtatggtgt ttctgcggat cgcattacaa ttgaatggaa gggctcatca   1080
gagcaaatct atgaagagaa cgcttggaat cgtattgtag taatgactgc agcggaataa   1140
```

<210> SEQ ID NO 51
<211> LENGTH: 1731
<212> TYPE: PRT
<213> ORGANISM: Porphyromonas gingivalis

<400> SEQUENCE: 51

```
Arg Lys Leu Leu Leu Leu Ile Ala Ala Ser Leu Leu Gly Val Gly Leu
1               5                   10                  15

Tyr Ala Gln Ser Ala Lys Ile Lys Leu Asp Ala Pro Thr Thr Arg Thr
            20                  25                  30

Thr Cys Thr Asn Asn Ser Phe Lys Gln Phe Asp Ala Ser Phe Ser Phe
        35                  40                  45

Asn Glu Val Glu Leu Thr Lys Val Glu Thr Lys Gly Gly Thr Phe Ala
    50                  55                  60

Ser Val Ser Ile Pro Gly Ala Phe Pro Thr Gly Glu Val Gly Ser Pro
65                  70                  75                  80

Glu Val Pro Ala Val Arg Lys Leu Ile Ala Val Pro Val Gly Ala Thr
                85                  90                  95

Pro Val Val Arg Val Lys Ser Phe Thr Glu Gln Val Tyr Ser Leu Asn
            100                 105                 110

Gln Tyr Gly Ser Glu Lys Leu Met Pro His Gln Pro Ser Met Ser Lys
        115                 120                 125

Ser Asp Asp Pro Glu Lys Val Pro Phe Val Tyr Asn Ala Ala Ala Tyr
    130                 135                 140

Ala Arg Lys Gly Phe Val Gly Gln Glu Leu Thr Gln Val Glu Met Leu
145                 150                 155                 160
```

```
Gly Thr Met Arg Gly Val Arg Ile Ala Ala Leu Thr Ile Asn Pro Val
                165                 170                 175

Gln Tyr Asp Val Val Ala Asn Gln Leu Lys Val Arg Asn Asn Ile Glu
            180                 185                 190

Ile Glu Val Ser Phe Gln Gly Ala Asp Glu Val Ala Thr Gln Arg Leu
        195                 200                 205

Tyr Asp Ala Ser Phe Ser Pro Tyr Phe Glu Thr Ala Tyr Lys Gln Leu
    210                 215                 220

Phe Asn Arg Asp Val Tyr Thr Asp His Gly Asp Leu Tyr Asn Thr Pro
225                 230                 235                 240

Val Arg Met Leu Val Val Ala Gly Ala Lys Phe Lys Glu Ala Leu Lys
                245                 250                 255

Pro Trp Leu Thr Trp Lys Ala Gln Lys Gly Phe Tyr Leu Asp Val His
            260                 265                 270

Tyr Thr Asp Glu Ala Glu Val Gly Thr Thr Asn Ala Ser Ile Lys Ala
        275                 280                 285

Phe Ile His Lys Lys Tyr Asn Asp Gly Leu Ala Ala Ser Ala Ala Pro
    290                 295                 300

Val Phe Leu Ala Leu Val Gly Asp Thr Asp Val Ile Ser Gly Glu Lys
305                 310                 315                 320

Gly Lys Lys Thr Lys Lys Val Thr Asp Leu Tyr Tyr Ser Ala Val Asp
                325                 330                 335

Gly Asp Tyr Phe Pro Glu Met Tyr Thr Phe Arg Met Ser Ala Ser Ser
            340                 345                 350

Pro Glu Glu Leu Thr Asn Ile Ile Asp Lys Val Leu Met Tyr Glu Lys
        355                 360                 365

Ala Thr Met Pro Asp Lys Ser Tyr Leu Glu Lys Val Leu Leu Ile Ala
    370                 375                 380

Gly Ala Asp Tyr Ser Trp Asn Ser Gln Val Gly Gln Pro Thr Ile Lys
385                 390                 395                 400

Tyr Gly Met Gln Tyr Tyr Tyr Asn Gln Glu His Gly Tyr Thr Asp Val
                405                 410                 415

Tyr Asn Tyr Leu Lys Ala Pro Tyr Thr Gly Cys Tyr Ser His Leu Asn
            420                 425                 430

Thr Gly Val Ser Phe Ala Asn Tyr Thr Ala His Gly Ser Glu Thr Ala
        435                 440                 445

Trp Ala Asp Pro Leu Leu Thr Thr Ser Gln Leu Lys Ala Leu Thr Asn
    450                 455                 460

Lys Asp Lys Tyr Phe Leu Ala Ile Gly Asn Cys Cys Ile Thr Ala Gln
465                 470                 475                 480

Phe Asp Tyr Val Gln Pro Cys Phe Gly Glu Val Ile Thr Arg Val Lys
                485                 490                 495

Glu Lys Gly Ala Tyr Ala Tyr Ile Gly Ser Ser Pro Asn Ser Tyr Trp
            500                 505                 510

Gly Glu Asp Tyr Tyr Trp Ser Val Gly Ala Asn Ala Val Phe Gly Val
        515                 520                 525

Gln Pro Thr Phe Glu Gly Thr Ser Met Gly Ser Tyr Asp Ala Thr Phe
    530                 535                 540

Leu Glu Asp Ser Tyr Asn Thr Val Asn Ser Ile Met Trp Ala Gly Asn
545                 550                 555                 560

Leu Ala Ala Thr His Ala Gly Asn Ile Gly Asn Ile Thr His Ile Gly
                565                 570                 575
```

```
Ala His Tyr Tyr Trp Glu Ala Tyr His Val Leu Gly Asp Gly Ser Val
            580                 585                 590

Met Pro Tyr Arg Ala Met Pro Lys Thr Asn Thr Tyr Thr Leu Pro Ala
        595                 600                 605

Ser Leu Pro Gln Asn Gln Ala Ser Tyr Ser Ile Gln Ala Ser Ala Gly
    610                 615                 620

Ser Tyr Val Ala Ile Ser Lys Asp Gly Val Leu Tyr Gly Thr Gly Val
625                 630                 635                 640

Ala Asn Ala Ser Gly Val Ala Thr Val Ser Met Thr Lys Gln Ile Thr
                645                 650                 655

Glu Asn Gly Asn Tyr Asp Val Val Ile Thr Arg Ser Asn Tyr Leu Pro
            660                 665                 670

Val Ile Lys Gln Ile Gln Val Gly Glu Pro Ser Pro Tyr Gln Pro Val
        675                 680                 685

Ser Asn Leu Thr Ala Thr Thr Gln Gly Gln Lys Val Thr Leu Lys Trp
    690                 695                 700

Glu Ala Pro Ser Ala Lys Lys Ala Glu Gly Ser Arg Glu Val Lys Arg
705                 710                 715                 720

Ile Gly Asp Gly Leu Phe Val Thr Ile Glu Pro Ala Asn Asp Val Arg
                725                 730                 735

Ala Asn Glu Ala Lys Val Val Leu Ala Ala Asp Asn Val Trp Gly Asp
            740                 745                 750

Asn Thr Gly Tyr Gln Phe Leu Leu Asp Ala Asp His Asn Thr Phe Gly
        755                 760                 765

Ser Val Ile Pro Ala Thr Gly Pro Leu Phe Thr Gly Thr Ala Ser Ser
    770                 775                 780

Asn Leu Tyr Ser Ala Asn Phe Glu Tyr Leu Ile Pro Ala Asn Ala Asp
785                 790                 795                 800

Pro Val Val Thr Thr Gln Asn Ile Ile Val Thr Gly Gln Gly Glu Val
                805                 810                 815

Val Ile Pro Gly Gly Val Tyr Asp Tyr Cys Ile Thr Asn Pro Glu Pro
            820                 825                 830

Ala Ser Gly Lys Met Trp Ile Ala Gly Asp Gly Gly Asn Gln Pro Ala
        835                 840                 845

Arg Tyr Asp Asp Phe Thr Phe Glu Ala Gly Lys Lys Tyr Thr Phe Thr
    850                 855                 860

Met Arg Arg Ala Gly Met Gly Asp Gly Thr Asp Met Glu Val Glu Asp
865                 870                 875                 880

Asp Ser Pro Ala Ser Tyr Thr Tyr Thr Val Tyr Arg Asp Gly Thr Lys
                885                 890                 895

Ile Lys Glu Gly Leu Thr Ala Thr Thr Phe Glu Glu Asp Gly Val Ala
            900                 905                 910

Ala Gly Asn His Glu Tyr Cys Val Glu Val Lys Tyr Thr Ala Gly Val
        915                 920                 925

Ser Pro Lys Val Cys Lys Asp Val Thr Val Glu Gly Ser Asn Glu Phe
    930                 935                 940

Ala Pro Val Gln Asn Leu Thr Gly Ser Ser Val Gly Gln Lys Val Thr
945                 950                 955                 960

Leu Lys Trp Asp Ala Pro Asn Gly Thr Pro Asn Pro Asn Pro Asn Pro
                965                 970                 975

Asn Pro Asn Pro Gly Thr Thr Leu Ser Glu Ser Phe Glu Asn Gly Ile
            980                 985                 990

Pro Ala Ser Trp Lys Thr Ile Asp  Ala Asp Gly Asp Gly  His Gly Trp
```

```
        995                 1000                1005

Lys Pro  Gly Asn Ala Pro Gly  Ile Ala Gly Tyr Asn  Ser Asn Gly
    1010                 1015                 1020

Cys Val  Tyr Ser Glu Ser Phe  Gly Leu Gly Gly Ile  Gly Val Leu
    1025                 1030                 1035

Thr Pro  Asp Asn Tyr Leu Ile  Thr Pro Ala Leu Asp  Leu Pro Asn
    1040                 1045                 1050

Gly Gly  Lys Leu Thr Phe Trp  Val Cys Ala Gln Asp  Ala Asn Tyr
    1055                 1060                 1065

Ala Ser  Glu His Tyr Ala Val  Tyr Ala Ser Ser Thr  Gly Asn Asp
    1070                 1075                 1080

Ala Ser  Asn Phe Thr Asn Ala  Leu Leu Glu Glu Thr  Ile Thr Ala
    1085                 1090                 1095

Lys Gly  Val Arg Ser Pro Lys  Ala Ile Arg Gly Arg  Ile Gln Gly
    1100                 1105                 1110

Thr Trp  Arg Gln Lys Thr Val  Asp Leu Pro Ala Gly  Thr Lys Tyr
    1115                 1120                 1125

Val Ala  Phe Arg His Phe Gln  Ser Thr Asp Met Phe  Tyr Ile Asp
    1130                 1135                 1140

Leu Asp  Glu Val Glu Ile Lys  Ala Asn Gly Lys Arg  Ala Asp Phe
    1145                 1150                 1155

Thr Glu  Thr Phe Glu Ser Ser  Thr His Gly Glu Ala  Pro Ala Glu
    1160                 1165                 1170

Trp Thr  Thr Ile Asp Ala Asp  Gly Asp Gly Gln Gly  Trp Leu Cys
    1175                 1180                 1185

Leu Ser  Ser Gly Gln Leu Asp  Trp Leu Thr Ala His  Gly Gly Ser
    1190                 1195                 1200

Asn Val  Val Ser Ser Phe Ser  Trp Asn Gly Met Ala  Leu Asn Pro
    1205                 1210                 1215

Asp Asn  Tyr Leu Ile Ser Lys  Asp Val Thr Gly Ala  Thr Lys Val
    1220                 1225                 1230

Lys Tyr  Tyr Tyr Ala Val Asn  Asp Gly Phe Pro Gly  Asp His Tyr
    1235                 1240                 1245

Ala Val  Met Ile Ser Lys Thr  Gly Thr Asn Ala Gly  Asp Phe Thr
    1250                 1255                 1260

Val Val  Phe Glu Glu Thr Pro  Asn Gly Ile Asn Lys  Gly Gly Ala
    1265                 1270                 1275

Arg Phe  Gly Leu Ser Thr Glu  Ala Asn Gly Ala Lys  Pro Gln Ser
    1280                 1285                 1290

Val Trp  Ile Glu Arg Thr Val  Asp Leu Pro Ala Gly  Thr Lys Tyr
    1295                 1300                 1305

Val Ala  Phe Arg His Tyr Asn  Cys Ser Asp Leu Asn  Tyr Ile Leu
    1310                 1315                 1320

Leu Asp  Asp Ile Gln Phe Thr  Met Gly Gly Ser Pro  Thr Pro Thr
    1325                 1330                 1335

Asp Tyr  Thr Tyr Thr Val Tyr  Arg Asp Gly Thr Lys  Ile Lys Glu
    1340                 1345                 1350

Gly Leu  Thr Glu Thr Thr Phe  Glu Glu Asp Gly Val  Ala Thr Gly
    1355                 1360                 1365

Asn His  Glu Tyr Cys Val Glu  Val Lys Tyr Thr Ala  Gly Val Ser
    1370                 1375                 1380

Pro Lys  Lys Cys Val Asn Val  Thr Val Asn Ser Thr  Gln Phe Asn
    1385                 1390                 1395
```

```
Pro Val Gln Asn Leu Thr Ala Glu Gln Ala Pro Asn Ser Met Asp
    1400                1405                1410

Ala Ile Leu Lys Trp Asn Ala Pro Ala Ser Lys Arg Ala Glu Val
    1415                1420                1425

Leu Asn Glu Asp Phe Glu Asn Gly Ile Pro Ala Ser Trp Lys Thr
    1430                1435                1440

Ile Asp Ala Asp Gly Asp Gly Asn Asn Trp Thr Thr Thr Pro Pro
    1445                1450                1455

Pro Gly Gly Ser Ser Phe Ala Gly His Asn Ser Ala Ile Cys Val
    1460                1465                1470

Ser Ser Ala Ser Tyr Ile Asn Phe Glu Gly Pro Gln Asn Pro Asp
    1475                1480                1485

Asn Tyr Leu Val Thr Pro Glu Leu Ser Leu Pro Gly Gly Gly Thr
    1490                1495                1500

Leu Thr Phe Trp Val Cys Ala Gln Asp Ala Asn Tyr Ala Ser Glu
    1505                1510                1515

His Tyr Ala Val Tyr Ala Ser Ser Thr Gly Asn Asp Ala Ser Asn
    1520                1525                1530

Phe Ala Asn Ala Leu Leu Glu Glu Val Leu Thr Ala Lys Thr Val
    1535                1540                1545

Val Thr Ala Pro Glu Ala Ile Arg Gly Thr Arg Ala Gln Gly Thr
    1550                1555                1560

Trp Tyr Gln Lys Thr Val Gln Leu Pro Ala Gly Thr Lys Tyr Val
    1565                1570                1575

Ala Phe Arg His Phe Gly Cys Thr Asp Phe Phe Trp Ile Asn Leu
    1580                1585                1590

Asp Asp Val Val Ile Thr Ser Gly Asn Ala Pro Ser Tyr Thr Tyr
    1595                1600                1605

Thr Ile Tyr Arg Asn Asn Thr Gln Ile Ala Ser Gly Val Thr Glu
    1610                1615                1620

Thr Thr Tyr Arg Asp Pro Asp Leu Ala Thr Gly Phe Tyr Thr Tyr
    1625                1630                1635

Gly Val Lys Val Val Tyr Pro Asn Gly Glu Ser Ala Ile Glu Thr
    1640                1645                1650

Ala Thr Leu Asn Ile Thr Ser Leu Ala Asp Val Thr Ala Gln Lys
    1655                1660                1665

Pro Tyr Thr Leu Thr Val Val Gly Lys Thr Ile Thr Val Thr Cys
    1670                1675                1680

Gln Gly Glu Ala Met Ile Tyr Asp Met Asn Gly Arg Arg Leu Ala
    1685                1690                1695

Ala Gly Arg Asn Thr Val Val Tyr Thr Ala Gln Gly Gly His Tyr
    1700                1705                1710

Ala Val Met Val Val Val Asp Gly Lys Ser Tyr Val Glu Lys Leu
    1715                1720                1725

Ala Ile Lys
    1730
```

<210> SEQ ID NO 52
<211> LENGTH: 5196
<212> TYPE: DNA
<213> ORGANISM: Porphyromonas gingivalis

<400> SEQUENCE: 52

```
aggaaattat tattgctgat cgcggcgtcc cttttgggag ttggtcttta cgcccaaagc      60
```

-continued gccaagatta agcttgatgc tccgactact cgaacgacat gtacgaacaa tagcttcaag 120
cagttcgatg caagcttttc gttcaatgaa gtcgagctga caaaggtgga gaccaaaggt 180
ggtactttcg cctcagtgtc aattccgggt gcattcccga ccggtgaggt tggttctccc 240
gaagtgccag cagttaggaa gttgattgct gtgcctgtcg gagccacacc tgttgttcgc 300
gtgaaaagtt ttaccgagca agtttactct ctgaaccaat acggttccga aaaactcatg 360
ccacatcaac cctctatgag caagagtgat gatcccgaaa aggttccctt cgtttacaat 420
gctgctgctt atgcacgcaa aggttttgtc ggacaagaac tgacccaagt agaaatgttg 480
gggacaatgc gtggtgttcg cattgcagct cttaccatta atcctgttca gtatgatgtg 540
gttgcaaacc aattgaaggt tagaaacaac atcgaaattg aagtaagctt tcaaggagct 600
gatgaagtag ctacacaacg tttgtatgat gcttctttta gcccttattt cgaaacagct 660
tataaacagc tcttcaatag agatgtttat acagatcatg gcgacttgta taatacgccg 720
gttcgtatgc ttgttgttgc aggtgcaaaa ttcaaagaag ctctcaagcc ttggctcact 780
tggaaggctc aaaagggctt ctatctggat gtgcattaca cagacgaagc tgaagtagga 840
acgacaaacg cctctatcaa ggcatttatt cacaagaaat acaatgatgg attggcagct 900
agtgctgctc cggtcttctt ggctttggtt ggtgacactg acgttattag cggagaaaaa 960
ggaaagaaaa caaaaaaagt taccgacttg tattacagtg cagtcgatgg cgactatttc 1020
cctgaaatgt atactttccg tatgtctgct tcttccccag aagaactgac gaacatcatt 1080
gataaggtat tgatgtatga aaaggctact atgccagata agagttattt ggagaaagtt 1140
ctcttgattg caggtgcaga ttatagctgg aattcccagg taggtcagcc aaccattaaa 1200
tacggtatgc agtactacta caaccaagag catggttata ccgacgtgta caactatctc 1260
aaagcccctt atacaggttg ctacagtcat ttgaataccg gagtcagctt tgcaaactat 1320
acagcgcatg gatctgagac cgcatgggct gatccacttc tgactacttc tcaactgaaa 1380
gcactcacta ataaggacaa atacttctta gctattggca actgctgtat tacagctcaa 1440
ttcgattatg tacagccttg cttcggagag gtaataactc gcgttaagga gaaaggggct 1500
tatgcctata tcggttcatc tccaaattct tattggggcg aggactacta ttggagtgtg 1560
ggtgctaatg ccgtatttgg tgttcagcct acttttgaag gtacgtctat gggttcttat 1620
gatgctacat tcttggagga ttcgtacaac acagtgaatt ctattatgtg ggcaggtaat 1680
cttgccgcta ctcatgctgg aaatatcggc aatattaccc atattggtgc tcattactat 1740
tgggaagctt atcatgtcct tggcgatggt tcggttatgc cttatcgtgc aatgcctaag 1800
accaatactt atacgcttcc tgcctctttg cctcagaatc aggcttctta tagcattcag 1860
gcttctgccg gttcttacgt agctatttct aaagatggag ttttgtatgg aacaggtgtt 1920
gctaatgcca gcggtgttgc gactgtgagt atgactaagc agattacgga aaatggtaat 1980
tatgatgtag ttatcactcg ctctaattat cttcctgtga tcaagcaaat tcaggtaggt 2040
gagcctagcc cctaccagcc cgtttccaac ttgacagcta caacgcaggg tcagaaagta 2100
acgctcaagt gggaagcacc gagcgcaaag aaggcagaag gttcccgtga agtaaaacgg 2160
atcggagacg gtcttttcgt tacgatcgaa cctgcaaacg atgtacgtgc caacgaagcc 2220
aaggttgtgc ttgcggcaga caacgtatgg ggagacaata cgggttacca gttcttgttg 2280
gatgccgatc acaatacatt cggaagtgtc attccggcaa ccggtcctct ctttaccgga 2340
acagcttctt ccaatcttta cagtgcgaac ttcgagtatt tgatcccggc caatgccgat 2400

-continued

```
cctgttgtta ctacacagaa tattatcgtt acaggacagg gtgaagttgt aatccccggt   2460
ggtgtttacg actattgcat tacgaacccg gaacctgcat ccggaaagat gtggatcgca   2520
ggagatggag gcaaccagcc tgcacgttat gacgatttca cattcgaagc aggcaagaag   2580
tacaccttca cgatgcgtcg cgccggaatg ggagatggaa ctgatatgga agtcgaagac   2640
gattcacctg caagctatac ctacacggtg tatcgtgacg gcacgaagat caaggaaggt   2700
ctgacagcta cgacattcga agaagacggt gtagctgcag gcaatcatga gtattgcgtg   2760
gaagttaagt acacagccgg cgtatctccg aaggtatgta aagacgttac ggtagaagga   2820
tccaatgaat ttgctcctgt acagaacctg accggtagtt cagtaggtca gaaagtaacg   2880
cttaagtggg atgcacctaa tggtaccccg aatccgaatc caaatccgaa tccgaatccg   2940
ggaacaacac tttccgaatc attcgaaaat ggtattccgg catcttggaa gacgatcgat   3000
gcagacggtg acgggcatgg ctggaaacct ggaaatgctc ccggaatcgc tggctacaat   3060
agcaatggtt gtgtatattc agagtcattc ggtcttggtg gtataggagt tcttacccct   3120
gacaactatc tgataacacc ggcattggat ttgcctaacg gaggtaagtt gactttctgg   3180
gtatgcgcac aggatgctaa ttatgcatcc gagcactatg cggtgtatgc atcttcgacc   3240
ggtaacgatg catccaactt cacgaatgct ttgttggaag agacgattac ggcaaaaggt   3300
gttcgctcgc cgaaagctat tcgtggtcgt atacagggta cttggcgcca gaagacggta   3360
gaccttcccg caggtacgaa atatgttgct ttccgtcact tccaaagcac ggatatgttc   3420
tacatcgacc ttgatgaggt tgagatcaag gccaatggca agcgcgcaga cttcacggaa   3480
acgttcgagt cttctactca tggagaggca ccagcggaat ggactactat cgatgccgat   3540
ggcgatggtc agggttggct ctgtctgtct tccggacaat tggactggct gacagctcat   3600
ggcggcagca acgtagtaag ctctttctca tggaatggaa tggctttgaa tcctgataac   3660
tatctcatct caaaggatgt tacaggcgca acgaaggtaa agtactacta tgcagtcaac   3720
gacggttttc ccggggatca ctatgcggtg atgatctcca agacgggcac gaacgccgga   3780
gacttcacgg ttgttttcga agaaacgcct aacggaataa ataagggcgg agcaagattc   3840
ggtctttcca cggaagccaa tggcgccaaa cctcaaagtg tatggatcga gcgtacggta   3900
gatttgcctg caggcacgaa gtatgttgct ttccgtcact acaattgctc ggatttgaac   3960
tacattcttt tggatgatat tcagttcacc atgggtggca gccccacccc gaccgattat   4020
acctacacgg tgtatcgtga tggtacgaag atcaaggaag gtttgaccga aacgaccttc   4080
gaagaagacg gcgtagctac gggcaatcat gagtattgcg tggaagtgaa gtacacagcc   4140
ggcgtatctc cgaagaaatg tgtaaacgta actgttaatt cgacacagtt caatcctgta   4200
cagaacctga cggcagaaca agctcctaac agcatggatg caatccttaa atggaatgca   4260
ccggcatcta agcgtgcgga agttctgaac gaagacttcg aaaatggtat tcctgcctca   4320
tggaagacga tcgatgcaga cggtgacggc aacaattgga cgacgacccc tcctcccgga   4380
ggctcctctt ttgcaggtca caacagtgcg atctgtgtct cttcagcttc ttatatcaac   4440
tttgaaggtc ctcagaaccc tgataactat ctggttacac cggagctttc tcttcctggc   4500
ggaggaacgc ttactttctg ggtatgtgca caagatgcca attatgcatc agagcactat   4560
gccgtgtacg catcttctac gggtaacgac gcttccaact tcgccaacgc tttgttggaa   4620
gaagtgctga cggccaagac agttgttacg gcacctgaag ccattcgtgg tactcgtgct   4680
cagggcacct ggtatcaaaa gacggtacag ttgcctgcgg gtactaagta tgttgccttc   4740
cgtcacttcg gctgtacgga cttcttctgg atcaaccttg atgatgttgt aatcacttca   4800
```

```
gggaacgctc cgtcttacac ctatacgatc tatcgtaata atacacagat agcatcaggc   4860

gtaacggaga ctacttaccg agatccggac ttggctaccg gtttttacac gtacggtgta   4920

aaggttgttt acccgaacgg agaatcagct atcgaaactg ctacgttgaa tatcacttcg   4980

ttggcagacg taacggctca gaagccttac acgctgacag ttgtaggaaa gacgatcacg   5040

gtaacttgcc aaggcgaagc tatgatctac gacatgaacg gtcgtcgtct ggcagcgggt   5100

cgcaacacgg ttgtttacac ggctcagggc ggccactatg cagtcatggt tgtcgttgac   5160

ggcaagtctt acgtagagaa actcgctatc aagtaa                             5196


<210> SEQ ID NO 53
<211> LENGTH: 555
<212> TYPE: PRT
<213> ORGANISM: Porphyromonas  gingivalis

<400> SEQUENCE: 53

Lys Lys Leu Leu Gln Ala Lys Ala Leu Ile Leu Ala Leu Gly Leu Phe
1               5                   10                  15

Gln Leu Pro Ala Ile Ala Gln Thr Gln Met Gln Ala Asp Arg Thr Asn
            20                  25                  30

Gly Gln Phe Ala Thr Glu Glu Met Gln Arg Ala Phe Gln Glu Thr Asn
        35                  40                  45

Pro Pro Ala Gly Pro Val Arg Ala Ile Ala Glu Tyr Glu Arg Ser Ala
    50                  55                  60

Ala Val Leu Val Arg Tyr Pro Phe Gly Ile Pro Met Glu Leu Ile Lys
65                  70                  75                  80

Glu Leu Ala Lys Asn Asp Lys Val Ile Thr Ile Val Ala Ser Glu Ser
                85                  90                  95

Gln Lys Asn Thr Val Ile Thr Gln Tyr Thr Gln Ser Gly Val Asn Leu
            100                 105                 110

Ser Asn Cys Asp Phe Ile Ile Ala Lys Thr Asp Ser Tyr Trp Thr Arg
        115                 120                 125

Asp Tyr Thr Gly Trp Phe Ala Met Tyr Asp Thr Asn Lys Val Gly Leu
    130                 135                 140

Val Asp Phe Ile Tyr Asn Arg Pro Arg Pro Asn Asp Asp Glu Phe Pro
145                 150                 155                 160

Lys Tyr Glu Ala Gln Tyr Leu Gly Ile Glu Met Phe Gly Met Lys Leu
                165                 170                 175

Lys Gln Thr Gly Gly Asn Tyr Met Thr Asp Gly Tyr Gly Ser Ala Val
            180                 185                 190

Gln Ser His Ile Ala Tyr Thr Glu Asn Ser Ser Leu Ser Gln Ala Gln
        195                 200                 205

Val Asn Gln Lys Met Lys Asp Tyr Leu Gly Ile Thr His His Asp Val
    210                 215                 220

Val Gln Asp Pro Asn Gly Glu Tyr Ile Asn His Val Asp Cys Trp Gly
225                 230                 235                 240

Lys Tyr Leu Ala Pro Asn Lys Ile Leu Ile Arg Lys Val Pro Asp Asn
                245                 250                 255

His Pro Gln His Gln Ala Leu Glu Asp Met Ala Ala Tyr Phe Ala Ala
            260                 265                 270

Gln Thr Cys Ala Trp Gly Thr Lys Tyr Glu Val Tyr Arg Ala Leu Ala
        275                 280                 285

Thr Asn Glu Gln Pro Tyr Thr Asn Ser Leu Ile Leu Asn Asn Arg Val
    290                 295                 300
```

```
Phe Val Pro Val Asn Gly Pro Ala Ser Val Asp Asn Asp Ala Leu Asn
305                 310                 315                 320

Val Tyr Lys Thr Ala Met Pro Gly Tyr Glu Ile Ile Gly Val Lys Gly
                325                 330                 335

Ala Ser Gly Thr Pro Trp Leu Gly Thr Asp Ala Leu His Cys Arg Thr
            340                 345                 350

His Glu Val Ala Asp Lys Gly Tyr Leu Tyr Ile Lys His Tyr Pro Ile
        355                 360                 365

Leu Gly Glu Gln Ala Gly Pro Asp Tyr Lys Ile Glu Ala Asp Val Val
    370                 375                 380

Ser Cys Ala Asn Ala Thr Ile Ser Pro Val Gln Cys Tyr Tyr Arg Ile
385                 390                 395                 400

Asn Gly Ser Gly Ser Phe Lys Ala Ala Asp Met Thr Met Glu Ser Thr
                405                 410                 415

Gly His Tyr Thr Tyr Ser Phe Thr Gly Leu Asn Lys Asn Asp Lys Val
            420                 425                 430

Glu Tyr Tyr Ile Ser Ala Ala Asp Asn Ser Gly Arg Lys Glu Thr Tyr
        435                 440                 445

Pro Phe Ile Gly Glu Pro Asp Pro Phe Lys Phe Thr Cys Met Asn Glu
    450                 455                 460

Thr Asn Thr Cys Thr Val Thr Gly Ala Ala Lys Ala Leu Arg Ala Trp
465                 470                 475                 480

Phe Asn Ala Gly Arg Ser Glu Leu Ala Val Ser Val Ser Leu Asn Ile
                485                 490                 495

Ala Gly Thr Tyr Arg Ile Lys Leu Tyr Asn Thr Ala Gly Glu Glu Val
            500                 505                 510

Ala Ala Met Thr Lys Glu Leu Val Ala Gly Thr Ser Val Phe Ser Met
        515                 520                 525

Asp Val Tyr Ser Gln Ala Pro Gly Thr Tyr Val Leu Val Val Glu Gly
    530                 535                 540

Asn Gly Ile Arg Glu Thr Met Lys Ile Leu Lys
545                 550                 555
```

```
<210> SEQ ID NO 54
<211> LENGTH: 1668
<212> TYPE: DNA
<213> ORGANISM: Porphyromonas gingivalis

<400> SEQUENCE: 54

aaaaagcttt tacaggctaa agccttgatt ctggcattgg gactcttcca actgcccgca      60

atcgcccaaa cgcaaatgca agcagaccga acaaacggtc aatttgcaac agaagagatg     120

caacgagcat tccaggaaac gaatccccct gcaggtcctg tgcgtgctat cgctgagtac     180

gaacgctctg cagccgtttt ggtacgctac ccgttcggta tcccgatgga attgatcaaa     240

gagctggcca agaacgacaa ggtgattacc attgtggcga gtgaaagcca aaaaaacacc     300

gttataaccc agtacaccca aagcggtgtg aatctctcta attgcgattt catcattgcg     360

aaaactgact cttactggac acgcgactat accggttggt tcgcaatgta cgatacgaac     420

aaagtaggtc tcgtggactt tatttataac cgccctcgtc ctaacgatga tgaattcccc     480

aaatacgaag cacaatatct gggcatcgag atgttcggga tgaagctcaa gcagaccggt     540

ggcaactaca tgacggacgg atatggatcc gctgtgcagt cacatatcgc atatacggag     600

aactcctctc tgtctcaagc tcaagtaaat caaaagatga aagactatct cggcatcaca     660
```

-continued

```
catcatgatg tggtacaaga tccgaacggc gaatatatca accatgtgga ctgttggggc    720
aagtatttgg caccgaacaa aatcctcatc aggaaagtgc ctgacaatca ccctcagcac    780
caagccctgg aagatatggc agcctacttc gcagcacaga cctgcgcatg ggaacgaag    840
tacgaggtat atcgcgcttt ggccaccaat gaacaaccgt acacgaactc tctgattctg    900
aacaacaggg tatttgttcc tgtcaatggc cccgcctccg tggacaacga tgctctgaac    960
gtctataaga cggcaatgcc cggttacgaa attataggtg tcaaaggggc ttcaggaaca   1020
ccttggttag gaacagatgc cctgcattgt cgtactcacg aggtagcgga taagggctat   1080
ctctatatca agcactaccc gatactgggc gaacaggcag gccctgatta taagatcgaa   1140
gcagatgtcg tctcatgcgc caatgctact atctcgccgg tacaatgtta ctatcgtatc   1200
aatggttccg gtagctttaa ggctgctgat atgacgatgg aatcaacagg tcactatact   1260
tatagcttta caggtcttaa caagaatgat aaggtagaat actatatctc tgccgctgac   1320
aatagtggtc gcaaagagac ttatcccttt atcggcgaac ctgatccttt caagtttacg   1380
tgtatgaacg aaaccaatac atgtactgtg accggagctg ccaaagctct tcgtgcatgg   1440
ttcaacgccg gtcgttcaga actggctgtt tcggtaagtt tgaatattgc cggcacatat   1500
cggataaagc tttataacac cgcaggagaa gaagtcgctg caatgaccaa ggaattagta   1560
gcagggacga gtgtcttcag tatggatgtg tattctcagg ctccgggcac atatgttctg   1620
gttgttgaag gaaatggaat ccgtgagaca atgaaaattc tcaaataa                1668
```

<210> SEQ ID NO 55
<211> LENGTH: 1016
<212> TYPE: PRT
<213> ORGANISM: Porphyromonas gingivalis

<400> SEQUENCE: 55

```
Lys Arg Met Thr Leu Phe Phe Leu Cys Leu Leu Thr Ser Ile Gly Trp
1               5                   10                  15

Ala Met Ala Gln Asn Arg Thr Val Lys Gly Thr Val Ile Ser Ser Glu
            20                  25                  30

Asp Asn Glu Pro Leu Ile Gly Ala Asn Val Val Val Val Gly Asn Thr
        35                  40                  45

Thr Ile Gly Ala Ala Thr Asp Leu Asp Gly Asn Phe Thr Leu Ser Val
    50                  55                  60

Pro Ala Asn Ala Lys Met Leu Arg Val Ser Tyr Ser Gly Met Thr Thr
65                  70                  75                  80

Lys Glu Val Ala Ile Ala Asn Val Met Lys Ile Val Leu Asp Pro Asp
                85                  90                  95

Ser Lys Val Leu Glu Gln Val Val Val Leu Gly Tyr Gly Thr Gly Gln
            100                 105                 110

Lys Leu Ser Thr Val Ser Gly Ser Val Ala Lys Val Ser Ser Glu Lys
        115                 120                 125

Leu Ala Glu Lys Pro Val Ala Asn Ile Met Asp Ala Leu Gln Gly Gln
    130                 135                 140

Val Ala Gly Met Gln Val Met Thr Thr Ser Gly Asp Pro Thr Ala Val
145                 150                 155                 160

Ala Ser Val Glu Ile His Gly Thr Gly Ser Leu Gly Ala Ser Ser Ala
                165                 170                 175

Pro Leu Tyr Ile Val Asp Gly Met Gln Thr Ser Leu Asp Val Val Ala
            180                 185                 190

Thr Met Asn Pro Asn Asp Phe Glu Ser Met Ser Val Leu Lys Asp Ala
```

```
        195                 200                 205

Ser Ala Thr Ser Ile Tyr Gly Ala Arg Ala Ala Asn Gly Val Val Phe
    210                 215                 220

Ile Gln Thr Lys Lys Gly Lys Met Ser Glu Arg Gly Arg Ile Thr Phe
225                 230                 235                 240

Asn Ala Ser Tyr Gly Ile Ser Gln Ile Leu Asn Thr Lys Pro Leu Asp
                245                 250                 255

Asn Met Met Thr Gly Asp Glu Leu Leu Asp Phe Gln Val Lys Ala Gly
            260                 265                 270

Phe Trp Gly Asn Asn Gln Thr Val Gln Lys Val Lys Asp Met Ile Leu
        275                 280                 285

Ala Gly Ala Glu Asp Leu Tyr Gly Asn Tyr Asp Ser Leu Lys Asp Glu
    290                 295                 300

Tyr Gly Lys Thr Leu Phe Pro Val Asp Phe Asn His Asp Ala Asp Trp
305                 310                 315                 320

Leu Lys Ala Leu Phe Lys Thr Ala Pro Thr Ser Gln Gly Asp Ile Ser
                325                 330                 335

Phe Ser Gly Gly Ser Gln Gly Thr Ser Tyr Tyr Ala Ser Ile Gly Tyr
            340                 345                 350

Phe Asp Gln Glu Gly Met Ala Arg Glu Pro Ala Asn Phe Lys Arg Tyr
        355                 360                 365

Ser Gly Arg Leu Asn Phe Glu Ser Arg Ile Asn Glu Trp Leu Lys Val
    370                 375                 380

Gly Ala Asn Leu Ser Gly Ala Ile Ala Asn Arg Arg Ser Ala Asp Tyr
385                 390                 395                 400

Phe Gly Lys Tyr Tyr Met Gly Ser Gly Thr Phe Gly Val Leu Thr Met
                405                 410                 415

Pro Arg Tyr Tyr Asn Pro Phe Asp Val Asn Gly Asp Leu Ala Asp Val
            420                 425                 430

Tyr Tyr Met Tyr Gly Ala Thr Arg Pro Ser Met Thr Glu Pro Tyr Phe
        435                 440                 445

Ala Lys Met Arg Pro Phe Ser Ser Glu Ser His Gln Ala Asn Val Asn
    450                 455                 460

Gly Phe Ala Gln Ile Thr Pro Ile Lys Gly Leu Thr Leu Lys Ala Gln
465                 470                 475                 480

Ala Gly Val Asp Ile Thr Asn Thr Arg Thr Ser Ser Lys Arg Met Pro
                485                 490                 495

Asn Asn Pro Tyr Asp Ser Thr Pro Leu Gly Glu Arg Arg Glu Arg Ala
            500                 505                 510

Tyr Arg Asp Val Ser Lys Ser Phe Thr Asn Thr Ala Glu Tyr Lys Phe
        515                 520                 525

Ser Ile Asp Glu Lys His Asp Leu Thr Ala Leu Met Gly His Glu Tyr
    530                 535                 540

Ile Glu Tyr Glu Gly Asp Val Ile Gly Ala Ser Ser Lys Gly Phe Glu
545                 550                 555                 560

Ser Asp Lys Leu Met Leu Leu Ser Gln Gly Lys Thr Gly Asn Ser Leu
                565                 570                 575

Ser Leu Pro Glu His Arg Val Ala Glu Tyr Ala Tyr Leu Ser Phe Phe
            580                 585                 590

Ser Arg Phe Asn Tyr Gly Phe Asp Lys Trp Met Tyr Ile Asp Phe Ser
        595                 600                 605

Val Arg Asn Asp Gln Ser Ser Arg Phe Gly Ser Asn Asn Arg Ser Ala
    610                 615                 620
```

```
Trp Phe Tyr Ser Val Gly Gly Met Phe Asp Ile Tyr Asn Lys Phe Ile
625                 630                 635                 640

Gln Glu Ser Asn Trp Leu Ser Asp Leu Arg Leu Lys Met Ser Tyr Gly
                645                 650                 655

Thr Thr Gly Asn Ser Glu Ile Gly Asn Tyr Asn His Gln Ala Leu Val
            660                 665                 670

Thr Val Asn Asn Tyr Thr Glu Asp Ala Met Gly Leu Ser Ile Ser Thr
        675                 680                 685

Ala Gly Asn Pro Asp Leu Ser Trp Glu Lys Gln Ser Gln Phe Asn Phe
    690                 695                 700

Gly Leu Ala Ala Gly Ala Phe Asn Asn Arg Leu Ser Ala Glu Val Asp
705                 710                 715                 720

Phe Tyr Val Arg Thr Thr Asn Asp Met Leu Ile Asp Val Pro Met Pro
                725                 730                 735

Tyr Ile Ser Gly Phe Phe Ser Gln Tyr Gln Asn Val Gly Ser Met Lys
            740                 745                 750

Asn Thr Gly Val Asp Leu Ser Leu Lys Gly Thr Ile Tyr Gln Asn Lys
        755                 760                 765

Asp Trp Asn Val Tyr Ala Ser Ala Asn Phe Asn Tyr Asn Arg Gln Glu
    770                 775                 780

Ile Thr Lys Leu Phe Phe Gly Leu Asn Lys Tyr Met Leu Pro Asn Thr
785                 790                 795                 800

Gly Thr Ile Trp Glu Ile Gly Tyr Pro Asn Ser Phe Tyr Met Ala Glu
                805                 810                 815

Tyr Ala Gly Ile Asp Lys Lys Thr Gly Lys Gln Leu Trp Tyr Val Pro
            820                 825                 830

Gly Gln Val Asp Ala Asp Gly Asn Lys Val Thr Thr Ser Gln Tyr Ser
        835                 840                 845

Ala Asp Leu Glu Thr Arg Ile Asp Lys Ser Val Thr Pro Pro Ile Thr
    850                 855                 860

Gly Gly Phe Ser Leu Gly Ala Ser Trp Lys Gly Leu Ser Leu Asp Ala
865                 870                 875                 880

Asp Phe Ala Tyr Ile Val Gly Lys Trp Met Ile Asn Asn Asp Arg Tyr
                885                 890                 895

Phe Thr Glu Asn Gly Gly Gly Leu Met Gln Leu Asn Lys Asp Lys Met
            900                 905                 910

Leu Leu Asn Ala Trp Thr Glu Asp Asn Lys Glu Thr Asp Val Pro Lys
        915                 920                 925

Leu Gly Gln Ser Pro Gln Phe Asp Thr His Leu Leu Glu Asn Ala Ser
    930                 935                 940

Phe Leu Arg Leu Lys Asn Leu Lys Leu Thr Tyr Val Leu Pro Asn Ser
945                 950                 955                 960

Leu Phe Ala Gly Gln Asn Val Ile Gly Gly Ala Arg Val Tyr Leu Met
                965                 970                 975

Ala Arg Asn Leu Leu Thr Val Thr Lys Tyr Lys Gly Phe Asp Pro Glu
            980                 985                 990

Ala Gly Gly Asn Val Gly Lys Asn  Gln Tyr Pro Asn Ser  Lys Gln Tyr
        995                 1000                1005

Val Ala  Gly Ile Gln Ile Ser  Phe
    1010                 1015
```

<210> SEQ ID NO 56
<211> LENGTH: 3051

<212> TYPE: DNA
<213> ORGANISM: Porphyromonas gingivalis

<400> SEQUENCE: 56

```
aaaagaatga cgctattctt cctttgcttg ctgacgagca ttgggtgggc tatggcccag     60
aatagaaccg tgaagggtac agttatctcc tccgaggata atgagcccct gatcggcgcg    120
aatgtcgtgg ttgtcggaaa caccactatc ggtgctgcaa ccgacttgga tggcaacttc    180
acgcttagcg tgcctgccaa tgccaaaatg ttgagagtgt cctattccgg tatgactacc    240
aaagaggtcg ccatcgctaa tgtgatgaag atcgtactgg atccggactc taaggttctg    300
gagcaggtag ttgtattggg ttacggtacg ggacagaaac tcagcactgt ttccggttct    360
gtggccaaag tgtccagcga aaagctcgcg gaaaagcccg ttgccaatat catggatgcc    420
ctccaaggtc aggtagccgg tatgcaggtt atgactacat ccggtgaccc tactgccgtc    480
gcttctgtgg agatccatgg tacagggtcg ttgggggcaa gctctgcacc attgtatatc    540
gtggatggta tgcaaacttc tttggatgtt gtggctacga tgaatccgaa tgattttgaa    600
tctatgtccg ttttgaaaga tgcttctgca acatctattt atggagctcg tgctgcaaac    660
ggagtcgttt tcattcaaac gaagaaaggt aaaatgagcg agagaggtcg tattaccttt    720
aatgccagtt acgggatttc tcaaatcctg aatactaagc cccttgataa tatgatgact    780
ggagatgaat tgctggattt tcaggtgaag gcaggttttt gggggaacaa tcaaaccgtt    840
cagaaggtta aagatatgat ccttgccgga gctgaagatt tgtatggcaa ttatgattct    900
ttgaaagatg agtatggtaa gacattgttc ccagtggatt ttaatcatga tgcagactgg    960
ctcaaggctt tgtttaaaac agcacccacc agtcaaggtg atatttcttt ctccggaggg   1020
tctcagggaa cttcatatta tgcctctata ggctacttcg atcaggaagg tatggctcgt   1080
gaaccggcaa attttaagcg ctatagtggc cggctcaact tcgaaagtcg tatcaatgaa   1140
tggctgaaag ttggtgcaaa tttgtctggt gcgatagcga atagacgatc tgccgactat   1200
tttggaaagt attatatggg gtcaggtact ttcggtgtgt taacgatgcc tcgttattat   1260
aaccctttg atgtgaatgg ggatttagca gatgtctatt acatgtatgg agctaccaga    1320
ccttctatga cagaaccgta cttcgcaaaa atgagaccgt tcagttccga atcacatcag   1380
gccaatgtaa atggtttcgc ccagattact ccgatcaaag gccttacttt aaaggcacag   1440
gctggtgttg atattactaa tactcgcact tcttctaaga gaatgcccaa taatccgtat   1500
gattctactc ctcttgggga aagaagagaa agagcttatc gagatgttag caagtctttt   1560
acaaatacgg ctgaatataa gttttcaatt gatgaaaaac atgatcttac agcattgatg   1620
gggcatgaat atattgaata tgaaggggat gttattgggg catcttctaa aggatttgaa   1680
agtgataagt tgatgttact gagccaggga aaaaccggaa atagtttgtc tttgcctgaa   1740
cacagagtcg ctgaatatgc ctatttgtct ttctttagtc gttttaatta cggttttgac   1800
aaatggatgt atatagattt ctctgttcgt aatgaccaat cctctcgatt cggatccaat   1860
aatagaagcg cgtggttcta ttctgtcggt ggaatgtttg acatatataa taaattcatt   1920
caagaaagta attggctcag tgatcttcga ctgaaaatga gttatggtac aacgggtaac   1980
tcggagattg gtaattacaa ccaccaagca ctcgttactg tgaacaatta tactgaagat   2040
gctatggggc ttagcatttc tacagcaggc aatcccgacc tctcgtggga aaagcagtct   2100
cagttcaact tcggtttggc tgcaggggct ttcaataatc gcttatctgc agaggtagat   2160
ttctatgtcc gcactacgaa tgatatgttg attgatgtcc cgatgcctta tatcagtggt   2220
```

```
ttcttctcac agtatcagaa tgtaggctct atgaaaaata cgggtgtaga cctttctctt   2280

aaggggacga tctaccaaaa taaggactgg aatgtatatg cttctgcgaa tttcaactac   2340

aatagacagg aaataacaaa gcttttcttc ggtctcaata agtacatgtt gcctaatacc   2400

ggtactatat gggaaattgg gtaccccaat tcgttctata tggctgaata tgctggaatc   2460

gacaaaaaaa ccggtaagca gttgtggtat gttcctggtc aagtcgatgc ggatggtaat   2520

aaagttacaa caagccagta ctcagctgac ttggagacac gaattgataa gtctgttact   2580

cctcctatta caggtggttt ctccttaggt gcttcttgga aaggactttc tttagatgct   2640

gattttgcct acatcgttgg taaatggatg atcaataatg accgttactt tacagagaat   2700

ggaggtggat tgatgcaatt aaataaagat aaaatgctat tgaatgcctg gacagaggat   2760

aataaagaaa cagatgttcc aaaattggga cagtctcctc agtttgatac gcatttgttg   2820

gagaatgctt ctttcctgcg tttgaagaat ctcaaactca cctatgtact ccccaatagt   2880

ctttttgctg ggcagaatgt gattggtgga gctcgtgtct atttgatggc gcgcaatctg   2940

ttaactgtta cgaagtataa aggctttgac cctgaagcag gggggaatgt gggaaaaaat   3000

caatatccta attctaagca gtacgttgcg ggtattcaga tttctttcta a            3051
```

<210> SEQ ID NO 57
<211> LENGTH: 1703
<212> TYPE: PRT
<213> ORGANISM: Porphyromonas gingivalis

<400> SEQUENCE: 57

```
Leu His Lys Phe Val Ser Ile Ala Leu Cys Ser Ser Leu Leu Gly Gly
1               5                   10                  15

Met Ala Phe Ala Gln Gln Thr Glu Leu Gly Arg Asn Pro Asn Val Arg
            20                  25                  30

Leu Leu Glu Ser Thr Gln Gln Ser Val Thr Lys Val Gln Phe Arg Met
        35                  40                  45

Asp Asn Leu Lys Phe Thr Glu Val Gln Thr Pro Lys Gly Met Ala Gln
    50                  55                  60

Val Pro Thr Tyr Thr Glu Gly Val Asn Leu Ser Glu Lys Gly Met Pro
65                  70                  75                  80

Thr Leu Pro Ile Leu Ser Arg Ser Leu Ala Val Ser Asp Thr Arg Glu
                85                  90                  95

Met Lys Val Glu Val Val Ser Ser Lys Phe Ile Glu Lys Lys Asn Val
            100                 105                 110

Leu Ile Ala Pro Ser Lys Gly Met Ile Met Arg Asn Glu Asp Pro Lys
        115                 120                 125

Lys Ile Pro Tyr Val Tyr Gly Lys Ser Tyr Ser Gln Asn Lys Phe Phe
    130                 135                 140

Pro Gly Glu Ile Ala Thr Leu Asp Asp Pro Phe Ile Leu Arg Asp Val
145                 150                 155                 160

Arg Gly Gln Val Val Asn Phe Ala Pro Leu Gln Tyr Asn Pro Val Thr
                165                 170                 175

Lys Thr Leu Arg Ile Tyr Thr Glu Ile Thr Val Ala Val Ser Glu Thr
            180                 185                 190

Ser Glu Gln Gly Lys Asn Ile Leu Asn Lys Lys Gly Thr Phe Ala Gly
        195                 200                 205

Phe Glu Asp Thr Tyr Lys Arg Met Phe Met Asn Tyr Glu Pro Gly Arg
    210                 215                 220

Tyr Thr Pro Val Glu Glu Lys Gln Asn Gly Arg Met Ile Val Ile Val
```

```
225                 230                 235                 240

Ala Lys Lys Tyr Glu Gly Asp Ile Lys Asp Phe Val Asp Trp Lys Asn
                245                 250                 255

Gln Arg Gly Leu Arg Thr Glu Val Lys Val Ala Glu Asp Ile Ala Ser
            260                 265                 270

Pro Val Thr Ala Asn Ala Ile Gln Gln Phe Val Lys Gln Glu Tyr Glu
        275                 280                 285

Lys Glu Gly Asn Asp Leu Thr Tyr Val Leu Leu Ile Gly Asp His Lys
    290                 295                 300

Asp Ile Pro Ala Lys Ile Thr Pro Gly Ile Lys Ser Asp Gln Val Tyr
305                 310                 315                 320

Gly Gln Ile Val Gly Asn Asp His Tyr Asn Glu Val Phe Ile Gly Arg
                325                 330                 335

Phe Ser Cys Glu Ser Lys Glu Asp Leu Lys Thr Gln Ile Asp Arg Thr
            340                 345                 350

Ile His Tyr Glu Arg Asn Ile Thr Thr Glu Asp Lys Trp Leu Gly Gln
        355                 360                 365

Ala Leu Cys Ile Ala Ser Ala Glu Gly Gly Pro Ser Ala Asp Asn Gly
    370                 375                 380

Glu Ser Asp Ile Gln His Glu Asn Val Ile Ala Asn Leu Leu Thr Gln
385                 390                 395                 400

Tyr Gly Tyr Thr Lys Ile Ile Lys Cys Tyr Asp Pro Gly Val Thr Pro
                405                 410                 415

Lys Asn Ile Ile Asp Ala Phe Asn Gly Gly Ile Ser Leu Ala Asn Tyr
            420                 425                 430

Thr Gly His Gly Ser Glu Thr Ala Trp Gly Thr Ser His Phe Gly Thr
        435                 440                 445

Thr His Val Lys Gln Leu Thr Asn Ser Asn Gln Leu Pro Phe Ile Phe
    450                 455                 460

Asp Val Ala Cys Val Asn Gly Asp Phe Leu Phe Ser Met Pro Cys Phe
465                 470                 475                 480

Ala Glu Ala Leu Met Arg Ala Gln Lys Asp Gly Lys Pro Thr Gly Thr
                485                 490                 495

Val Ala Ile Ile Ala Ser Thr Ile Asn Gln Ser Trp Ala Ser Pro Met
            500                 505                 510

Arg Gly Gln Asp Glu Met Asn Glu Ile Leu Cys Glu Lys His Pro Asn
        515                 520                 525

Asn Ile Lys Arg Thr Phe Gly Gly Val Thr Met Asn Gly Met Phe Ala
    530                 535                 540

Met Val Glu Lys Tyr Lys Lys Asp Gly Glu Lys Met Leu Asp Thr Trp
545                 550                 555                 560

Thr Val Phe Gly Asp Pro Ser Leu Leu Val Arg Thr Leu Val Pro Thr
                565                 570                 575

Lys Met Gln Val Thr Ala Pro Ala Gln Ile Asn Leu Thr Asp Ala Ser
            580                 585                 590

Val Asn Val Ser Cys Asp Tyr Asn Gly Ala Ile Ala Thr Ile Ser Ala
        595                 600                 605

Asn Gly Lys Met Phe Gly Ser Ala Val Val Glu Asn Gly Thr Ala Thr
    610                 615                 620

Ile Asn Leu Thr Gly Leu Thr Asn Glu Ser Thr Leu Thr Leu Thr Val
625                 630                 635                 640

Val Gly Tyr Asn Lys Glu Thr Val Ile Lys Thr Ile Asn Thr Asn Gly
                645                 650                 655
```

```
Glu Pro Asn Pro Tyr Gln Pro Val Ser Asn Leu Thr Ala Thr Thr Gln
            660                 665                 670

Gly Gln Lys Val Thr Leu Lys Trp Asp Ala Pro Ser Thr Lys Thr Asn
        675                 680                 685

Ala Thr Thr Asn Thr Ala Arg Ser Val Asp Gly Ile Arg Glu Leu Val
    690                 695                 700

Leu Leu Ser Val Ser Asp Ala Pro Glu Leu Leu Arg Ser Gly Gln Ala
705                 710                 715                 720

Glu Ile Val Leu Glu Ala His Asp Val Trp Asn Asp Gly Ser Gly Tyr
                725                 730                 735

Gln Ile Leu Leu Asp Ala Asp His Asp Gln Tyr Gly Gln Val Ile Pro
            740                 745                 750

Ser Asp Thr His Thr Leu Trp Pro Asn Cys Ser Val Pro Ala Asn Leu
        755                 760                 765

Phe Ala Pro Phe Glu Tyr Thr Val Pro Glu Asn Ala Asp Pro Ser Cys
    770                 775                 780

Ser Pro Thr Asn Met Ile Met Asp Gly Thr Ala Ser Val Asn Ile Pro
785                 790                 795                 800

Ala Gly Thr Tyr Asp Phe Ala Ile Ala Ala Pro Gln Ala Asn Ala Lys
                805                 810                 815

Ile Trp Ile Ala Gly Gln Gly Pro Thr Lys Glu Asp Asp Tyr Val Phe
            820                 825                 830

Glu Ala Gly Lys Lys Tyr His Phe Leu Met Lys Lys Met Gly Ser Gly
        835                 840                 845

Asp Gly Thr Glu Leu Thr Ile Ser Glu Gly Gly Gly Ser Asp Tyr Thr
    850                 855                 860

Tyr Thr Val Tyr Arg Asp Gly Thr Lys Ile Lys Glu Gly Leu Thr Ala
865                 870                 875                 880

Thr Thr Phe Glu Glu Asp Gly Val Ala Ala Gly Asn His Glu Tyr Cys
                885                 890                 895

Val Glu Val Lys Tyr Thr Ala Gly Val Ser Pro Lys Val Cys Lys Asp
            900                 905                 910

Val Thr Val Glu Gly Ser Asn Glu Phe Ala Pro Val Gln Asn Leu Thr
        915                 920                 925

Gly Ser Ala Val Gly Gln Lys Val Thr Leu Lys Trp Asp Ala Pro Asn
    930                 935                 940

Gly Thr Pro Asn Pro Asn Pro Asn Pro Asn Pro Asn Pro Asn Pro Gly
945                 950                 955                 960

Thr Thr Thr Leu Ser Glu Ser Phe Glu Asn Gly Ile Pro Ala Ser Trp
                965                 970                 975

Lys Thr Ile Asp Ala Asp Gly Asp Gly His Gly Trp Lys Pro Gly Asn
            980                 985                 990

Ala Pro Gly Ile Ala Gly Tyr Asn  Ser Asn Gly Cys Val  Tyr Ser Glu
        995                 1000                1005

Ser Phe  Gly Leu Gly Gly Ile  Gly Val Leu Thr Pro  Asp Asn Tyr
    1010                 1015                 1020

Leu Ile  Thr Pro Ala Leu Asp  Leu Pro Asn Gly Gly  Lys Leu Thr
    1025                 1030                 1035

Phe Trp  Val Cys Ala Gln Asp  Ala Asn Tyr Ala Ser  Glu His Tyr
    1040                 1045                 1050

Ala Val  Tyr Ala Ser Ser Thr  Gly Asn Asp Ala Ser  Asn Phe Thr
    1055                 1060                 1065
```

```
Asn Ala  Leu Leu Glu Glu Thr  Ile Thr Ala Lys Gly  Val Arg Ser
    1070                 1075                 1080

Pro Glu  Ala Ile Arg Gly Arg  Ile Gln Gly Thr Trp  Arg Gln Lys
    1085                 1090                 1095

Thr Val  Asp Leu Pro Ala Gly  Thr Lys Tyr Val Ala  Phe Arg His
    1100                 1105                 1110

Phe Gln  Ser Thr Asp Met Phe  Tyr Ile Asp Leu Asp  Glu Val Glu
    1115                 1120                 1125

Ile Lys  Ala Asn Gly Lys Arg  Ala Asp Phe Thr Glu  Thr Phe Glu
    1130                 1135                 1140

Ser Ser  Thr His Gly Glu Ala  Pro Ala Glu Trp Thr  Thr Ile Asp
    1145                 1150                 1155

Ala Asp  Gly Asp Gly Gln Gly  Trp Leu Cys Leu Ser  Ser Gly Gln
    1160                 1165                 1170

Leu Asp  Trp Leu Thr Ala His  Gly Gly Thr Asn Val  Val Ser Ser
    1175                 1180                 1185

Phe Ser  Trp Asn Gly Met Ala  Leu Asn Pro Asp Asn  Tyr Leu Ile
    1190                 1195                 1200

Ser Lys  Asp Val Thr Gly Ala  Thr Lys Val Lys Tyr  Tyr Tyr Ala
    1205                 1210                 1215

Val Asn  Asp Gly Phe Pro Gly  Asp His Tyr Ala Val  Met Ile Ser
    1220                 1225                 1230

Lys Thr  Gly Thr Asn Ala Gly  Asp Phe Thr Val Val  Phe Glu Glu
    1235                 1240                 1245

Thr Pro  Asn Gly Ile Asn Lys  Gly Gly Ala Arg Phe  Gly Leu Ser
    1250                 1255                 1260

Thr Glu  Ala Asp Gly Ala Lys  Pro Gln Ser Val Trp  Ile Glu Arg
    1265                 1270                 1275

Thr Val  Asp Leu Pro Ala Gly  Thr Lys Tyr Val Ala  Phe Arg His
    1280                 1285                 1290

Tyr Asn  Cys Ser Asp Leu Asn  Tyr Ile Leu Leu Asp  Asp Ile Gln
    1295                 1300                 1305

Phe Thr  Met Gly Gly Ser Pro  Thr Pro Thr Asp Tyr  Thr Tyr Thr
    1310                 1315                 1320

Val Tyr  Arg Asp Gly Thr Lys  Ile Lys Glu Gly Leu  Thr Glu Thr
    1325                 1330                 1335

Thr Phe  Glu Glu Asp Gly Val  Ala Thr Gly Asn His  Glu Tyr Cys
    1340                 1345                 1350

Val Glu  Val Lys Tyr Thr Ala  Gly Val Ser Pro Lys  Lys Cys Val
    1355                 1360                 1365

Asn Val  Thr Val Asn Ser Thr  Gln Phe Asn Pro Val  Lys Asn Leu
    1370                 1375                 1380

Lys Ala  Gln Pro Asp Gly Gly  Asp Val Val Leu Lys  Trp Glu Ala
    1385                 1390                 1395

Pro Ser  Ala Lys Lys Thr Glu  Gly Ser Arg Glu Val  Lys Arg Ile
    1400                 1405                 1410

Gly Asp  Gly Leu Phe Val Thr  Ile Glu Pro Ala Asn  Asp Val Arg
    1415                 1420                 1425

Ala Asn  Glu Ala Lys Val Val  Leu Ala Ala Asp Asn  Val Trp Gly
    1430                 1435                 1440

Asp Asn  Thr Gly Tyr Gln Phe  Leu Leu Asp Ala Asp  His Asn Thr
    1445                 1450                 1455

Phe Gly  Ser Val Ile Pro Ala  Thr Gly Pro Leu Phe  Thr Gly Thr
```

```
    1460                1465                1470

Ala Ser Ser Asp Leu Tyr Ser Ala Asn Phe Glu Tyr Leu Ile Pro
    1475                1480                1485

Ala Asn Ala Asp Pro Val Val Thr Thr Gln Asn Ile Ile Val Thr
    1490                1495                1500

Gly Gln Gly Glu Val Val Ile Pro Gly Gly Val Tyr Asp Tyr Cys
    1505                1510                1515

Ile Thr Asn Pro Glu Pro Ala Ser Gly Lys Met Trp Ile Ala Gly
    1520                1525                1530

Asp Gly Gly Asn Gln Pro Ala Arg Tyr Asp Asp Phe Thr Phe Glu
    1535                1540                1545

Ala Gly Lys Lys Tyr Thr Phe Thr Met Arg Arg Ala Gly Met Gly
    1550                1555                1560

Asp Gly Thr Asp Met Glu Val Glu Asp Asp Ser Pro Ala Ser Tyr
    1565                1570                1575

Thr Tyr Thr Val Tyr Arg Asp Gly Thr Lys Ile Lys Glu Gly Leu
    1580                1585                1590

Thr Glu Thr Thr Tyr Arg Asp Ala Gly Met Ser Ala Gln Ser His
    1595                1600                1605

Glu Tyr Cys Val Glu Val Lys Tyr Thr Ala Gly Val Ser Pro Lys
    1610                1615                1620

Val Cys Val Asp Tyr Ile Pro Asp Gly Val Ala Asp Val Thr Ala
    1625                1630                1635

Gln Lys Pro Tyr Thr Leu Thr Val Val Gly Lys Thr Ile Thr Val
    1640                1645                1650

Thr Cys Gln Gly Glu Ala Met Ile Tyr Asp Met Asn Gly Arg Arg
    1655                1660                1665

Leu Ala Ala Gly Arg Asn Thr Val Val Tyr Thr Ala Gln Gly Gly
    1670                1675                1680

Tyr Tyr Ala Val Met Val Val Val Asp Gly Lys Ser Tyr Val Glu
    1685                1690                1695

Lys Leu Ala Val Lys
    1700
```

<210> SEQ ID NO 58
<211> LENGTH: 5112
<212> TYPE: DNA
<213> ORGANISM: Porphyromonas gingivalis

<400> SEQUENCE: 58

```
ttgcacaagt ttgtttcgat tgctctttgc tcttccttat taggaggaat ggcatttgcg      60

cagcagacag agttgggacg caatccgaat gtgagattgc tcgaatccac tcagcaatcg     120

gtgacaaagg ttcagttccg tatggacaac ctcaagttca ccgaagttca aacccctaag     180

ggaatggcac aagtgccgac ctatacagaa ggggttaatc tttctgaaaa agggatgcct     240

acgcttccca ttctatcacg ctctttggcg gtttcagaca ctcgtgagat gaaggtagag     300

gttgtttcct caaagttcat cgaaaagaaa aatgtcctga ttgcaccctc caagggcatg     360

attatgcgta acgaagatcc gaaaaagatc ccttacgttt atggaaagag ctactcgcaa     420

aacaaattct tcccgggaga gatcgccacg cttgatgatc cttttatcct tcgtgatgtg     480

cgtggacagg ttgtaaactt tgcgcctttg cagtataacc ctgtgacaaa gacgttgcgc     540

atctatacgg aaatcactgt ggcagtgagc gaaacttcgg agcaaggcaa aaatattctg     600

aacaagaaag gtacatttgc cggctttgaa gacacataca agcgcatgtt catgaactac     660
```

```
gagccagggc gttacacacc ggtagaggaa aaacaaaatg gtcgtatgat cgtcatcgta    720
gccaaaaagt atgagggaga tattaaagat ttcgttgatt ggaaaaacca acgcggtctc    780
cgtaccgagg tgaaagtggc agaagatatt gcttctcccg ttacagctaa tgctattcag    840
caattcgtta agcaagaata cgagaaagaa ggtaatgatt tgacctatgt tcttttgatt    900
ggcgatcaca aagatattcc tgccaaaatt actccgggga tcaaatccga ccaggtatat    960
ggacaaatag taggtaatga ccactacaac gaagtcttca tcggtcgttt ctcatgtgag   1020
agcaaagagg atctgaagac acaaatcgat cggactattc actatgagcg caatataacc   1080
acggaagaca aatggctcgg tcaggctctt tgtattgctt cggctgaagg aggcccatcc   1140
gcagacaatg gtgaaagtga tatccagcat gagaatgtaa tcgccaatct gcttacccag   1200
tatggttata ccaagattat caaatgttat gatccgggag taactcctaa aaacattatt   1260
gatgctttca acggaggaat ctcgttggcc aactatacgg gccacggtag cgaaacagct   1320
tggggtacgt ctcacttcgg caccactcat gtgaagcagc ttaccaacag caaccagcta   1380
ccgtttattt tcgacgtagc ttgtgtgaat ggcgatttcc tattcagcat gccttgtttc   1440
gcagaagcat tgatgcgtgc acaaaaagat ggtaagccga caggtactgt tgctatcata   1500
gcgtctacga tcaaccagtc ttgggcttct cctatgcgcg ggcaggatga gatgaacgaa   1560
attctgtgcg aaaaacaccc gaacaacatc aagcgtactt tcggtggtgt caccatgaac   1620
ggtatgtttg ctatggtgga aaagtataaa aaggatggtg agaagatgct cgacacatgg   1680
actgtattcg gcgacccctc gctgctcgtt cgtacacttg tcccgaccaa aatgcaggtt   1740
acggctccgg ctcagattaa tttgacggat gcttcagtca acgtatcttg cgattataat   1800
ggtgctattg ctaccatttc agccaatgga aagatgttcg gttctgcagt tgtcgaaaat   1860
ggaacagcta caatcaatct gacaggtctg acaaatgaaa gcacgcttac ccttacagta   1920
gttggttaca acaaagagac ggttattaag accatcaaca ctaatggtga gcctaacccc   1980
taccagcctg tttccaactt gactgctaca acgcagggtc agaaagtaac gctcaagtgg   2040
gatgcaccga gcacgaaaac caatgcaacc actaataccg ctcgcagcgt ggatggcata   2100
cgagaactgg ttcttctgtc agtcagcgat gcccccgaac ttcttcgcag cggtcaggcc   2160
gagattgttc ttgaagctca cgatgtttgg aatgatggat ccggttatca gattcttttg   2220
gatgcagacc atgatcaata tggacaggtt atacccagtg atacccatac tctttggccg   2280
aactgtagtg tcccggccaa tctgttcgct ccgttcgaat atacggttcc ggaaaatgca   2340
gatccttctt gttcccctac caatatgata atggatggta ctgcatccgt taatataccg   2400
gccggaactt atgactttgc aattgctgct cctcaagcaa atgcaaagat ttggattgcc   2460
ggacaaggac cgacgaaaga agatgattat gtatttgaag ccggtaaaaa ataccatttc   2520
cttatgaaga agatgggtag cggtgatgga actgaattga ctataagcga aggtggtgga   2580
agcgattaca cctatactgt ctatcgtgac ggcacgaaga tcaaggaagg tctgacggct   2640
acgacattcg aagaagacgg tgtagctgca ggcaatcatg agtattgcgt ggaagttaag   2700
tacacagccg gcgtatctcc gaaggtatgt aaagacgtta cggtagaagg atccaatgaa   2760
tttgctcctg tacagaacct gaccggtagt gcagtcggcc agaaagtaac gcttaagtgg   2820
gatgcaccta atggtacccc gaatccaaat ccaaatccga atccaaatcc gaatcccgga   2880
acaactacac tttccgaatc attcgaaaat ggtattcctg cctcatggaa gacgatcgat   2940
gcagacggtg acgggcatgg ctggaagcct ggaaatgctc ccggaatcgc tggctacaat   3000
```

```
agcaatggtt gtgtatattc agagtcattc ggtcttggtg gtataggagt tcttacccct   3060

gacaactatc tgataacacc ggcattggat ttgcctaacg gaggtaagtt gactttctgg   3120

gtatgcgcac aggatgctaa ttatgcatcc gagcactatg cggtgtatgc atcttcgacc   3180

ggtaacgatg catccaactt cacgaatgct ttgttggaag agacgattac ggcaaaaggt   3240

gttcgctcgc cggaagctat tcgtggtcgt atacagggta cttggcgcca gaagacggta   3300

gaccttcccg caggtacgaa atatgttgct ttccgtcact tccaaagcac ggatatgttc   3360

tacatcgacc ttgatgaggt tgagatcaag gccaatggca agcgcgcaga cttcacggaa   3420

acgttcgagt cttctactca tggagaggca ccagcggaat ggactactat cgatgccgat   3480

ggcgatggtc agggttggct ctgtctgtct tccggacaat tggactggct gacagctcat   3540

ggcggcacca acgtagtaag ctctttctca tggaatggaa tggctttgaa tcctgataac   3600

tatctcatct caaaggatgt tacaggcgca acgaaggtaa agtactacta tgcagtcaac   3660

gacggttttc ccggggatca ctatgcggtg atgatctcca agacgggcac gaacgccgga   3720

gacttcacgg ttgttttcga agaaacgcct aacggaataa ataagggcgg agcaagattc   3780

ggtctttcca cggaagccga tggcgccaaa cctcaaagtg tatggatcga gcgtacggta   3840

gatttgcctg cgggcacgaa gtatgttgct ttccgtcact acaattgctc ggatttgaac   3900

tacattcttt tggatgatat tcagttcacc atgggtggca gccccacccc gaccgattat   3960

acctacacgg tgtatcgtga tggtacgaag atcaaggaag gtttgaccga aacgaccttc   4020

gaagaagacg gcgtagctac gggcaatcat gagtattgcg tggaagtgaa gtacacagcc   4080

ggcgtatctc cgaagaaatg tgtaaacgta actgttaatt cgacacagtt caatcctgta   4140

aagaacctga aggcacaacc ggatggcggc gacgtggttc tcaagtggga agccccgagc   4200

gcaaagaaga cagaaggttc tcgtgaagta aaacggatcg gagacggtct tttcgttacg   4260

atcgaacctg caaacgatgt acgtgccaac gaagccaagg ttgtgctcgc agcagacaac   4320

gtatggggag acaatacggg ttaccagttc ttgttggatg ccgatcacaa tacattcgga   4380

agtgtcattc cggcaaccgg tcctctcttt accggaacag cttcttccga tctttacagt   4440

gcgaacttcg agtatttgat cccggccaat gccgatcctg ttgttactac acagaatatt   4500

atcgttacag gacagggtga agttgtaatc cccggtggtg tttacgacta ttgcattacg   4560

aacccggaac ctgcatccgg aaagatgtgg atcgcaggag atggaggcaa ccagcctgca   4620

cgttatgacg atttcacatt cgaagcaggc aagaagtaca ccttcacgat gcgtcgcgcc   4680

ggaatgggag atggaactga tatggaagtc gaagacgatt cacctgcaag ctatacctat   4740

acagtctatc gtgacggcac gaagatcaag gaaggtctga ccgaaacgac ctaccgcgat   4800

gcaggaatga gtgcacaatc tcatgagtat tgcgtggaag ttaagtacac agccggcgta   4860

tctccgaagg tttgtgtgga ttatattcct gacggagtgg cagacgtaac ggctcagaag   4920

ccttacacgc tgacagttgt aggaaagacg atcacggtaa cttgccaagg cgaagctatg   4980

atctacgaca tgaacggtcg tcgtctggca gccggtcgca acacggttgt ttacacggct   5040

cagggcggct actatgcagt tatggttgtc gttgacggca agtcttacgt agagaaactc   5100

gctgtaaagt aa                                                       5112
```

<210> SEQ ID NO 59
<211> LENGTH: 390
<212> TYPE: PRT
<213> ORGANISM: Porphyromonas gingivalis

<400> SEQUENCE: 59

```
Lys Val Lys Tyr Leu Met Leu Thr Leu Val Gly Ala Ile Ala Leu Asn
1               5                   10                  15

Ala Ser Ala Gln Glu Asn Thr Val Pro Ala Thr Gly Gln Leu Pro Ala
            20                  25                  30

Lys Asn Val Ala Phe Ala Arg Asn Lys Ala Gly Ser Asn Trp Phe Val
        35                  40                  45

Thr Leu Gln Gly Gly Val Ala Ala Gln Phe Leu Asn Asp Asn Asn Asn
    50                  55                  60

Lys Asp Leu Met Asp Arg Leu Gly Ala Ile Gly Ser Leu Ser Val Gly
65                  70                  75                  80

Lys Tyr His Ser Pro Phe Phe Ala Thr Arg Leu Gln Ile Asn Gly Gly
                85                  90                  95

Gln Ala His Thr Phe Leu Gly Lys Asn Gly Glu Gln Glu Ile Asn Thr
            100                 105                 110

Asn Phe Gly Ala Ala His Phe Asp Phe Met Phe Asp Val Val Asn Tyr
        115                 120                 125

Phe Ala Pro Tyr Arg Glu Asn Arg Phe Phe His Leu Ile Pro Trp Val
    130                 135                 140

Gly Val Gly Tyr Gln His Lys Phe Ile Gly Ser Glu Trp Ser Lys Asp
145                 150                 155                 160

Asn Val Glu Ser Leu Thr Ala Asn Val Gly Val Met Met Ala Phe Arg
                165                 170                 175

Leu Gly Lys Arg Val Asp Phe Val Ile Glu Ala Gln Ala Ala His Ser
            180                 185                 190

Asn Leu Asn Leu Ser Arg Ala Tyr Asn Ala Lys Lys Thr Pro Val Phe
        195                 200                 205

Glu Asp Pro Ala Gly Arg Tyr Tyr Asn Gly Phe Gln Gly Met Ala Thr
    210                 215                 220

Ala Gly Leu Asn Phe Arg Leu Gly Ala Val Gly Phe Asn Ala Ile Glu
225                 230                 235                 240

Pro Met Asp Tyr Ala Leu Ile Asn Asp Leu Asn Gly Gln Ile Asn Arg
                245                 250                 255

Leu Arg Ser Glu Val Glu Glu Leu Ser Lys Arg Pro Val Ser Cys Pro
            260                 265                 270

Glu Cys Pro Glu Val Thr Pro Val Thr Lys Thr Glu Asn Ile Leu Thr
        275                 280                 285

Glu Lys Ala Val Leu Phe Arg Phe Asp Ser His Val Val Asp Lys Asp
    290                 295                 300

Gln Leu Ile Asn Leu Tyr Asp Val Ala Gln Phe Val Lys Glu Thr Asn
305                 310                 315                 320

Glu Pro Ile Thr Val Val Gly Tyr Ala Asp Pro Thr Gly Asn Thr Gln
                325                 330                 335

Tyr Asn Glu Lys Leu Ser Glu Arg Arg Ala Lys Ala Val Val Asp Val
            340                 345                 350

Leu Thr Gly Lys Tyr Gly Val Pro Ser Glu Leu Ile Ser Val Glu Trp
        355                 360                 365

Lys Gly Asp Ser Thr Gln Pro Phe Ser Lys Lys Ala Trp Asn Arg Val
    370                 375                 380

Val Ile Val Arg Ser Lys
385                 390
```

<210> SEQ ID NO 60
<211> LENGTH: 1173

<212> TYPE: DNA
<213> ORGANISM: Porphyromonas gingivalis

<400> SEQUENCE: 60

```
aaggtaaagt acttaatgct cacattggtt ggagcaattg cactgaacgc aagtgcacag     60
gagaatactg taccggcaac gggtcagtta cccgctaaga atgttgcttt tgctcgcaat    120
aaagcaggca gcaattggtt tgtaacactg caaggcggtg ttgcagcgca gttcctcaat    180
gacaacaaca acaaagacct catggaccgc ttaggagcca taggttctct ttctgtcgga    240
aagtatcaca gccctttctt tgcaactcgt ttgcaaatta acggaggtca agcccacact    300
ttcctcggaa aaaatggcga acaagaaatc aacaccaatt ttggtgcagc tcacttcgac    360
tttatgtttg atgtggttaa ctactttgca ccatatcgcg aaaatcgttt cttccattta    420
attccatggg taggtgttgg ctaccaacac aaattcatcg gtagcgaatg gagcaaagac    480
aatgtggaat cactgacggc gaatgtagga gttatgatgg ctttcagatt aggaaagcga    540
gtagactttg tgatcgaagc acaagcagct cactccaatc tcaatctaag tcgcgcatac    600
aatgccaaga aaactcccgt attcgaagat cccgcaggac gttattacaa tggattccag    660
gggatggcta cagcaggtct taatttccgc ctgggagccg taggcttcaa tgccattgaa    720
ccaatggact acgcacttat caatgatctg aatggtcaga ttaaccgttt gcgcagcgag    780
gtcgaagaac tctcaaaacg tcctgtatca tgccccgaat gtcctgaagt aactcctgtt    840
actaagacag aaaatatact gacggaaaaa gctgtactgt tccgtttcga cagccacgtt    900
gtggacaaag atcaattgat caacctgtat gacgtagctc agtttgtaaa agaaactaac    960
gagccgatta ccgttgttgg ttatgctgat cctacgggta atactcaata caacgagaaa   1020
ttgtctgagc gtcgggctaa agccgttgtt gatgttctga caggtaaata tggtgtgcct   1080
tccgaattaa tctctgtaga atggaagggc gactctacgc aaccgttcag caagaaagct   1140
tggaatcgtg ttgtaatcgt tcgctccaag taa                                1173
```

<210> SEQ ID NO 61
<211> LENGTH: 500
<212> TYPE: PRT
<213> ORGANISM: Porphyromonas gingivalis

<400> SEQUENCE: 61

```
Lys Lys Ile Ile Tyr Trp Val Ala Thr Val Phe Leu Ala Ala Ser Val
1               5                   10                  15

Ser Ser Cys Glu Leu Asp Arg Asp Pro Glu Gly Lys Asp Phe Gln Gln
            20                  25                  30

Pro Tyr Thr Ser Phe Val Gln Thr Lys Gln Asn Arg Asp Gly Leu Tyr
        35                  40                  45

Ala Leu Leu Arg Asn Thr Glu Asn Pro Arg Met His Phe Tyr Gln Glu
    50                  55                  60

Leu Gln Ser Asp Met Tyr Cys Thr Thr Ile Thr Asp Gly Asn Ser Leu
65                  70                  75                  80

Ala Pro Phe Val Asn Trp Asp Leu Gly Ile Leu Asn Asp His Gly Arg
                85                  90                  95

Ala Asp Glu Asp Glu Val Ser Gly Ile Ala Gly Tyr Tyr Phe Val Tyr
            100                 105                 110

Asn Arg Leu Asn Gln Gln Ala Asn Ala Phe Val Asn Asn Thr Glu Ala
        115                 120                 125

Ala Leu Gln Asn Gln Val Tyr Lys Asn Ser Thr Glu Ile Ala Asn Ala
    130                 135                 140
```

```
Lys Ser Phe Leu Ala Glu Gly Lys Val Leu Gln Ala Leu Ala Ile Trp
145                 150                 155                 160

Arg Leu Met Asp Arg Phe Ser Phe His Glu Ser Val Thr Glu Val Asn
                165                 170                 175

Ser Gly Ala Lys Asp Leu Gly Val Ile Leu Leu Lys Glu Tyr Asn Pro
            180                 185                 190

Gly Tyr Ile Gly Pro Arg Ala Thr Lys Ala Gln Cys Tyr Asp Tyr Ile
        195                 200                 205

Leu Ser Arg Leu Ser Glu Ala Ile Glu Val Leu Pro Glu Asn Arg Glu
    210                 215                 220

Ser Val Leu Tyr Val Ser Arg Asp Tyr Ala Tyr Ala Leu Arg Ala Arg
225                 230                 235                 240

Ile Tyr Leu Ala Leu Gly Glu Tyr Gly Lys Ala Ala Ala Asp Ala Lys
                245                 250                 255

Met Val Val Asp Lys Tyr Pro Leu Ile Gly Ala Ala Asp Ala Ser Glu
            260                 265                 270

Phe Glu Asn Ile Tyr Arg Ser Asp Ala Asn Asn Pro Glu Ile Ile Phe
        275                 280                 285

Arg Gly Phe Ala Ser Ala Thr Leu Gly Ser Phe Thr Ala Thr Thr Leu
    290                 295                 300

Asn Gly Ala Ala Pro Ala Gly Lys Asp Ile Lys Tyr Asn Pro Ser Ala
305                 310                 315                 320

Val Pro Phe Gln Trp Val Val Asp Leu Tyr Glu Asn Glu Asp Phe Arg
                325                 330                 335

Lys Ser Val Tyr Ile Ala Lys Val Val Lys Lys Asp Lys Gly Tyr Leu
            340                 345                 350

Val Asn Lys Phe Leu Glu Asp Lys Ala Tyr Arg Asp Val Gln Asp Lys
        355                 360                 365

Pro Asn Leu Lys Val Gly Ala Arg Tyr Phe Ser Val Ala Glu Val Tyr
    370                 375                 380

Leu Ile Leu Val Glu Ser Ala Leu Gln Thr Gly Asp Thr Pro Thr Ala
385                 390                 395                 400

Glu Lys Tyr Leu Lys Ala Leu Ser Lys Ala Arg Gly Ala Glu Val Ser
                405                 410                 415

Val Val Asn Met Glu Ala Leu Gln Ala Glu Arg Thr Arg Glu Leu Ile
            420                 425                 430

Gly Glu Gly Ser Arg Leu Arg Asp Met Val Arg Trp Ser Ile Pro Asn
        435                 440                 445

Asn His Asp Ala Phe Glu Thr Gln Pro Gly Leu Glu Gly Phe Ala Asn
    450                 455                 460

Thr Thr Pro Leu Lys Ala Gln Ala Pro Val Gly Phe Tyr Ala Tyr Thr
465                 470                 475                 480

Trp Glu Phe Pro Gln Arg Asp Arg Gln Thr Asn Pro Gln Leu Ile Lys
                485                 490                 495

Asn Trp Pro Ile
            500
```

<210> SEQ ID NO 62
<211> LENGTH: 1503
<212> TYPE: DNA
<213> ORGANISM: Porphyromonas gingivalis

<400> SEQUENCE: 62

```
aaaaaaataa tttattgggt tgcgacagtt ttcttagcag cgagcgtatc ctcttgcgag     60
```

```
cttgaccgcg accccgaagg aaaagatttc caacagccat atacttcttt cgtgcagacg    120

aaacaaaaca gagatggtct ttacgcactt ttgcgtaata ctgaaaatcc acgaatgcat    180

ttttatcagg aacttcaatc cgatatgtat tgcactacca ttactgatgg taactcctta    240

gctccgttcg tgaattggga tttaggcata cttaacgacc atggacgtgc tgatgaggac    300

gaagtctccg gtatagctgg ctactatttc gtatacaatc gactaaatca gcaagcgaat    360

gcttttgtta acaatacgga agctgcgttg cagaatcaag tgtataaaaa ttccaccgag    420

atcgccaatg ctaagagctt tttggcggaa ggaaaagttt tacaagcatt ggctatttgg    480

cgactgatgg atcgttttag cttccatgaa agcgtgacag aagttaattc cggtgcgaaa    540

gatcttggcg ttattctgtt gaaagaatat aatcctggtt atatcggtcc ccgtgcaacg    600

aaggcacaat gttatgatta cattttgtca cgtttgtctg aggctattga agttttgccc    660

gaaaacaggg aaagcgttct ttatgtgagc cgtgattacg cctatgccct ccgagcaaga    720

atttacctcg cgttgggtga atatggaaaa gctgcagcag atgctaagat ggttgttgat    780

aagtatcctt tgattggtgc agcagatgct tctgagtttg agaatattta tcgatcagat    840

gctaataatc ccgaaattat ttttcgtggt tttgcttctg cgactcttgg ctcgtttact    900

gctacgacac taaatggtgc tgcgccagca ggtaaggata taaaatataa tccgagcgca    960

gtcccttttcc aatgggtagt ggatctttat gaaaacgaag atttccgcaa atccgtatat   1020

atcgcgaaag ttgtgaaaaa ggataagggg tatttagtaa ataaattcct tgaggacaag   1080

gcttatcgtg atgttcagga taagccaaac cttaaagtcg gagctcgtta ttttagcgtt   1140

gctgaggtct acttaatttt ggtagagtct gctcttcaga ctggagatac cccaacagcc   1200

gaaaaatatc tcaaggcttt gagtaaagct cgtggagcag aagtttcagt cgttaatatg   1260

gaagcactgc aagcagagcg tacgcgtgag cttataggtg agggtagtcg tttgcgtgat   1320

atggtccgct ggagtatccc taataatcat gatgcttttg agactcagcc tggtttagaa   1380

ggttttgcaa atactactcc tttgaaagct caagctcctg taggctttta tgcatatact   1440

tgggagttcc cacagcgaga tcgacaaact aatccgcagt taataaagaa ctggccgata   1500

taa                                                                  1503
```

<210> SEQ ID NO 63
<211> LENGTH: 1731
<212> TYPE: PRT
<213> ORGANISM: Porphyromonas gingivalis

<400> SEQUENCE: 63

```
Arg Lys Leu Leu Leu Leu Ile Ala Ala Ser Leu Leu Gly Val Gly Leu
1               5                   10                  15

Tyr Ala Gln Ser Ala Lys Ile Lys Leu Asp Ala Pro Thr Thr Arg Thr
            20                  25                  30

Thr Cys Thr Asn Asn Ser Phe Lys Gln Phe Asp Ala Ser Phe Ser Phe
        35                  40                  45

Asn Glu Val Glu Leu Thr Lys Val Glu Thr Lys Gly Gly Thr Phe Ala
    50                  55                  60

Ser Val Ser Ile Pro Gly Ala Phe Pro Thr Gly Glu Val Gly Ser Pro
65                  70                  75                  80

Glu Val Pro Ala Val Arg Lys Leu Ile Ala Val Pro Val Gly Ala Thr
                85                  90                  95

Pro Val Val Arg Val Lys Ser Phe Thr Glu Gln Val Tyr Ser Leu Asn
            100                 105                 110
```

```
Gln Tyr Gly Ser Glu Lys Leu Met Pro His Gln Pro Ser Met Ser Lys
        115                 120                 125

Ser Asp Asp Pro Glu Lys Val Pro Phe Val Tyr Asn Ala Ala Ala Tyr
    130                 135                 140

Ala Arg Lys Gly Phe Val Gly Gln Glu Leu Thr Gln Val Glu Met Leu
145                 150                 155                 160

Gly Thr Met Arg Gly Val Arg Ile Ala Ala Leu Thr Ile Asn Pro Val
                165                 170                 175

Gln Tyr Asp Val Val Ala Asn Gln Leu Lys Val Arg Asn Asn Ile Glu
            180                 185                 190

Ile Glu Val Ser Phe Gln Gly Ala Asp Glu Val Ala Thr Gln Arg Leu
        195                 200                 205

Tyr Asp Ala Ser Phe Ser Pro Tyr Phe Glu Thr Ala Tyr Lys Gln Leu
    210                 215                 220

Phe Asn Arg Asp Val Tyr Thr Asp His Gly Asp Leu Tyr Asn Thr Pro
225                 230                 235                 240

Val Arg Met Leu Val Val Ala Gly Ala Lys Phe Lys Glu Ala Leu Lys
                245                 250                 255

Pro Trp Leu Thr Trp Lys Ala Gln Lys Gly Phe Tyr Leu Asp Val His
            260                 265                 270

Tyr Thr Asp Glu Ala Glu Val Gly Thr Thr Asn Ala Ser Ile Lys Ala
        275                 280                 285

Phe Ile His Lys Lys Tyr Asn Asp Gly Leu Ala Ala Ser Ala Ala Pro
    290                 295                 300

Val Phe Leu Ala Leu Val Gly Asp Thr Asp Val Ile Ser Gly Glu Lys
305                 310                 315                 320

Gly Lys Lys Thr Lys Lys Val Thr Asp Leu Tyr Tyr Ser Ala Val Asp
                325                 330                 335

Gly Asp Tyr Phe Pro Glu Met Tyr Thr Phe Arg Met Ser Ala Ser Ser
            340                 345                 350

Pro Glu Glu Leu Thr Asn Ile Ile Asp Lys Val Leu Met Tyr Glu Lys
        355                 360                 365

Ala Thr Met Pro Asp Lys Ser Tyr Leu Glu Lys Val Leu Leu Ile Ala
    370                 375                 380

Gly Ala Asp Tyr Ser Trp Asn Ser Gln Val Gly Gln Pro Thr Ile Lys
385                 390                 395                 400

Tyr Gly Met Gln Tyr Tyr Tyr Asn Gln Glu His Gly Tyr Thr Asp Val
                405                 410                 415

Tyr Asn Tyr Leu Lys Ala Pro Tyr Thr Gly Cys Tyr Ser His Leu Asn
            420                 425                 430

Thr Gly Val Ser Phe Ala Asn Tyr Thr Ala His Gly Ser Glu Thr Ala
        435                 440                 445

Trp Ala Asp Pro Leu Leu Thr Thr Ser Gln Leu Lys Ala Leu Thr Asn
    450                 455                 460

Lys Asp Lys Tyr Phe Leu Ala Ile Gly Asn Cys Ala Ile Thr Ala Gln
465                 470                 475                 480

Phe Asp Tyr Val Gln Pro Cys Phe Gly Glu Val Ile Thr Arg Val Lys
                485                 490                 495

Glu Lys Gly Ala Tyr Ala Tyr Ile Gly Ser Ser Pro Asn Ser Tyr Trp
            500                 505                 510

Gly Glu Asp Tyr Tyr Trp Ser Val Gly Ala Asn Ala Val Phe Gly Val
        515                 520                 525
```

-continued

```
Gln Pro Thr Phe Glu Gly Thr Ser Met Gly Ser Tyr Asp Ala Thr Phe
    530                 535                 540

Leu Glu Asp Ser Tyr Asn Thr Val Asn Ser Ile Met Trp Ala Gly Asn
545                 550                 555                 560

Leu Ala Ala Thr His Ala Gly Asn Ile Gly Asn Ile Thr His Ile Gly
                565                 570                 575

Ala His Tyr Tyr Trp Glu Ala Tyr His Val Leu Gly Asp Gly Ser Val
            580                 585                 590

Met Pro Tyr Arg Ala Met Pro Lys Thr Asn Thr Tyr Thr Leu Pro Ala
        595                 600                 605

Ser Leu Pro Gln Asn Gln Ala Ser Tyr Ser Ile Gln Ala Ser Ala Gly
    610                 615                 620

Ser Tyr Val Ala Ile Ser Lys Asp Gly Val Leu Tyr Gly Thr Gly Val
625                 630                 635                 640

Ala Asn Ala Ser Gly Val Ala Thr Val Ser Met Thr Lys Gln Ile Thr
                645                 650                 655

Glu Asn Gly Asn Tyr Asp Val Val Ile Thr Arg Ser Asn Tyr Leu Pro
            660                 665                 670

Val Ile Lys Gln Ile Gln Val Gly Glu Pro Ser Pro Tyr Gln Pro Val
        675                 680                 685

Ser Asn Leu Thr Ala Thr Thr Gln Gly Gln Lys Val Thr Leu Lys Trp
    690                 695                 700

Glu Ala Pro Ser Ala Lys Lys Ala Glu Gly Ser Arg Glu Val Lys Arg
705                 710                 715                 720

Ile Gly Asp Gly Leu Phe Val Thr Ile Glu Pro Ala Asn Asp Val Arg
                725                 730                 735

Ala Asn Glu Ala Lys Val Val Leu Ala Ala Asp Asn Val Trp Gly Asp
            740                 745                 750

Asn Thr Gly Tyr Gln Phe Leu Leu Asp Ala Asp His Asn Thr Phe Gly
        755                 760                 765

Ser Val Ile Pro Ala Thr Gly Pro Leu Phe Thr Gly Thr Ala Ser Ser
    770                 775                 780

Asn Leu Tyr Ser Ala Asn Phe Glu Tyr Leu Ile Pro Ala Asn Ala Asp
785                 790                 795                 800

Pro Val Val Thr Thr Gln Asn Ile Ile Val Thr Gly Gln Gly Glu Val
                805                 810                 815

Val Ile Pro Gly Gly Val Tyr Asp Tyr Cys Ile Thr Asn Pro Glu Pro
            820                 825                 830

Ala Ser Gly Lys Met Trp Ile Ala Gly Asp Gly Gly Asn Gln Pro Ala
        835                 840                 845

Arg Tyr Asp Asp Phe Thr Phe Glu Ala Gly Lys Lys Tyr Thr Phe Thr
    850                 855                 860

Met Arg Arg Ala Gly Met Gly Asp Gly Thr Asp Met Glu Val Glu Asp
865                 870                 875                 880

Asp Ser Pro Ala Ser Tyr Thr Tyr Thr Val Tyr Arg Asp Gly Thr Lys
                885                 890                 895

Ile Lys Glu Gly Leu Thr Ala Thr Thr Phe Glu Glu Asp Gly Val Ala
            900                 905                 910

Ala Gly Asn His Glu Tyr Cys Val Glu Val Lys Tyr Thr Ala Gly Val
        915                 920                 925

Ser Pro Lys Val Cys Lys Asp Val Thr Val Glu Gly Ser Asn Glu Phe
    930                 935                 940

Ala Pro Val Gln Asn Leu Thr Gly Ser Ser Val Gly Gln Lys Val Thr
```

```
945                 950                 955                 960

Leu Lys Trp Asp Ala Pro Asn Gly Thr Pro Asn Pro Asn Pro Asn Pro
                965                 970                 975

Asn Pro Asn Pro Gly Thr Thr Leu Ser Glu Ser Phe Glu Asn Gly Ile
            980                 985                 990

Pro Ala Ser Trp Lys Thr Ile Asp  Ala Asp Gly Asp Gly  His Gly Trp
        995                 1000                1005

Lys Pro  Gly Asn Ala Pro Gly  Ile Ala Gly Tyr Asn  Ser Asn Gly
    1010                 1015                 1020

Cys Val  Tyr Ser Glu Ser Phe  Gly Leu Gly Gly Ile  Gly Val Leu
    1025                 1030                 1035

Thr Pro  Asp Asn Tyr Leu Ile  Thr Pro Ala Leu Asp  Leu Pro Asn
    1040                 1045                 1050

Gly Gly  Lys Leu Thr Phe Trp  Val Cys Ala Gln Asp  Ala Asn Tyr
    1055                 1060                 1065

Ala Ser  Glu His Tyr Ala Val  Tyr Ala Ser Ser Thr  Gly Asn Asp
    1070                 1075                 1080

Ala Ser  Asn Phe Thr Asn Ala  Leu Leu Glu Glu Thr  Ile Thr Ala
    1085                 1090                 1095

Lys Gly  Val Arg Ser Pro Lys  Ala Ile Arg Gly Arg  Ile Gln Gly
    1100                 1105                 1110

Thr Trp  Arg Gln Lys Thr Val  Asp Leu Pro Ala Gly  Thr Lys Tyr
    1115                 1120                 1125

Val Ala  Phe Arg His Phe Gln  Ser Thr Asp Met Phe  Tyr Ile Asp
    1130                 1135                 1140

Leu Asp  Glu Val Glu Ile Lys  Ala Asn Gly Lys Arg  Ala Asp Phe
    1145                 1150                 1155

Thr Glu  Thr Phe Glu Ser Ser  Thr His Gly Glu Ala  Pro Ala Glu
    1160                 1165                 1170

Trp Thr  Thr Ile Asp Ala Asp  Gly Asp Gly Gln Gly  Trp Leu Cys
    1175                 1180                 1185

Leu Ser  Ser Gly Gln Leu Asp  Trp Leu Thr Ala His  Gly Gly Ser
    1190                 1195                 1200

Asn Val  Val Ser Ser Phe Ser  Trp Asn Gly Met Ala  Leu Asn Pro
    1205                 1210                 1215

Asp Asn  Tyr Leu Ile Ser Lys  Asp Val Thr Gly Ala  Thr Lys Val
    1220                 1225                 1230

Lys Tyr  Tyr Tyr Ala Val Asn  Asp Gly Phe Pro Gly  Asp His Tyr
    1235                 1240                 1245

Ala Val  Met Ile Ser Lys Thr  Gly Thr Asn Ala Gly  Asp Phe Thr
    1250                 1255                 1260

Val Val  Phe Glu Glu Thr Pro  Asn Gly Ile Asn Lys  Gly Gly Ala
    1265                 1270                 1275

Arg Phe  Gly Leu Ser Thr Glu  Ala Asn Gly Ala Lys  Pro Gln Ser
    1280                 1285                 1290

Val Trp  Ile Glu Arg Thr Val  Asp Leu Pro Ala Gly  Thr Lys Tyr
    1295                 1300                 1305

Val Ala  Phe Arg His Tyr Asn  Cys Ser Asp Leu Asn  Tyr Ile Leu
    1310                 1315                 1320

Leu Asp  Asp Ile Gln Phe Thr  Met Gly Gly Ser Pro  Thr Pro Thr
    1325                 1330                 1335

Asp Tyr  Thr Tyr Thr Val Tyr  Arg Asp Gly Thr Lys  Ile Lys Glu
    1340                 1345                 1350
```

```
Gly Leu  Thr Glu Thr Thr Phe  Glu Glu Asp Gly Val  Ala Thr Gly
    1355                 1360                 1365

Asn His  Glu Tyr Cys Val Glu  Val Lys Tyr Thr Ala  Gly Val Ser
    1370                 1375                 1380

Pro Lys  Lys Cys Val Asn Val  Thr Val Asn Ser Thr  Gln Phe Asn
    1385                 1390                 1395

Pro Val  Gln Asn Leu Thr Ala  Glu Gln Ala Pro Asn  Ser Met Asp
    1400                 1405                 1410

Ala Ile  Leu Lys Trp Asn Ala  Pro Ala Ser Lys Arg  Ala Glu Val
    1415                 1420                 1425

Leu Asn  Glu Asp Phe Glu Asn  Gly Ile Pro Ala Ser  Trp Lys Thr
    1430                 1435                 1440

Ile Asp  Ala Asp Gly Asp Gly  Asn Asn Trp Thr Thr  Thr Pro Pro
    1445                 1450                 1455

Pro Gly  Gly Ser Ser Phe Ala  Gly His Asn Ser Ala  Ile Cys Val
    1460                 1465                 1470

Ser Ser  Ala Ser Tyr Ile Asn  Phe Glu Gly Pro Gln  Asn Pro Asp
    1475                 1480                 1485

Asn Tyr  Leu Val Thr Pro Glu  Leu Ser Leu Pro Gly  Gly Gly Thr
    1490                 1495                 1500

Leu Thr  Phe Trp Val Cys Ala  Gln Asp Ala Asn Tyr  Ala Ser Glu
    1505                 1510                 1515

His Tyr  Ala Val Tyr Ala Ser  Ser Thr Gly Asn Asp  Ala Ser Asn
    1520                 1525                 1530

Phe Ala  Asn Ala Leu Leu Glu  Glu Val Leu Thr Ala  Lys Thr Val
    1535                 1540                 1545

Val Thr  Ala Pro Glu Ala Ile  Arg Gly Thr Arg Ala  Gln Gly Thr
    1550                 1555                 1560

Trp Tyr  Gln Lys Thr Val Gln  Leu Pro Ala Gly Thr  Lys Tyr Val
    1565                 1570                 1575

Ala Phe  Arg His Phe Gly Cys  Thr Asp Phe Phe Trp  Ile Asn Leu
    1580                 1585                 1590

Asp Asp  Val Val Ile Thr Ser  Gly Asn Ala Pro Ser  Tyr Thr Tyr
    1595                 1600                 1605

Thr Ile  Tyr Arg Asn Asn Thr  Gln Ile Ala Ser Gly  Val Thr Glu
    1610                 1615                 1620

Thr Thr  Tyr Arg Asp Pro Asp  Leu Ala Thr Gly Phe  Tyr Thr Tyr
    1625                 1630                 1635

Gly Val  Lys Val Val Tyr Pro  Asn Gly Glu Ser Ala  Ile Glu Thr
    1640                 1645                 1650

Ala Thr  Leu Asn Ile Thr Ser  Leu Ala Asp Val Thr  Ala Gln Lys
    1655                 1660                 1665

Pro Tyr  Thr Leu Thr Val Val  Gly Lys Thr Ile Thr  Val Thr Cys
    1670                 1675                 1680

Gln Gly  Glu Ala Met Ile Tyr  Asp Met Asn Gly Arg  Arg Leu Ala
    1685                 1690                 1695

Ala Gly  Arg Asn Thr Val Val  Tyr Thr Ala Gln Gly  Gly His Tyr
    1700                 1705                 1710

Ala Val  Met Val Val Val Asp  Gly Lys Ser Tyr Val  Glu Lys Leu
    1715                 1720                 1725

Ala Ile  Lys
    1730
```

<210> SEQ ID NO 64
<211> LENGTH: 5196
<212> TYPE: DNA
<213> ORGANISM: Porphyromonas gingivalis

<400> SEQUENCE: 64

```
aggaaattat tattgctgat cgcggcgtcc cttttgggag ttggtcttta cgcccaaagc     60
gccaagatta agcttgatgc tccgactact cgaacgacat gtacgaacaa tagcttcaag    120
cagttcgatg caagcttttc gttcaatgaa gtcgagctga caaaggtgga gaccaaaggt    180
ggtactttcg cctcagtgtc aattccgggt gcattcccga ccggtgaggt tggttctccc    240
gaagtgccag cagttaggaa gttgattgct gtgcctgtcg gagccacacc tgttgttcgc    300
gtgaaaagtt ttaccgagca agtttactct ctgaaccaat acggttccga aaaactcatg    360
ccacatcaac cctctatgag caagagtgat gatcccgaaa aggttccctt cgtttacaat    420
gctgctgctt atgcacgcaa aggttttgtc ggacaagaac tgacccaagt agaaatgttg    480
gggacaatgc gtggtgttcg cattgcagct cttaccatta atcctgttca gtatgatgtg    540
gttgcaaacc aattgaaggt tagaaacaac atcgaaattg aagtaagctt tcaaggagct    600
gatgaagtag ctacacaacg tttgtatgat gcttctttta gcccttattt cgaaacagct    660
tataaacagc tcttcaatag agatgtttat acagatcatg gcgacttgta taatacgccg    720
gttcgtatgc ttgttgttgc aggtgcaaaa ttcaaagaag ctctcaagcc ttggctcact    780
tggaaggctc aaaagggctt ctatctggat gtgcattaca cagacgaagc tgaagtagga    840
acgacaaacg cctctatcaa ggcatttatt cacaagaaat acaatgatgg attggcagct    900
agtgctgctc cggtcttctt ggctttggtt ggtgacactg acgttattag cggagaaaaa    960
ggaaagaaaa caaaaaaagt taccgacttg tattacagtg cagtcgatgg cgactatttc   1020
cctgaaatgt atactttccg tatgtctgct tcttccccag aagaactgac gaacatcatt   1080
gataaggtat tgatgtatga aaaggctact atgccagata agagttattt ggagaaagtt   1140
ctcttgattg caggtgcaga ttatagctgg aattcccagg taggtcagcc aaccattaaa   1200
tacggtatgc agtactacta caaccaagag catggttata ccgacgtgta caactatctc   1260
aaagcccctt atacaggttg ctacagtcat ttgaataccg gagtcagctt tgcaaactat   1320
acagcgcatg gatctgagac cgcatgggct gatccacttc tgactacttc tcaactgaaa   1380
gcactcacta ataaggacaa atacttctta gctattggca actgcgctat tacagctcaa   1440
ttcgattatg tacagccttg cttcggagag gtaataactc gcgttaagga gaaaggggct   1500
tatgcctata tcggttcatc tccaaattct tattggggcg aggactacta ttggagtgtg   1560
ggtgctaatg ccgtatttgg tgttcagcct acttttgaag gtacgtctat gggttcttat   1620
gatgctacat tcttggagga ttcgtacaac acagtgaatt ctattatgtg ggcaggtaat   1680
cttgccgcta ctcatgctgg aaatatcggc aatattaccc atattggtgc tcattactat   1740
tgggaagctt atcatgtcct tggcgatggt tcggttatgc cttatcgtgc aatgcctaag   1800
accaatactt atacgcttcc tgcctctttg cctcagaatc aggcttctta tagcattcag   1860
gcttctgccg gttcttacgt agctatttct aaagatggag ttttgtatgg aacaggtgtt   1920
gctaatgcca gcggtgttgc gactgtgagt atgactaagc agattacgga aaatggtaat   1980
tatgatgtag ttatcactcg ctctaattat cttcctgtga tcaagcaaat tcaggtaggt   2040
gagcctagcc cctaccagcc cgtttccaac ttgacagcta caacgcaggg tcagaaagta   2100
acgctcaagt gggaagcacc gagcgcaaag aaggcagaag gttcccgtga agtaaaacgg   2160
```

```
atcggagacg gtcttttcgt tacgatcgaa cctgcaaacg atgtacgtgc caacgaagcc   2220
aaggttgtgc ttgcggcaga caacgtatgg ggagacaata cgggttacca gttcttgttg   2280
gatgccgatc acaatacatt cggaagtgtc attccggcaa ccggtcctct ctttaccgga   2340
acagcttctt ccaatcttta cagtgcgaac ttcgagtatt tgatcccggc caatgccgat   2400
cctgttgtta ctacacagaa tattatcgtt acaggacagg gtgaagttgt aatccccggt   2460
ggtgtttacg actattgcat tacgaacccg gaacctgcat ccggaaagat gtggatcgca   2520
ggagatggag gcaaccagcc tgcacgttat gacgatttca cattcgaagc aggcaagaag   2580
tacaccttca cgatgcgtcg cgccggaatg ggagatggaa ctgatatgga agtcgaagac   2640
gattcacctg caagctatac ctacacggtg tatcgtgacg gcacgaagat caaggaaggt   2700
ctgacagcta cgacattcga agaagacggt gtagctgcag gcaatcatga gtattgcgtg   2760
gaagttaagt acacagccgg cgtatctccg aaggtatgta aagacgttac ggtagaagga   2820
tccaatgaat ttgctcctgt acagaacctg accggtagtt cagtaggtca gaaagtaacg   2880
cttaagtggg atgcacctaa tggtaccccg aatccgaatc caaatccgaa tccgaatccg   2940
ggaacaacac tttccgaatc attcgaaaat ggtattccgg catcttggaa gacgatcgat   3000
gcagacggtg acgggcatgg ctggaaacct ggaaatgctc ccggaatcgc tggctacaat   3060
agcaatggtt gtgtatattc agagtcattc ggtcttggtg gtataggagt tcttacccct   3120
gacaactatc tgataacacc ggcattggat ttgcctaacg gaggtaagtt gactttctgg   3180
gtatgcgcac aggatgctaa ttatgcatcc gagcactatg cggtgtatgc atcttcgacc   3240
ggtaacgatg catccaactt cacgaatgct ttgttggaag agacgattac ggcaaaaggt   3300
gttcgctcgc cgaaagctat tcgtggtcgt atacagggta cttggcgcca gaagacggta   3360
gaccttcccg caggtacgaa atatgttgct ttccgtcact tccaaagcac ggatatgttc   3420
tacatcgacc ttgatgaggt tgagatcaag gccaatggca agcgcgcaga cttcacggaa   3480
acgttcgagt cttctactca tggagaggca ccagcggaat ggactactat cgatgccgat   3540
ggcgatggtc agggttggct ctgtctgtct tccggacaat tggactggct gacagctcat   3600
ggcggcagca acgtagtaag ctctttctca tggaatggaa tggctttgaa tcctgataac   3660
tatctcatct caaaggatgt tacaggcgca acgaaggtaa agtactacta tgcagtcaac   3720
gacggttttc ccggggatca ctatgcggtg atgatctcca agacgggcac gaacgccgga   3780
gacttcacgg ttgttttcga agaaacgcct aacggaataa ataagggcgg agcaagattc   3840
ggtctttcca cggaagccaa tggcgccaaa cctcaaagtg tatggatcga gcgtacggta   3900
gatttgcctg caggcacgaa gtatgttgct ttccgtcact acaattgctc ggatttgaac   3960
tacattcttt tggatgatat tcagttcacc atgggtggca gccccacccc gaccgattat   4020
acctacacgg tgtatcgtga tggtacgaag atcaaggaag gtttgaccga aacgaccttc   4080
gaagaagacg gcgtagctac gggcaatcat gagtattgcg tggaagtgaa gtacacagcc   4140
ggcgtatctc cgaagaaatg tgtaaacgta actgttaatt cgacacagtt caatcctgta   4200
cagaacctga cggcagaaca agctcctaac agcatggatg caatccttaa atggaatgca   4260
ccggcatcta agcgtgcgga agttctgaac gaagacttcg aaaatggtat tcctgcctca   4320
tggaagacga tcgatgcaga cggtgacggc aacaattgga cgacgacccc tcctcccgga   4380
ggctcctctt ttgcaggtca caacagtgcg atctgtgtct cttcagcttc ttatatcaac   4440
tttgaaggtc ctcagaaccc tgataactat ctggttacac cggagctttc tcttcctggc   4500
```

```
ggaggaacgc ttactttctg ggtatgtgca caagatgcca attatgcatc agagcactat   4560

gccgtgtacg catcttctac gggtaacgac gcttccaact tcgccaacgc tttgttggaa   4620

gaagtgctga cggccaagac agttgttacg gcacctgaag ccattcgtgg tactcgtgct   4680

cagggcacct ggtatcaaaa gacggtacag ttgcctgcgg gtactaagta tgttgccttc   4740

cgtcacttcg gctgtacgga cttcttctgg atcaaccttg atgatgttgt aatcacttca   4800

gggaacgctc cgtcttacac ctatacgatc tatcgtaata atacacagat agcatcaggc   4860

gtaacggaga ctacttaccg agatccggac ttggctaccg gtttttacac gtacggtgta   4920

aaggttgttt acccgaacgg agaatcagct atcgaaactg ctacgttgaa tatcacttcg   4980

ttggcagacg taacggctca gaagccttac acgctgacag ttgtaggaaa gacgatcacg   5040

gtaacttgcc aaggcgaagc tatgatctac gacatgaacg gtcgtcgtct ggcagcgggt   5100

cgcaacacgg ttgtttacac ggctcagggc ggccactatg cagtcatggt tgtcgttgac   5160

ggcaagtctt acgtagagaa actcgctatc aagtaa                             5196


<210> SEQ ID NO 65
<211> LENGTH: 1731
<212> TYPE: PRT
<213> ORGANISM: Porphyromonas gingivalis

<400> SEQUENCE: 65

Arg Lys Leu Leu Leu Leu Ile Ala Ala Ser Leu Leu Gly Val Gly Leu
1               5                   10                  15

Tyr Ala Gln Ser Ala Lys Ile Lys Leu Asp Ala Pro Thr Thr Arg Thr
            20                  25                  30

Thr Cys Thr Asn Asn Ser Phe Lys Gln Phe Asp Ala Ser Phe Ser Phe
        35                  40                  45

Asn Glu Val Glu Leu Thr Lys Val Glu Thr Lys Gly Gly Thr Phe Ala
    50                  55                  60

Ser Val Ser Ile Pro Gly Ala Phe Pro Thr Gly Glu Val Gly Ser Pro
65                  70                  75                  80

Glu Val Pro Ala Val Arg Lys Leu Ile Ala Val Pro Val Gly Ala Thr
                85                  90                  95

Pro Val Val Arg Val Lys Ser Phe Thr Glu Gln Val Tyr Ser Leu Asn
            100                 105                 110

Gln Tyr Gly Ser Glu Lys Leu Met Pro His Gln Pro Ser Met Ser Lys
        115                 120                 125

Ser Asp Asp Pro Glu Lys Val Pro Phe Val Tyr Asn Ala Ala Ala Tyr
    130                 135                 140

Ala Arg Lys Gly Phe Val Gly Gln Glu Leu Thr Gln Val Glu Met Leu
145                 150                 155                 160

Gly Thr Met Arg Gly Val Arg Ile Ala Ala Leu Thr Ile Asn Pro Val
                165                 170                 175

Gln Tyr Asp Val Val Ala Asn Gln Leu Lys Val Arg Asn Asn Ile Glu
            180                 185                 190

Ile Glu Val Ser Phe Gln Gly Ala Asp Glu Val Ala Thr Gln Arg Leu
        195                 200                 205

Tyr Asp Ala Ser Phe Ser Pro Tyr Phe Glu Thr Ala Tyr Lys Gln Leu
    210                 215                 220

Phe Asn Arg Asp Val Tyr Thr Asp His Gly Asp Leu Tyr Asn Thr Pro
225                 230                 235                 240

Val Arg Met Leu Val Val Ala Gly Ala Lys Phe Lys Glu Ala Leu Lys
                245                 250                 255
```

```
Pro Trp Leu Thr Trp Lys Ala Gln Lys Gly Phe Tyr Leu Asp Val His
            260                 265                 270

Tyr Thr Asp Glu Ala Glu Val Gly Thr Thr Asn Ala Ser Ile Lys Ala
        275                 280                 285

Phe Ile His Lys Lys Tyr Asn Asp Gly Leu Ala Ala Ser Ala Ala Pro
    290                 295                 300

Val Phe Leu Ala Leu Val Gly Asp Thr Asp Val Ile Ser Gly Glu Lys
305                 310                 315                 320

Gly Lys Lys Thr Lys Lys Val Thr Asp Leu Tyr Tyr Ser Ala Val Asp
                325                 330                 335

Gly Asp Tyr Phe Pro Glu Met Tyr Thr Phe Arg Met Ser Ala Ser Ser
            340                 345                 350

Pro Glu Glu Leu Thr Asn Ile Ile Asp Lys Val Leu Met Tyr Glu Lys
        355                 360                 365

Ala Thr Met Pro Asp Lys Ser Tyr Leu Glu Lys Val Leu Leu Ile Ala
    370                 375                 380

Gly Ala Asp Tyr Ser Trp Asn Ser Gln Val Gly Gln Pro Thr Ile Lys
385                 390                 395                 400

Tyr Gly Met Gln Tyr Tyr Tyr Asn Gln Glu His Gly Tyr Thr Asp Val
                405                 410                 415

Tyr Asn Tyr Leu Lys Ala Pro Tyr Thr Gly Cys Tyr Ser His Leu Asn
            420                 425                 430

Thr Gly Val Ser Phe Ala Asn Tyr Thr Ala His Gly Ser Glu Thr Ala
        435                 440                 445

Trp Ala Asp Pro Leu Leu Thr Thr Ser Gln Leu Lys Ala Leu Thr Asn
    450                 455                 460

Lys Asp Lys Tyr Phe Leu Ala Ile Gly Asn Cys Cys Ile Thr Ala Gln
465                 470                 475                 480

Phe Asp Tyr Val Gln Pro Ala Phe Gly Glu Val Ile Thr Arg Val Lys
                485                 490                 495

Glu Lys Gly Ala Tyr Ala Tyr Ile Gly Ser Ser Pro Asn Ser Tyr Trp
            500                 505                 510

Gly Glu Asp Tyr Tyr Trp Ser Val Gly Ala Asn Ala Val Phe Gly Val
        515                 520                 525

Gln Pro Thr Phe Glu Gly Thr Ser Met Gly Ser Tyr Asp Ala Thr Phe
    530                 535                 540

Leu Glu Asp Ser Tyr Asn Thr Val Asn Ser Ile Met Trp Ala Gly Asn
545                 550                 555                 560

Leu Ala Ala Thr His Ala Gly Asn Ile Gly Asn Ile Thr His Ile Gly
                565                 570                 575

Ala His Tyr Tyr Trp Glu Ala Tyr His Val Leu Gly Asp Gly Ser Val
            580                 585                 590

Met Pro Tyr Arg Ala Met Pro Lys Thr Asn Thr Tyr Thr Leu Pro Ala
        595                 600                 605

Ser Leu Pro Gln Asn Gln Ala Ser Tyr Ser Ile Gln Ala Ser Ala Gly
    610                 615                 620

Ser Tyr Val Ala Ile Ser Lys Asp Gly Val Leu Tyr Gly Thr Gly Val
625                 630                 635                 640

Ala Asn Ala Ser Gly Val Ala Thr Val Ser Met Thr Lys Gln Ile Thr
                645                 650                 655

Glu Asn Gly Asn Tyr Asp Val Val Ile Thr Arg Ser Asn Tyr Leu Pro
            660                 665                 670
```

```
Val Ile Lys Gln Ile Gln Val Gly Glu Pro Ser Pro Tyr Gln Pro Val
        675                 680                 685

Ser Asn Leu Thr Ala Thr Thr Gln Gly Gln Lys Val Thr Leu Lys Trp
    690                 695                 700

Glu Ala Pro Ser Ala Lys Lys Ala Glu Gly Ser Arg Glu Val Lys Arg
705                 710                 715                 720

Ile Gly Asp Gly Leu Phe Val Thr Ile Glu Pro Ala Asn Asp Val Arg
                725                 730                 735

Ala Asn Glu Ala Lys Val Val Leu Ala Ala Asp Asn Val Trp Gly Asp
            740                 745                 750

Asn Thr Gly Tyr Gln Phe Leu Leu Asp Ala Asp His Asn Thr Phe Gly
        755                 760                 765

Ser Val Ile Pro Ala Thr Gly Pro Leu Phe Thr Gly Thr Ala Ser Ser
    770                 775                 780

Asn Leu Tyr Ser Ala Asn Phe Glu Tyr Leu Ile Pro Ala Asn Ala Asp
785                 790                 795                 800

Pro Val Val Thr Thr Gln Asn Ile Ile Val Thr Gly Gln Gly Glu Val
                805                 810                 815

Val Ile Pro Gly Gly Val Tyr Asp Tyr Cys Ile Thr Asn Pro Glu Pro
            820                 825                 830

Ala Ser Gly Lys Met Trp Ile Ala Gly Asp Gly Gly Asn Gln Pro Ala
        835                 840                 845

Arg Tyr Asp Asp Phe Thr Phe Glu Ala Gly Lys Lys Tyr Thr Phe Thr
    850                 855                 860

Met Arg Arg Ala Gly Met Gly Asp Gly Thr Asp Met Glu Val Glu Asp
865                 870                 875                 880

Asp Ser Pro Ala Ser Tyr Thr Tyr Thr Val Tyr Arg Asp Gly Thr Lys
                885                 890                 895

Ile Lys Glu Gly Leu Thr Ala Thr Thr Phe Glu Glu Asp Gly Val Ala
            900                 905                 910

Ala Gly Asn His Glu Tyr Cys Val Glu Val Lys Tyr Thr Ala Gly Val
        915                 920                 925

Ser Pro Lys Val Cys Lys Asp Val Thr Val Glu Gly Ser Asn Glu Phe
    930                 935                 940

Ala Pro Val Gln Asn Leu Thr Gly Ser Ser Val Gly Gln Lys Val Thr
945                 950                 955                 960

Leu Lys Trp Asp Ala Pro Asn Gly Thr Pro Asn Pro Asn Pro Asn Pro
                965                 970                 975

Asn Pro Asn Pro Gly Thr Thr Leu Ser Glu Ser Phe Glu Asn Gly Ile
            980                 985                 990

Pro Ala Ser Trp Lys Thr Ile Asp  Ala Asp Gly Asp Gly  His Gly Trp
        995                 1000                 1005

Lys Pro  Gly Asn Ala Pro Gly  Ile Ala Gly Tyr Asn  Ser Asn Gly
    1010                 1015                 1020

Cys Val  Tyr Ser Glu Ser Phe  Gly Leu Gly Gly Ile  Gly Val Leu
    1025                 1030                 1035

Thr Pro  Asp Asn Tyr Leu Ile  Thr Pro Ala Leu Asp  Leu Pro Asn
    1040                 1045                 1050

Gly Gly  Lys Leu Thr Phe Trp  Val Cys Ala Gln Asp  Ala Asn Tyr
    1055                 1060                 1065

Ala Ser  Glu His Tyr Ala Val  Tyr Ala Ser Ser Thr  Gly Asn Asp
    1070                 1075                 1080

Ala Ser  Asn Phe Thr Asn Ala  Leu Leu Glu Glu Thr  Ile Thr Ala
```

```
    1085                1090                1095

Lys Gly  Val Arg Ser Pro Lys  Ala Ile Arg Gly Arg  Ile Gln Gly
    1100                1105                1110

Thr Trp  Arg Gln Lys Thr Val  Asp Leu Pro Ala Gly  Thr Lys Tyr
    1115                1120                1125

Val Ala  Phe Arg His Phe Gln  Ser Thr Asp Met Phe  Tyr Ile Asp
    1130                1135                1140

Leu Asp  Glu Val Glu Ile Lys  Ala Asn Gly Lys Arg  Ala Asp Phe
    1145                1150                1155

Thr Glu  Thr Phe Glu Ser Ser  Thr His Gly Glu Ala  Pro Ala Glu
    1160                1165                1170

Trp Thr  Thr Ile Asp Ala Asp  Gly Asp Gly Gln Gly  Trp Leu Cys
    1175                1180                1185

Leu Ser  Ser Gly Gln Leu Asp  Trp Leu Thr Ala His  Gly Gly Ser
    1190                1195                1200

Asn Val  Val Ser Ser Phe Ser  Trp Asn Gly Met Ala  Leu Asn Pro
    1205                1210                1215

Asp Asn  Tyr Leu Ile Ser Lys  Asp Val Thr Gly Ala  Thr Lys Val
    1220                1225                1230

Lys Tyr  Tyr Tyr Ala Val Asn  Asp Gly Phe Pro Gly  Asp His Tyr
    1235                1240                1245

Ala Val  Met Ile Ser Lys Thr  Gly Thr Asn Ala Gly  Asp Phe Thr
    1250                1255                1260

Val Val  Phe Glu Glu Thr Pro  Asn Gly Ile Asn Lys  Gly Gly Ala
    1265                1270                1275

Arg Phe  Gly Leu Ser Thr Glu  Ala Asn Gly Ala Lys  Pro Gln Ser
    1280                1285                1290

Val Trp  Ile Glu Arg Thr Val  Asp Leu Pro Ala Gly  Thr Lys Tyr
    1295                1300                1305

Val Ala  Phe Arg His Tyr Asn  Cys Ser Asp Leu Asn  Tyr Ile Leu
    1310                1315                1320

Leu Asp  Asp Ile Gln Phe Thr  Met Gly Gly Ser Pro  Thr Pro Thr
    1325                1330                1335

Asp Tyr  Thr Tyr Thr Val Tyr  Arg Asp Gly Thr Lys  Ile Lys Glu
    1340                1345                1350

Gly Leu  Thr Glu Thr Thr Phe  Glu Glu Asp Gly Val  Ala Thr Gly
    1355                1360                1365

Asn His  Glu Tyr Cys Val Glu  Val Lys Tyr Thr Ala  Gly Val Ser
    1370                1375                1380

Pro Lys  Lys Cys Val Asn Val  Thr Val Asn Ser Thr  Gln Phe Asn
    1385                1390                1395

Pro Val  Gln Asn Leu Thr Ala  Glu Gln Ala Pro Asn  Ser Met Asp
    1400                1405                1410

Ala Ile  Leu Lys Trp Asn Ala  Pro Ala Ser Lys Arg  Ala Glu Val
    1415                1420                1425

Leu Asn  Glu Asp Phe Glu Asn  Gly Ile Pro Ala Ser  Trp Lys Thr
    1430                1435                1440

Ile Asp  Ala Asp Gly Asp Gly  Asn Asn Trp Thr Thr  Thr Pro Pro
    1445                1450                1455

Pro Gly  Gly Ser Ser Phe Ala  Gly His Asn Ser Ala  Ile Cys Val
    1460                1465                1470

Ser Ser  Ala Ser Tyr Ile Asn  Phe Glu Gly Pro Gln  Asn Pro Asp
    1475                1480                1485
```

```
Asn Tyr  Leu Val Thr Pro Glu  Leu Ser Leu Pro Gly  Gly Gly Thr
    1490                 1495                 1500

Leu Thr  Phe Trp Val Cys Ala  Gln Asp Ala Asn Tyr  Ala Ser Glu
    1505                 1510                 1515

His Tyr  Ala Val Tyr Ala Ser  Ser Thr Gly Asn Asp  Ala Ser Asn
    1520                 1525                 1530

Phe Ala  Asn Ala Leu Leu Glu  Glu Val Leu Thr Ala  Lys Thr Val
    1535                 1540                 1545

Val Thr  Ala Pro Glu Ala Ile  Arg Gly Thr Arg Ala  Gln Gly Thr
    1550                 1555                 1560

Trp Tyr  Gln Lys Thr Val Gln  Leu Pro Ala Gly Thr  Lys Tyr Val
    1565                 1570                 1575

Ala Phe  Arg His Phe Gly Cys  Thr Asp Phe Phe Trp  Ile Asn Leu
    1580                 1585                 1590

Asp Asp  Val Val Ile Thr Ser  Gly Asn Ala Pro Ser  Tyr Thr Tyr
    1595                 1600                 1605

Thr Ile  Tyr Arg Asn Asn Thr  Gln Ile Ala Ser Gly  Val Thr Glu
    1610                 1615                 1620

Thr Thr  Tyr Arg Asp Pro Asp  Leu Ala Thr Gly Phe  Tyr Thr Tyr
    1625                 1630                 1635

Gly Val  Lys Val Val Tyr Pro  Asn Gly Glu Ser Ala  Ile Glu Thr
    1640                 1645                 1650

Ala Thr  Leu Asn Ile Thr Ser  Leu Ala Asp Val Thr  Ala Gln Lys
    1655                 1660                 1665

Pro Tyr  Thr Leu Thr Val Val  Gly Lys Thr Ile Thr  Val Thr Cys
    1670                 1675                 1680

Gln Gly  Glu Ala Met Ile Tyr  Asp Met Asn Gly Arg  Arg Leu Ala
    1685                 1690                 1695

Ala Gly  Arg Asn Thr Val Val  Tyr Thr Ala Gln Gly  Gly His Tyr
    1700                 1705                 1710

Ala Val  Met Val Val Val Asp  Gly Lys Ser Tyr Val  Glu Lys Leu
    1715                 1720                 1725

Ala Ile  Lys
    1730
```

<210> SEQ ID NO 66
<211> LENGTH: 5196
<212> TYPE: DNA
<213> ORGANISM: Porphyromonas gingivalis

<400> SEQUENCE: 66

```
aggaaattat tattgctgat cgcggcgtcc cttttgggag ttggtcttta cgcccaaagc     60

gccaagatta agcttgatgc tccgactact cgaacgacat gtacgaacaa tagcttcaag    120

cagttcgatg caagcttttc gttcaatgaa gtcgagctga caaaggtgga gaccaaaggt    180

ggtactttcg cctcagtgtc aattccgggt gcattcccga ccggtgaggt tggttctccc    240

gaagtgccag cagttaggaa gttgattgct gtgcctgtcg gagccacacc tgttgttcgc    300

gtgaaaagtt ttaccgagca agtttactct ctgaaccaat acggttccga aaaactcatg    360

ccacatcaac cctctatgag caagagtgat gatcccgaaa aggttccctt cgtttacaat    420

gctgctgctt atgcacgcaa aggttttgtc ggacaagaac tgacccaagt agaaatgttg    480

gggacaatgc gtggtgttcg cattgcagct cttaccatta atcctgttca gtatgatgtg    540

gttgcaaacc aattgaaggt tagaaacaac atcgaaattg aagtaagctt tcaaggagct    600
```

```
gatgaagtag ctacacaacg tttgtatgat gcttctttta gcccttattt cgaaacagct    660
tataaacagc tcttcaatag agatgtttat acagatcatg gcgacttgta taatacgccg    720
gttcgtatgc ttgttgttgc aggtgcaaaa ttcaaagaag ctctcaagcc ttggctcact    780
tggaaggctc aaaagggctt ctatctggat gtgcattaca cagacgaagc tgaagtagga    840
acgacaaacg cctctatcaa ggcatttatt cacaagaaat acaatgatgg attggcagct    900
agtgctgctc cggtcttctt ggctttggtt ggtgacactg acgttattag cggagaaaaa    960
ggaaagaaaa caaaaaaagt taccgacttg tattacagtg cagtcgatgg cgactatttc   1020
cctgaaatgt atactttccg tatgtctgct tcttccccag aagaactgac gaacatcatt   1080
gataaggtat tgatgtatga aaaggctact atgccagata agagttattt ggagaaagtt   1140
ctcttgattg caggtgcaga ttatagctgg aattcccagg taggtcagcc aaccattaaa   1200
tacggtatgc agtactacta caaccaagag catggttata ccgacgtgta caactatctc   1260
aaagcccctt atacaggttg ctacagtcat ttgaataccg gagtcagctt tgcaaactat   1320
acagcgcatg gatctgagac cgcatgggct gatccacttc tgactacttc tcaactgaaa   1380
gcactcacta ataaggacaa atacttctta gctattggca actgctgtat tacagctcaa   1440
ttcgattatg tacagcctgc cttcggagag gtaataactc gcgttaagga gaaaggggct   1500
tatgcctata tcggttcatc tccaaattct tattggggcg aggactacta ttggagtgtg   1560
ggtgctaatg ccgtatttgg tgttcagcct actttttgaag gtacgtctat gggttcttat   1620
gatgctacat tcttggagga ttcgtacaac acagtgaatt ctattatgtg ggcaggtaat   1680
cttgccgcta ctcatgctgg aaatatcggc aatattaccc atattggtgc tcattactat   1740
tgggaagctt atcatgtcct tggcgatggt tcggttatgc cttatcgtgc aatgcctaag   1800
accaatactt atacgcttcc tgcctctttg cctcagaatc aggcttctta tagcattcag   1860
gcttctgccg gttcttacgt agctatttct aaagatggag ttttgtatgg aacaggtgtt   1920
gctaatgcca gcggtgttgc gactgtgagt atgactaagc agattacgga aaatggtaat   1980
tatgatgtag ttatcactcg ctctaattat cttcctgtga tcaagcaaat tcaggtaggt   2040
gagcctagcc cctaccagcc cgtttccaac ttgacagcta caacgcaggg tcagaaagta   2100
acgctcaagt gggaagcacc gagcgcaaag aaggcagaag gttcccgtga agtaaaacgg   2160
atcggagacg gtcttttcgt tacgatcgaa cctgcaaacg atgtacgtgc caacgaagcc   2220
aaggttgtgc ttgcggcaga caacgtatgg ggagacaata cgggttacca gttcttgttg   2280
gatgccgatc acaatacatt cggaagtgtc attccggcaa ccggtcctct ctttaccgga   2340
acagcttctt ccaatcttta cagtgcgaac ttcgagtatt tgatcccggc caatgccgat   2400
cctgttgtta ctacacagaa tattatcgtt acaggacagg gtgaagttgt aatccccggt   2460
ggtgtttacg actattgcat tacgaacccg gaacctgcat ccggaaagat gtggatcgca   2520
ggagatggag gcaaccagcc tgcacgttat gacgatttca cattcgaagc aggcaagaag   2580
tacaccttca cgatgcgtcg cgccggaatg ggagatggaa ctgatatgga agtcgaagac   2640
gattcacctg caagctatac ctacacggtg tatcgtgacg gcacgaagat caaggaaggt   2700
ctgacagcta cgacattcga agaagacggt gtagctgcag gcaatcatga gtattgcgtg   2760
gaagttaagt acacagccgg cgtatctccg aaggtatgta aagacgttac ggtagaagga   2820
tccaatgaat ttgctcctgt acagaacctg accggtagtt cagtaggtca gaaagtaacg   2880
cttaagtggg atgcacctaa tggtaccccg aatccgaatc caaatccgaa tccgaatccg   2940
```

```
ggaacaacac tttccgaatc attcgaaaat ggtattccgg catcttggaa gacgatcgat   3000

gcagacggtg acgggcatgg ctggaaacct ggaaatgctc ccggaatcgc tggctacaat   3060

agcaatggtt gtgtatattc agagtcattc ggtcttggtg gtataggagt tcttacccct   3120

gacaactatc tgataacacc ggcattggat ttgcctaacg gaggtaagtt gactttctgg   3180

gtatgcgcac aggatgctaa ttatgcatcc gagcactatg cggtgtatgc atcttcgacc   3240

ggtaacgatg catccaactt cacgaatgct ttgttggaag agacgattac ggcaaaaggt   3300

gttcgctcgc cgaaagctat tcgtggtcgt atacagggta cttggcgcca gaagacggta   3360

gaccttcccg caggtacgaa atatgttgct ttccgtcact tccaaagcac ggatatgttc   3420

tacatcgacc ttgatgaggt tgagatcaag gccaatggca agcgcgcaga cttcacggaa   3480

acgttcgagt cttctactca tggagaggca ccagcggaat ggactactat cgatgccgat   3540

ggcgatggtc agggttggct ctgtctgtct tccggacaat tggactggct gacagctcat   3600

ggcggcagca acgtagtaag ctctttctca tggaatggaa tggctttgaa tcctgataac   3660

tatctcatct caaaggatgt tacaggcgca acgaaggtaa agtactacta tgcagtcaac   3720

gacggttttc ccggggatca ctatgcggtg atgatctcca agacgggcac gaacgccgga   3780

gacttcacgg ttgttttcga agaaacgcct aacggaataa ataagggcgg agcaagattc   3840

ggtctttcca cggaagccaa tggcgccaaa cctcaaagtg tatggatcga gcgtacggta   3900

gatttgcctg caggcacgaa gtatgttgct ttccgtcact acaattgctc ggatttgaac   3960

tacattcttt tggatgatat tcagttcacc atgggtggca gccccacccc gaccgattat   4020

acctacacgg tgtatcgtga tggtacgaag atcaaggaag gtttgaccga aacgaccttc   4080

gaagaagacg gcgtagctac gggcaatcat gagtattgcg tggaagtgaa gtacacagcc   4140

ggcgtatctc cgaagaaatg tgtaaacgta actgttaatt cgacacagtt caatcctgta   4200

cagaacctga cggcagaaca agctcctaac agcatggatg caatccttaa atggaatgca   4260

ccggcatcta agcgtgcgga agttctgaac gaagacttcg aaaatggtat tcctgcctca   4320

tggaagacga tcgatgcaga cggtgacggc aacaattgga cgacgacccc tcctcccgga   4380

ggctcctctt ttgcaggtca caacagtgcg atctgtgtct cttcagcttc ttatatcaac   4440

tttgaaggtc ctcagaaccc tgataactat ctggttacac cggagctttc tcttcctggc   4500

ggaggaacgc ttactttctg ggtatgtgca caagatgcca attatgcatc agagcactat   4560

gccgtgtacg catcttctac gggtaacgac gcttccaact tcgccaacgc tttgttggaa   4620

gaagtgctga cggccaagac agttgttacg gcacctgaag ccattcgtgg tactcgtgct   4680

cagggcacct ggtatcaaaa gacggtacag ttgcctgcgg gtactaagta tgttgccttc   4740

cgtcacttcg gctgtacgga cttcttctgg atcaaccttg atgatgttgt aatcacttca   4800

gggaacgctc cgtcttacac ctatacgatc tatcgtaata atacacagat agcatcaggc   4860

gtaacggaga ctacttaccg agatccggac ttggctaccg gtttttacac gtacggtgta   4920

aaggttgttt acccgaacgg agaatcagct atcgaaactg ctacgttgaa tatcacttcg   4980

ttggcagacg taacggctca gaagccttac acgctgacag ttgtaggaaa gacgatcacg   5040

gtaacttgcc aaggcgaagc tatgatctac gacatgaacg gtcgtcgtct ggcagcgggt   5100

cgcaacacgg ttgtttacac ggctcagggc ggccactatg cagtcatggt tgtcgttgac   5160

ggcaagtctt acgtagagaa actcgctatc aagtaa                              5196
```

<210> SEQ ID NO 67
<211> LENGTH: 1703

```
<212> TYPE: PRT
<213> ORGANISM: Porphyromonas gingivalis

<400> SEQUENCE: 67

Leu His Lys Phe Val Ser Ile Ala Leu Cys Ser Ser Leu Leu Gly Gly
1               5                   10                  15

Met Ala Phe Ala Gln Gln Thr Glu Leu Gly Arg Asn Pro Asn Val Arg
            20                  25                  30

Leu Leu Glu Ser Thr Gln Gln Ser Val Thr Lys Val Gln Phe Arg Met
        35                  40                  45

Asp Asn Leu Lys Phe Thr Glu Val Gln Thr Pro Lys Gly Met Ala Gln
    50                  55                  60

Val Pro Thr Tyr Thr Glu Gly Val Asn Leu Ser Glu Lys Gly Met Pro
65                  70                  75                  80

Thr Leu Pro Ile Leu Ser Arg Ser Leu Ala Val Ser Asp Thr Arg Glu
                85                  90                  95

Met Lys Val Glu Val Val Ser Ser Lys Phe Ile Glu Lys Lys Asn Val
            100                 105                 110

Leu Ile Ala Pro Ser Lys Gly Met Ile Met Arg Asn Glu Asp Pro Lys
        115                 120                 125

Lys Ile Pro Tyr Val Tyr Gly Lys Ser Tyr Ser Gln Asn Lys Phe Phe
    130                 135                 140

Pro Gly Glu Ile Ala Thr Leu Asp Asp Pro Phe Ile Leu Arg Asp Val
145                 150                 155                 160

Arg Gly Gln Val Val Asn Phe Ala Pro Leu Gln Tyr Asn Pro Val Thr
                165                 170                 175

Lys Thr Leu Arg Ile Tyr Thr Glu Ile Thr Val Ala Val Ser Glu Thr
            180                 185                 190

Ser Glu Gln Gly Lys Asn Ile Leu Asn Lys Lys Gly Thr Phe Ala Gly
        195                 200                 205

Phe Glu Asp Thr Tyr Lys Arg Met Phe Met Asn Tyr Glu Pro Gly Arg
    210                 215                 220

Tyr Thr Pro Val Glu Glu Lys Gln Asn Gly Arg Met Ile Val Ile Val
225                 230                 235                 240

Ala Lys Lys Tyr Glu Gly Asp Ile Lys Asp Phe Val Asp Trp Lys Asn
                245                 250                 255

Gln Arg Gly Leu Arg Thr Glu Val Lys Val Ala Glu Asp Ile Ala Ser
            260                 265                 270

Pro Val Thr Ala Asn Ala Ile Gln Gln Phe Val Lys Gln Glu Tyr Glu
        275                 280                 285

Lys Glu Gly Asn Asp Leu Thr Tyr Val Leu Leu Ile Gly Asp His Lys
    290                 295                 300

Asp Ile Pro Ala Lys Ile Thr Pro Gly Ile Lys Ser Asp Gln Val Tyr
305                 310                 315                 320

Gly Gln Ile Val Gly Asn Asp His Tyr Asn Glu Val Phe Ile Gly Arg
                325                 330                 335

Phe Ser Cys Glu Ser Lys Glu Asp Leu Lys Thr Gln Ile Asp Arg Thr
            340                 345                 350

Ile His Tyr Glu Arg Asn Ile Thr Thr Glu Asp Lys Trp Leu Gly Gln
        355                 360                 365

Ala Leu Cys Ile Ala Ser Ala Glu Gly Gly Pro Ser Ala Asp Asn Gly
    370                 375                 380

Glu Ser Asp Ile Gln His Glu Asn Val Ile Ala Asn Leu Leu Thr Gln
385                 390                 395                 400
```

```
Tyr Gly Tyr Thr Lys Ile Ile Lys Cys Tyr Asp Pro Gly Val Thr Pro
                405                 410                 415

Lys Asn Ile Ile Asp Ala Phe Asn Gly Gly Ile Ser Leu Ala Asn Tyr
            420                 425                 430

Thr Gly His Gly Ser Glu Thr Ala Trp Gly Thr Ser His Phe Gly Thr
        435                 440                 445

Thr His Val Lys Gln Leu Thr Asn Ser Asn Gln Leu Pro Phe Ile Phe
    450                 455                 460

Asp Val Ala Ala Val Asn Gly Asp Phe Leu Phe Ser Met Pro Cys Phe
465                 470                 475                 480

Ala Glu Ala Leu Met Arg Ala Gln Lys Asp Gly Lys Pro Thr Gly Thr
                485                 490                 495

Val Ala Ile Ile Ala Ser Thr Ile Asn Gln Ser Trp Ala Ser Pro Met
            500                 505                 510

Arg Gly Gln Asp Glu Met Asn Glu Ile Leu Cys Glu Lys His Pro Asn
        515                 520                 525

Asn Ile Lys Arg Thr Phe Gly Gly Val Thr Met Asn Gly Met Phe Ala
    530                 535                 540

Met Val Glu Lys Tyr Lys Lys Asp Gly Glu Lys Met Leu Asp Thr Trp
545                 550                 555                 560

Thr Val Phe Gly Asp Pro Ser Leu Leu Val Arg Thr Leu Val Pro Thr
                565                 570                 575

Lys Met Gln Val Thr Ala Pro Ala Gln Ile Asn Leu Thr Asp Ala Ser
            580                 585                 590

Val Asn Val Ser Cys Asp Tyr Asn Gly Ala Ile Ala Thr Ile Ser Ala
        595                 600                 605

Asn Gly Lys Met Phe Gly Ser Ala Val Val Glu Asn Gly Thr Ala Thr
    610                 615                 620

Ile Asn Leu Thr Gly Leu Thr Asn Glu Ser Thr Leu Thr Leu Thr Val
625                 630                 635                 640

Val Gly Tyr Asn Lys Glu Thr Val Ile Lys Thr Ile Asn Thr Asn Gly
                645                 650                 655

Glu Pro Asn Pro Tyr Gln Pro Val Ser Asn Leu Thr Ala Thr Thr Gln
            660                 665                 670

Gly Gln Lys Val Thr Leu Lys Trp Asp Ala Pro Ser Thr Lys Thr Asn
        675                 680                 685

Ala Thr Thr Asn Thr Ala Arg Ser Val Asp Gly Ile Arg Glu Leu Val
    690                 695                 700

Leu Leu Ser Val Ser Asp Ala Pro Glu Leu Leu Arg Ser Gly Gln Ala
705                 710                 715                 720

Glu Ile Val Leu Glu Ala His Asp Val Trp Asn Asp Gly Ser Gly Tyr
                725                 730                 735

Gln Ile Leu Leu Asp Ala Asp His Asp Gln Tyr Gly Gln Val Ile Pro
            740                 745                 750

Ser Asp Thr His Thr Leu Trp Pro Asn Cys Ser Val Pro Ala Asn Leu
        755                 760                 765

Phe Ala Pro Phe Glu Tyr Thr Val Pro Glu Asn Ala Asp Pro Ser Cys
    770                 775                 780

Ser Pro Thr Asn Met Ile Met Asp Gly Thr Ala Ser Val Asn Ile Pro
785                 790                 795                 800

Ala Gly Thr Tyr Asp Phe Ala Ile Ala Ala Pro Gln Ala Asn Ala Lys
                805                 810                 815
```

```
Ile Trp Ile Ala Gly Gln Gly Pro Thr Lys Glu Asp Asp Tyr Val Phe
            820                 825                 830

Glu Ala Gly Lys Lys Tyr His Phe Leu Met Lys Lys Met Gly Ser Gly
        835                 840                 845

Asp Gly Thr Glu Leu Thr Ile Ser Glu Gly Gly Gly Ser Asp Tyr Thr
    850                 855                 860

Tyr Thr Val Tyr Arg Asp Gly Thr Lys Ile Lys Glu Gly Leu Thr Ala
865                 870                 875                 880

Thr Thr Phe Glu Glu Asp Gly Val Ala Ala Gly Asn His Glu Tyr Cys
                885                 890                 895

Val Glu Val Lys Tyr Thr Ala Gly Val Ser Pro Lys Val Cys Lys Asp
            900                 905                 910

Val Thr Val Glu Gly Ser Asn Glu Phe Ala Pro Val Gln Asn Leu Thr
        915                 920                 925

Gly Ser Ala Val Gly Gln Lys Val Thr Leu Lys Trp Asp Ala Pro Asn
    930                 935                 940

Gly Thr Pro Asn Pro Asn Pro Asn Pro Asn Pro Asn Pro Asn Pro Gly
945                 950                 955                 960

Thr Thr Thr Leu Ser Glu Ser Phe Glu Asn Gly Ile Pro Ala Ser Trp
                965                 970                 975

Lys Thr Ile Asp Ala Asp Gly Asp Gly His Gly Trp Lys Pro Gly Asn
            980                 985                 990

Ala Pro Gly Ile Ala Gly Tyr Asn  Ser Asn Gly Cys Val  Tyr Ser Glu
        995                 1000                1005

Ser Phe  Gly Leu Gly Gly Ile  Gly Val Leu Thr Pro  Asp Asn Tyr
    1010                1015                1020

Leu Ile  Thr Pro Ala Leu Asp  Leu Pro Asn Gly Gly  Lys Leu Thr
    1025                1030                1035

Phe Trp  Val Cys Ala Gln Asp  Ala Asn Tyr Ala Ser  Glu His Tyr
    1040                1045                1050

Ala Val  Tyr Ala Ser Ser Thr  Gly Asn Asp Ala Ser  Asn Phe Thr
    1055                1060                1065

Asn Ala  Leu Leu Glu Glu Thr  Ile Thr Ala Lys Gly  Val Arg Ser
    1070                1075                1080

Pro Glu  Ala Ile Arg Gly Arg  Ile Gln Gly Thr Trp  Arg Gln Lys
    1085                1090                1095

Thr Val  Asp Leu Pro Ala Gly  Thr Lys Tyr Val Ala  Phe Arg His
    1100                1105                1110

Phe Gln  Ser Thr Asp Met Phe  Tyr Ile Asp Leu Asp  Glu Val Glu
    1115                1120                1125

Ile Lys  Ala Asn Gly Lys Arg  Ala Asp Phe Thr Glu  Thr Phe Glu
    1130                1135                1140

Ser Ser  Thr His Gly Glu Ala  Pro Ala Glu Trp Thr  Thr Ile Asp
    1145                1150                1155

Ala Asp  Gly Asp Gly Gln Gly  Trp Leu Cys Leu Ser  Ser Gly Gln
    1160                1165                1170

Leu Asp  Trp Leu Thr Ala His  Gly Gly Thr Asn Val  Val Ser Ser
    1175                1180                1185

Phe Ser  Trp Asn Gly Met Ala  Leu Asn Pro Asp Asn  Tyr Leu Ile
    1190                1195                1200

Ser Lys  Asp Val Thr Gly Ala  Thr Lys Val Lys Tyr  Tyr Tyr Ala
    1205                1210                1215

Val Asn  Asp Gly Phe Pro Gly  Asp His Tyr Ala Val  Met Ile Ser
```

```
    1220                1225                1230

Lys Thr  Gly Thr Asn Ala Gly  Asp Phe Thr Val Val  Phe Glu Glu
    1235                1240                1245

Thr Pro  Asn Gly Ile Asn Lys  Gly Gly Ala Arg Phe  Gly Leu Ser
    1250                1255                1260

Thr Glu  Ala Asp Gly Ala Lys  Pro Gln Ser Val Trp  Ile Glu Arg
    1265                1270                1275

Thr Val  Asp Leu Pro Ala Gly  Thr Lys Tyr Val Ala  Phe Arg His
    1280                1285                1290

Tyr Asn  Cys Ser Asp Leu Asn  Tyr Ile Leu Leu Asp  Asp Ile Gln
    1295                1300                1305

Phe Thr  Met Gly Gly Ser Pro  Thr Pro Thr Asp Tyr  Thr Tyr Thr
    1310                1315                1320

Val Tyr  Arg Asp Gly Thr Lys  Ile Lys Glu Gly Leu  Thr Glu Thr
    1325                1330                1335

Thr Phe  Glu Glu Asp Gly Val  Ala Thr Gly Asn His  Glu Tyr Cys
    1340                1345                1350

Val Glu  Val Lys Tyr Thr Ala  Gly Val Ser Pro Lys  Lys Cys Val
    1355                1360                1365

Asn Val  Thr Val Asn Ser Thr  Gln Phe Asn Pro Val  Lys Asn Leu
    1370                1375                1380

Lys Ala  Gln Pro Asp Gly Gly  Asp Val Val Leu Lys  Trp Glu Ala
    1385                1390                1395

Pro Ser  Ala Lys Lys Thr Glu  Gly Ser Arg Glu Val  Lys Arg Ile
    1400                1405                1410

Gly Asp  Gly Leu Phe Val Thr  Ile Glu Pro Ala Asn  Asp Val Arg
    1415                1420                1425

Ala Asn  Glu Ala Lys Val Val  Leu Ala Ala Asp Asn  Val Trp Gly
    1430                1435                1440

Asp Asn  Thr Gly Tyr Gln Phe  Leu Leu Asp Ala Asp  His Asn Thr
    1445                1450                1455

Phe Gly  Ser Val Ile Pro Ala  Thr Gly Pro Leu Phe  Thr Gly Thr
    1460                1465                1470

Ala Ser  Ser Asp Leu Tyr Ser  Ala Asn Phe Glu Tyr  Leu Ile Pro
    1475                1480                1485

Ala Asn  Ala Asp Pro Val Val  Thr Thr Gln Asn Ile  Ile Val Thr
    1490                1495                1500

Gly Gln  Gly Glu Val Val Ile  Pro Gly Gly Val Tyr  Asp Tyr Cys
    1505                1510                1515

Ile Thr  Asn Pro Glu Pro Ala  Ser Gly Lys Met Trp  Ile Ala Gly
    1520                1525                1530

Asp Gly  Gly Asn Gln Pro Ala  Arg Tyr Asp Asp Phe  Thr Phe Glu
    1535                1540                1545

Ala Gly  Lys Lys Tyr Thr Phe  Thr Met Arg Arg Ala  Gly Met Gly
    1550                1555                1560

Asp Gly  Thr Asp Met Glu Val  Glu Asp Asp Ser Pro  Ala Ser Tyr
    1565                1570                1575

Thr Tyr  Thr Val Tyr Arg Asp  Gly Thr Lys Ile Lys  Glu Gly Leu
    1580                1585                1590

Thr Glu  Thr Thr Tyr Arg Asp  Ala Gly Met Ser Ala  Gln Ser His
    1595                1600                1605

Glu Tyr  Cys Val Glu Val Lys  Tyr Thr Ala Gly Val  Ser Pro Lys
    1610                1615                1620
```

Val Cys Val Asp Tyr Ile Pro Asp Gly Val Ala Asp Val Thr Ala
1625 1630 1635

Gln Lys Pro Tyr Thr Leu Thr Val Val Gly Lys Thr Ile Thr Val
1640 1645 1650

Thr Cys Gln Gly Glu Ala Met Ile Tyr Asp Met Asn Gly Arg Arg
1655 1660 1665

Leu Ala Ala Gly Arg Asn Thr Val Val Tyr Thr Ala Gln Gly Gly
1670 1675 1680

Tyr Tyr Ala Val Met Val Val Val Asp Gly Lys Ser Tyr Val Glu
1685 1690 1695

Lys Leu Ala Val Lys
1700

<210> SEQ ID NO 68
<211> LENGTH: 5112
<212> TYPE: DNA
<213> ORGANISM: Porphyromonas gingivalis

<400> SEQUENCE: 68
ttgcacaagt ttgtttcgat tgctctttgc tcttccttat taggaggaat ggcatttgcg 60
cagcagacag agttgggacg caatccgaat gtgagattgc tcgaatccac tcagcaatcg 120
gtgacaaagg ttcagttccg tatggacaac ctcaagttca ccgaagttca aacccctaag 180
ggaatggcac aagtgccgac ctatacagaa ggggttaatc tttctgaaaa agggatgcct 240
acgcttccca ttctatcacg ctctttggcg gtttcagaca ctcgtgagat gaaggtagag 300
gttgtttcct caaagttcat cgaaaagaaa aatgtcctga ttgcaccctc caagggcatg 360
attatgcgta acgaagatcc gaaaaagatc ccttacgttt atggaaagag ctactcgcaa 420
aacaaattct tcccgggaga gatcgccacg cttgatgatc cttttatcct tcgtgatgtg 480
cgtggacagg ttgtaaactt tgcgcctttg cagtataacc ctgtgacaaa gacgttgcgc 540
atctatacgg aaatcactgt ggcagtgagc gaaacttcgg agcaaggcaa aaatattctg 600
aacaagaaag gtacatttgc cggctttgaa gacacataca agcgcatgtt catgaactac 660
gagccagggc gttacacacc ggtagaggaa aaacaaaatg gtcgtatgat cgtcatcgta 720
gccaaaaagt atgagggaga tattaaagat ttcgttgatt ggaaaaacca acgcggtctc 780
cgtaccgagg tgaaagtggc agaagatatt gcttctcccg ttacagctaa tgctattcag 840
caattcgtta agcaagaata cgagaaagaa ggtaatgatt tgacctatgt tcttttgatt 900
ggcgatcaca aagatattcc tgccaaaatt actccgggga tcaaatccga ccaggtatat 960
ggacaaatag taggtaatga ccactacaac gaagtcttca tcggtcgttt ctcatgtgag 1020
agcaaagagg atctgaagac acaaatcgat cggactattc actatgagcg caatataacc 1080
acggaagaca aatggctcgg tcaggctctt tgtattgctt cggctgaagg aggcccatcc 1140
gcagacaatg gtgaaagtga tatccagcat gagaatgtaa tcgccaatct gcttacccag 1200
tatggttata ccaagattat caaatgttat gatccgggag taactcctaa aaacattatt 1260
gatgctttca acggaggaat ctcgttggcc aactatacgg gccacggtag cgaaacagct 1320
tggggtacgt ctcacttcgg caccactcat gtgaagcagc ttaccaacag caaccagcta 1380
ccgtttattt tcgacgtagc tgctgtgaat ggcgatttcc tattcagcat gccttgtttc 1440
gcagaagcat tgatgcgtgc acaaaaagat ggtaagccga caggtactgt tgctatcata 1500
gcgtctacga tcaaccagtc ttgggcttct cctatgcgcg ggcaggatga gatgaacgaa 1560

```
attctgtgcg aaaaacaccc gaacaacatc aagcgtactt tcggtggtgt caccatgaac   1620
ggtatgtttg ctatggtgga aaagtataaa aaggatggtg agaagatgct cgacacatgg   1680
actgtattcg gcgacccctc gctgctcgtt cgtacacttg tcccgaccaa aatgcaggtt   1740
acggctccgg ctcagattaa tttgacggat gcttcagtca acgtatcttg cgattataat   1800
ggtgctattg ctaccatttc agccaatgga aagatgttcg gttctgcagt tgtcgaaaat   1860
ggaacagcta caatcaatct gacaggtctg acaaatgaaa gcacgcttac ccttacagta   1920
gttggttaca acaaagagac ggttattaag accatcaaca ctaatggtga gcctaacccc   1980
taccagcctg tttccaactt gactgctaca acgcagggtc agaaagtaac gctcaagtgg   2040
gatgcaccga gcacgaaaac caatgcaacc actaataccg ctcgcagcgt ggatggcata   2100
cgagaactgg ttcttctgtc agtcagcgat gcccccgaac ttcttcgcag cggtcaggcc   2160
gagattgttc ttgaagctca cgatgtttgg aatgatggat ccggttatca gattcttttg   2220
gatgcagacc atgatcaata tggacaggtt atacccagtg atacccatac tctttggccg   2280
aactgtagtg tcccggccaa tctgttcgct ccgttcgaat atacggttcc ggaaaatgca   2340
gatccttctt gttcccctac caatatgata atggatggta ctgcatccgt taatataccg   2400
gccggaactt atgactttgc aattgctgct cctcaagcaa atgcaaagat ttggattgcc   2460
ggacaaggac cgacgaaaga agatgattat gtatttgaag ccggtaaaaa ataccatttc   2520
cttatgaaga agatgggtag cggtgatgga actgaattga ctataagcga aggtggtgga   2580
agcgattaca cctatactgt ctatcgtgac ggcacgaaga tcaaggaagg tctgacggct   2640
acgacattcg aagaagacgg tgtagctgca ggcaatcatg agtattgcgt ggaagttaag   2700
tacacagccg gcgtatctcc gaaggtatgt aaagacgtta cggtagaagg atccaatgaa   2760
tttgctcctg tacagaacct gaccggtagt gcagtcggcc agaaagtaac gcttaagtgg   2820
gatgcaccta atggtacccc gaatccaaat ccaaatccga atccaaatcc gaatcccgga   2880
acaactacac tttccgaatc attcgaaaat ggtattcctg cctcatggaa gacgatcgat   2940
gcagacggtg acgggcatgg ctggaagcct ggaaatgctc ccggaatcgc tggctacaat   3000
agcaatggtt gtgtatattc agagtcattc ggtcttggtg gtataggagt tcttacccct   3060
gacaactatc tgataacacc ggcattggat ttgcctaacg gaggtaagtt gactttctgg   3120
gtatgcgcac aggatgctaa ttatgcatcc gagcactatg cggtgtatgc atcttcgacc   3180
ggtaacgatg catccaactt cacgaatgct ttgttggaag agacgattac ggcaaaaggt   3240
gttcgctcgc cggaagctat tcgtggtcgt atacagggta cttggcgcca gaagacggta   3300
gaccttcccg caggtacgaa atatgttgct ttccgtcact tccaaagcac ggatatgttc   3360
tacatcgacc ttgatgaggt tgagatcaag gccaatggca agcgcgcaga cttcacggaa   3420
acgttcgagt cttctactca tggagaggca ccagcggaat ggactactat cgatgccgat   3480
ggcgatggtc agggttggct ctgtctgtct tccggacaat tggactggct gacagctcat   3540
ggcggcacca acgtagtaag ctctttctca tggaatggaa tggctttgaa tcctgataac   3600
tatctcatct caaaggatgt tacaggcgca acgaaggtaa agtactacta tgcagtcaac   3660
gacggttttc ccggggatca ctatgcggtg atgatctcca agacgggcac gaacgccgga   3720
gacttcacgg ttgttttcga agaaacgcct aacggaataa ataagggcgg agcaagattc   3780
ggtctttcca cggaagccga tggcgccaaa cctcaaagtg tatggatcga gcgtacggta   3840
gatttgcctg cgggcacgaa gtatgttgct ttccgtcact acaattgctc ggatttgaac   3900
tacattcttt tggatgatat tcagttcacc atgggtggca gccccacccc gaccgattat   3960
```

```
acctacacgg tgtatcgtga tggtacgaag atcaaggaag gtttgaccga aacgaccttc   4020

gaagaagacg gcgtagctac gggcaatcat gagtattgcg tggaagtgaa gtacacagcc   4080

ggcgtatctc cgaagaaatg tgtaaacgta actgttaatt cgacacagtt caatcctgta   4140

aagaacctga aggcacaacc ggatggcggc gacgtggttc tcaagtggga agccccgagc   4200

gcaaagaaga cagaaggttc tcgtgaagta aaacggatcg gagacggtct tttcgttacg   4260

atcgaacctg caaacgatgt acgtgccaac gaagccaagg ttgtgctcgc agcagacaac   4320

gtatggggag acaatacggg ttaccagttc ttgttggatg ccgatcacaa tacattcgga   4380

agtgtcattc cggcaaccgg tcctctcttt accggaacag cttcttccga tctttacagt   4440

gcgaacttcg agtatttgat cccggccaat gccgatcctg ttgttactac acagaatatt   4500

atcgttacag gacagggtga agttgtaatc cccggtggtg tttacgacta ttgcattacg   4560

aacccggaac ctgcatccgg aaagatgtgg atcgcaggag atggaggcaa ccagcctgca   4620

cgttatgacg atttcacatt cgaagcaggc aagaagtaca ccttcacgat gcgtcgcgcc   4680

ggaatgggag atggaactga tatggaagtc gaagacgatt cacctgcaag ctatacctat   4740

acagtctatc gtgacggcac gaagatcaag gaaggtctga ccgaaacgac ctaccgcgat   4800

gcaggaatga gtgcacaatc tcatgagtat tgcgtggaag ttaagtacac agccggcgta   4860

tctccgaagg tttgtgtgga ttatattcct gacggagtgg cagacgtaac ggctcagaag   4920

ccttacacgc tgacagttgt aggaaagacg atcacggtaa cttgccaagg cgaagctatg   4980

atctacgaca tgaacggtcg tcgtctggca gccggtcgca acacggttgt ttacacggct   5040

cagggcggct actatgcagt tatggttgtc gttgacggca agtcttacgt agagaaactc   5100

gctgtaaagt aa                                                       5112
```

<210> SEQ ID NO 69
<211> LENGTH: 1703
<212> TYPE: PRT
<213> ORGANISM: Porphyromonas gingivalis

<400> SEQUENCE: 69

```
Leu His Lys Phe Val Ser Ile Ala Leu Cys Ser Ser Leu Leu Gly Gly
1               5                   10                  15

Met Ala Phe Ala Gln Gln Thr Glu Leu Gly Arg Asn Pro Asn Val Arg
            20                  25                  30

Leu Leu Glu Ser Thr Gln Gln Ser Val Thr Lys Val Gln Phe Arg Met
        35                  40                  45

Asp Asn Leu Lys Phe Thr Glu Val Gln Thr Pro Lys Gly Met Ala Gln
    50                  55                  60

Val Pro Thr Tyr Thr Glu Gly Val Asn Leu Ser Glu Lys Gly Met Pro
65                  70                  75                  80

Thr Leu Pro Ile Leu Ser Arg Ser Leu Ala Val Ser Asp Thr Arg Glu
                85                  90                  95

Met Lys Val Glu Val Val Ser Ser Lys Phe Ile Glu Lys Lys Asn Val
            100                 105                 110

Leu Ile Ala Pro Ser Lys Gly Met Ile Met Arg Asn Glu Asp Pro Lys
        115                 120                 125

Lys Ile Pro Tyr Val Tyr Gly Lys Ser Tyr Ser Gln Asn Lys Phe Phe
    130                 135                 140

Pro Gly Glu Ile Ala Thr Leu Asp Asp Pro Phe Ile Leu Arg Asp Val
145                 150                 155                 160
```

```
Arg Gly Gln Val Val Asn Phe Ala Pro Leu Gln Tyr Asn Pro Val Thr
                165                 170                 175

Lys Thr Leu Arg Ile Tyr Thr Glu Ile Thr Val Ala Val Ser Glu Thr
            180                 185                 190

Ser Glu Gln Gly Lys Asn Ile Leu Asn Lys Lys Gly Thr Phe Ala Gly
        195                 200                 205

Phe Glu Asp Thr Tyr Lys Arg Met Phe Met Asn Tyr Glu Pro Gly Arg
    210                 215                 220

Tyr Thr Pro Val Glu Glu Lys Gln Asn Gly Arg Met Ile Val Ile Val
225                 230                 235                 240

Ala Lys Lys Tyr Glu Gly Asp Ile Lys Asp Phe Val Asp Trp Lys Asn
                245                 250                 255

Gln Arg Gly Leu Arg Thr Glu Val Lys Val Ala Glu Asp Ile Ala Ser
            260                 265                 270

Pro Val Thr Ala Asn Ala Ile Gln Gln Phe Val Lys Gln Glu Tyr Glu
        275                 280                 285

Lys Glu Gly Asn Asp Leu Thr Tyr Val Leu Leu Ile Gly Asp His Lys
    290                 295                 300

Asp Ile Pro Ala Lys Ile Thr Pro Gly Ile Lys Ser Asp Gln Val Tyr
305                 310                 315                 320

Gly Gln Ile Val Gly Asn Asp His Tyr Asn Glu Val Phe Ile Gly Arg
                325                 330                 335

Phe Ser Cys Glu Ser Lys Glu Asp Leu Lys Thr Gln Ile Asp Arg Thr
            340                 345                 350

Ile His Tyr Glu Arg Asn Ile Thr Thr Glu Asp Lys Trp Leu Gly Gln
        355                 360                 365

Ala Leu Cys Ile Ala Ser Ala Glu Gly Gly Pro Ser Ala Asp Asn Gly
    370                 375                 380

Glu Ser Asp Ile Gln His Glu Asn Val Ile Ala Asn Leu Leu Thr Gln
385                 390                 395                 400

Tyr Gly Tyr Thr Lys Ile Ile Lys Cys Tyr Asp Pro Gly Val Thr Pro
                405                 410                 415

Lys Asn Ile Ile Asp Ala Phe Asn Gly Gly Ile Ser Leu Ala Asn Tyr
            420                 425                 430

Thr Gly His Gly Ser Glu Thr Ala Trp Gly Thr Ser His Phe Gly Thr
        435                 440                 445

Thr His Val Lys Gln Leu Thr Asn Ser Asn Gln Leu Pro Phe Ile Phe
    450                 455                 460

Asp Val Ala Cys Val Asn Gly Asp Phe Leu Phe Ser Met Pro Ala Phe
465                 470                 475                 480

Ala Glu Ala Leu Met Arg Ala Gln Lys Asp Gly Lys Pro Thr Gly Thr
                485                 490                 495

Val Ala Ile Ile Ala Ser Thr Ile Asn Gln Ser Trp Ala Ser Pro Met
            500                 505                 510

Arg Gly Gln Asp Glu Met Asn Glu Ile Leu Cys Glu Lys His Pro Asn
        515                 520                 525

Asn Ile Lys Arg Thr Phe Gly Gly Val Thr Met Asn Gly Met Phe Ala
    530                 535                 540

Met Val Glu Lys Tyr Lys Lys Asp Gly Glu Lys Met Leu Asp Thr Trp
545                 550                 555                 560

Thr Val Phe Gly Asp Pro Ser Leu Leu Val Arg Thr Leu Val Pro Thr
                565                 570                 575

Lys Met Gln Val Thr Ala Pro Ala Gln Ile Asn Leu Thr Asp Ala Ser
```

```
            580                 585                 590

Val Asn Val Ser Cys Asp Tyr Asn Gly Ala Ile Ala Thr Ile Ser Ala
        595                 600                 605

Asn Gly Lys Met Phe Gly Ser Ala Val Val Glu Asn Gly Thr Ala Thr
    610                 615                 620

Ile Asn Leu Thr Gly Leu Thr Asn Glu Ser Thr Leu Thr Leu Thr Val
625                 630                 635                 640

Val Gly Tyr Asn Lys Glu Thr Val Ile Lys Thr Ile Asn Thr Asn Gly
                645                 650                 655

Glu Pro Asn Pro Tyr Gln Pro Val Ser Asn Leu Thr Ala Thr Thr Gln
            660                 665                 670

Gly Gln Lys Val Thr Leu Lys Trp Asp Ala Pro Ser Thr Lys Thr Asn
        675                 680                 685

Ala Thr Thr Asn Thr Ala Arg Ser Val Asp Gly Ile Arg Glu Leu Val
    690                 695                 700

Leu Leu Ser Val Ser Asp Ala Pro Glu Leu Leu Arg Ser Gly Gln Ala
705                 710                 715                 720

Glu Ile Val Leu Glu Ala His Asp Val Trp Asn Asp Gly Ser Gly Tyr
                725                 730                 735

Gln Ile Leu Leu Asp Ala Asp His Asp Gln Tyr Gly Gln Val Ile Pro
            740                 745                 750

Ser Asp Thr His Thr Leu Trp Pro Asn Cys Ser Val Pro Ala Asn Leu
        755                 760                 765

Phe Ala Pro Phe Glu Tyr Thr Val Pro Glu Asn Ala Asp Pro Ser Cys
    770                 775                 780

Ser Pro Thr Asn Met Ile Met Asp Gly Thr Ala Ser Val Asn Ile Pro
785                 790                 795                 800

Ala Gly Thr Tyr Asp Phe Ala Ile Ala Ala Pro Gln Ala Asn Ala Lys
                805                 810                 815

Ile Trp Ile Ala Gly Gln Gly Pro Thr Lys Glu Asp Asp Tyr Val Phe
            820                 825                 830

Glu Ala Gly Lys Lys Tyr His Phe Leu Met Lys Lys Met Gly Ser Gly
        835                 840                 845

Asp Gly Thr Glu Leu Thr Ile Ser Glu Gly Gly Gly Ser Asp Tyr Thr
    850                 855                 860

Tyr Thr Val Tyr Arg Asp Gly Thr Lys Ile Lys Glu Gly Leu Thr Ala
865                 870                 875                 880

Thr Thr Phe Glu Glu Asp Gly Val Ala Ala Gly Asn His Glu Tyr Cys
                885                 890                 895

Val Glu Val Lys Tyr Thr Ala Gly Val Ser Pro Lys Val Cys Lys Asp
            900                 905                 910

Val Thr Val Glu Gly Ser Asn Glu Phe Ala Pro Val Gln Asn Leu Thr
        915                 920                 925

Gly Ser Ala Val Gly Gln Lys Val Thr Leu Lys Trp Asp Ala Pro Asn
    930                 935                 940

Gly Thr Pro Asn Pro Asn Pro Asn Pro Asn Pro Asn Pro Asn Pro Gly
945                 950                 955                 960

Thr Thr Thr Leu Ser Glu Ser Phe Glu Asn Gly Ile Pro Ala Ser Trp
                965                 970                 975

Lys Thr Ile Asp Ala Asp Gly Asp Gly His Gly Trp Lys Pro Gly Asn
            980                 985                 990

Ala Pro Gly Ile Ala Gly Tyr Asn  Ser Asn Gly Cys Val  Tyr Ser Glu
        995                 1000                 1005
```

```
Ser Phe  Gly Leu Gly Gly Ile  Gly Val Leu Thr Pro  Asp Asn Tyr
    1010                 1015                 1020

Leu Ile  Thr Pro Ala Leu Asp  Leu Pro Asn Gly Gly  Lys Leu Thr
    1025                 1030                 1035

Phe Trp  Val Cys Ala Gln Asp  Ala Asn Tyr Ala Ser  Glu His Tyr
    1040                 1045                 1050

Ala Val  Tyr Ala Ser Ser Thr  Gly Asn Asp Ala Ser  Asn Phe Thr
    1055                 1060                 1065

Asn Ala  Leu Leu Glu Glu Thr  Ile Thr Ala Lys Gly  Val Arg Ser
    1070                 1075                 1080

Pro Glu  Ala Ile Arg Gly Arg  Ile Gln Gly Thr Trp  Arg Gln Lys
    1085                 1090                 1095

Thr Val  Asp Leu Pro Ala Gly  Thr Lys Tyr Val Ala  Phe Arg His
    1100                 1105                 1110

Phe Gln  Ser Thr Asp Met Phe  Tyr Ile Asp Leu Asp  Glu Val Glu
    1115                 1120                 1125

Ile Lys  Ala Asn Gly Lys Arg  Ala Asp Phe Thr Glu  Thr Phe Glu
    1130                 1135                 1140

Ser Ser  Thr His Gly Glu Ala  Pro Ala Glu Trp Thr  Thr Ile Asp
    1145                 1150                 1155

Ala Asp  Gly Asp Gly Gln Gly  Trp Leu Cys Leu Ser  Ser Gly Gln
    1160                 1165                 1170

Leu Asp  Trp Leu Thr Ala His  Gly Gly Thr Asn Val  Val Ser Ser
    1175                 1180                 1185

Phe Ser  Trp Asn Gly Met Ala  Leu Asn Pro Asp Asn  Tyr Leu Ile
    1190                 1195                 1200

Ser Lys  Asp Val Thr Gly Ala  Thr Lys Val Lys Tyr  Tyr Tyr Ala
    1205                 1210                 1215

Val Asn  Asp Gly Phe Pro Gly  Asp His Tyr Ala Val  Met Ile Ser
    1220                 1225                 1230

Lys Thr  Gly Thr Asn Ala Gly  Asp Phe Thr Val Val  Phe Glu Glu
    1235                 1240                 1245

Thr Pro  Asn Gly Ile Asn Lys  Gly Gly Ala Arg Phe  Gly Leu Ser
    1250                 1255                 1260

Thr Glu  Ala Asp Gly Ala Lys  Pro Gln Ser Val Trp  Ile Glu Arg
    1265                 1270                 1275

Thr Val  Asp Leu Pro Ala Gly  Thr Lys Tyr Val Ala  Phe Arg His
    1280                 1285                 1290

Tyr Asn  Cys Ser Asp Leu Asn  Tyr Ile Leu Leu Asp  Asp Ile Gln
    1295                 1300                 1305

Phe Thr  Met Gly Gly Ser Pro  Thr Pro Thr Asp Tyr  Thr Tyr Thr
    1310                 1315                 1320

Val Tyr  Arg Asp Gly Thr Lys  Ile Lys Glu Gly Leu  Thr Glu Thr
    1325                 1330                 1335

Thr Phe  Glu Glu Asp Gly Val  Ala Thr Gly Asn His  Glu Tyr Cys
    1340                 1345                 1350

Val Glu  Val Lys Tyr Thr Ala  Gly Val Ser Pro Lys  Lys Cys Val
    1355                 1360                 1365

Asn Val  Thr Val Asn Ser Thr  Gln Phe Asn Pro Val  Lys Asn Leu
    1370                 1375                 1380

Lys Ala  Gln Pro Asp Gly Gly  Asp Val Val Leu Lys  Trp Glu Ala
    1385                 1390                 1395
```

```
Pro Ser  Ala Lys Lys Thr Glu  Gly Ser Arg Glu Val  Lys Arg Ile
    1400                 1405                 1410

Gly Asp  Gly Leu Phe Val Thr  Ile Glu Pro Ala Asn  Asp Val Arg
    1415                 1420                 1425

Ala Asn  Glu Ala Lys Val Val  Leu Ala Ala Asp Asn  Val Trp Gly
    1430                 1435                 1440

Asp Asn  Thr Gly Tyr Gln Phe  Leu Leu Asp Ala Asp  His Asn Thr
    1445                 1450                 1455

Phe Gly  Ser Val Ile Pro Ala  Thr Gly Pro Leu Phe  Thr Gly Thr
    1460                 1465                 1470

Ala Ser  Ser Asp Leu Tyr Ser  Ala Asn Phe Glu Tyr  Leu Ile Pro
    1475                 1480                 1485

Ala Asn  Ala Asp Pro Val Val  Thr Thr Gln Asn Ile  Ile Val Thr
    1490                 1495                 1500

Gly Gln  Gly Glu Val Val Ile  Pro Gly Gly Val Tyr  Asp Tyr Cys
    1505                 1510                 1515

Ile Thr  Asn Pro Glu Pro Ala  Ser Gly Lys Met Trp  Ile Ala Gly
    1520                 1525                 1530

Asp Gly  Gly Asn Gln Pro Ala  Arg Tyr Asp Asp Phe  Thr Phe Glu
    1535                 1540                 1545

Ala Gly  Lys Lys Tyr Thr Phe  Thr Met Arg Arg Ala  Gly Met Gly
    1550                 1555                 1560

Asp Gly  Thr Asp Met Glu Val  Glu Asp Asp Ser Pro  Ala Ser Tyr
    1565                 1570                 1575

Thr Tyr  Thr Val Tyr Arg Asp  Gly Thr Lys Ile Lys  Glu Gly Leu
    1580                 1585                 1590

Thr Glu  Thr Thr Tyr Arg Asp  Ala Gly Met Ser Ala  Gln Ser His
    1595                 1600                 1605

Glu Tyr  Cys Val Glu Val Lys  Tyr Thr Ala Gly Val  Ser Pro Lys
    1610                 1615                 1620

Val Cys  Val Asp Tyr Ile Pro  Asp Gly Val Ala Asp  Val Thr Ala
    1625                 1630                 1635

Gln Lys  Pro Tyr Thr Leu Thr  Val Val Gly Lys Thr  Ile Thr Val
    1640                 1645                 1650

Thr Cys  Gln Gly Glu Ala Met  Ile Tyr Asp Met Asn  Gly Arg Arg
    1655                 1660                 1665

Leu Ala  Ala Gly Arg Asn Thr  Val Val Tyr Thr Ala  Gln Gly Gly
    1670                 1675                 1680

Tyr Tyr  Ala Val Met Val Val  Val Asp Gly Lys Ser  Tyr Val Glu
    1685                 1690                 1695

Lys Leu  Ala Val Lys
    1700
```

<210> SEQ ID NO 70
<211> LENGTH: 5112
<212> TYPE: DNA
<213> ORGANISM: Porphyromonas gingivalis

<400> SEQUENCE: 70

```
ttgcacaagt ttgtttcgat tgctctttgc tcttccttat taggaggaat ggcatttgcg     60

cagcagacag agttgggacg caatccgaat gtgagattgc tcgaatccac tcagcaatcg    120

gtgacaaagg ttcagttccg tatggacaac ctcaagttca ccgaagttca aacccctaag    180

ggaatggcac aagtgccgac ctatacagaa ggggttaatc tttctgaaaa agggatgcct    240
```

```
acgcttccca ttctatcacg ctctttggcg gtttcagaca ctcgtgagat gaaggtagag    300
gttgtttcct caaagttcat cgaaaagaaa aatgtcctga ttgcaccctc caagggcatg    360
attatgcgta acgaagatcc gaaaaagatc ccttacgttt atggaaagag ctactcgcaa    420
aacaaattct tcccgggaga gatcgccacg cttgatgatc cttttatcct tcgtgatgtg    480
cgtggacagg ttgtaaactt tgcgcctttg cagtataacc ctgtgacaaa gacgttgcgc    540
atctatacgg aaatcactgt ggcagtgagc gaaacttcgg agcaaggcaa aaatattctg    600
aacaagaaag gtacatttgc cggctttgaa gacacataca agcgcatgtt catgaactac    660
gagccagggc gttacacacc ggtagaggaa aaacaaaatg gtcgtatgat cgtcatcgta    720
gccaaaaagt atgagggaga tattaaagat ttcgttgatt ggaaaaacca acgcggtctc    780
cgtaccgagg tgaaagtggc agaagatatt gcttctcccg ttacagctaa tgctattcag    840
caattcgtta agcaagaata cgagaaagaa ggtaatgatt tgacctatgt tcttttgatt    900
ggcgatcaca aagatattcc tgccaaaatt actccgggga tcaaatccga ccaggtatat    960
ggacaaatag taggtaatga ccactacaac gaagtcttca tcggtcgttt ctcatgtgag   1020
agcaaagagg atctgaagac acaaatcgat cggactattc actatgagcg caatataacc   1080
acggaagaca aatggctcgg tcaggctctt tgtattgctt cggctgaagg aggcccatcc   1140
gcagacaatg gtgaaagtga tatccagcat gagaatgtaa tcgccaatct gcttacccag   1200
tatggttata ccaagattat caaatgttat gatccgggag taactcctaa aaacattatt   1260
gatgctttca acggaggaat ctcgttggcc aactatacgg gccacggtag cgaaacagct   1320
tggggtacgt ctcacttcgg caccactcat gtgaagcagc ttaccaacag caaccagcta   1380
ccgtttattt tcgacgtagc ttgtgtgaat ggcgatttcc tattcagcat gcctgctttc   1440
gcagaagcat tgatgcgtgc acaaaaagat ggtaagccga caggtactgt tgctatcata   1500
gcgtctacga tcaaccagtc ttgggcttct cctatgcgcg ggcaggatga gatgaacgaa   1560
attctgtgcg aaaaacaccc gaacaacatc aagcgtactt tcggtggtgt caccatgaac   1620
ggtatgtttg ctatggtgga aaagtataaa aaggatggtg agaagatgct cgacacatgg   1680
actgtattcg gcgacccctc gctgctcgtt cgtacacttg tcccgaccaa aatgcaggtt   1740
acggctccgg ctcagattaa tttgacggat gcttcagtca acgtatcttg cgattataat   1800
ggtgctattg ctaccatttc agccaatgga aagatgttcg gttctgcagt tgtcgaaaat   1860
ggaacagcta caatcaatct gacaggtctg acaaatgaaa gcacgcttac ccttacagta   1920
gttggttaca acaaagagac ggttattaag accatcaaca ctaatggtga gcctaacccc   1980
taccagcctg tttccaactt gactgctaca acgcagggtc agaaagtaac gctcaagtgg   2040
gatgcaccga gcacgaaaac caatgcaacc actaataccg ctcgcagcgt ggatggcata   2100
cgagaactgg ttcttctgtc agtcagcgat gcccccgaac ttcttcgcag cggtcaggcc   2160
gagattgttc ttgaagctca cgatgtttgg aatgatggat ccggttatca gattcttttg   2220
gatgcagacc atgatcaata tggacaggtt atacccagtg atacccatac tctttggccg   2280
aactgtagtg tcccggccaa tctgttcgct ccgttcgaat atacggttcc ggaaaatgca   2340
gatccttctt gttcccctac caatatgata atggatggta ctgcatccgt taatataccg   2400
gccggaactt atgactttgc aattgctgct cctcaagcaa atgcaaagat ttggattgcc   2460
ggacaaggac cgacgaaaga agatgattat gtatttgaag ccggtaaaaa ataccatttc   2520
cttatgaaga agatgggtag cggtgatgga actgaattga ctataagcga aggtggtgga   2580
agcgattaca cctatactgt ctatcgtgac ggcacgaaga tcaaggaagg tctgacggct   2640
```

```
acgacattcg aagaagacgg tgtagctgca ggcaatcatg agtattgcgt ggaagttaag   2700
tacacagccg gcgtatctcc gaaggtatgt aaagacgtta cggtagaagg atccaatgaa   2760
tttgctcctg tacagaacct gaccggtagt gcagtcggcc agaaagtaac gcttaagtgg   2820
gatgcaccta atggtacccc gaatccaaat ccaaatccga atccaaatcc gaatcccgga   2880
acaactacac tttccgaatc attcgaaaat ggtattcctg cctcatggaa gacgatcgat   2940
gcagacggtg acgggcatgg ctggaagcct ggaaatgctc ccggaatcgc tggctacaat   3000
agcaatggtt gtgtatattc agagtcattc ggtcttggtg gtataggagt tcttacccct   3060
gacaactatc tgataacacc ggcattggat ttgcctaacg gaggtaagtt gactttctgg   3120
gtatgcgcac aggatgctaa ttatgcatcc gagcactatg cggtgtatgc atcttcgacc   3180
ggtaacgatg catccaactt cacgaatgct ttgttggaag agacgattac ggcaaaaggt   3240
gttcgctcgc cggaagctat tcgtggtcgt atacagggta cttggcgcca gaagacggta   3300
gaccttcccg caggtacgaa atatgttgct ttccgtcact tccaaagcac ggatatgttc   3360
tacatcgacc ttgatgaggt tgagatcaag gccaatggca agcgcgcaga cttcacggaa   3420
acgttcgagt cttctactca tggagaggca ccagcggaat ggactactat cgatgccgat   3480
ggcgatggtc agggttggct ctgtctgtct tccggacaat tggactggct gacagctcat   3540
ggcggcacca acgtagtaag ctctttctca tggaatggaa tggctttgaa tcctgataac   3600
tatctcatct caaaggatgt tacaggcgca acgaaggtaa agtactacta tgcagtcaac   3660
gacggttttc ccggggatca ctatgcggtg atgatctcca agacgggcac gaacgccgga   3720
gacttcacgg ttgttttcga agaaacgcct aacggaataa ataagggcgg agcaagattc   3780
ggtctttcca cggaagccga tggcgccaaa cctcaaagtg tatggatcga gcgtacggta   3840
gatttgcctg cgggcacgaa gtatgttgct ttccgtcact acaattgctc ggatttgaac   3900
tacattcttt tggatgatat tcagttcacc atgggtggca gccccacccc gaccgattat   3960
acctacacgg tgtatcgtga tggtacgaag atcaaggaag gtttgaccga aacgaccttc   4020
gaagaagacg gcgtagctac gggcaatcat gagtattgcg tggaagtgaa gtacacagcc   4080
ggcgtatctc cgaagaaatg tgtaaacgta actgttaatt cgacacagtt caatcctgta   4140
aagaacctga aggcacaacc ggatggcggc gacgtggttc tcaagtggga agccccgagc   4200
gcaaagaaga cagaaggttc tcgtgaagta aaacggatcg gagacggtct tttcgttacg   4260
atcgaacctg caaacgatgt acgtgccaac gaagccaagg ttgtgctcgc agcagacaac   4320
gtatggggag acaatacggg ttaccagttc ttgttggatg ccgatcacaa tacattcgga   4380
agtgtcattc cggcaaccgg tcctctcttt accggaacag cttcttccga tctttacagt   4440
gcgaacttcg agtatttgat cccggccaat gccgatcctg ttgttactac acagaatatt   4500
atcgttacag gacagggtga agttgtaatc cccggtggtg tttacgacta ttgcattacg   4560
aacccggaac ctgcatccgg aaagatgtgg atcgcaggag atggaggcaa ccagcctgca   4620
cgttatgacg atttcacatt cgaagcaggc aagaagtaca ccttcacgat gcgtcgcgcc   4680
ggaatgggag atggaactga tatggaagtc gaagacgatt cacctgcaag ctatacctat   4740
acagtctatc gtgacggcac gaagatcaag gaaggtctga ccgaaacgac ctaccgcgat   4800
gcaggaatga gtgcacaatc tcatgagtat tgcgtggaag ttaagtacac agccggcgta   4860
tctccgaagg tttgtgtgga ttatattcct gacggagtgg cagacgtaac ggctcagaag   4920
ccttacacgc tgacagttgt aggaaagacg atcacggtaa cttgccaagg cgaagctatg   4980
```

```
atctacgaca tgaacggtcg tcgtctggca gccggtcgca acacggttgt ttacacggct   5040

cagggcggct actatgcagt tatggttgtc gttgacggca agtcttacgt agagaaactc   5100

gctgtaaagt aa                                                        5112


<210> SEQ ID NO 71
<211> LENGTH: 64
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 71

ggggacaagt ttgtacaaaa aagcaggctc aggatccaag aaaaagaatt ttttgcttct     60

tggc                                                                  64


<210> SEQ ID NO 72
<211> LENGTH: 62
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 72

ggggaccact ttgtacaaga aagctgggtc gcggccgctt acccgatatg gatctttttcc    60

gt                                                                    62


<210> SEQ ID NO 73
<211> LENGTH: 64
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 73

ggggacaagt ttgtacaaaa aagcaggctc aggatccctt acgaaactaa aaacactgct     60

actt                                                                  64


<210> SEQ ID NO 74
<211> LENGTH: 60
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 74

ggggaccact ttgtacaaga aagctgggtc gcggccgcct acagatccac gtcctgctcg     60


<210> SEQ ID NO 75
<211> LENGTH: 63
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 75

ggggacaagt ttgtacaaaa aagcaggctc actcgagatg aaacgatata caataattct     60

tgc                                                                   63
```

<210> SEQ ID NO 76
<211> LENGTH: 62
<212> TYPE: DNA
<213> ORGANISM: Artificial Sequence
<220> FEATURE:
<223> OTHER INFORMATION: Description of Artificial Sequence: Synthetic DNA

<400> SEQUENCE: 76
ggggaccact ttgtacaaga aagctgggtc gcggccgctt agaaacgagc cccggaatct 60
cc 62

<210> SEQ ID NO 77
<211> LENGTH: 63
<212> TYPE: DNA
<213> ORGANISM: Artificial Sequence
<220> FEATURE:
<223> OTHER INFORMATION: Description of Artificial Sequence: Synthetic DNA

<400> SEQUENCE: 77
ggggacaagt ttgtacaaaa aagcaggctc actcgagcaa atgaaattaa aaagtattct 60
tct 63

<210> SEQ ID NO 78
<211> LENGTH: 63
<212> TYPE: DNA
<213> ORGANISM: Artificial Sequence
<220> FEATURE:
<223> OTHER INFORMATION: Description of Artificial Sequence: Synthetic DNA

<400> SEQUENCE: 78
ggggaccact ttgtacaaga aagctgggtc gcggccgctt agatcaactt cagctcttgg 60
atg 63

<210> SEQ ID NO 79
<211> LENGTH: 62
<212> TYPE: DNA
<213> ORGANISM: Artificial Sequence
<220> FEATURE:
<223> OTHER INFORMATION: Description of Artificial Sequence: Synthetic DNA

<400> SEQUENCE: 79
ggggacaagt ttgtacaaaa aagcaggctc actcgagaaa agaaaaccgc tattctcagc 60
cc 62

<210> SEQ ID NO 80
<211> LENGTH: 59
<212> TYPE: DNA
<213> ORGANISM: Artificial Sequence
<220> FEATURE:
<223> OTHER INFORMATION: Description of Artificial Sequence: Synthetic DNA

<400> SEQUENCE: 80
ggggaccact ttgtacaaga aagctgggtc actagtttac ggcatcgcgg ttttgatcg 59

<210> SEQ ID NO 81
<211> LENGTH: 64
<212> TYPE: DNA
<213> ORGANISM: Artificial Sequence
<220> FEATURE:

<223> OTHER INFORMATION: Description of Artificial Sequence: Synthetic
DNA

<400> SEQUENCE: 81
ggggacaagt ttgtacaaaa aagcaggctc aggatccagg atcaagccct ctctgaaaac 60
gatg 64

<210> SEQ ID NO 82
<211> LENGTH: 64
<212> TYPE: DNA
<213> ORGANISM: Artificial Sequence
<220> FEATURE:
<223> OTHER INFORMATION: Description of Artificial Sequence: Synthetic
DNA

<400> SEQUENCE: 82
ggggaccact ttgtacaaga aagctgggtc gcggccgctc agaagcgata cgacattgtc 60
attg 64

<210> SEQ ID NO 83
<211> LENGTH: 62
<212> TYPE: DNA
<213> ORGANISM: Artificial Sequence
<220> FEATURE:
<223> OTHER INFORMATION: Description of Artificial Sequence: Synthetic
DNA

<400> SEQUENCE: 83
ggggacaagt ttgtacaaaa aagcaggctc aggatccaaa gtaaaacatc tattagctgc 60
at 62

<210> SEQ ID NO 84
<211> LENGTH: 64
<212> TYPE: DNA
<213> ORGANISM: Artificial Sequence
<220> FEATURE:
<223> OTHER INFORMATION: Description of Artificial Sequence: Synthetic
DNA

<400> SEQUENCE: 84
ggggaccact ttgtacaaga aagctgggtc gcggccgctc agaatgctac ctgcacctgt 60
gtta 64

<210> SEQ ID NO 85
<211> LENGTH: 60
<212> TYPE: DNA
<213> ORGANISM: Artificial Sequence
<220> FEATURE:
<223> OTHER INFORMATION: Description of Artificial Sequence: Synthetic
DNA

<400> SEQUENCE: 85
ggggacaagt ttgtacaaaa aagcaggctc acccgggatg tcgttaccgc agcacaatcg 60

<210> SEQ ID NO 86
<211> LENGTH: 60
<212> TYPE: DNA
<213> ORGANISM: Artificial Sequence
<220> FEATURE:
<223> OTHER INFORMATION: Description of Artificial Sequence: Synthetic
DNA

<400> SEQUENCE: 86
ggggaccact ttgtacaaga aagctgggtc actagtttag aattcgatat catagttatg 60

<210> SEQ ID NO 87
<211> LENGTH: 63
<212> TYPE: DNA
<213> ORGANISM: Artificial Sequence
<220> FEATURE:
<223> OTHER INFORMATION: Description of Artificial Sequence: Synthetic DNA

<400> SEQUENCE: 87
ggggacaagt ttgtacaaaa aagcaggctc aggatccaaa agattattac tctctgctgc 60
tat 63

<210> SEQ ID NO 88
<211> LENGTH: 64
<212> TYPE: DNA
<213> ORGANISM: Artificial Sequence
<220> FEATURE:
<223> OTHER INFORMATION: Description of Artificial Sequence: Synthetic DNA

<400> SEQUENCE: 88
ggggaccact ttgtacaaga aagctgggtc gcggccgctc aaggaactaa gactttaagg 60
aaat 64

<210> SEQ ID NO 89
<211> LENGTH: 59
<212> TYPE: DNA
<213> ORGANISM: Artificial Sequence
<220> FEATURE:
<223> OTHER INFORMATION: Description of Artificial Sequence: Synthetic DNA

<400> SEQUENCE: 89
ggggacaagt ttgtacaaaa aagcaggctc aggatccaaa aaactgattt tagcgactt 59

<210> SEQ ID NO 90
<211> LENGTH: 63
<212> TYPE: DNA
<213> ORGANISM: Artificial Sequence
<220> FEATURE:
<223> OTHER INFORMATION: Description of Artificial Sequence: Synthetic DNA

<400> SEQUENCE: 90
ggggaccact ttgtacaaga aagctgggtc gcggccgctt agcgagcaga ggtggctttc 60
ata 63

<210> SEQ ID NO 91
<211> LENGTH: 62
<212> TYPE: DNA
<213> ORGANISM: Artificial Sequence
<220> FEATURE:
<223> OTHER INFORMATION: Description of Artificial Sequence: Synthetic DNA

<400> SEQUENCE: 91
ggggacaagt ttgtacaaaa aagcaggctc aggatccaag acccaagaaa ttatgacaat 60
gc 62

<210> SEQ ID NO 92
<211> LENGTH: 63
<212> TYPE: DNA
<213> ORGANISM: Artificial Sequence
<220> FEATURE:
<223> OTHER INFORMATION: Description of Artificial Sequence: Synthetic
DNA

<400> SEQUENCE: 92
ggggaccact ttgtacaaga aagctgggtc gcggccgctt agcaaacgcc ctgagctacc 60
ata 63

<210> SEQ ID NO 93
<211> LENGTH: 63
<212> TYPE: DNA
<213> ORGANISM: Artificial Sequence
<220> FEATURE:
<223> OTHER INFORMATION: Description of Artificial Sequence: Synthetic
DNA

<400> SEQUENCE: 93
ggggacaagt ttgtacaaaa aagcaggctc aggatccaag aagcacaatt tcaccgcagg 60
acc 63

<210> SEQ ID NO 94
<211> LENGTH: 65
<212> TYPE: DNA
<213> ORGANISM: Artificial Sequence
<220> FEATURE:
<223> OTHER INFORMATION: Description of Artificial Sequence: Synthetic
DNA

<400> SEQUENCE: 94
ggggaccact ttgtacaaga aagctgggtc gcggccgctt agtgcttagc ttcgaattcc 60
ttcat 65

<210> SEQ ID NO 95
<211> LENGTH: 63
<212> TYPE: DNA
<213> ORGANISM: Artificial Sequence
<220> FEATURE:
<223> OTHER INFORMATION: Description of Artificial Sequence: Synthetic
DNA

<400> SEQUENCE: 95
ggggacaagt ttgtacaaaa aagcaggctc actcgagaaa aagtttttct tcgcgctact 60
atc 63

<210> SEQ ID NO 96
<211> LENGTH: 63
<212> TYPE: DNA
<213> ORGANISM: Artificial Sequence
<220> FEATURE:
<223> OTHER INFORMATION: Description of Artificial Sequence: Synthetic
DNA

<400> SEQUENCE: 96
ggggaccact ttgtacaaga aagctgggtc actagtttag aagttgacca taaccttacc 60
cat 63

<210> SEQ ID NO 97
<211> LENGTH: 63
<212> TYPE: DNA
<213> ORGANISM: Artificial Sequence
<220> FEATURE:
<223> OTHER INFORMATION: Description of Artificial Sequence: Synthetic
DNA

<400> SEQUENCE: 97
ggggacaagt ttgtacaaaa aagcaggctc aggatccaaa aaaacaaagt ttttcttgtt 60
ggg 63

<210> SEQ ID NO 98
<211> LENGTH: 71
<212> TYPE: DNA
<213> ORGANISM: Artificial Sequence
<220> FEATURE:
<223> OTHER INFORMATION: Description of Artificial Sequence: Synthetic DNA

<400> SEQUENCE: 98
ggggaccact ttgtacaaga aagctgggtc gcggccgctt accaagtagc agcctgatta 60
acaacaaccc a 71

<210> SEQ ID NO 99
<211> LENGTH: 62
<212> TYPE: DNA
<213> ORGANISM: Artificial Sequence
<220> FEATURE:
<223> OTHER INFORMATION: Description of Artificial Sequence: Synthetic DNA

<400> SEQUENCE: 99
ggggacaagt ttgtacaaaa aagcaggctc aggatccaaa aaattgctat atatactgtt 60
gc 62

<210> SEQ ID NO 100
<211> LENGTH: 65
<212> TYPE: DNA
<213> ORGANISM: Artificial Sequence
<220> FEATURE:
<223> OTHER INFORMATION: Description of Artificial Sequence: Synthetic DNA

<400> SEQUENCE: 100
ggggaccact ttgtacaaga aagctgggtc gcggccgctt acggattcgc caccgttatc 60
gtctg 65

<210> SEQ ID NO 101
<211> LENGTH: 62
<212> TYPE: DNA
<213> ORGANISM: Artificial Sequence
<220> FEATURE:
<223> OTHER INFORMATION: Description of Artificial Sequence: Synthetic DNA

<400> SEQUENCE: 101
ggggacaagt ttgtacaaaa aagcaggctc aggatccaaa aaaatcattt tctccgcact 60
ct 62

<210> SEQ ID NO 102
<211> LENGTH: 62
<212> TYPE: DNA
<213> ORGANISM: Artificial Sequence
<220> FEATURE:
<223> OTHER INFORMATION: Description of Artificial Sequence: Synthetic DNA

<400> SEQUENCE: 102
ggggaccact ttgtacaaga aagctgggtc gcggccgctt atttaacggg gtatgtataa 60
gc 62

<210> SEQ ID NO 103
<211> LENGTH: 64
<212> TYPE: DNA
<213> ORGANISM: Artificial Sequence
<220> FEATURE:
<223> OTHER INFORMATION: Description of Artificial Sequence: Synthetic DNA

<400> SEQUENCE: 103
ggggacaagt ttgtacaaaa aagcaggctc aggatccaca aacgatatct tgcagcgtct 60
tgcg 64

<210> SEQ ID NO 104
<211> LENGTH: 64
<212> TYPE: DNA
<213> ORGANISM: Artificial Sequence
<220> FEATURE:
<223> OTHER INFORMATION: Description of Artificial Sequence: Synthetic DNA

<400> SEQUENCE: 104
ggggaccact ttgtacaaga aagctgggtc gcggccgctt agatagtctg agttttctct 60
ttga 64

<210> SEQ ID NO 105
<211> LENGTH: 62
<212> TYPE: DNA
<213> ORGANISM: Artificial Sequence
<220> FEATURE:
<223> OTHER INFORMATION: Description of Artificial Sequence: Synthetic DNA

<400> SEQUENCE: 105
ggggacaagt ttgtacaaaa aagcaggctc aggatccacg aaagtaggta ttaacggctt 60
tg 62

<210> SEQ ID NO 106
<211> LENGTH: 63
<212> TYPE: DNA
<213> ORGANISM: Artificial Sequence
<220> FEATURE:
<223> OTHER INFORMATION: Description of Artificial Sequence: Synthetic DNA

<400> SEQUENCE: 106
ggggaccact ttgtacaaga aagctgggtc gcggccgctt atgcgtttac cttagccatg 60
tag 63

<210> SEQ ID NO 107
<211> LENGTH: 63
<212> TYPE: DNA
<213> ORGANISM: Artificial Sequence
<220> FEATURE:
<223> OTHER INFORMATION: Description of Artificial Sequence: Synthetic DNA

<400> SEQUENCE: 107
ggggacaagt ttgtacaaaa aagcaggctc aggatccaaa ataagcgaaa acgtaactaa 60
agc 63

<210> SEQ ID NO 108

<211> LENGTH: 66
<212> TYPE: DNA
<213> ORGANISM: Artificial Sequence
<220> FEATURE:
<223> OTHER INFORMATION: Description of Artificial Sequence: Synthetic DNA

<400> SEQUENCE: 108
ggggaccact ttgtacaaga aagctgggtc gcggccgctt atctccgggc gagctgatga 60
tcgatg 66

<210> SEQ ID NO 109
<211> LENGTH: 61
<212> TYPE: DNA
<213> ORGANISM: Artificial Sequence
<220> FEATURE:
<223> OTHER INFORMATION: Description of Artificial Sequence: Synthetic DNA

<400> SEQUENCE: 109
ggggacaagt ttgtacaaaa aagcaggctc acccgggaaa aaagacagcg taattttcga 60
t 61

<210> SEQ ID NO 110
<211> LENGTH: 63
<212> TYPE: DNA
<213> ORGANISM: Artificial Sequence
<220> FEATURE:
<223> OTHER INFORMATION: Description of Artificial Sequence: Synthetic DNA

<400> SEQUENCE: 110
ggggaccact ttgtacaaga aagctgggtc actagtttac caagcaaaga gaggataatc 60
ggc 63

<210> SEQ ID NO 111
<211> LENGTH: 61
<212> TYPE: DNA
<213> ORGANISM: Artificial Sequence
<220> FEATURE:
<223> OTHER INFORMATION: Description of Artificial Sequence: Synthetic DNA

<400> SEQUENCE: 111
ggggacaagt ttgtacaaaa aagcaggctc acccgggaaa aagctatttc tctcgctcac 60
g 61

<210> SEQ ID NO 112
<211> LENGTH: 62
<212> TYPE: DNA
<213> ORGANISM: Artificial Sequence
<220> FEATURE:
<223> OTHER INFORMATION: Description of Artificial Sequence: Synthetic DNA

<400> SEQUENCE: 112
ggggaccact ttgtacaaga aagctgggtc actagtttat ttgccatcgg attgcggatt 60
ga 62

<210> SEQ ID NO 113
<211> LENGTH: 62
<212> TYPE: DNA
<213> ORGANISM: Artificial Sequence
<220> FEATURE:

<223> OTHER INFORMATION: Description of Artificial Sequence: Synthetic DNA

<400> SEQUENCE: 113

```
ggggacaagt ttgtacaaaa aagcaggctc acccgggaac aaattttaca aatcactttt     60

gc                                                                     62
```

<210> SEQ ID NO 114
<211> LENGTH: 64
<212> TYPE: DNA
<213> ORGANISM: Artificial Sequence
<220> FEATURE:
<223> OTHER INFORMATION: Description of Artificial Sequence: Synthetic DNA

<400> SEQUENCE: 114

```
ggggaccact ttgtacaaga aagctgggtc actagtctac tgcttcacga tcttttggct     60

caca                                                                   64
```

<210> SEQ ID NO 115
<211> LENGTH: 59
<212> TYPE: DNA
<213> ORGANISM: Artificial Sequence
<220> FEATURE:
<223> OTHER INFORMATION: Description of Artificial Sequence: Synthetic DNA

<400> SEQUENCE: 115

```
ggggacaagt ttgtacaaaa aagcaggctc acccgggaaa aaaacgctcg taatagtcg      59
```

<210> SEQ ID NO 116
<211> LENGTH: 58
<212> TYPE: DNA
<213> ORGANISM: Artificial Sequence
<220> FEATURE:
<223> OTHER INFORMATION: Description of Artificial Sequence: Synthetic DNA

<400> SEQUENCE: 116

```
ggggaccact ttgtacaaga aagctgggtc actagttcat tctcctttga taaagcgg       58
```

<210> SEQ ID NO 117
<211> LENGTH: 61
<212> TYPE: DNA
<213> ORGANISM: Artificial Sequence
<220> FEATURE:
<223> OTHER INFORMATION: Description of Artificial Sequence: Synthetic DNA

<400> SEQUENCE: 117

```
ggggacaagt ttgtacaaaa aagcaggctc actcgagaaa aagattcttg aagtaacggg     60

t                                                                      61
```

<210> SEQ ID NO 118
<211> LENGTH: 61
<212> TYPE: DNA
<213> ORGANISM: Artificial Sequence
<220> FEATURE:
<223> OTHER INFORMATION: Description of Artificial Sequence: Synthetic DNA

<400> SEQUENCE: 118

```
ggggaccact ttgtacaaga aagctgggtc actagtttac ttggtagcgt aggcagacag     60

c                                                                      61
```

<210> SEQ ID NO 119
<211> LENGTH: 63
<212> TYPE: DNA
<213> ORGANISM: Artificial Sequence
<220> FEATURE:
<223> OTHER INFORMATION: Description of Artificial Sequence: Synthetic DNA

<400> SEQUENCE: 119
ggggacaagt ttgtacaaaa aagcaggctc actcgagaaa gctaaatctt tattattagc 60
act 63

<210> SEQ ID NO 120
<211> LENGTH: 62
<212> TYPE: DNA
<213> ORGANISM: Artificial Sequence
<220> FEATURE:
<223> OTHER INFORMATION: Description of Artificial Sequence: Synthetic DNA

<400> SEQUENCE: 120
ggggaccact ttgtacaaga aagctgggtc actagtttat tccgctgcag tcattactac 60
aa 62

<210> SEQ ID NO 121
<211> LENGTH: 63
<212> TYPE: DNA
<213> ORGANISM: Artificial Sequence
<220> FEATURE:
<223> OTHER INFORMATION: Description of Artificial Sequence: Synthetic DNA

<400> SEQUENCE: 121
ggggacaagt ttgtacaaaa aagcaggctc actcgagagg aaattattat tgctgatcgc 60
ggc 63

<210> SEQ ID NO 122
<211> LENGTH: 61
<212> TYPE: DNA
<213> ORGANISM: Artificial Sequence
<220> FEATURE:
<223> OTHER INFORMATION: Description of Artificial Sequence: Synthetic DNA

<400> SEQUENCE: 122
ggggaccact ttgtacaaga aagctgggtc actagtttac ttgatagcga gtttctctac 60
g 61

<210> SEQ ID NO 123
<211> LENGTH: 59
<212> TYPE: DNA
<213> ORGANISM: Artificial Sequence
<220> FEATURE:
<223> OTHER INFORMATION: Description of Artificial Sequence: Synthetic DNA

<400> SEQUENCE: 123
ggggacaagt ttgtacaaaa aagcaggctc actcgagaaa aagcttttac aggctaaag 59

<210> SEQ ID NO 124
<211> LENGTH: 65
<212> TYPE: DNA
<213> ORGANISM: Artificial Sequence
<220> FEATURE:
<223> OTHER INFORMATION: Description of Artificial Sequence: Synthetic DNA

<400> SEQUENCE: 124
ggggaccact ttgtacaaga aagctgggtc gcggccgctt atttgagaat tttcattgtc 60
tcacg 65

<210> SEQ ID NO 125
<211> LENGTH: 63
<212> TYPE: DNA
<213> ORGANISM: Artificial Sequence
<220> FEATURE:
<223> OTHER INFORMATION: Description of Artificial Sequence: Synthetic DNA

<400> SEQUENCE: 125
ggggacaagt ttgtacaaaa aagcaggctc actcgagaaa agaatgacgc tattcttcct 60
ttg 63

<210> SEQ ID NO 126
<211> LENGTH: 59
<212> TYPE: DNA
<213> ORGANISM: Artificial Sequence
<220> FEATURE:
<223> OTHER INFORMATION: Description of Artificial Sequence: Synthetic DNA

<400> SEQUENCE: 126
ggggaccact ttgtacaaga aagctgggtc gcggccgctt agaaagaaat ctgaatacc 59

<210> SEQ ID NO 127
<211> LENGTH: 61
<212> TYPE: DNA
<213> ORGANISM: Artificial Sequence
<220> FEATURE:
<223> OTHER INFORMATION: Description of Artificial Sequence: Synthetic DNA

<400> SEQUENCE: 127
ggggacaagt ttgtacaaaa aagcaggctc actcgagttg aacaagtttg tttcgattgc 60
t 61

<210> SEQ ID NO 128
<211> LENGTH: 61
<212> TYPE: DNA
<213> ORGANISM: Artificial Sequence
<220> FEATURE:
<223> OTHER INFORMATION: Description of Artificial Sequence: Synthetic DNA

<400> SEQUENCE: 128
ggggaccact ttgtacaaga aagctgggtc actagtttac tttacagcga gtttctctac 60
g 61

<210> SEQ ID NO 129
<211> LENGTH: 61
<212> TYPE: DNA
<213> ORGANISM: Artificial Sequence
<220> FEATURE:
<223> OTHER INFORMATION: Description of Artificial Sequence: Synthetic DNA

<400> SEQUENCE: 129 gggggacaagt ttgtacaaaa aagcaggctc actcgagaag gtaaagtact taatgctcac 60
a 61

<210> SEQ ID NO 130
<211> LENGTH: 63
<212> TYPE: DNA
<213> ORGANISM: Artificial Sequence
<220> FEATURE:
<223> OTHER INFORMATION: Description of Artificial Sequence: Synthetic DNA

<400> SEQUENCE: 130
ggggaccact ttgtacaaga aagctgggtc actagtttac ttggagcgaa cgattacaac 60
acg 63

<210> SEQ ID NO 131
<211> LENGTH: 68
<212> TYPE: DNA
<213> ORGANISM: Artificial Sequence
<220> FEATURE:
<223> OTHER INFORMATION: Description of Artificial Sequence: Synthetic DNA

<400> SEQUENCE: 131
ggggacaagt ttgtacaaaa aagcaggctc actcgagaaa aaaataattt attgggttgc 60
gacagttt 68

<210> SEQ ID NO 132
<211> LENGTH: 69
<212> TYPE: DNA
<213> ORGANISM: Artificial Sequence
<220> FEATURE:
<223> OTHER INFORMATION: Description of Artificial Sequence: Synthetic DNA

<400> SEQUENCE: 132
ggggaccact ttgtacaaga aagctgggtc actagtttat atcggccagt tctttattaa 60
ctgcggatt 69

<210> SEQ ID NO 133
<211> LENGTH: 20
<212> TYPE: DNA
<213> ORGANISM: Artificial Sequence
<220> FEATURE:
<223> OTHER INFORMATION: Description of Artificial Sequence: Synthetic DNA

<400> SEQUENCE: 133
attacagctc aattcgatta 20

<210> SEQ ID NO 134
<211> LENGTH: 20
<212> TYPE: DNA
<213> ORGANISM: Artificial Sequence
<220> FEATURE:
<223> OTHER INFORMATION: Description of Artificial Sequence: Synthetic DNA

<400> SEQUENCE: 134
agcgcagttg ccaatagcta 20

<210> SEQ ID NO 135
<211> LENGTH: 20
<212> TYPE: DNA

<213> ORGANISM: Artificial Sequence
<220> FEATURE:
<223> OTHER INFORMATION: Description of Artificial Sequence: Synthetic DNA

<400> SEQUENCE: 135
ccttcggaga ggtaataact 20

<210> SEQ ID NO 136
<211> LENGTH: 20
<212> TYPE: DNA
<213> ORGANISM: Artificial Sequence
<220> FEATURE:
<223> OTHER INFORMATION: Description of Artificial Sequence: Synthetic DNA

<400> SEQUENCE: 136
caggctgtac ataatcgaat 20

<210> SEQ ID NO 137
<211> LENGTH: 20
<212> TYPE: DNA
<213> ORGANISM: Artificial Sequence
<220> FEATURE:
<223> OTHER INFORMATION: Description of Artificial Sequence: Synthetic DNA

<400> SEQUENCE: 137
gtgaatggcg atttcctatt 20

<210> SEQ ID NO 138
<211> LENGTH: 20
<212> TYPE: DNA
<213> ORGANISM: Artificial Sequence
<220> FEATURE:
<223> OTHER INFORMATION: Description of Artificial Sequence: Synthetic DNA

<400> SEQUENCE: 138
agcagctacg tcgaaaataa 20

<210> SEQ ID NO 139
<211> LENGTH: 20
<212> TYPE: DNA
<213> ORGANISM: Artificial Sequence
<220> FEATURE:
<223> OTHER INFORMATION: Description of Artificial Sequence: Synthetic DNA

<400> SEQUENCE: 139
ctttcgcaga agcattgatg 20

<210> SEQ ID NO 140
<211> LENGTH: 20
<212> TYPE: DNA
<213> ORGANISM: Artificial Sequence
<220> FEATURE:
<223> OTHER INFORMATION: Description of Artificial Sequence: Synthetic DNA

<400> SEQUENCE: 140
caggcatgct gaataggaaa 20

<210> SEQ ID NO 141
<211> LENGTH: 860
<212> TYPE: PRT
<213> ORGANISM: Porphyromonas gingivalis

<400> SEQUENCE: 141

```
Arg Lys Leu Leu Leu Leu Ile Ala Ala Ser Leu Leu Gly Val Gly Leu
1               5                   10                  15

Tyr Ala Gln Ser Ala Lys Ile Lys Leu Asp Ala Pro Thr Thr Arg Thr
            20                  25                  30

Thr Cys Thr Asn Asn Ser Phe Lys Gln Phe Asp Ala Ser Phe Ser Phe
        35                  40                  45

Asn Glu Val Glu Leu Thr Lys Val Glu Thr Lys Gly Gly Thr Phe Ala
    50                  55                  60

Ser Val Ser Ile Pro Gly Ala Phe Pro Thr Gly Glu Val Gly Ser Pro
65                  70                  75                  80

Glu Val Pro Ala Val Arg Lys Leu Ile Ala Val Pro Val Gly Ala Thr
                85                  90                  95

Pro Val Val Arg Val Lys Ser Phe Thr Glu Gln Val Tyr Ser Leu Asn
            100                 105                 110

Gln Tyr Gly Ser Glu Lys Leu Met Pro His Gln Pro Ser Met Ser Lys
        115                 120                 125

Ser Asp Asp Pro Glu Lys Val Pro Phe Val Tyr Asn Ala Ala Ala Tyr
    130                 135                 140

Ala Arg Lys Gly Phe Val Gly Gln Glu Leu Thr Gln Val Glu Met Leu
145                 150                 155                 160

Gly Thr Met Arg Gly Val Arg Ile Ala Ala Leu Thr Ile Asn Pro Val
                165                 170                 175

Gln Tyr Asp Val Val Ala Asn Gln Leu Lys Val Arg Asn Asn Ile Glu
            180                 185                 190

Ile Glu Val Ser Phe Gln Gly Ala Asp Glu Val Ala Thr Gln Arg Leu
        195                 200                 205

Tyr Asp Ala Ser Phe Ser Pro Tyr Phe Glu Thr Ala Tyr Lys Gln Leu
    210                 215                 220

Phe Asn Arg Asp Val Tyr Thr Asp His Gly Asp Leu Tyr Asn Thr Pro
225                 230                 235                 240

Val Arg Met Leu Val Val Ala Gly Ala Lys Phe Lys Glu Ala Leu Lys
                245                 250                 255

Pro Trp Leu Thr Trp Lys Ala Gln Lys Gly Phe Tyr Leu Asp Val His
            260                 265                 270

Tyr Thr Asp Glu Ala Glu Val Gly Thr Thr Asn Ala Ser Ile Lys Ala
        275                 280                 285

Phe Ile His Lys Lys Tyr Asn Asp Gly Leu Ala Ala Ser Ala Ala Pro
    290                 295                 300

Val Phe Leu Ala Leu Val Gly Asp Thr Asp Val Ile Ser Gly Glu Lys
305                 310                 315                 320

Gly Lys Lys Thr Lys Lys Val Thr Asp Leu Tyr Tyr Ser Ala Val Asp
                325                 330                 335

Gly Asp Tyr Phe Pro Glu Met Tyr Thr Phe Arg Met Ser Ala Ser Ser
            340                 345                 350

Pro Glu Glu Leu Thr Asn Ile Ile Asp Lys Val Leu Met Tyr Glu Lys
        355                 360                 365

Ala Thr Met Pro Asp Lys Ser Tyr Leu Glu Lys Val Leu Leu Ile Ala
    370                 375                 380

Gly Ala Asp Tyr Ser Trp Asn Ser Gln Val Gly Gln Pro Thr Ile Lys
385                 390                 395                 400

Tyr Gly Met Gln Tyr Tyr Tyr Asn Gln Glu His Gly Tyr Thr Asp Val
```

```
                405                 410                 415

Tyr Asn Tyr Leu Lys Ala Pro Tyr Thr Gly Cys Tyr Ser His Leu Asn
            420                 425                 430

Thr Gly Val Ser Phe Ala Asn Tyr Thr Ala His Gly Ser Glu Thr Ala
        435                 440                 445

Trp Ala Asp Pro Leu Leu Thr Thr Ser Gln Leu Lys Ala Leu Thr Asn
    450                 455                 460

Lys Asp Lys Tyr Phe Leu Ala Ile Gly Asn Cys Ala Ile Thr Ala Gln
465                 470                 475                 480

Phe Asp Tyr Val Gln Pro Cys Phe Gly Glu Val Ile Thr Arg Val Lys
                485                 490                 495

Glu Lys Gly Ala Tyr Ala Tyr Ile Gly Ser Ser Pro Asn Ser Tyr Trp
            500                 505                 510

Gly Glu Asp Tyr Tyr Trp Ser Val Gly Ala Asn Ala Val Phe Gly Val
        515                 520                 525

Gln Pro Thr Phe Glu Gly Thr Ser Met Gly Ser Tyr Asp Ala Thr Phe
    530                 535                 540

Leu Glu Asp Ser Tyr Asn Thr Val Asn Ser Ile Met Trp Ala Gly Asn
545                 550                 555                 560

Leu Ala Ala Thr His Ala Gly Asn Ile Gly Asn Ile Thr His Ile Gly
                565                 570                 575

Ala His Tyr Tyr Trp Glu Ala Tyr His Val Leu Gly Asp Gly Ser Val
            580                 585                 590

Met Pro Tyr Arg Ala Met Pro Lys Thr Asn Thr Tyr Thr Leu Pro Ala
        595                 600                 605

Ser Leu Pro Gln Asn Gln Ala Ser Tyr Ser Ile Gln Ala Ser Ala Gly
    610                 615                 620

Ser Tyr Val Ala Ile Ser Lys Asp Gly Val Leu Tyr Gly Thr Gly Val
625                 630                 635                 640

Ala Asn Ala Ser Gly Val Ala Thr Val Ser Met Thr Lys Gln Ile Thr
                645                 650                 655

Glu Asn Gly Asn Tyr Asp Val Val Ile Thr Arg Ser Asn Tyr Leu Pro
            660                 665                 670

Val Ile Lys Gln Ile Gln Val Gly Glu Pro Ser Pro Tyr Gln Pro Val
        675                 680                 685

Ser Asn Leu Thr Ala Thr Thr Gln Gly Gln Lys Val Thr Leu Lys Trp
    690                 695                 700

Glu Ala Pro Ser Ala Lys Lys Ala Glu Gly Ser Arg Glu Val Lys Arg
705                 710                 715                 720

Ile Gly Asp Gly Leu Phe Val Thr Ile Glu Pro Ala Asn Asp Val Arg
                725                 730                 735

Ala Asn Glu Ala Lys Val Val Leu Ala Ala Asp Asn Val Trp Gly Asp
            740                 745                 750

Asn Thr Gly Tyr Gln Phe Leu Leu Asp Ala Asp His Asn Thr Phe Gly
        755                 760                 765

Ser Val Ile Pro Ala Thr Gly Pro Leu Phe Thr Gly Thr Ala Ser Ser
    770                 775                 780

Asn Leu Tyr Ser Ala Asn Phe Glu Tyr Leu Ile Pro Ala Asn Ala Asp
785                 790                 795                 800

Pro Val Val Thr Thr Gln Asn Ile Ile Val Thr Gly Gln Gly Glu Val
                805                 810                 815

Val Ile Pro Gly Gly Val Tyr Asp Tyr Cys Ile Thr Asn Pro Glu Pro
            820                 825                 830
```

```
Ala Ser Gly Lys Met Trp Ile Ala Gly Asp Gly Gly Asn Gln Pro Ala
        835                 840                 845

Arg Tyr Asp Asp Phe Thr Phe Glu Ala Gly Lys Lys
    850                 855                 860


<210> SEQ ID NO 142
<211> LENGTH: 2583
<212> TYPE: DNA
<213> ORGANISM: Porphyromonas  gingivalis

<400> SEQUENCE: 142

aggaaattat tattgctgat cgcggcgtcc cttttgggag ttggtcttta cgcccaaagc     60

gccaagatta agcttgatgc tccgactact cgaacgacat gtacgaacaa tagcttcaag    120

cagttcgatg caagcttttc gttcaatgaa gtcgagctga caaaggtgga gaccaaaggt    180

ggtactttcg cctcagtgtc aattccgggt gcattcccga ccggtgaggt tggttctccc    240

gaagtgccag cagttaggaa gttgattgct gtgcctgtcg gagccacacc tgttgttcgc    300

gtgaaaagtt ttaccgagca agtttactct ctgaaccaat acggttccga aaaactcatg    360

ccacatcaac cctctatgag caagagtgat gatcccgaaa aggttccctt cgtttacaat    420

gctgctgctt atgcacgcaa aggttttgtc ggacaagaac tgacccaagt agaaatgttg    480

gggacaatgc gtggtgttcg cattgcagct cttaccatta atcctgttca gtatgatgtg    540

gttgcaaacc aattgaaggt tagaaacaac atcgaaattg aagtaagctt tcaaggagct    600

gatgaagtag ctacacaacg tttgtatgat gcttctttta gcccttattt cgaaacagct    660

tataaacagc tcttcaatag agatgtttat acagatcatg gcgacttgta taatacgccg    720

gttcgtatgc ttgttgttgc aggtgcaaaa ttcaaagaag ctctcaagcc ttggctcact    780

tggaaggctc aaaagggctt ctatctggat gtgcattaca cagacgaagc tgaagtagga    840

acgacaaacg cctctatcaa ggcatttatt cacaagaaat acaatgatgg attggcagct    900

agtgctgctc cggtcttctt ggctttggtt ggtgacactg acgttattag cggagaaaaa    960

ggaaagaaaa caaaaaaagt taccgacttg tattacagtg cagtcgatgg cgactatttc   1020

cctgaaatgt atactttccg tatgtctgct tcttccccag aagaactgac gaacatcatt   1080

gataaggtat tgatgtatga aaaggctact atgccagata agagttattt ggagaaagtt   1140

ctcttgattg caggtgcaga ttatagctgg aattcccagg taggtcagcc aaccattaaa   1200

tacggtatgc agtactacta caaccaagag catggttata ccgacgtgta caactatctc   1260

aaagcccctt atacaggttg ctacagtcat ttgaataccg gagtcagctt tgcaaactat   1320

acagcgcatg gatctgagac cgcatgggct gatccacttc tgactacttc tcaactgaaa   1380

gcactcacta ataaggacaa atacttctta gctattggca actgcgctat tacagctcaa   1440

ttcgattatg tacagccttg cttcggagag gtaataactc gcgttaagga gaaaggggct   1500

tatgcctata tcggttcatc tccaaattct tattggggcg aggactacta ttggagtgtg   1560

ggtgctaatg ccgtatttgg tgttcagcct acttttgaag gtacgtctat gggttcttat   1620

gatgctacat tcttggagga ttcgtacaac acagtgaatt ctattatgtg ggcaggtaat   1680

cttgccgcta ctcatgctgg aaatatcggc aatattaccc atattggtgc tcattactat   1740

tgggaagctt atcatgtcct tggcgatggt tcggttatgc cttatcgtgc aatgcctaag   1800

accaatactt atacgcttcc tgcctctttg cctcagaatc aggcttctta tagcattcag   1860

gcttctgccg gttcttacgt agctatttct aaagatggag ttttgtatgg aacaggtgtt   1920
```

```
gctaatgcca gcggtgttgc gactgtgagt atgactaagc agattacgga aaatggtaat   1980

tatgatgtag ttatcactcg ctctaattat cttcctgtga tcaagcaaat tcaggtaggt   2040

gagcctagcc cctaccagcc cgtttccaac ttgacagcta caacgcaggg tcagaaagta   2100

acgctcaagt gggaagcacc gagcgcaaag aaggcagaag gttcccgtga agtaaaacgg   2160

atcggagacg gtcttttcgt tacgatcgaa cctgcaaacg atgtacgtgc caacgaagcc   2220

aaggttgtgc ttgcggcaga caacgtatgg ggagacaata cgggttacca gttcttgttg   2280

gatgccgatc acaatacatt cggaagtgtc attccggcaa ccggtcctct ctttaccgga   2340

acagcttctt ccaatcttta cagtgcgaac ttcgagtatt tgatcccggc caatgccgat   2400

cctgttgtta ctacacagaa tattatcgtt acaggacagg gtgaagttgt aatccccggt   2460

ggtgtttacg actattgcat tacgaacccg gaacctgcat ccggaaagat gtggatcgca   2520

ggagatggag gcaaccagcc tgcacgttat gacgatttca cattcgaagc aggcaagaag   2580

taa                                                                 2583
```

<210> SEQ ID NO 143
<211> LENGTH: 871
<212> TYPE: PRT
<213> ORGANISM: Porphyromonas gingivalis

<400> SEQUENCE: 143

```
Tyr Thr Phe Thr Met Arg Arg Ala Gly Met Gly Asp Gly Thr Asp Met
1               5                   10                  15

Glu Val Glu Asp Asp Ser Pro Ala Ser Tyr Thr Tyr Thr Val Tyr Arg
            20                  25                  30

Asp Gly Thr Lys Ile Lys Glu Gly Leu Thr Ala Thr Thr Phe Glu Glu
        35                  40                  45

Asp Gly Val Ala Ala Gly Asn His Glu Tyr Cys Val Glu Val Lys Tyr
    50                  55                  60

Thr Ala Gly Val Ser Pro Lys Val Cys Lys Asp Val Thr Val Glu Gly
65                  70                  75                  80

Ser Asn Glu Phe Ala Pro Val Gln Asn Leu Thr Gly Ser Ser Val Gly
                85                  90                  95

Gln Lys Val Thr Leu Lys Trp Asp Ala Pro Asn Gly Thr Pro Asn Pro
            100                 105                 110

Asn Pro Asn Pro Asn Pro Asn Pro Gly Thr Thr Leu Ser Glu Ser Phe
        115                 120                 125

Glu Asn Gly Ile Pro Ala Ser Trp Lys Thr Ile Asp Ala Asp Gly Asp
    130                 135                 140

Gly His Gly Trp Lys Pro Gly Asn Ala Pro Gly Ile Ala Gly Tyr Asn
145                 150                 155                 160

Ser Asn Gly Cys Val Tyr Ser Glu Ser Phe Gly Leu Gly Gly Ile Gly
                165                 170                 175

Val Leu Thr Pro Asp Asn Tyr Leu Ile Thr Pro Ala Leu Asp Leu Pro
            180                 185                 190

Asn Gly Gly Lys Leu Thr Phe Trp Val Cys Ala Gln Asp Ala Asn Tyr
        195                 200                 205

Ala Ser Glu His Tyr Ala Val Tyr Ala Ser Ser Thr Gly Asn Asp Ala
    210                 215                 220

Ser Asn Phe Thr Asn Ala Leu Leu Glu Glu Thr Ile Thr Ala Lys Gly
225                 230                 235                 240

Val Arg Ser Pro Lys Ala Ile Arg Gly Arg Ile Gln Gly Thr Trp Arg
                245                 250                 255
```

```
Gln Lys Thr Val Asp Leu Pro Ala Gly Thr Lys Tyr Val Ala Phe Arg
            260                 265                 270

His Phe Gln Ser Thr Asp Met Phe Tyr Ile Asp Leu Asp Glu Val Glu
        275                 280                 285

Ile Lys Ala Asn Gly Lys Arg Ala Asp Phe Thr Glu Thr Phe Glu Ser
    290                 295                 300

Ser Thr His Gly Glu Ala Pro Ala Glu Trp Thr Thr Ile Asp Ala Asp
305                 310                 315                 320

Gly Asp Gly Gln Gly Trp Leu Cys Leu Ser Ser Gly Gln Leu Asp Trp
                325                 330                 335

Leu Thr Ala His Gly Gly Ser Asn Val Val Ser Ser Phe Ser Trp Asn
            340                 345                 350

Gly Met Ala Leu Asn Pro Asp Asn Tyr Leu Ile Ser Lys Asp Val Thr
        355                 360                 365

Gly Ala Thr Lys Val Lys Tyr Tyr Tyr Ala Val Asn Asp Gly Phe Pro
    370                 375                 380

Gly Asp His Tyr Ala Val Met Ile Ser Lys Thr Gly Thr Asn Ala Gly
385                 390                 395                 400

Asp Phe Thr Val Val Phe Glu Glu Thr Pro Asn Gly Ile Asn Lys Gly
                405                 410                 415

Gly Ala Arg Phe Gly Leu Ser Thr Glu Ala Asn Gly Ala Lys Pro Gln
            420                 425                 430

Ser Val Trp Ile Glu Arg Thr Val Asp Leu Pro Ala Gly Thr Lys Tyr
        435                 440                 445

Val Ala Phe Arg His Tyr Asn Cys Ser Asp Leu Asn Tyr Ile Leu Leu
    450                 455                 460

Asp Asp Ile Gln Phe Thr Met Gly Gly Ser Pro Thr Pro Thr Asp Tyr
465                 470                 475                 480

Thr Tyr Thr Val Tyr Arg Asp Gly Thr Lys Ile Lys Glu Gly Leu Thr
                485                 490                 495

Glu Thr Thr Phe Glu Glu Asp Gly Val Ala Thr Gly Asn His Glu Tyr
            500                 505                 510

Cys Val Glu Val Lys Tyr Thr Ala Gly Val Ser Pro Lys Lys Cys Val
        515                 520                 525

Asn Val Thr Val Asn Ser Thr Gln Phe Asn Pro Val Gln Asn Leu Thr
    530                 535                 540

Ala Glu Gln Ala Pro Asn Ser Met Asp Ala Ile Leu Lys Trp Asn Ala
545                 550                 555                 560

Pro Ala Ser Lys Arg Ala Glu Val Leu Asn Glu Asp Phe Glu Asn Gly
                565                 570                 575

Ile Pro Ala Ser Trp Lys Thr Ile Asp Ala Asp Gly Asp Gly Asn Asn
            580                 585                 590

Trp Thr Thr Thr Pro Pro Pro Gly Gly Ser Ser Phe Ala Gly His Asn
        595                 600                 605

Ser Ala Ile Cys Val Ser Ser Ala Ser Tyr Ile Asn Phe Glu Gly Pro
    610                 615                 620

Gln Asn Pro Asp Asn Tyr Leu Val Thr Pro Glu Leu Ser Leu Pro Gly
625                 630                 635                 640

Gly Gly Thr Leu Thr Phe Trp Val Cys Ala Gln Asp Ala Asn Tyr Ala
                645                 650                 655

Ser Glu His Tyr Ala Val Tyr Ala Ser Ser Thr Gly Asn Asp Ala Ser
            660                 665                 670
```

```
Asn Phe Ala Asn Ala Leu Leu Glu Glu Val Leu Thr Ala Lys Thr Val
        675                 680                 685

Val Thr Ala Pro Glu Ala Ile Arg Gly Thr Arg Ala Gln Gly Thr Trp
    690                 695                 700

Tyr Gln Lys Thr Val Gln Leu Pro Ala Gly Thr Lys Tyr Val Ala Phe
705                 710                 715                 720

Arg His Phe Gly Cys Thr Asp Phe Phe Trp Ile Asn Leu Asp Asp Val
                725                 730                 735

Val Ile Thr Ser Gly Asn Ala Pro Ser Tyr Thr Tyr Thr Ile Tyr Arg
            740                 745                 750

Asn Asn Thr Gln Ile Ala Ser Gly Val Thr Glu Thr Thr Tyr Arg Asp
        755                 760                 765

Pro Asp Leu Ala Thr Gly Phe Tyr Thr Tyr Gly Val Lys Val Val Tyr
    770                 775                 780

Pro Asn Gly Glu Ser Ala Ile Glu Thr Ala Thr Leu Asn Ile Thr Ser
785                 790                 795                 800

Leu Ala Asp Val Thr Ala Gln Lys Pro Tyr Thr Leu Thr Val Val Gly
                805                 810                 815

Lys Thr Ile Thr Val Thr Cys Gln Gly Glu Ala Met Ile Tyr Asp Met
            820                 825                 830

Asn Gly Arg Arg Leu Ala Ala Gly Arg Asn Thr Val Val Tyr Thr Ala
        835                 840                 845

Gln Gly Gly His Tyr Ala Val Met Val Val Val Asp Gly Lys Ser Tyr
    850                 855                 860

Val Glu Lys Leu Ala Val Lys
865                 870
```

<210> SEQ ID NO 144
<211> LENGTH: 2616
<212> TYPE: DNA
<213> ORGANISM: Porphyromonas gingivalis

<400> SEQUENCE: 144

```
tacaccttca cgatgcgtcg cgccggaatg ggagatggaa ctgatatgga agtcgaagac      60

gattcacctg caagctatac ctacacggtg tatcgtgacg gcacgaagat caaggaaggt     120

ctgacagcta cgacattcga agaagacggt gtagctgcag gcaatcatga gtattgcgtg     180

gaagttaagt acacagccgg cgtatctccg aaggtatgta aagacgttac ggtagaagga     240

tccaatgaat ttgctcctgt acagaacctg accggtagtt cagtaggtca gaaagtaacg     300

cttaagtggg atgcacctaa tggtaccccg aatccgaatc caaatccgaa tccgaatccg     360

ggaacaacac tttccgaatc attcgaaaat ggtattccgg catcttggaa gacgatcgat     420

gcagacggtg acgggcatgg ctggaaacct ggaaatgctc ccggaatcgc tggctacaat     480

agcaatggtt gtgtatattc agagtcattc ggtcttggtg gtataggagt tcttacccct     540

gacaactatc tgataacacc ggcattggat ttgcctaacg gaggtaagtt gactttctgg     600

gtatgcgcac aggatgctaa ttatgcatcc gagcactatg cggtgtatgc atcttcgacc     660

ggtaacgatg catccaactt cacgaatgct ttgttggaag agacgattac ggcaaaaggt     720

gttcgctcgc cgaaagctat tcgtggtcgt atacagggta cttggcgcca gaagacggta     780

gaccttcccg caggtacgaa atatgttgct ttccgtcact tccaaagcac ggatatgttc     840

tacatcgacc ttgatgaggt tgagatcaag gccaatggca agcgcgcaga cttcacggaa     900

acgttcgagt cttctactca tggagaggca ccagcggaat ggactactat cgatgccgat     960
```

```
ggcgatggtc agggttggct ctgtctgtct tccggacaat tggactggct gacagctcat   1020
ggcggcagca acgtagtaag ctctttctca tggaatggaa tggctttgaa tcctgataac   1080
tatctcatct caaaggatgt tacaggcgca acgaaggtaa agtactacta tgcagtcaac   1140
gacggttttc ccggggatca ctatgcggtg atgatctcca agacgggcac gaacgccgga   1200
gacttcacgg ttgttttcga agaaacgcct aacggaataa ataagggcgg agcaagattc   1260
ggtctttcca cggaagccaa tggcgccaaa cctcaaagtg tatggatcga gcgtacggta   1320
gatttgcctg caggcacgaa gtatgttgct ttccgtcact acaattgctc ggatttgaac   1380
tacattcttt tggatgatat tcagttcacc atgggtggca gccccacccc gaccgattat   1440
acctacacgg tgtatcgtga tggtacgaag atcaaggaag gtttgaccga aacgaccttc   1500
gaagaagacg gcgtagctac gggcaatcat gagtattgcg tggaagtgaa gtacacagcc   1560
ggcgtatctc cgaagaaatg tgtaaacgta actgttaatt cgacacagtt caatcctgta   1620
cagaacctga cggcagaaca agctcctaac agcatggatg caatccttaa atggaatgca   1680
ccggcatcta agcgtgcgga agttctgaac gaagacttcg aaaatggtat tcctgcctca   1740
tggaagacga tcgatgcaga cggtgacggc aacaattgga cgacgacccc tcctcccgga   1800
ggctcctctt ttgcaggtca caacagtgcg atctgtgtct cttcagcttc ttatatcaac   1860
tttgaaggtc ctcagaaccc tgataactat ctggttacac cggagctttc tcttcctggc   1920
ggaggaacgc ttactttctg ggtatgtgca caagatgcca attatgcatc agagcactat   1980
gccgtgtacg catcttctac gggtaacgac gcttccaact tcgccaacgc tttgttggaa   2040
gaagtgctga cggccaagac agttgttacg gcacctgaag ccattcgtgg tactcgtgct   2100
cagggcacct ggtatcaaaa gacggtacag ttgcctgcgg gtactaagta tgttgccttc   2160
cgtcacttcg gctgtacgga cttcttctgg atcaaccttg atgatgttgt aatcacttca   2220
gggaacgctc cgtcttacac ctatacgatc tatcgtaata atacacagat agcatcaggc   2280
gtaacggaga ctacttaccg agatccggac ttggctaccg gtttttacac gtacggtgta   2340
aaggttgttt acccgaacgg agaatcagct atcgaaactg ctacgttgaa tatcacttcg   2400
ttggcagacg taacggctca gaagccttac acgctgacag ttgtaggaaa gacgatcacg   2460
gtaacttgcc aaggcgaagc tatgatctac gacatgaacg gtcgtcgtct ggcagcgggt   2520
cgcaacacgg ttgtttacac ggctcagggc ggccactatg cagtcatggt tgtcgttgac   2580
ggcaagtctt acgtagagaa actcgctgta aagtaa                              2616
```

<210> SEQ ID NO 145
<211> LENGTH: 860
<212> TYPE: PRT
<213> ORGANISM: Porphyromonas gingivalis

<400> SEQUENCE: 145

```
Lys Asn Leu Asn Lys Phe Val Ser Ile Ala Leu Cys Ser Ser Leu Leu
1               5                   10                  15

Gly Gly Met Ala Phe Ala Gln Gln Thr Glu Leu Gly Arg Asn Pro Asn
            20                  25                  30

Val Arg Leu Leu Glu Ser Thr Gln Gln Ser Val Thr Lys Val Gln Phe
        35                  40                  45

Arg Met Asp Asn Leu Lys Phe Thr Glu Val Gln Thr Pro Lys Gly Met
    50                  55                  60

Ala Gln Val Pro Thr Tyr Thr Glu Gly Val Asn Leu Ser Glu Lys Gly
65                  70                  75                  80
```

```
Met Pro Thr Leu Pro Ile Leu Ser Arg Ser Leu Ala Val Ser Asp Thr
                85                  90                  95

Arg Glu Met Lys Val Glu Val Val Ser Ser Lys Phe Ile Glu Lys Lys
            100                 105                 110

Asn Val Leu Ile Ala Pro Ser Lys Gly Met Ile Met Arg Asn Glu Asp
        115                 120                 125

Pro Lys Lys Ile Pro Tyr Val Tyr Gly Lys Ser Tyr Ser Gln Asn Lys
    130                 135                 140

Phe Phe Pro Gly Glu Ile Ala Thr Leu Asp Asp Pro Phe Ile Leu Arg
145                 150                 155                 160

Asp Val Arg Gly Gln Val Val Asn Phe Ala Pro Leu Gln Tyr Asn Pro
                165                 170                 175

Val Thr Lys Thr Leu Arg Ile Tyr Thr Glu Ile Thr Val Ala Val Ser
            180                 185                 190

Glu Thr Ser Glu Gln Gly Lys Asn Ile Leu Asn Lys Lys Gly Thr Phe
        195                 200                 205

Ala Gly Phe Glu Asp Thr Tyr Lys Arg Met Phe Met Asn Tyr Glu Pro
    210                 215                 220

Gly Arg Tyr Thr Pro Val Glu Glu Lys Gln Asn Gly Arg Met Ile Val
225                 230                 235                 240

Ile Val Ala Lys Lys Tyr Glu Gly Asp Ile Lys Asp Phe Val Asp Trp
                245                 250                 255

Lys Asn Gln Arg Gly Leu Arg Thr Glu Val Lys Val Ala Glu Asp Ile
            260                 265                 270

Ala Ser Pro Val Thr Ala Asn Ala Ile Gln Gln Phe Val Lys Gln Glu
        275                 280                 285

Tyr Glu Lys Glu Gly Asn Asp Leu Thr Tyr Val Leu Leu Ile Gly Asp
    290                 295                 300

His Lys Asp Ile Pro Ala Lys Ile Thr Pro Gly Ile Lys Ser Asp Gln
305                 310                 315                 320

Val Tyr Gly Gln Ile Val Gly Asn Asp His Tyr Asn Glu Val Phe Ile
                325                 330                 335

Gly Arg Phe Ser Cys Glu Ser Lys Glu Asp Leu Lys Thr Gln Ile Asp
            340                 345                 350

Arg Thr Ile His Tyr Glu Arg Asn Ile Thr Thr Glu Asp Lys Trp Leu
        355                 360                 365

Gly Gln Ala Leu Cys Ile Ala Ser Ala Glu Gly Gly Pro Ser Ala Asp
    370                 375                 380

Asn Gly Glu Ser Asp Ile Gln His Glu Asn Val Ile Ala Asn Leu Leu
385                 390                 395                 400

Thr Gln Tyr Gly Tyr Thr Lys Ile Ile Lys Cys Tyr Asp Pro Gly Val
                405                 410                 415

Thr Pro Lys Asn Ile Ile Asp Ala Phe Asn Gly Gly Ile Ser Leu Ala
            420                 425                 430

Asn Tyr Thr Gly His Gly Ser Glu Thr Ala Trp Gly Thr Ser His Phe
        435                 440                 445

Gly Thr Thr His Val Lys Gln Leu Thr Asn Ser Asn Gln Leu Pro Phe
    450                 455                 460

Ile Phe Asp Val Ala Ala Val Asn Gly Asp Phe Leu Phe Ser Met Pro
465                 470                 475                 480

Cys Phe Ala Glu Ala Leu Met Arg Ala Gln Lys Asp Gly Lys Pro Thr
                485                 490                 495

Gly Thr Val Ala Ile Ile Ala Ser Thr Ile Asn Gln Ser Trp Ala Ser
```

```
            500                 505                 510

Pro Met Arg Gly Gln Asp Glu Met Asn Glu Ile Leu Cys Glu Lys His
        515                 520                 525

Pro Asn Asn Ile Lys Arg Thr Phe Gly Gly Val Thr Met Asn Gly Met
    530                 535                 540

Phe Ala Met Val Glu Lys Tyr Lys Lys Asp Gly Glu Lys Met Leu Asp
545                 550                 555                 560

Thr Trp Thr Val Phe Gly Asp Pro Ser Leu Leu Val Arg Thr Leu Val
                565                 570                 575

Pro Thr Lys Met Gln Val Thr Ala Pro Ala Gln Ile Asn Leu Thr Asp
            580                 585                 590

Ala Ser Val Asn Val Ser Cys Asp Tyr Asn Gly Ala Ile Ala Thr Ile
        595                 600                 605

Ser Ala Asn Gly Lys Met Phe Gly Ser Ala Val Val Glu Asn Gly Thr
    610                 615                 620

Ala Thr Ile Asn Leu Thr Gly Leu Thr Asn Glu Ser Thr Leu Thr Leu
625                 630                 635                 640

Thr Val Val Gly Tyr Asn Lys Glu Thr Val Ile Lys Thr Ile Asn Thr
                645                 650                 655

Asn Gly Glu Pro Asn Pro Tyr Gln Pro Val Ser Asn Leu Thr Ala Thr
            660                 665                 670

Thr Gln Gly Gln Lys Val Thr Leu Lys Trp Asp Ala Pro Ser Thr Lys
        675                 680                 685

Thr Asn Ala Thr Thr Asn Thr Ala Arg Ser Val Asp Gly Ile Arg Glu
    690                 695                 700

Leu Val Leu Leu Ser Val Ser Asp Ala Pro Glu Leu Leu Arg Ser Gly
705                 710                 715                 720

Gln Ala Glu Ile Val Leu Glu Ala His Asp Val Trp Asn Asp Gly Ser
                725                 730                 735

Gly Tyr Gln Ile Leu Leu Asp Ala Asp His Asp Gln Tyr Gly Gln Val
            740                 745                 750

Ile Pro Ser Asp Thr His Thr Leu Trp Pro Asn Cys Ser Val Pro Ala
        755                 760                 765

Asn Leu Phe Ala Pro Phe Glu Tyr Thr Val Pro Glu Asn Ala Asp Pro
    770                 775                 780

Ser Cys Ser Pro Thr Asn Met Ile Met Asp Gly Thr Ala Ser Val Asn
785                 790                 795                 800

Ile Pro Ala Gly Thr Tyr Asp Phe Ala Ile Ala Ala Pro Gln Ala Asn
                805                 810                 815

Ala Lys Ile Trp Ile Ala Gly Gln Gly Pro Thr Lys Glu Asp Asp Tyr
            820                 825                 830

Val Phe Glu Ala Gly Lys Lys Tyr His Phe Leu Met Lys Lys Met Gly
        835                 840                 845

Ser Gly Asp Gly Thr Glu Leu Thr Ile Ser Glu Gly
    850                 855                 860


<210> SEQ ID NO 146
<211> LENGTH: 2583
<212> TYPE: DNA
<213> ORGANISM: Porphyromonas gingivalis

<400> SEQUENCE: 146

aaaaacttga acaagtttgt ttcgattgct ctttgctctt ccttattagg aggaatggca      60

tttgcgcagc agacagagtt gggacgcaat ccgaatgtga gattgctcga atccactcag     120
```

```
caatcggtga caaaggttca gttccgtatg gacaacctca agttcaccga agttcaaacc    180
cctaagggaa tggcacaagt gccgacctat acagaagggg ttaatctttc tgaaaaaggg    240
atgcctacgc ttcccattct atcacgctct ttggcggttt cagacactcg tgagatgaag    300
gtagaggttg tttcctcaaa gttcatcgaa aagaaaaatg tcctgattgc accctccaag    360
ggcatgatta tgcgtaacga agatccgaaa aagatccctt acgtttatgg aaagagctac    420
tcgcaaaaca aattcttccc gggagagatc gccacgcttg atgatccttt tatccttcgt    480
gatgtgcgtg gacaggttgt aaactttgcg cctttgcagt ataaccctgt gacaaagacg    540
ttgcgcatct atacggaaat cactgtggca gtgagcgaaa cttcggagca aggcaaaaat    600
attctgaaca agaaaggtac atttgccggc tttgaagaca catacaagcg catgttcatg    660
aactacgagc cagggcgtta cacaccggta gaggaaaaac aaaatggtcg tatgatcgtc    720
atcgtagcca aaaagtatga gggagatatt aaagatttcg ttgattggaa aaaccaacgc    780
ggtctccgta ccgaggtgaa agtggcagaa gatattgctt ctcccgttac agctaatgct    840
attcagcaat tcgttaagca agaatacgag aaagaaggta atgatttgac ctatgttctt    900
ttgattggcg atcacaaaga tattcctgcc aaaattactc cggggatcaa atccgaccag    960
gtatatggac aaatagtagg taatgaccac tacaacgaag tcttcatcgg tcgtttctca   1020
tgtgagagca aagaggatct gaagacacaa atcgatcgga ctattcacta tgagcgcaat   1080
ataaccacgg aagacaaatg gctcggtcag gctctttgta ttgcttcggc tgaaggaggc   1140
ccatccgcag acaatggtga aagtgatatc cagcatgaga atgtaatcgc caatctgctt   1200
acccagtatg gttataccaa gattatcaaa tgttatgatc cgggagtaac tcctaaaaac   1260
attattgatg ctttcaacgg aggaatctcg ttggccaact atacgggcca cggtagcgaa   1320
acagcttggg gtacgtctca cttcggcacc actcatgtga agcagcttac caacagcaac   1380
cagctaccgt ttattttcga cgtagctgct gtgaatggcg atttcctatt cagcatgcct   1440
tgtttcgcag aagcattgat gcgtgcacaa aaagatggta agccgacagg tactgttgct   1500
atcatagcgt ctacgatcaa ccagtcttgg gcttctccta tgcgcgggca ggatgagatg   1560
aacgaaattc tgtgcgaaaa acacccgaac aacatcaagc gtactttcgg tggtgtcacc   1620
atgaacggta tgtttgctat ggtggaaaag tataaaaagg atggtgagaa gatgctcgac   1680
acatggactg tattcggcga cccctcgctg ctcgttcgta cacttgtccc gaccaaaatg   1740
caggttacgg ctccggctca gattaatttg acggatgctt cagtcaacgt atcttgcgat   1800
tataatggtg ctattgctac catttcagcc aatggaaaga tgttcggttc tgcagttgtc   1860
gaaaatggaa cagctacaat caatctgaca ggtctgacaa atgaaagcac gcttaccctt   1920
acagtagttg gttacaacaa agagacggtt attaagacca tcaacactaa tggtgagcct   1980
aacccctacc agcctgtttc caacttgact gctacaacgc agggtcagaa agtaacgctc   2040
aagtgggatg caccgagcac gaaaaccaat gcaaccacta ataccgctcg cagcgtggat   2100
ggcatacgag aactggttct tctgtcagtc agcgatgccc ccgaacttct tcgcagcggt   2160
caggccgaga ttgttcttga agctcacgat gtttggaatg atggatccgg ttatcagatt   2220
cttttggatg cagaccatga tcaatatgga caggttatac ccagtgatac ccatactctt   2280
tggccgaact gtagtgtccc ggccaatctg ttcgctccgt tcgaatatac ggttccggaa   2340
aatgcagatc cttcttgttc ccctaccaat atgataatgg atggtactgc atccgttaat   2400
ataccggccg gaacttatga ctttgcaatt gctgctcctc aagcaaatgc aaagatttgg   2460
```

```
attgccggac aaggaccgac gaaagaagat gattatgtat ttgaagccgg taaaaaatac   2520

catttcctta tgaagaagat gggtagcggt gatggaactg aattgactat aagcgaaggt   2580

taa                                                                  2583


<210> SEQ ID NO 147
<211> LENGTH: 845
<212> TYPE: PRT
<213> ORGANISM: Porphyromonas  gingivalis

<400> SEQUENCE: 147

Gly Gly Ser Asp Tyr Thr Tyr Thr Val Tyr Arg Asp Gly Thr Lys Ile
1               5                   10                  15

Lys Glu Gly Leu Thr Ala Thr Thr Phe Glu Glu Asp Gly Val Ala Ala
            20                  25                  30

Gly Asn His Glu Tyr Cys Val Glu Val Lys Tyr Thr Ala Gly Val Ser
        35                  40                  45

Pro Lys Val Cys Lys Asp Val Thr Val Glu Gly Ser Asn Glu Phe Ala
    50                  55                  60

Pro Val Gln Asn Leu Thr Gly Ser Ala Val Gly Gln Lys Val Thr Leu
65                  70                  75                  80

Lys Trp Asp Ala Pro Asn Gly Thr Pro Asn Pro Asn Pro Asn Pro Asn
                85                  90                  95

Pro Asn Pro Asn Pro Gly Thr Thr Thr Leu Ser Glu Ser Phe Glu Asn
            100                 105                 110

Gly Ile Pro Ala Ser Trp Lys Thr Ile Asp Ala Asp Gly Asp Gly His
        115                 120                 125

Gly Trp Lys Pro Gly Asn Ala Pro Gly Ile Ala Gly Tyr Asn Ser Asn
    130                 135                 140

Gly Cys Val Tyr Ser Glu Ser Phe Gly Leu Gly Gly Ile Gly Val Leu
145                 150                 155                 160

Thr Pro Asp Asn Tyr Leu Ile Thr Pro Ala Leu Asp Leu Pro Asn Gly
                165                 170                 175

Gly Lys Leu Thr Phe Trp Val Cys Ala Gln Asp Ala Asn Tyr Ala Ser
            180                 185                 190

Glu His Tyr Ala Val Tyr Ala Ser Ser Thr Gly Asn Asp Ala Ser Asn
        195                 200                 205

Phe Thr Asn Ala Leu Leu Glu Glu Thr Ile Thr Ala Lys Gly Val Arg
    210                 215                 220

Ser Pro Glu Ala Ile Arg Gly Arg Ile Gln Gly Thr Trp Arg Gln Lys
225                 230                 235                 240

Thr Val Asp Leu Pro Ala Gly Thr Lys Tyr Val Ala Phe Arg His Phe
                245                 250                 255

Gln Ser Thr Asp Met Phe Tyr Ile Asp Leu Asp Glu Val Glu Ile Lys
            260                 265                 270

Ala Asn Gly Lys Arg Ala Asp Phe Thr Glu Thr Phe Glu Ser Ser Thr
        275                 280                 285

His Gly Glu Ala Pro Ala Glu Trp Thr Thr Ile Asp Ala Asp Gly Asp
    290                 295                 300

Gly Gln Gly Trp Leu Cys Leu Ser Ser Gly Gln Leu Asp Trp Leu Thr
305                 310                 315                 320

Ala His Gly Gly Thr Asn Val Val Ser Ser Phe Ser Trp Asn Gly Met
                325                 330                 335

Ala Leu Asn Pro Asp Asn Tyr Leu Ile Ser Lys Asp Val Thr Gly Ala
            340                 345                 350
```

```
Thr Lys Val Lys Tyr Tyr Tyr Ala Val Asn Asp Gly Phe Pro Gly Asp
        355                 360                 365

His Tyr Ala Val Met Ile Ser Lys Thr Gly Thr Asn Ala Gly Asp Phe
    370                 375                 380

Thr Val Val Phe Glu Glu Thr Pro Asn Gly Ile Asn Lys Gly Gly Ala
385                 390                 395                 400

Arg Phe Gly Leu Ser Thr Glu Ala Asp Gly Ala Lys Pro Gln Ser Val
                405                 410                 415

Trp Ile Glu Arg Thr Val Asp Leu Pro Ala Gly Thr Lys Tyr Val Ala
            420                 425                 430

Phe Arg His Tyr Asn Cys Ser Asp Leu Asn Tyr Ile Leu Leu Asp Asp
        435                 440                 445

Ile Gln Phe Thr Met Gly Gly Ser Pro Thr Pro Thr Asp Tyr Thr Tyr
    450                 455                 460

Thr Val Tyr Arg Asp Gly Thr Lys Ile Lys Glu Gly Leu Thr Glu Thr
465                 470                 475                 480

Thr Phe Glu Glu Asp Gly Val Ala Thr Gly Asn His Glu Tyr Cys Val
                485                 490                 495

Glu Val Lys Tyr Thr Ala Gly Val Ser Pro Lys Lys Cys Val Asn Val
            500                 505                 510

Thr Val Asn Ser Thr Gln Phe Asn Pro Val Lys Asn Leu Lys Ala Gln
        515                 520                 525

Pro Asp Gly Gly Asp Val Val Leu Lys Trp Glu Ala Pro Ser Ala Lys
    530                 535                 540

Lys Thr Glu Gly Ser Arg Glu Val Lys Arg Ile Gly Asp Gly Leu Phe
545                 550                 555                 560

Val Thr Ile Glu Pro Ala Asn Asp Val Arg Ala Asn Glu Ala Lys Val
                565                 570                 575

Val Leu Ala Ala Asp Asn Val Trp Gly Asp Asn Thr Gly Tyr Gln Phe
            580                 585                 590

Leu Leu Asp Ala Asp His Asn Thr Phe Gly Ser Val Ile Pro Ala Thr
        595                 600                 605

Gly Pro Leu Phe Thr Gly Thr Ala Ser Ser Asp Leu Tyr Ser Ala Asn
    610                 615                 620

Phe Glu Tyr Leu Ile Pro Ala Asn Ala Asp Pro Val Val Thr Thr Gln
625                 630                 635                 640

Asn Ile Ile Val Thr Gly Gln Gly Glu Val Val Ile Pro Gly Gly Val
                645                 650                 655

Tyr Asp Tyr Cys Ile Thr Asn Pro Glu Pro Ala Ser Gly Lys Met Trp
            660                 665                 670

Ile Ala Gly Asp Gly Gly Asn Gln Pro Ala Arg Tyr Asp Asp Phe Thr
        675                 680                 685

Phe Glu Ala Gly Lys Lys Tyr Thr Phe Thr Met Arg Arg Ala Gly Met
    690                 695                 700

Gly Asp Gly Thr Asp Met Glu Val Glu Asp Asp Ser Pro Ala Ser Tyr
705                 710                 715                 720

Thr Tyr Thr Val Tyr Arg Asp Gly Thr Lys Ile Lys Glu Gly Leu Thr
                725                 730                 735

Glu Thr Thr Tyr Arg Asp Ala Gly Met Ser Ala Gln Ser His Glu Tyr
            740                 745                 750

Cys Val Glu Val Lys Tyr Thr Ala Gly Val Ser Pro Lys Val Cys Val
        755                 760                 765
```

```
Asp Tyr Ile Pro Asp Gly Val Ala Asp Val Thr Ala Gln Lys Pro Tyr
    770                 775                 780

Thr Leu Thr Val Val Gly Lys Thr Ile Thr Val Thr Cys Gln Gly Glu
785                 790                 795                 800

Ala Met Ile Tyr Asp Met Asn Gly Arg Arg Leu Ala Ala Gly Arg Asn
                805                 810                 815

Thr Val Val Tyr Thr Ala Gln Gly Gly Tyr Tyr Ala Val Met Val Val
            820                 825                 830

Val Asp Gly Lys Ser Tyr Val Glu Lys Leu Ala Ile Lys
        835                 840                 845


<210> SEQ ID NO 148
<211> LENGTH: 2538
<212> TYPE: DNA
<213> ORGANISM: Porphyromonas gingivalis

<400> SEQUENCE: 148

ggtggaagcg attacaccta tactgtctat cgtgacggca cgaagatcaa ggaaggtctg     60

acggctacga cattcgaaga agacggtgta gctgcaggca atcatgagta ttgcgtggaa    120

gttaagtaca cagccggcgt atctccgaag gtatgtaaag acgttacggt agaaggatcc    180

aatgaatttg ctcctgtaca gaacctgacc ggtagtgcag tcggccagaa agtaacgctt    240

aagtgggatg cacctaatgg taccccgaat ccaaatccaa atccgaatcc aaatccgaat    300

cccggaacaa ctacactttc cgaatcattc gaaaatggta ttcctgcctc atggaagacg    360

atcgatgcag acggtgacgg gcatggctgg aagcctggaa atgctcccgg aatcgctggc    420

tacaatagca atggttgtgt atattcagag tcattcggtc ttggtggtat aggagttctt    480

acccctgaca actatctgat aacaccggca ttggatttgc ctaacggagg taagttgact    540

ttctgggtat gcgcacagga tgctaattat gcatccgagc actatgcggt gtatgcatct    600

tcgaccggta acgatgcatc caacttcacg aatgctttgt tggaagagac gattacggca    660

aaaggtgttc gctcgccgga agctattcgt ggtcgtatac agggtacttg gcgccagaag    720

acggtagacc ttcccgcagg tacgaaatat gttgctttcc gtcacttcca aagcacggat    780

atgttctaca tcgaccttga tgaggttgag atcaaggcca atggcaagcg cgcagacttc    840

acggaaacgt tcgagtcttc tactcatgga gaggcaccag cggaatggac tactatcgat    900

gccgatggcg atggtcaggg ttggctctgt ctgtcttccg gacaattgga ctggctgaca    960

gctcatggcg gcaccaacgt agtaagctct ttctcatgga atggaatggc tttgaatcct   1020

gataactatc tcatctcaaa ggatgttaca ggcgcaacga aggtaaagta ctactatgca   1080

gtcaacgacg gttttcccgg ggatcactat gcggtgatga tctccaagac gggcacgaac   1140

gccggagact tcacggttgt tttcgaagaa acgcctaacg gaataaataa gggcggagca   1200

agattcggtc tttccacgga agccgatggc gccaaacctc aaagtgtatg gatcgagcgt   1260

acggtagatt tgcctgcggg cacgaagtat gttgctttcc gtcactacaa ttgctcggat   1320

ttgaactaca ttcttttgga tgatattcag ttcaccatgg gtggcagccc caccccgacc   1380

gattatacct acacggtgta tcgtgatggt acgaagatca aggaaggttt gaccgaaacg   1440

accttcgaag aagacggcgt agctacgggc aatcatgagt attgcgtgga agtgaagtac   1500

acagccggcg tatctccgaa gaaatgtgta aacgtaactg ttaattcgac acagttcaat   1560

cctgtaaaga acctgaaggc acaaccggat ggcggcgacg tggttctcaa gtgggaagcc   1620

ccgagcgcaa agaagacaga aggttctcgt gaagtaaaac ggatcggaga cggtcttttc   1680
```

```
gttacgatcg aacctgcaaa cgatgtacgt gccaacgaag ccaaggttgt gctcgcagca   1740

gacaacgtat ggggagacaa tacgggttac cagttcttgt tggatgccga tcacaataca   1800

ttcggaagtg tcattccggc aaccggtcct ctctttaccg gaacagcttc ttccgatctt   1860

tacagtgcga acttcgagta tttgatcccg gccaatgccg atcctgttgt tactacacag   1920

aatattatcg ttacaggaca gggtgaagtt gtaatccccg gtggtgttta cgactattgc   1980

attacgaacc cggaacctgc atccggaaag atgtggatcg caggagatgg aggcaaccag   2040

cctgcacgtt atgacgattt cacattcgaa gcaggcaaga agtacacctt cacgatgcgt   2100

cgcgccggaa tgggagatgg aactgatatg gaagtcgaag acgattcacc tgcaagctat   2160

acctatacag tctatcgtga cggcacgaag atcaaggaag gtctgaccga aacgacctac   2220

cgcgatgcag gaatgagtgc acaatctcat gagtattgcg tggaagttaa gtacacagcc   2280

ggcgtatctc cgaaggtttg tgtggattat attcctgacg gagtggcaga cgtaacggct   2340

cagaagcctt acacgctgac agttgtagga aagacgatca cggtaacttg ccaaggcgaa   2400

gctatgatct acgacatgaa cggtcgtcgt ctggcagccg gtcgcaacac ggttgtttac   2460

acggctcagg gcggctacta tgcagttatg gttgtcgttg acggcaagtc ttacgtagag   2520

aaactcgcta tcaagtaa                                                 2538
```

```
<210> SEQ ID NO 149
<211> LENGTH: 387
<212> TYPE: PRT
<213> ORGANISM: Porphyromonas  gingivalis

<400> SEQUENCE: 149

Lys Lys Thr Lys Phe Phe Leu Leu Gly Leu Ala Ala Leu Ala Met Thr
1               5                   10                  15

Ala Cys Asn Lys Asp Asn Glu Ala Glu Pro Val Val Glu Thr Asn Ala
            20                  25                  30

Thr Val Ser Phe Ile Ile Lys Ser Gly Glu Ser Arg Ala Val Gly Asp
        35                  40                  45

Asp Leu Thr Asp Ala Lys Ile Thr Lys Leu Thr Ala Met Val Tyr Ala
    50                  55                  60

Gly Gln Val Gln Glu Gly Ile Lys Thr Val Glu Glu Asp Gly Gly Val
65                  70                  75                  80

Leu Lys Val Glu Gly Ile Pro Cys Lys Ser Gly Ala Asn Arg Val Leu
                85                  90                  95

Val Val Val Ala Asn His Asn Tyr Glu Leu Thr Gly Lys Ser Leu Asn
            100                 105                 110

Glu Val Glu Ala Leu Thr Thr Ser Leu Thr Ala Glu Asn Gln Asn Ala
        115                 120                 125

Lys Asn Leu Ile Met Thr Gly Lys Ser Ala Ala Phe Thr Ile Lys Pro
    130                 135                 140

Gly Ser Asn His Tyr Gly Tyr Pro Gly Gly Thr Ala Ser Asp Asn Leu
145                 150                 155                 160

Val Ser Ala Gly Thr Pro Leu Ala Val Thr Arg Val His Ala Gly Ile
                165                 170                 175

Ser Phe Ala Gly Val Glu Val Asn Met Ala Thr Gln Tyr Gln Asn Tyr
            180                 185                 190

Tyr Ser Phe Lys Pro Ala Asp Ala Lys Ile Ala Ala Leu Val Ala Lys
        195                 200                 205

Lys Asp Ser Lys Ile Phe Gly Asn Ser Leu Val Ser Asn Thr Asn Ala
    210                 215                 220
```

```
Tyr Leu Tyr Gly Val Gln Thr Pro Ala Gly Leu Tyr Thr Pro Asp Ala
225                 230                 235                 240

Ala Gly Glu Thr Tyr Glu Leu Glu Ala Ser Leu Asn Thr Asn Tyr Ala
                245                 250                 255

Val Gly Ala Gly Phe Tyr Val Leu Glu Ser Lys Tyr Asp Ala Ser Asn
            260                 265                 270

Glu Leu Arg Pro Thr Ile Leu Cys Ile Tyr Gly Lys Leu Leu Asp Lys
        275                 280                 285

Asp Gly Asn Pro Leu Thr Glu Pro Ala Leu Thr Asp Ala Ile Asn Ala
    290                 295                 300

Gly Phe Cys Asp Gly Asp Gly Thr Thr Tyr Tyr Pro Val Leu Val Asn
305                 310                 315                 320

Tyr Asp Gly Asn Gly Tyr Ile Tyr Ser Gly Ala Ile Thr Gln Gly Gln
                325                 330                 335

Asn Lys Ile Val Arg Asn Asn His Tyr Lys Ile Thr Leu Asn Ile Thr
            340                 345                 350

Gly Pro Gly Thr Asn Thr Pro Glu Asn Pro Gln Pro Val Gln Ala Asn
        355                 360                 365

Leu Asn Val Thr Cys Gln Val Thr Pro Trp Val Val Val Asn Gln Ala
    370                 375                 380

Ala Thr Trp
385


<210> SEQ ID NO 150
<211> LENGTH: 1164
<212> TYPE: DNA
<213> ORGANISM: Porphyromonas  gingivalis

<400> SEQUENCE: 150

aaaaaaacaa agtttttctt gttgggactt gctgctcttg ctatgacagc ttgtaacaaa      60

gacaacgagg cagaacccgt tgtagaaact aacgctactg ttagtttcat aattaagagc     120

ggtgagagcc gcgctgtagg cgatgacctt acagatgcta agatcacaaa gctcaccgcc     180

atggtctatg caggtcaagt tcaagaaggt attaagacag tggaagagga cggcggagtc     240

cttaaagtag aaggaattcc gtgtaaatct ggagccaacc gtgtcctcgt cgttgtagcc     300

aatcacaatt atgagcttac cggtaaaagt ttgaatgagg ttgaggcctt gacgacttct     360

ttgacagctg aaaaccaaaa tgccaaaaac ttgatcatga caggtaagtc agcagctttt     420

acaatcaaac cgggctccaa ccactatggc tatcctggtg ggactgcatc cgacaacctt     480

gtttctgctg gaactcctct tgccgttact cgcgtgcatg ccggtatctc attcgcagga     540

gtagaggtaa atatggctac acagtatcaa aactactatt cttttaaacc agctgacgct     600

aaaatcgcag cccttgtcgc aaagaaagat tctaagattt tcggcaattc tttggtctca     660

aacactaatg catatttgta tggagtccaa acgcctgccg gtctttacac tccggatgct     720

gcaggagaaa catacgaatt ggaggcgtct ttgaatacga attatgctgt aggtgccggc     780

ttctatgtgc tggaaagtaa atatgatgca agcaacgagc ttcgtccgac gatcctttgt     840

atctatggaa agctgctcga taaggacggc aaccctctca cggaaccagc cttgacggat     900

gctataaatg ccggattctg cgacggagat ggcacgactt actatccggt attggtgaac     960

tatgatggca atggctacat ctattcaggt gctattaccc aaggacaaaa caaaatcgtt    1020

cgcaacaacc actacaagat tacgctgaac atcaccggcc ccggtacgaa tactcctgaa    1080

aatcctcaac cggtacaagc caacctgaat gttacttgcc aagttacacc ttgggttgtt    1140
```

```
gttaatcagg ctgctacttg gtaa                                          1164

<210> SEQ ID NO 151
<211> LENGTH: 549
<212> TYPE: PRT
<213> ORGANISM: Porphyromonas  gingivalis

<400> SEQUENCE: 151

Lys Ser Lys Ser Ile Ile Ala Gln Leu Leu Tyr Val Leu Ile Ala Phe
1               5                   10                  15

Met Ala Val Ser Cys Val Ala Asp Lys Ser Glu Pro Cys Pro Ser Gly
            20                  25                  30

Glu Pro Thr Arg Val Ser Gly Ser Ile Val Ser Leu Glu His His Gly
        35                  40                  45

Leu Arg Gly Ala Ser Ala Asp Lys Glu Asn Ser Val Glu Arg Leu Glu
    50                  55                  60

Leu Trp Val Phe Asp Glu Asp Gly His Phe Leu Glu Arg Ala Val Ala
65                  70                  75                  80

Asp Leu Ser Gly Phe Thr Phe Thr Ala Lys Ile Ile Pro Ser Glu Val
                85                  90                  95

Glu Arg Arg Ile His Phe Ile Ala Asn Tyr Glu Leu Ala Asp Pro Ser
            100                 105                 110

Val Trp Val Gly Arg Ser Glu Arg Glu Met Leu Pro Ser Ile Ser Val
        115                 120                 125

Ala Asp Asp Leu Glu Thr Ile Arg Met Trp Ala Arg Ile Ser Tyr Pro
    130                 135                 140

Ser Ile Ala Pro Asn Gln Asn Leu Gly Gln Ile Gln Leu Leu Arg Asn
145                 150                 155                 160

Met Ala Lys Phe Ser Leu Ser Val Thr Pro Pro Ala Glu Ser Lys Leu
                165                 170                 175

Tyr Asp Ala Ser Tyr Ala Leu Tyr Asn Ser Trp Asn Lys Gly Thr Leu
            180                 185                 190

Ala Pro Phe Asp Pro Asn Thr Gly Ser Phe Pro Gln Gly Gln Ile Thr
        195                 200                 205

Glu Pro Ala Gly Val Val Phe Ala Asn Pro Thr Ser Glu Ala Ala Phe
    210                 215                 220

Lys Glu Ala Asp Gly Ala His Phe Phe Tyr Gly Phe Glu Arg Asp Gln
225                 230                 235                 240

Ser Asn Ile Gly Thr Gly Ala Gly Ile Thr Cys Leu Ile Leu Lys Ala
                245                 250                 255

Arg Tyr Asn Leu Pro Asn Ala Asp Tyr Thr Tyr Tyr Lys Leu Asp Phe
            260                 265                 270

Val Asp Ala Asn Lys Val Arg Tyr Asn Ile Thr Arg Asn His Phe Tyr
        275                 280                 285

Lys Met Ile Leu Lys Lys Ala Lys Ala Pro Gly Arg Pro Thr Leu Gln
    290                 295                 300

Glu Ala Leu Asp Gly Ala Ala Ala Asn Asn Ile Phe Leu Ser Ala Glu
305                 310                 315                 320

Val Gln Ala Leu Pro Ala Phe Ser Asp Gly Ser Gly Met Leu Thr Val
                325                 330                 335

Asp His Thr Tyr Met Val Phe Val Gln Gly Glu Pro Ser Gly Thr Phe
            340                 345                 350

Gln Ala Thr Tyr Ile Pro Gln Gly Gln Asn Asn Pro Asp Tyr Ser Lys
        355                 360                 365
```

```
Leu Thr Val Ser Val Ser Thr Pro Thr Gly Gln Gln Ala Ala Val Thr
    370                 375                 380

Ser Ala Gln His Glu Gly Asn Gly Lys Ile Lys Leu Thr Leu Ala Gln
385                 390                 395                 400

Gln Glu Asn Leu Thr Lys Arg Ser Asp Val Val Ile Gly Val Gln Gly
                405                 410                 415

Asn Pro Asp Leu Lys Arg Ser Val Thr Val Leu Val Arg Glu Lys Tyr
            420                 425                 430

Gln Tyr Asp Phe Phe Lys Ala Asn Thr Ser Ser Ala Glu Asn Asn Gln
        435                 440                 445

Val Thr Thr Gln Ile Ser Ala Gly Gln Gly Asn Glu Leu Leu Ile Ser
    450                 455                 460

Ala Lys Leu Pro Asp Val Leu Asn Ala Ala Leu Leu Pro Ile Thr Phe
465                 470                 475                 480

Lys Val Tyr Thr Glu His Phe Tyr Pro Lys Thr Gly Gly Met Ile Leu
                485                 490                 495

Gly Ile Glu Gly Gly Lys Thr Leu Tyr Lys Tyr Val Leu Thr Thr Met
            500                 505                 510

Pro Gln Asn Lys Glu Leu Gln Phe Ser Phe Lys Ser Asn Lys Val Asn
        515                 520                 525

Ser Ala Glu Asn Ile Ala Val Lys Met Asp Tyr Phe His Asp Gln Thr
    530                 535                 540

Ile His Val Thr Asn
545
```

```
<210> SEQ ID NO 152
<211> LENGTH: 1650
<212> TYPE: DNA
<213> ORGANISM: Porphyromonas  gingivalis

<400> SEQUENCE: 152

aaaagtaaaa gcataatcgc acaattactg tatgtgctca tagcattcat ggctgtatct      60

tgtgtggctg acaagtcgga accctgtcca tcgggagagc ctactcgggt aagcggtagc     120

attgtttcat tagaacatca tggtttacga ggtgcttcag cggacaaaga gaacagcgta     180

gaaaggctcg agctttgggt tttcgatgaa gatgggcact ttctggaaag agctgtagcc     240

gatctgtctg gatttacatt tacagccaaa atcattcctt cggaggtcga acgcagaatt     300

cattttattg caaactatga attggcagac ccttctgttt gggtcggtcg ttccgaacgg     360

gaaatgctgc catcgatctc agtggccgat gatttggaaa cgatccgtat gtgggcgcgt     420

atctcttatc cgtccatagc ccctaatcag aatctcggtc agattcaatt gctacgcaac     480

atggctaagt tctctctttc tgtgacacct cctgcagaaa gcaagctcta cgacgccagc     540

tatgctctgt acaattcctg gaacaaaggg accttagctc catttgaccc gaatacaggc     600

tcttttcctc agggacagat caccgagccg gcaggcgtgg tgtttgcaaa cccgacatcg     660

gaagcagcct ttaaggaggc agacggtgcc cattttttct atggattcga acgtgaccaa     720

tccaatatag gaacaggggc aggaatcaca tgtctgattc taaaagcacg atacaatctt     780

cccaatgcgg actataccta ttataagctt gactttgtag atgcaaacaa ggtgcgttat     840

aatattacgc gcaaccactt ctacaaaatg attcttaaga aagccaaggc tccgggaaga     900

cctacgctac aggaagcatt ggacggagcc gccgcaaaca atatatttct ctcggcagaa     960

gtacaagctt tacctgcttt ttccgatggg tccggtatgc tgactgtgga tcatacctat    1020
```

```
atggttttttg tccaaggaga gccatccggc acttttcaag ccacatacat tcctcaggga   1080

caaaacaatc cggattattc caaactgacc gtatcagtct ccacccctac aggccaacag   1140

gcggctgtta cttcagctca acacgaaggc aacggcaaga tcaagctcac attggctcag   1200

caggaaaacc ttaccaagag gtccgacgtg gtcatcggtg tacaaggcaa tcctgacctc   1260

aaacgttcgg ttacggtatt ggtacgcgag aaatatcagt atgatttttt caaagccaat   1320

acatcttcgg cagagaacaa ccaagtaact actcaaattt cggcaggaca aggaaatgag   1380

ctcctcatta gtgccaaact gccggacgta cttaatgcgg cccttctgcc tatcacgttt   1440

aaagtatata ccgaacactt ctatccgaag accggcggga tgatattagg gatagaagga   1500

ggaaagactt tgtacaaata cgtattgacg acaatgcctc agaacaagga actgcaattt   1560

agctttaagt cgaataaagt gaactcggct gaaaacattg cagtcaagat ggattacttt   1620

catgaccaaa cgattcacgt gacgaattag                                    1650
```

<210> SEQ ID NO 153
<211> LENGTH: 1045
<212> TYPE: PRT
<213> ORGANISM: Porphyromonas gingivalis

<400> SEQUENCE: 153

```
Lys Arg Met Thr Leu Phe Phe Leu Cys Leu Leu Thr Ser Ile Gly Trp
1               5                   10                  15

Ala Met Ala Gln Asn Arg Thr Val Lys Gly Thr Val Ile Ser Ser Glu
            20                  25                  30

Asp Asn Glu Pro Leu Ile Gly Ala Asn Val Val Val Val Gly Asn Thr
        35                  40                  45

Thr Ile Gly Ala Ala Thr Asp Leu Asp Gly Asn Phe Thr Leu Ser Val
    50                  55                  60

Pro Ala Asn Ala Lys Met Leu Arg Val Ser Tyr Ser Gly Met Thr Thr
65                  70                  75                  80

Lys Glu Val Ala Ile Ala Asn Val Met Lys Ile Val Leu Asp Pro Asp
                85                  90                  95

Ser Lys Val Leu Glu Gln Val Val Val Leu Gly Tyr Gly Thr Gly Gln
            100                 105                 110

Lys Leu Ser Thr Val Ser Gly Ser Val Ala Lys Val Ser Ser Glu Lys
        115                 120                 125

Leu Ala Glu Lys Pro Val Ala Asn Ile Met Asp Ala Leu Gln Gly Gln
    130                 135                 140

Val Ala Gly Met Gln Val Ile Thr Gly Ser Gly Asp Pro Thr Ala Val
145                 150                 155                 160

Ala Ser Val Lys Ile His Gly Ser Gly Ser Leu Thr Ser Ser Ser Ala
                165                 170                 175

Pro Leu Tyr Ile Val Asp Gly Val Pro Thr Asp Leu Gly Val Val Ala
            180                 185                 190

Gly Met Asn Pro Asn Asp Phe Glu Ser Phe Thr Ile Leu Lys Asp Ala
        195                 200                 205

Ser Ser Thr Ser Ile Tyr Gly Ala Arg Ala Ala Asn Gly Val Ile Val
    210                 215                 220

Ile Thr Thr Lys Arg Gly Lys Met Gly Glu Arg Gly Arg Ile Thr Phe
225                 230                 235                 240

Asn Ala Ser Tyr Gly Val Ser Ser Ile Ile Asn Lys Lys Pro Phe Lys
                245                 250                 255

Ser Met Met Thr Gly Asp Glu Phe Ala Arg Trp Gln Tyr Gly Val Gly
```

```
            260                 265                 270

Tyr Ala Ala Ala Asp Gln Tyr Ser Thr Phe Glu Ala Trp Lys Asp His
        275                 280                 285

Ile Lys Glu Asp Ala Lys Gln Ala Leu Ile Asn Tyr Ser Pro Tyr Leu
    290                 295                 300

Glu Asp Gln Ile Lys Lys Gly Ile Leu Asp Pro Ile Asn Phe Asp Lys
305                 310                 315                 320

Asp Thr Asp Trp Leu Gly Tyr His Phe Arg Thr Ala Pro Thr Thr Gln
                325                 330                 335

Gly Asp Val Ser Ile Gln Gly Gly Ser Gln Gly Thr Ser Tyr Phe Leu
            340                 345                 350

Ser Leu Glu Tyr Phe Asp Gln Glu Gly Ile Ser Arg Ser Glu Ser Leu
        355                 360                 365

Leu Lys Arg Tyr Thr Gly Arg Leu Asn Leu Glu Ser Arg Val Asn Asp
    370                 375                 380

Trp Leu Lys Val Gly Ala Asn Met Ser Ala Ala Leu Ala Lys Arg Arg
385                 390                 395                 400

Ala Ser Gly Phe Ala Ser Ser Ala Tyr Ile Ser Glu Gly Ser Phe Ala
                405                 410                 415

Ala Leu Val Ala Ala Pro Tyr Leu Asn Pro Tyr Thr Thr Ser Gly Asp
            420                 425                 430

Phe Ala Glu Ala Tyr Tyr Met Asp Phe Gln Asp Lys Val Ile Phe Gly
        435                 440                 445

Ile Pro His Arg Asp Ser Tyr Arg Pro Tyr Asn Arg Glu Ala Tyr Gln
    450                 455                 460

Ala Thr Met Ser Gly Tyr Ala Gln Leu Thr Pro Ile Lys Gly Leu Thr
465                 470                 475                 480

Leu Lys Ala Gln Ala Gly Phe Asp Phe Leu Gln Glu Arg Thr Ser Ser
                485                 490                 495

Lys Leu Leu Pro Asn Asn Pro Leu Ala Leu Asp Pro Leu Gly Thr Ser
            500                 505                 510

Arg Gly Arg Phe Tyr His Tyr Leu Thr Lys Thr Phe Thr Asn Thr Ala
        515                 520                 525

Glu Tyr Lys Phe Ser Val Glu Asp Lys His Asp Val Thr Leu Leu Ala
    530                 535                 540

Gly His Glu Phe Ile Asp Tyr Glu Tyr Asp Met Phe Gly Ala Leu Gly
545                 550                 555                 560

Lys Gly Tyr Glu Asn Pro Lys Phe Met Met Leu Ser Gln Ala Lys Gly
                565                 570                 575

Asp Thr Tyr Leu Thr Leu Pro Glu Gln Ala Lys Ala Glu Tyr Ala Tyr
            580                 585                 590

Leu Ser Phe Phe Gly Arg Gly Ser Tyr Gly Phe Asp Lys Trp Leu Tyr
        595                 600                 605

Val Asp Leu Ser Val Arg Asn Asp Arg Ser Ser Arg Phe Gly Ala Asn
    610                 615                 620

Lys Arg Ser Ala Met Phe Gly Ser Gly Gly Val Met Met Asp Val Phe
625                 630                 635                 640

Asn Lys Phe Ile Lys Glu Ser Thr Trp Leu Ser Asp Leu Arg Phe Lys
                645                 650                 655

Met Ser Tyr Gly Thr Thr Gly Asn Ser Glu Met Arg Asn Tyr Thr Thr
            660                 665                 670

Gly Asn Pro Glu Tyr Tyr Ala His Leu Ala Leu Val Gly Ser Asn Pro
        675                 680                 685
```

```
Tyr Thr Asp Asn Ala Leu Gly Leu Ser Val Ala Thr Pro Gly Asn Pro
    690                 695                 700

Asn Leu Ser Trp Glu Gln Gln Ser Gln Phe Asn Val Gly Val Ala Ser
705                 710                 715                 720

Ser Phe Phe Asp Gly Arg Leu Asn Ala Glu Leu Asp Phe Tyr Val Arg
                725                 730                 735

Ala Thr Asp Asp Met Leu Ile Glu Val Pro Leu Pro Tyr Leu Ser Gly
            740                 745                 750

Phe Thr Ala Gln Leu Gln Asn Val Gly Ala Met Lys Asn Thr Gly Phe
        755                 760                 765

Asp Ile Thr Val Ser Gly Asp Ile Val Arg Ser Lys Asp Phe Lys Val
    770                 775                 780

Tyr Gly Ser Ala Thr Phe Asn Tyr Asn Arg Glu Glu Ile Thr Arg Leu
785                 790                 795                 800

Phe Ser Gly Leu Lys Glu Tyr Val Arg Asp Gly Tyr Ser Tyr Ser Trp
                805                 810                 815

Ile Val Gly Lys Pro Thr Val Phe Tyr Cys Ala Glu Tyr Ala Gly Val
            820                 825                 830

Tyr Lys Gly Gln Ala Gly Pro Asn Tyr Val Asp Ala Glu Gly Lys Pro
        835                 840                 845

Phe Lys Gly Gly Asp Gln Met Trp Tyr Val Pro Gly Glu Tyr Asn Glu
    850                 855                 860

Asp Gly Ser Arg Lys Leu Thr Asn Lys Tyr Ser Ser Ser Leu Glu His
865                 870                 875                 880

Ala Leu Thr Asp Lys Ala Leu Thr Pro Pro Val Thr Gly Gly Phe Ser
                885                 890                 895

Leu Gly Ala Ser Trp Lys Asp Leu Ser Leu Asp Ala Asp Phe Ser Tyr
            900                 905                 910

Ile Leu Gly Lys Trp Met Ile Asn Asn Asp Arg Tyr Phe Thr Glu Asn
        915                 920                 925

Thr Ser Pro Gly Phe Asn Phe Thr Asn Lys Asp Lys Met Ile Leu Asn
    930                 935                 940

Ala Trp Thr Gln Gln Asn Ser Asp Ser Asp Val Pro Arg Ile Gly Gln
945                 950                 955                 960

Ser Met His Phe Asp Ser Arg Leu Leu Glu Asn Ala Ser Phe Leu Arg
                965                 970                 975

Met Lys Asn Leu Lys Leu Thr Tyr Asn Leu Pro Gln Asn Leu Phe Ala
            980                 985                 990

Gly Gln Asn Val Leu Ser Gly Ala  Arg Val Tyr Leu Met  Ala Arg Asn
        995                 1000                1005

Leu Phe  Thr Ile Thr Lys Phe  Lys Gly Phe Asp Pro  Glu Ala Gly
    1010                1015                1020

Ala Asn  Leu Ser Met Asn Gln  Tyr Pro Asn Thr Lys  Gln Tyr Val
    1025                1030                1035

Ala Gly  Ile Gln Ile Ser Phe
    1040                1045
```

<210> SEQ ID NO 154
<211> LENGTH: 3138
<212> TYPE: DNA
<213> ORGANISM: Porphyromonas gingivalis

<400> SEQUENCE: 154

```
aaaagaatga cgctattctt cctttgcttg ctgacgagca ttgggtgggc tatggcccag     60
```

```
aatagaaccg tgaagggtac agttatctcc tccgaggata atgagcccct gatcggcgcg    120
aatgtcgtgg ttgtcggaaa caccactatc ggtgctgcaa ccgacttgga tggcaacttc    180
acgcttagcg tgcctgccaa tgccaaaatg ttgagagtgt catattccgg tatgactacc    240
aaagaggtcg ccatcgctaa tgtgatgaag atcgtactgg atccggactc taaggttctg    300
gagcaggtag ttgtattggg ttatggtacg ggacagaaac tcagcaccgt ttccggttct    360
gtggccaaag tgtccagcga aaagctcgcg gaaaagcctg ttgccaacat catggatgcc    420
ctccaaggtc aggtagccgg tatgcaggtt attaccggtt ccggtgaccc tactgccgtc    480
gcttctgtga agatccacgg ttcagggtct ttgacttcaa gttcagcccc tctctacatc    540
gtggatggtg tgccgactga tttgggtgta gttgccggta tgaaccctaa tgacttcgaa    600
tcgtttacga ttcttaaaga cgcttcttct acttctatct atggtgcgcg tgcagccaat    660
ggcgttattg tcattacgac caaacgcgga aagatgggag agcgtggccg tattacgttc    720
aacgccagct atggagtgtc ttctattatt aataaaaaac ccttcaagag catgatgacg    780
ggagatgaat tcgcccgttg gcagtatggt gtcggctatg ctgcagcaga tcaatacagt    840
actttcgagg catggaaaga ccacattaaa gaggatgcta agcaagcatt gataaactac    900
tcaccttatc ttgaggatca aatcaagaaa ggtatacttg atccgataaa ctttgataaa    960
gatacggatt ggctgggata ccatttccgc actgctccta ccactcaagg agatgtttct   1020
atccagggag gttcgcaagg cacttcttac ttcttatctt tggaatattt tgaccaagag   1080
ggtatctctc gctcggaatc tcttttgaag cgttatacag gtcgtcttaa cttggaaagc   1140
cgtgtgaacg attggttgaa ggttggagcc aatatgtcgg cagctcttgc caaaagacgt   1200
gcctctggtt ttgcttcttc tgcgtatatc tcagaaggat catttgctgc tttggttgct   1260
gctccttatc tgaatcccta tacaacatca ggcgattttg ctgaagcgta ttacatggat   1320
tttcaagaca aagtaatatt cggaattccg caccgtgaca gctatcgtcc ttataatcgt   1380
gaagcttatc aagcaacgat gagtggatat gcacaactca caccgataaa ggggctgacg   1440
ctcaaggcac aagccggctt cgactttttg caagaacgca cttcttctaa actgcttccc   1500
aataacccct tggcattgga cccgttgggt acaagtcggg ggcgttttta tcactatttg   1560
accaaaactt ttaccaacac ggcagagtat aagttctcgg tagaagataa gcatgacgtg   1620
actcttttgg caggccatga gtttatcgat tacgaatatg atatgtttgg agccttagga   1680
aagggttacg aaaatccgaa attcatgatg cttagccaag caaaaggtga tacttatttg   1740
actttgcccg aacaggcaaa agccgaatat gcctatctct ctttcttcgg ccgtggtagc   1800
tatggttttg acaagtggct ttatgtagac ctctctgttc gtaatgatag atcttctcgc   1860
tttggtgcca ataaacgcag tgcgatgttt ggatctggtg gcgttatgat ggatgttttc   1920
aacaaattca ttaaagaaag cacgtggctc agtgatctgc gctttaagat gagctatggt   1980
actaccggta actccgaaat gagaaattac acaactggaa accctgaata ttatgctcat   2040
ttggctttgg ttggtagcaa tccatatacg gacaacgctt tgggcctttc ggtggctaca   2100
ccgggtaacc ctaatctttc atgggaacaa caatctcagt tcaatgtagg tgttgcttct   2160
tcattctttg atggtcgact caacgctgaa ttggatttct atgttcgtgc tacagacgat   2220
atgcttatcg aggtgcctct gccttatttg agcggattca cggctcagtt gcagaatgtg   2280
ggtgctatga agaataccgg tttcgatatt actgttagtg gggatattgt tcgaagcaag   2340
gacttcaagg tgtacggatc agctacattt aactataacc gtgaagaaat tacacgtcta   2400
```

```
ttctccggtc tcaaggagta cgttcgtgat ggatatagct attcatggat tgttggcaag   2460

cctacagtat tctattgtgc tgaatatgct ggcgtttata aaggccaagc cggccccaat   2520

tatgtggatg ctgaaggcaa gccctttaag ggtggagacc aaatgtggta tgtccccgga   2580

gaatacaatg aagatgggag tcgcaagctt accaataaat attcttcttc attggagcat   2640

gctctgacag ataaggctct cactcctccc gttacaggag gattttcctt aggtgcttca   2700

tggaaagacc tttctttgga tgcagatttc tcttatattc tgggtaagtg gatgattaat   2760

aatgaccggt attttacaga aaatacttcc cccggtttta actttacaaa taaagacaag   2820

atgatactga atgcatggac gcagcagaat tctgattcgg atgtgccccg tatcggtcag   2880

tcgatgcatt ttgactctcg cttgttagaa aacgcttctt tcttgcgtat gaagaatctg   2940

aaattgactt acaacctgcc ccaaaatctc ttcgccggtc agaatgtcct ctcgggagcg   3000

cgtgtctact tgatggctcg taacttgttt acaattacaa agttcaaagg ttttgaccct   3060

gaagcaggag caaatctatc tatgaaccag tatcctaata ctaaacagta cgtggctggt   3120

attcagattt ctttctaa                                                 3138
```

<210> SEQ ID NO 155
<211> LENGTH: 498
<212> TYPE: PRT
<213> ORGANISM: Porphyromonas gingivalis

<400> SEQUENCE: 155

```
Lys Lys Ile Ile Asn Tyr Ala Val Ala Gly Leu Leu Leu Val Ser Ser
1               5                   10                  15

Phe Ala Ala Cys Asp Leu Asp Arg Thr Pro His Asn Ser Gly Val Gln
            20                  25                  30

Lys Pro Tyr Glu Asp Met Ala Thr Thr Val Gln Tyr Arg Asp Gly Leu
        35                  40                  45

Tyr Ser Val Leu Arg Gly Ala Glu Asn Ala Gly Arg Tyr Thr Leu Ser
    50                  55                  60

Glu Tyr Met Ser Asp Met Tyr Cys Val Met Gln Gly Asp Gly Gly His
65                  70                  75                  80

Ala Thr Pro Tyr Val Thr Trp Thr Ile Pro Arg Ile Glu Thr Ala Asp
                85                  90                  95

His Ala Ser Asn Tyr Tyr Phe Gly Phe Asn Arg Leu Ile Gln Gln Ala
            100                 105                 110

Asn Ala Phe Val Gly Asn Val Lys Leu Ala Ile Ala Asn Gly Val Tyr
        115                 120                 125

Lys Thr Glu Val Asp Lys Thr Asn Ala Gln Ile Tyr Leu Ala Glu Ala
    130                 135                 140

Lys Thr Leu Gln Ala Leu Ala Leu Phe Arg Leu Met Glu Arg Phe Ala
145                 150                 155                 160

Tyr Pro Tyr Asp Pro Asn Glu Thr Thr Ser Pro Lys Asn Leu Gly Val
                165                 170                 175

Val Leu Ile Lys Glu Tyr Asp Pro Trp Ala Val Gly Ala Arg Ala Thr
            180                 185                 190

Gln Thr Glu Thr Tyr Ser Tyr Ile Met Ser Leu Leu Asp Glu Ala Ile
        195                 200                 205

Ser Val Leu Pro Glu Thr Asn Ala Asn Asn Met Tyr Val Ser Arg Asp
    210                 215                 220

Tyr Ala Leu Gly Leu Arg Ala Arg Val His Met Ala Met Asp Asn Tyr
225                 230                 235                 240
```

```
Ala Glu Ala Ala Asn Asp Ile Arg Ala Phe Tyr Lys Lys Tyr Asn Leu
                245                 250                 255

Ile Ser Ala Ala Asn Ser Asp Glu Phe Glu Glu Ala Tyr Arg Lys Met
            260                 265                 270

Ser Ser Asn Pro Glu Leu Ile Phe Arg Gly Tyr Ala Ser Val Thr Asn
        275                 280                 285

Gly Tyr Leu Val Tyr Gln Asp Leu Met Gly Ala Thr Ala Ser Gly Thr
    290                 295                 300

Asn Val Lys Tyr Asn Pro Arg Val Thr Pro Leu Gln Trp Val Cys Asp
305                 310                 315                 320

Leu Tyr Asp Ala Ala Asp Tyr Arg Lys Lys Val Tyr Ile Val Asp Lys
                325                 330                 335

Val Asn Gly Asp Gly Gly Lys Gly Tyr Val Val Asn Lys Phe Leu Gly
            340                 345                 350

Asp Pro Glu Leu Arg Glu Asp Pro Lys Lys Glu Asn Phe Lys Thr Gly
        355                 360                 365

Cys Arg Phe Phe Ser Leu Ala Glu Ala Tyr Leu Ile Leu Ala Glu Ala
    370                 375                 380

Asp Ile Met Thr Gly Asn Thr Ala Glu Ala Met Glu Val Leu Lys Glu
385                 390                 395                 400

Leu Ser Lys Ser Arg Gly Ala Glu Val Ser Gly Ala Asp Tyr Met Gln
                405                 410                 415

Ile Leu Lys Asp Glu Arg Thr Arg Glu Met Ile Gly Glu Gly Ser Arg
            420                 425                 430

Leu Asn Asp Met Ile Arg Trp Asn Met Asp Leu Val Val Ser Pro Val
        435                 440                 445

Gln Ala Val Leu His Lys Ile Ala Val Pro Thr Ile Leu Gln Thr Asp
    450                 455                 460

Asp Pro Thr Arg Val Pro Ala Gly Phe Tyr Ala Phe Thr Trp Glu Ile
465                 470                 475                 480

Pro Asn Arg Asp Leu Val Val Ile Pro Glu Leu Val Arg Asn Trp Pro
                485                 490                 495

Lys Gln


<210> SEQ ID NO 156
<211> LENGTH: 1497
<212> TYPE: DNA
<213> ORGANISM: Porphyromonas gingivalis

<400> SEQUENCE: 156

aaaaaaataa ttaattatgc tgtggccgga ttgctactcg tttcaagctt tgccgcttgt     60

gacttggatc gcactcctca caattctggt gtccaaaagc cttatgaaga tatggccacc    120

acagttcagt atagagatgg attgtattct gttcttcgtg gtgcagagaa tgccggacgg    180

tatactttgt cagaatatat gtccgatatg tattgtgtaa tgcaaggaga tggtggccat    240

gctacgcctt atgttacatg gacgattcct cgcattgaga ctgctgacca cgcatcgaat    300

tattactttg gttttaatcg gttaattcag caagccaatg cttttgtcgg aaatgttaag    360

ctggcaatcg caaatggggt ttataagaca gaagttgata aaaccaatgc tcaaatttat    420

ttggctgagg ccaagacttt gcaggcttta gctttgttcc gtcttatgga gcgctttgcc    480

tatccctatg atccaaacga aaccacttct ccgaaaaact tgggggtggt tttgataaag    540

gaatatgatc cttgggctgt gggtgcacga gctacgcaga cggaaacgta tagctatatt    600

atgagccttc ttgatgaggc catctctgtt ttgcctgaaa cgaatgcgaa caatatgtat    660
```

```
gtgagtcggg attatgcttt aggcttgcgt gctcgcgtac acatggcgat ggataactat    720

gctgaagccg ccaatgatat cagagctttt tataaaaagt acaatctgat ttctgctgct    780

aattccgatg aatttgagga ggcttataga aagatgagct ccaatcctga gcttattttc    840

cgcggatatg cttccgttac taacggatac cttgtgtatc aggatttgat gggagcaaca    900

gcttctggaa ctaatgtgaa gtacaaccct cgtgttaccc ctctgcaatg ggtttgcgac    960

ctttatgatg cggctgatta tcgtaagaaa gtgtacattg tagacaaggt gaacggtgac   1020

ggtggcaaag gttatgtcgt aaataagttc cttggagacc ctgaacttcg tgaagaccct   1080

aagaaggaaa atttcaaaac cggttgtcgt ttcttctctc tcgcagaagc ctatcttatc   1140

ttggcagaag cagatattat gactggtaat acagccgagg ctatggaagt tctgaaagag   1200

ctgagtaagt ctcgtggagc agaggtttcc ggtgcagatt atatgcaaat cctcaaggat   1260

gagcgtacac gagaaatgat cggtgaaggt tctcgtctca atgacatgat tcgctggaat   1320

atggatttgg tggtatctcc cgttcaggct gttcttcata aaatagctgt cccgactatc   1380

cttcagactg atgacccgac acgtgttcct gccggcttct atgctttcac gtgggaaatt   1440

cccaatcgtg atcttgtagt tattcccgag ctggttcgca actggccaaa acagtaa      1497
```

```
<210> SEQ ID NO 157
<211> LENGTH: 59
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 157

ggggacaagt ttgtacaaaa aagcaggctc actcgagagg aaattattat tgctgatcg      59
```

```
<210> SEQ ID NO 158
<211> LENGTH: 61
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 158

ggggaccact ttgtacaaga aagctgggtc actagtttac ttcttgcctg cttcgaatgt     60

g                                                                     61
```

```
<210> SEQ ID NO 159
<211> LENGTH: 57
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 159

ggggacaagt ttgtacaaaa aagcaggctc actcgagtac accttcacga tgcgtcg        57
```

```
<210> SEQ ID NO 160
<211> LENGTH: 57
<212> TYPE: DNA
<213> ORGANISM: Artificial Sequence
<220> FEATURE:
<223> OTHER INFORMATION: Description of Artificial Sequence: Synthetic
      DNA
```

<400> SEQUENCE: 160 gggaccact ttgtacaaga aagctgggtc actagtttac tttacagcga gtttctc 57

<210> SEQ ID NO 161
<211> LENGTH: 57
<212> TYPE: DNA
<213> ORGANISM: Artificial Sequence
<220> FEATURE:
<223> OTHER INFORMATION: Description of Artificial Sequence: Synthetic DNA

<400> SEQUENCE: 161
ggggacaagt ttgtacaaaa aagcaggctc actcgagaaa aacttgaaca agtttgt 57

<210> SEQ ID NO 162
<211> LENGTH: 60
<212> TYPE: DNA
<213> ORGANISM: Artificial Sequence
<220> FEATURE:
<223> OTHER INFORMATION: Description of Artificial Sequence: Synthetic DNA

<400> SEQUENCE: 162
ggggaccact ttgtacaaga aagctgggtc actagtttaa ccttcgctta tagtcaattc 60

<210> SEQ ID NO 163
<211> LENGTH: 57
<212> TYPE: DNA
<213> ORGANISM: Artificial Sequence
<220> FEATURE:
<223> OTHER INFORMATION: Description of Artificial Sequence: Synthetic DNA

<400> SEQUENCE: 163
ggggacaagt ttgtacaaaa aagcaggctc actcgagggt ggaagcgatt acaccta 57

<210> SEQ ID NO 164
<211> LENGTH: 57
<212> TYPE: DNA
<213> ORGANISM: Artificial Sequence
<220> FEATURE:
<223> OTHER INFORMATION: Description of Artificial Sequence: Synthetic DNA

<400> SEQUENCE: 164
ggggaccact ttgtacaaga aagctgggtc actagtttac ttgatagcga gtttctc 57

<210> SEQ ID NO 165
<211> LENGTH: 63
<212> TYPE: DNA
<213> ORGANISM: Artificial Sequence
<220> FEATURE:
<223> OTHER INFORMATION: Description of Artificial Sequence: Synthetic DNA

<400> SEQUENCE: 165
ggggacaagt ttgtacaaaa aagcaggctc aggatccaaa aaaacaaagt ttttcttgtt 60
ggg 63

<210> SEQ ID NO 166
<211> LENGTH: 71
<212> TYPE: DNA
<213> ORGANISM: Artificial Sequence
<220> FEATURE:
<223> OTHER INFORMATION: Description of Artificial Sequence: Synthetic DNA

<400> SEQUENCE: 166

```
ggggaccact ttgtacaaga aagctgggtc gcggccgctt accaagtagc agcctgatta     60

acaacaaccc a                                                           71
```

<210> SEQ ID NO 167
<211> LENGTH: 62
<212> TYPE: DNA
<213> ORGANISM: Artificial Sequence
<220> FEATURE:
<223> OTHER INFORMATION: Description of Artificial Sequence: Synthetic DNA

<400> SEQUENCE: 167

```
ggggacaagt ttgtacaaaa aagcaggctc aggatccaaa agtaaaagca taatcgcaca     60

at                                                                     62
```

<210> SEQ ID NO 168
<211> LENGTH: 65
<212> TYPE: DNA
<213> ORGANISM: Artificial Sequence
<220> FEATURE:
<223> OTHER INFORMATION: Description of Artificial Sequence: Synthetic DNA

<400> SEQUENCE: 168

```
ggggaccact ttgtacaaga aagctgggtc gcggccgcct aattcgtcac gtgaatcgtt     60

tggtc                                                                  65
```

<210> SEQ ID NO 169
<211> LENGTH: 63
<212> TYPE: DNA
<213> ORGANISM: Artificial Sequence
<220> FEATURE:
<223> OTHER INFORMATION: DDescription of Artificial Sequence: Synthetic DNA

<400> SEQUENCE: 169

```
ggggacaagt ttgtacaaaa aagcaggctc actcgagaaa agaatgacgc tattcttcct     60

ttg                                                                    63
```

<210> SEQ ID NO 170
<211> LENGTH: 59
<212> TYPE: DNA
<213> ORGANISM: Artificial Sequence
<220> FEATURE:
<223> OTHER INFORMATION: Description of Artificial Sequence: Synthetic DNA

<400> SEQUENCE: 170

```
ggggaccact ttgtacaaga aagctgggtc gcggccgctt agaaagaaat ctgaatacc      59
```

<210> SEQ ID NO 171
<211> LENGTH: 64
<212> TYPE: DNA
<213> ORGANISM: Artificial
<220> FEATURE:
<223> OTHER INFORMATION: Description of Artificial Sequence: Synthetic DNA

<400> SEQUENCE: 171

```
ggggacaagt ttgtacaaaa aagcaggctc aggatccaaa aaaataatta attatgctgt     60

ggcc                                                                   64
```

-continued

```
<210> SEQ ID NO 172
<211> LENGTH: 68
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 172

ggggaccact ttgtacaaga aagctgggtc gcggccgctt actgttttgg ccagttgcga     60

accagctc                                                              68
```

TEST KIT FOR PLASMA OR SERUM ANTIBODY TITER AGAINST PERIODONTAL DISEASE-CAUSING BACTERIA

TECHNICAL FIELD

The present invention relates to: a test kit for a plasma or serum antibody titer against a periodontal disease-causing bacterium, more specifically a test kit for a plasma or serum antibody titer against a periodontal disease-causing bacterium which is suitable for automated testing using a device and comprises a specific periodontal disease-causing bacterium antigen protein; a modified polypeptide for use in the kit; and a method for measuring an antibody titer against a periodontal disease-causing bacterium in a blood sample.

BACKGROUND OF THE INVENTION

A periodontal disease is a bacterial infection that is developed through an infection of periodontal tissue with oral bacterium.

The diagnosis of periodontal disease in a dental clinical site is carried out based on overall results of clinical tests such as a clinical condition, a photograph of oral cavity, a radiographic image or a periodontal tissue test. Among these tests, the photograph of oral cavity and the radiographic image exploration visually evaluate the morphological change of periodontal tissue, and periodontal tissue test evaluates by measuring various clinical items such as the state of the formation of plaque, the depth of a periodontal pocket, the presence of bleeding during probing or the degree of tooth mobility. Therefore, these tests require complicated operations and a practitioner must have advanced technique for accurately diagnosing the periodontal disease pathologic condition of patients.

In other words, in some cases, a test result may vary depending on the skill level of practitioners, and therefore different diagnoses may be given to a patient. Further, in the clinical dental tests as mentioned above, in spite of a fact that a periodontal disease is a bacterial infection, the periodontal disease is evaluated not at "a level of infection" with a periodontal disease-causing bacterium but at a level of "the morphological change" of periodontal tissue; in other words, the test is carried out by the practitioner's subjectivity. Therefore, there have been a demand for an objective periodontal disease test method which is reasonable from the bacteriological and immunological viewpoints and in which difference in a test result would not occur depending on the skill level of practitioners.

In these situations, a periodontal disease test system is carried out, in which a serum antibody titer against a periodontal disease-causing bacterium is employed as a measure for the periodontal disease testing (Chieko KUDO, Journal of Okayama Dental Society, vol. 28 (1) (2009), pp. 1-14). In this periodontal disease test system, the state of infection with a periodontal disease-causing bacterium or the severity of a periodontal disease (the state of inflammation) is evaluated by detecting/quantifying "a specific antibody" against the periodontal disease-causing bacterium from a trace amount of blood that is collected from a finger tip of a patient and then is separated. According to this system, it is possible to objectively and uniformly evaluate the disease condition of a periodontal disease by employing an immunological technique.

Further, in this periodontal disease test system, plasma is separated from the blood collected from a finger tip, a sample of the plasma is mailed to an inspection agency, an IgG antibody titer against a periodontal disease-causing bacterium is measured in the inspection agency, the severity of a periodontal disease is evaluated, and then a result of the periodontal disease test is notified to each patient (a test on a plasma antibody titer against a periodontal disease-causing bacterium). Thus, the periodontal disease test can be assisted in general practitioners or at home. Further, since test data are comprehensively collected and analyzed, it becomes possible to correlate the test data with disease conditions using an enormous quantity of data.

Meanwhile, in the periodontal disease test system mentioned above, since a large quantity of samples is handled, it is required to treat the samples automatically and at a high speed.

In the test system, the correlation between test results and a periodontal disease become higher with the increase in the types of antibodies against an antigen to be tested in a (blood) sample, and thus the periodontal disease can be tested with higher accuracy. In addition, in a human suffering from periodontal disease, the type of periodontal disease-causing bacterium antigen to be recognized is varied due to the inter-individual differences in the periodontal disease-causing bacteria and the human. Also in this regard, a periodontal disease can be tested with higher accuracy with the increase in the types of antibodies to be tested.

However, if the antibody titers of a variety of antibodies are to be measured, it is difficult to treat samples at a high speed, which is not suitable for automated test using a device.

The antigen used in the current antibody titer measurements is a solution prepared by disrupting a periodontal disease-causing bacterium such as *Porphyromonas gingivalis*, which is a mixture containing a wide variety of bacterial proteins (including LPSs and membrane lipids). Therefore, it has been difficult to treat a large quantity of samples automatically and at a high speed using a device.

DISCLOSURE OF INVENTION

The object of the present invention is to provide: a test kit for a plasma or serum antibody titer against a periodontal disease-causing bacterium, which can cover a various antigen-antibody reactions occurring due to changing antigenicity of periodontal disease-causing bacterium and a various of immunological reactions of a substance to be tested, which can test periodontal diseases in a wide scope of patients having various immunotypes with high accuracy, and which can be treated by an automated device at a high speed; a periodontal disease-causing bacterium antigen protein which can be suitably used in the kit; and a method for testing a plasma or serum antibody titer against a periodontal disease-causing bacterium in a blood sample, which uses the kit.

Under these problems, the present inventors have studied on the selection of periodontal disease-causing bacterium proteins, which can cover a various antigen-antibody reactions even when the number of types of the protein is small and therefore can evaluate a periodontal disease with high accuracy. As a result, it is found that a specific combination of periodontal disease-causing bacterium proteins can specifically react with plasma antibody in a blood sample separated from a periodontal disease patient, various antigen-antibody reactions are covered and the blood sample can be tested with high accuracy by selectively using the combination of the bacterial proteins, and the blood sample can be treated using an automated device at a high speed. These findings led to the accomplishment of the present invention.

That is, the present invention provides:

[1]

a test kit for a plasma or serum antibody titer against a periodontal disease-causing bacterium, comprising a set of polypeptides having the amino acid sequences represented by SEQ ID NOs: 1, 3, 9, 15, 19, 31, 41, 43, 63, 65 and 67;

[2]

the test kit for a plasma or serum antibody titer against a periodontal disease-causing bacterium according to [1], wherein the test kit further comprises polypeptides having the amino acid sequences represented by SEQ ID NOs: 5 and 37;

[3]

the test kit for a plasma or serum antibody titer against a periodontal disease-causing bacterium according to [1] or [2], wherein the test kit further comprises polypeptides having the amino acid sequences represented by SEQ ID NOs: 23, 35 and 47;

[4]

the test kit for a plasma or serum antibody titer against a periodontal disease-causing bacterium according to any one of [1] to [3], wherein the test kit further comprises a polypeptide having the amino acid sequence represented by SEQ ID NO: 17;

[5]

a modified polypeptide having the amino acid sequence represented by SEQ ID NO: 63;

[6]

the modified polypeptide according to [5], comprising an amino acid sequence encoded by the nucleotide sequence represented by SEQ ID NO: 64;

[7]

a modified polypeptide having the amino acid sequence represented by SEQ ID NO: 65;

[8]

the modified polypeptide according to [7], comprising an amino acid sequence encoded by the nucleotide sequence represented by SEQ ID NO: 66;

[9]

a modified polypeptide having the amino acid sequence represented by SEQ ID NO: 67;

[10]

the modified polypeptide according to [9], comprising an amino acid sequence encoded by the nucleotide sequence represented by SEQ ID NO: 68;

[11]

a modified polypeptide having the amino acid sequence represented by SEQ ID NO: 141;

[12]

the modified polypeptide according to [11], comprising an amino acid sequence encoded by the nucleotide sequence represented by SEQ ID NO: 142;

[13]

a modified polypeptide having the amino acid sequence represented by SEQ ID NO: 145;

[14]

the modified polypeptide according to [13], comprising an amino acid sequence encoded by the nucleotide sequence represented by SEQ ID NO: 146;

[15]

a test kit for a plasma or serum antibody titer against a periodontal disease-causing bacterium, comprising a polypeptide having at least one amino acid sequence selected from the group consisting of the amino acid sequences represented by SEQ ID NOs: 1, 3, 5, 9, 15, 17, 19, 23, 31, 35, 37, 41, 43, 47, 63, 65, 67, 141, 143, 145, 147, 151, 153 and 155;

[16]

the test kit for a plasma or serum antibody titer against a periodontal disease-causing bacterium according to [15], wherein the polypeptide is a polypeptide having at least one amino acid sequence selected from the group consisting of the amino acid sequences represented by SEQ ID NOs: 3, 5, 15, 19, 31, 41, 141 and 145;

[17]

the test kit for a plasma or serum antibody titer against a periodontal disease-causing bacterium according to [15], wherein the polypeptide is a polypeptide encoded by at least one polynucleotide sequence selected from the group consisting of the polynucleotide sequences represented by SEQ ID NOs: 2, 4, 6, 10, 16, 18, 20, 24, 32, 36, 38, 42, 44, 48, 64, 66, 68, 142, 144, 146, 148, 152, 154 and 156;

[18]

a method for measuring an antibody titer against a periodontal disease-causing bacterium in a blood sample separated from a human body, comprising bringing the blood sample into contact with a periodontal disease-causing bacterium antigen polypeptide, said method being characterized in that the periodontal disease-causing bacterium antigen polypeptide is a polypeptide having at least one amino acid sequence selected from the group consisting of the amino acid sequences represented by SEQ ID NOs: 1, 3, 5, 9, 15, 17, 19, 23, 31, 35, 37, 41, 43, 47, 63, 65, 67, 141, 143, 145, 147, 151, 153 and 155;

[19]

a method for determining the presence of an antibody against a periodontal disease-causing bacterium in a blood sample separated from a human body, comprising bringing the blood sample into contact with a periodontal disease-causing bacterium antigen polypeptide, said method being characterized in that the periodontal disease-causing bacterium antigen polypeptide is a polypeptide having at least one amino acid sequence selected from the group consisting of the amino acid sequences represented by SEQ ID NOs: 3, 5, 15, 19, 31, 41, 141 and 145;

[20]

the method according to [19], wherein the polypeptide is a polypeptide encoded by at least one polynucleotide sequence selected from the group consisting of the polynucleotide sequences represented by SEQ ID NOs: 4, 6, 16, 20, 32, 42, 142 and 146;

[21]

a typing kit for strains of Porphyromonas gingivalis, comprising a polypeptide having at least one amino acid sequence selected from the group consisting of the amino acid sequences represented by SEQ ID NOs: 151, 153 and 155;

[22]

the typing kit according to [21], wherein the polypeptide is a polypeptide encoded by at least one polynucleotide sequence selected from the group consisting of the polynucleotide sequences represented by SEQ ID NOs: 152, 154 and 156;

[23]

a polypeptide having the amino acid sequence represented by SEQ ID NO: 151;

[24]

the polypeptide according to [23], comprising an amino acid sequence encoded by the nucleotide sequence represented by SEQ ID NO: 152;

[25]

a polypeptide having the amino acid sequence represented by SEQ ID NO: 153;

[26]

the polypeptide according to [25], comprising an amino acid sequence encoded by the nucleotide sequence represented by SEQ ID NO: 154;

[27]

a polypeptide having the amino acid sequence represented by SEQ ID NO: 155;

[28]

the polypeptide according to [27], comprising an amino acid sequence encoded by the nucleotide sequence represented by SEQ ID NO: 156.

In a first aspect, the present invention provides a test kit for a plasma or serum antibody titer against a periodontal disease-causing bacterium, which comprises a specific antigen protein.

According to the test kit for a plasma or serum antibody titer against a periodontal disease-causing bacterium of the present invention, the specific antigen protein is reacted with a small amount of blood separated from a human body and the IgG antibody titer against a periodontal disease-causing bacterium in a blood sample (plasma or serum) is measured, thereby testing the infection with the periodontal disease-causing bacterium of the subject. Generally, the following embodiments are included.

In one embodiment, the test kit comprises:

(1) a lancet for cutting the body of the subject to make a small wound to cause slight bleeding;

(2) a capillary for collecting the blood;

(3) a bottle in which a solution containing a specific periodontal disease-causing bacterium antigen protein is placed;

(4) a cylinder for compressing the inside of the bottle to separate plasma from the blood; and (5) a cap for hermetically sealing the bottle, wherein the blood collected using the capillary is mixed with the solution in the bottle to cause an antigen-antibody reaction between the antigen protein in the bottle and an IgG antibody against a periodontal disease-causing bacterium when the IgG antibody is present in the blood sample, and immunoprecipitation is measured, thereby testing the infection with the periodontal disease-causing bacterium.

In another embodiment, the test kit is used in an ELISA method, in which:

(1) an antigen protein is immobilized onto a 96-well plate for immobilizing;

(2) a blood sample (plasma or serum) is added to the 96-well plate to cause an antigen-antibody reaction;

(3) the 96-well plate is washed, and then an anti-human IgG secondary antibody is added thereto to cause an antigen-antibody reaction; and (4) the 96-well plate is washed, and then a light-developing or luminous reaction caused by the presence of the specifically bound anti-human IgG secondary antibody is carried out, thereby detecting a signal thereof.

In still another embodiment, the test kit is used in an antigen immobilization filter method, in which:

(1) an antigen protein is immobilized onto a filter (through biotinylation, etc.);

(2) a blood sample (plasma or serum) is added to the filter to cause an antigen-antibody reaction in the filter;

(3) the filter is washed, and then an anti-human IgG secondary antibody is added thereto to cause an antigen-antibody reaction;

(4) the filter is washed, and then a light-developing or luminous reaction caused by the presence of the specifically bound anti-human IgG secondary antibody is carried out, thereby detecting a signal thereof.

The characteristic feature of this aspect of the present invention resides in the periodontal disease-causing bacterium Porphyromonas gingivalis antigen protein contained in the test kit, and the antigen protein specifically reacts with an antibody against a periodontal disease-causing bacterium in a periodontal disease patient and also reacts with antibodies in a wide scope of periodontal disease patients.

That is, the periodontal disease-causing bacterium antigen protein contained in the test kit for a plasma or serum antibody titer against a periodontal disease-causing bacterium according to the present invention is a polypeptide having at least one amino acid sequence selected from the group consisting of the amino acid sequences represented by SEQ ID NOs: 1, 3, 5, 9, 15, 17, 19, 23, 31, 35, 37, 41, 43, 47, 141, 143, 145, 147, 151, 153 and 155 shown in the Sequence Listing. When one of these antigen proteins or a combination of two or more of these antigen proteins is used, the antibody titer or the type of an antibody in a periodontal disease patient can be tested and the degree or type of the infection with a periodontal disease-causing bacterium can also be tested. Further, there is inter-individual variability in the periodontal disease-causing bacterium antigen proteins and the immunotypes of individual periodontal disease patients (types of antibodies against periodontal disease-causing bacteria). However, when the antigen proteins of the present invention are used in combination, periodontal disease patients having an extensive immunotypes can be covered. Furthermore, a periodontal disease-causing bacterium strain SU63, which is a risk factor for cardiovascular diseases or cerebrovascular diseases, can be detected.

Preferably, the periodontal disease-causing bacterium antigen protein to be used in the present invention is a polypeptide encoded by at least one nucleotide sequence selected from the group consisting of nucleotide sequences represented by SEQ ID NOs: 2, 4, 6, 10, 16, 18, 20, 24, 32, 36, 38, 42, 44, 48, 142, 144, 146, 148, 152, 154 and 156 shown in the Sequence Listing.

More preferably, the periodontal disease-causing bacterium antigen protein contained in the test kit for a plasma or serum antibody titer against a periodontal disease-causing bacterium of the present invention is a polypeptide having at least one amino acid sequence selected from the group consisting of the amino acid sequences represented by SEQ ID NOs: 3, 5, 15, 19, 31, 41, 63 and 67 shown in the Sequence Listing, and preferably is a polypeptide encoded by at least one polynucleotide sequence selected from the group consisting of the polynucleotide sequences represented by SEQ ID NOs: 4, 6, 16, 20, 32, 42, 64 and 68.

In a second aspect, the present invention provides a modified polypeptide for use in the above-mentioned test kit for a plasma or serum antibody titer against a periodontal disease-causing bacterium.

During discovering periodontal disease-causing bacterium antigen proteins suitable for the antibody titer test kit, the present inventors find that some of the antigen proteins have a protease activity, in spite of the fact that the antigen proteins can react with antibodies in a wide scope of periodontal disease patients, and therefore often adversely affect the testing due to the self-digestion activity or the decomposing activity on other antigen proteins thereof. Then, the present inventors produced a modified polypeptide in which the protease activity is eliminated while keeping the antigenicity of these antigen proteins by a genetic engineering technique.

That is, the modified polypeptide for use in the test kit for a plasma or serum antibody titer against a periodontal disease-causing bacterium of the present invention is a polypeptide having the amino acid sequence represented by SEQ ID NO: 63, 65 or 67, and includes a modified polypeptide produced by deleting a cysteine residue at position-477 or position-488 in a wild-type polypeptide represented by SEQ ID NO: 51 or substituting the cysteine residue by another amino acid residue, preferably an alanine residue (i.e., a polypeptide represented by SEQ ID NO: 63 and 65 respectively) and a modified polypeptide produced by deleting a cysteine residue at position-471 in a wild-type polypeptide represented by SEQ ID NO: 57 or substituting the cysteine residue by another amino acid residue, preferably an alanine residue (i.e., a polypeptide represented by SEQ ID NO: 67). When one of these modified polypeptides or a combination of two or more of these modified polypeptides is used, antibodies against particularly more extensive types of periodontal disease-causing bacteria can be tested.

In a third aspect, the present invention provides a method for measuring an antibody titer against a periodontal disease-causing bacterium in a blood sample separated from a human body, comprising bringing the blood sample into contact with a periodontal disease-causing bacterium antigen polypeptide, wherein the blood sample to be used in the method is preferably blood, serum or plasma collected from a fingertip capillary or a vein, the periodontal disease-causing bacterium antigen polypeptide is a polypeptide having at least one amino acid sequence selected from the group consisting of the amino acid sequences represented by SEQ ID NOs: 1, 3, 5, 9, 15, 17, 19, 23, 31, 35, 37, 41, 43, 47, 63, 65, 67, 141, 143, 145, 147, 151, 153 and 155. The periodontal disease-causing bacterium antigen polypeptide is preferably a polypeptide having at least one amino acid sequence selected from the group consisting of the amino acid sequences represented by SEQ ID NOs: 3, 5, 15, 19, 31, 41, 63 and 67.

The method according to this aspect of the present invention can be suitably carried out using the test kit for a plasma or serum antibody titer against a periodontal disease-causing bacterium of the first aspect, preferably the periodontal disease-causing bacterium plasma antibody titer test.

Further, it also becomes possible to test the degree of progression (severity) of a periodontal disease on the basis of the antibody titer.

In a fourth aspect, the present invention provides a typing kit for a Porphyromonas gingivalis strain. The kit enables the typing of Porphyromonas gingivalis strains, particularly strain FDC381 and strain SU63, occurring in a blood sample separated from a human body to examine whether or not any one of the strains is present in the sample. The kit comprises a polypeptide having at least one amino acid sequence selected from the group consisting of the amino acid sequences represented by SEQ ID NOs: 151, 153 and 155, and the polypeptide is preferably encoded by at least one polynucleotide selected from the group consisting of the polynucleotides represented by SEQ ID NOs: 152, 154 and 156.

Effect of the Invention

According to the present invention, it becomes possible to provide a periodontal disease test kit, which enables the high speeded and highly accurate testing on a periodontal disease. It also becomes possible to provide a periodontal disease test kit, which enables the objective testing on a periodontal disease without depending on the skill level of practitioners.

Further, when the periodontal disease test kit of the present invention becomes widely used, a periodontal disease can be tested in a unified manner in dental clinics across the country. Further, by making a database of the measurement results obtained in the test, it becomes possible to establish or modify the determination criteria or treatment guidelines for periodontal diseases.

Furthermore, the periodontal disease test kit of the present invention can detect a risk factor for cardiovascular or cerebrovascular diseases.

BRIEF DESCRIPTION OF DRAWINGS

FIG. 6 illustrates the results of the Mascot search of antigen proteins.

FIG. 7 illustrates the genetic information on identified antigen proteins and the results of selection thereof.

FIG. 8 illustrates antigen-antibody reactions between sera and synthetic antigen proteins.

FIG. 9 illustrates signal values of the antigen-antibody reactions between sera and synthetic antigen proteins.

FIG. 11 illustrates signal values of the antigen-antibody reactions between healthy subject sera and synthetic antigen proteins.

FIG. 12 illustrates signal values of the antigen-antibody reactions between diverse patient sera and antigen proteins.

FIG. 13 illustrates the summary of the antigen-antibody reactions between diverse patient sera and antigen proteins.

FIG. 16 illustrates signal values of the antigen-antibody reactions between sera and synthetic antigen proteins.

FIG. 17 illustrates the summary of the antigen-antibody reactions between diverse sera and antigen proteins.

FIG. 18 illustrates signal average values and S/N values of the antigen-antibody reactions between healthy subject sera and patient sera and antigen proteins.

FIG. 21 illustrates the summary of the antigen-antibody reactions between sera and antigen proteins (strain SU63).

DETAILED DESCRIPTION OF THE PREFERRED EMBODIMENTS

Figure 1:
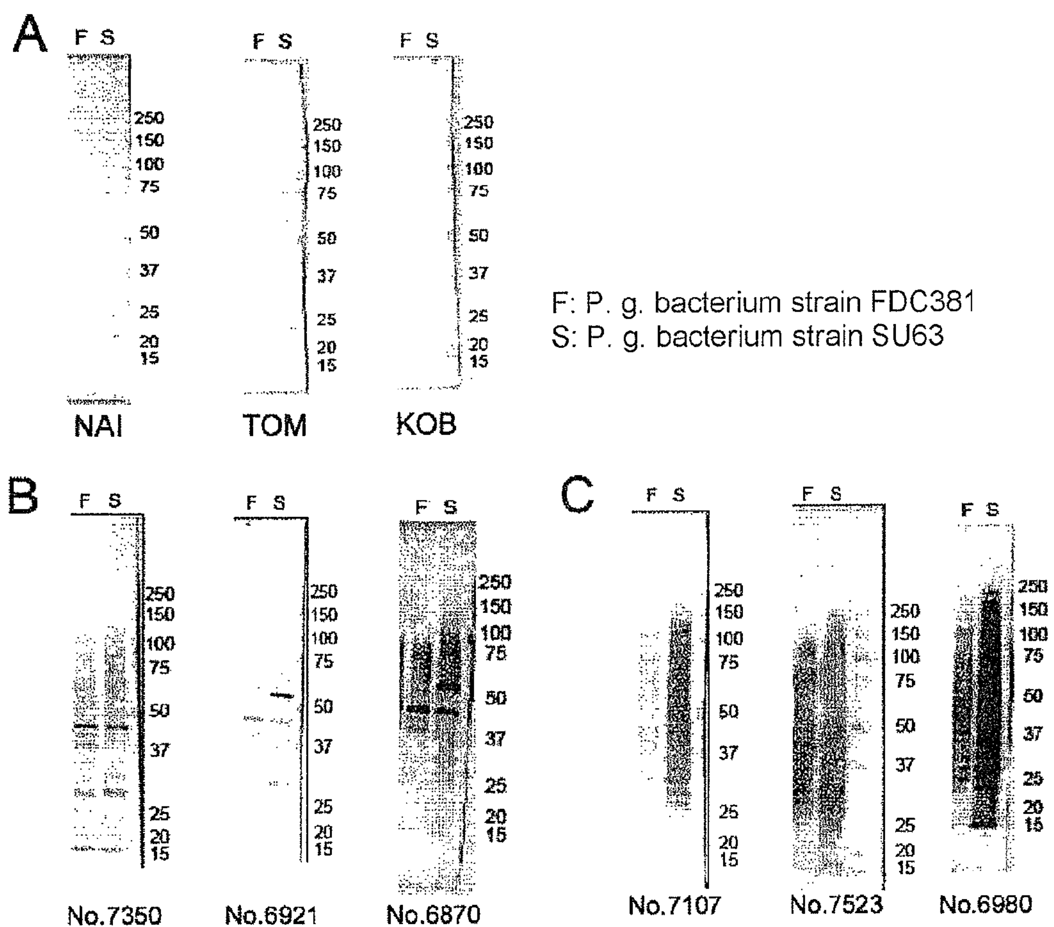
FIG. 1 illustrates antigen-antibody reactions between periodontal disease-causing bacterium antigen proteins and human sera. A: an antigen-antibody reaction with healthy subject sera; and B and C: antigen-antibody reactions with periodontal disease patient sera.

The present invention is described more in detail with reference to examples hereinbelow. However, the present invention is not limited by the examples.

Throughout the whole of the examples, *Porphyromonas gingivalis* strain FDC381 and strain SU63 are used as the periodontal disease-causing bacteria. Strain FDC381 is sold by Summit Pharmaceuticals International Corporation, and strain SU63 is available in the form of a type-II or type-IV fimbriated strain.

Production of an Antibody Column

When a human is infected with a periodontal bacterium, a variety of antibodies against the periodontal disease-causing bacterium antigen are produced in the human body through an immune response. Antigens recognized by the produced antibodies are varied depending on the difference in immune responses in the individuals.

Therefore, it is examined as to what type of antigen among the components in a periodontal disease-causing bacterium antigen preparation solution is targeted by the antibodies, and sera for use in the purification of more antigens are selected on the basis of the results of the examination.

Preparation of Antigen Proteins

An antigen preparation solution (Institute of Immunology Co., Ltd., 200 μg protein equivalent), which was prepared by disrupting cells of Porphyromonas gingivalis (strain FDC381 and strain SU63) with ultrasonic waves and then subjecting to ultracentrifugation to collect a supernatant fraction, was added with phosphate-buffered saline (PBS) to prepare a solution having a volume of 270 μl. Trichloroacetic acid was added to the solution, the resultant mixture was allowed to stand in ice and then centrifuged at a low temperature, and then a supernatant was removed therefrom. Ice-cold ethanol was added to a precipitate to wash, the resultant solution was centrifuged again at a low temperature, and then a supernatant was removed therefrom. The above-mentioned procedure was repeated two times. The precipitate was air-dried, and then added with 120 μl of PBS containing 0.06% of sodium dodecyl sulfate (SDS) to dissolve the precipitate. In this manner, an antigen protein solution for each of the strains was prepared.

Quantification of Antigen Proteins

Each of prepared standards (concentrations: 1000, 500, 250, 125, 62.5 or 31.25 ng/μl) (25 μl), an antigen protein solution diluted with PBS (25 μl) as a control was added to each well of a 96-well plate, and then a protein working solution (a mixture of Thermo scientific, Reagent A:B=50:1) (200 μl) was added to each well. Subsequently, the reaction solution was stirred with a shaker and then incubated in a constant-temperature-humidity unit at 37° C. for 30 minutes. Subsequently, an absorbance at 577 nm was measured using a plate reader (Intermed, NJ2000). In this manner, the collected antigen proteins were quantified.

SDS-PAGE Electrophoresis

Each of the quantified *P. gingivalis* bacteria (strain FDC381 and strain SU63) antigen proteins was prepared into a solution having a protein concentration of 400 ng/μl using a sample buffer (Invitrogen). The prepared sample was thermally denatured and then subjected to SDS-PAGE electrophoresis (a protein solution: 5 μl).

A gel that had been subjected to SDS-PAGE electrophoresis was subjected to blotting on a polyvinylidene fluoride membrane (a PVDF membrane) using an iBlot dry blotting system (Invitrogen).

After transferring onto the PVDF membrane, the electrophoresed layout (a molecular weight marker, strain FDC381, strain SU63) was cleaved as one set. A cleaved one set of slits was subjected to Ponceau staining to confirm the occurrence of blotting of proteins. The remaining slits were placed in a Falcon tube and then immersed in a blocking solution (Tris-buffered saline (abbreviated as "TBS", hereinbelow) containing 3% of skim milk and 0.1% of Tween 20).

Antigen-Antibody Reaction Using Serum

After the removal of the blocking solution from the blocked slit, a serum reaction solution (a solution prepared by adding 8 μl of a serum collected from a healthy subject or a periodontal disease patient to 20 ml of TBS containing 3% of skim milk) was added to the slit, and the resultant solution was shaken at room temperature. Subsequently, the slit was washed with TBS containing 0.05% of Tween 20. After washing, a 5000-fold-diluted horseradish peroxidase-conjugated goat anti-human IgG antibody reaction solution (a solution prepared by adding an anti-human secondary antibody (CHEMICON) to TBS containing 3% of skim milk) was added to the slit, and the resultant product was shaken at room temperature. Subsequently, the slit was washed with TBS containing 0.05% of Tween 20. After washing, the slit was immersed in TBS containing 0.61 mg/mL of 4-methoxy-1-naphthol and 0.018% of aqueous hydrogen peroxide, the development of a color was confirmed, and the slit was washed with purified water and then dried.

The results of the reactions between the antigen proteins and the human sera are shown in FIG. 1.

Almost no signal was observed in the antigen-antibody reaction with the healthy subject sera (FIG. 1A: normal subject sera).

On the other hand, clear signals were observed in the antigen-antibody reaction with periodontal disease patient sera, and the patterns of the signals were various (FIGS. 1B and 1C). The various signals observed in the antigen-antibody reaction with patient sera could be roughly classified into two groups, i.e., signals having clear bands (FIG. 1B) and signals showing wholly spread smears (FIG. 1C). The various antigen-antibody reaction patterns are formed due to the difference in sizes and specificity to the strains.

Signals having the below-mentioned sizes were observed specifically strong in many of the patient sera.

46 kDa (antigen proteins of strain FDC381 and strain SU63)

25 to 37 kDa (antigen proteins of strain FDC381 and strain SU63)

100 to 110 kDa (antigen proteins of strain FDC381 and strain SU63)

57 kDa (an antigen protein of strain SU63)

150 to 250 kDa (an antigen protein of strain SU63)

Reviewing the results of the antigen-antibody reactions using periodontal disease patient sera, roughly two types of signal patterns (clear bands and wholly spread smears) were observed, and various antigen-antibody reaction patterns were formed depending on the combinations (sizes, types of strains) of the antigens. That is, it was demonstrated that the antibodies produced in persons infected with *P. gingivalis* bacteria were varied and there were cases in which some proteins were recognized as antigen proteins in some sera but were not at all recognized in the other sera. This fact agrees with a report that antibodies contained in varied periodontal disease patient sera utilize a variety of proteins as antigen thereof. Therefore, it was demonstrated that, for the purpose of measuring the infection with *P. gingivalis* bacteria employing antibody titers, various test antigen proteins were needed.

Further, it is considered that, when an antigen protein that is common between strain FDC381 and strain SU63 is used in the test, it is difficult so far as to identify the strains. On the other hand, when only an antigen protein specific to a strain is used in the test, if positive results are obtained, it is suspected that the infection with the strain may occur.

Although the antigen-antibody reaction patterns observed in patient sera were various, no significant difference in patterns was observed between sera from first-visit patients (FV) and sera from maintenance patients (SPT). Thus, antigen proteins that showed strong signals in patient sera were identified and they were made candidates for the antigens to be used in the test.

As shown in the results, a group of antigen proteins of 46 kDa, 25 to 37 kDa, 100 to 110 kDa, 57 kDa and 150 to 250 kDa are mentioned as the band showing strong signals against many patient sera. Then, the presence of antigenicity of the group of proteins against sera from various patients was determined. The results are shown in

TABLE 1

Reactions of patient sera against antigen protein groups

| | | | Plasma antibody titer | | Common antigen | | | SU63-specific antigen | |
|---|---|---|---|---|---|---|---|---|---|
| | | Patient serum No. | FDC381: | SU63: | 46 kDa | 25-37 kDa | 100-110 kDa | 57 kDa | 150-250 kDa |
| FV | 381 ≥ 1 | 7056 | 7.36 | 0.1 | ○ | | | | |
| | SU < 1 | 7457 | 6.18 | 0.6 | ○ | ○ | ○ | | ○ |
| | | 6991 | 4.43 | 0.9 | | | | ○ | |
| | | 7492 | 3.76 | 0.59 | ○ | | ○ | | ○ |
| | | 6809 | 3.35 | 0.9 | | ○ | ○ | ○ | |
| | | 6816 | 1.89 | 0.76 | ○ | | | | |
| | | 7125 | 1.89 | 0.09 | ○ | ○ | ○ | | ○ |
| | | 7500 | 1.87 | 0.93 | | ○ | ○ | | ○ |
| | | 7107 | 1.8 | 0.06 | | ○ | ○ | | ○ |
| | | 7835 | 1.64 | 0.19 | ○ | | | | |
| | 381 ≥ 1 | 7350 | 5.45 | 10.18 | ○ | | | | |
| | SU ≥ 1 | 7523 | 15.11 | 9.08 | | ○ | ○ | | ○ |
| | | 7524 | 44.9 | 7.35 | | ○ | ○ | ○ | ○ |
| | | 6921 | 7.55 | 5.07 | ○ | | ○ | ○ | |
| | | 6896 | 4.36 | 4.37 | | ○ | ○ | | ○ |
| | | 6975 | 7.98 | 4.31 | ○ | ○ | ○ | ○ | ○ |
| | | 6923 | 5.2 | 4.11 | ○ | ○ | ○ | ○ | |
| | | 7393 | 15.2 | 4.07 | ○ | ○ | | | ○ |
| | | 6926 | 5.63 | 3.61 | ○ | | | ○ | |
| | | 7495 | 11.38 | 2.61 | | | ○ | ○ | |
| | 381 < 1 | 6817 | 0.11 | 1.32 | | ○ | | | |
| | SU ≥ 1 | 6820 | 0.68 | 2.01 | ○ | | ○ | | ○ |
| | | 6828 | 0.55 | 1.97 | | | | | |
| | | 6855 | 0.58 | 1.03 | | ○ | ○ | | |
| | | 6863 | −0.32 | 2.2 | ○ | | | | |
| | | 6867 | 0.93 | 1.46 | ○ | | | ○ | |
| | | 6874 | 0.03 | 2.83 | ○ | | ○ | ○ | |
| | | 6881 | 0.66 | 1.4 | ○ | ○ | ○ | | |
| | | 6889 | 0.28 | 2.23 | ○ | ○ | ○ | | |
| | | 6904 | 0.88 | 1.51 | ○ | | | | |
| | | 6935 | 0.63 | 1.31 | ○ | | | | |
| | | 6968 | 0.08 | 1.93 | ○ | ○ | | | ○ |
| SPT | 381 ≥ 1 | 7082 | 133.77 | 39.79 | ○ | ○ | ○ | | |
| | SU ≥ 1 | 6918 | 30.24 | 6.71 | ○ | ○ | ○ | ○ | |
| | | 6870 | 13.32 | 5.85 | ○ | ○ | ○ | ○ | |
| | | 6980 | 13.36 | 5.52 | ○ | ○ | ○ | | ○ |
| | | 6872 | 6.19 | 4.66 | ○ | | ○ | ○ | |
| | | 7001 | 3.77 | 3.32 | ○ | ○ | ○ | | ○ |
| | | 6802 | 1.16 | 3.05 | ○ | ○ | ○ | | |
| | | 7268 | 23.57 | 2.87 | ○ | ○ | ○ | ○ | |
| | | 7004 | 1.54 | 2.31 | | ○ | ○ | | ○ |
| | 381 ≥ 1 | 6823 | 4.57 | 0.44 | | ○ | ○ | | |
| | SU < 1 | 7234 | 3.25 | 0.63 | ○ | | ○ | ○ | |
| | | 7230 | 3.22 | 0.87 | ○ | | ○ | | |
| | | 7381 | 3.22 | 0.09 | ○ | ○ | ○ | ○ | |
| | | 7210 | 1.74 | 0.32 | ○ | ○ | ○ | ○ | |
| | | 7253 | 1.57 | −0.19 | ○ | | | | ○ |
| | | 7263 | 1.49 | 0.07 | | | | ○ | |
| | | 7135 | 1.49 | 0.14 | ○ | ○ | ○ | | |

As apparent from Table 1, it was demonstrated that, when combinations of these five types of antigen protein groups were used, it became possible to confirm the presence of an antibody against a *P. gingivalis* bacterium in all of the patient sera and the testing on extensive periodontal disease patients could be covered.

Selection of Sera to be Used in Production of Immunoaffinity Column

Next, for the purpose of purifying the five types of antigen protein groups using an immunoaffinity column, sera to be used for the production of the column were selected. In this selection, two types of patient serum pools were used for the production of the antibody column with taking the antigen-antibody reaction patterns and the plasma antibody titer measurements in patient sera into consideration. That is, No. 7350, No. 6921 and No. 6870 serum pools, which showed clear bands against target antigens and had high plasma antibody titers, were used for the production of the antibody column for purifying antigen protein groups of 46 kDa (strain FDC381 and strain SU63) and 57 kDa (strain SU63). On the other hand, No. 7107, No. 7523 and No. 6980 serum pools, which showed wholly spread smear-like band patterns but showed strong signals against target antigens and had high plasma antibody titers, were used for the production of the antibody column for purifying antigen protein groups of 25 to 37 kDa (strain FDC381 and strain SU63), 100 to 110 kDa (strain FDC381 and strain SU63) and 150 to 250 kDa (strain SU63). As controls for comparison purposes, serum pools of healthy subjects NAI, TOM and KOB were used in the production of the antibody column for purifying antigen proteins from healthy subjects.

On the other hand, as antigen proteins to be used in the plasma antibody titer test, five types of antigen protein groups (46 kDa, 25 to 37 kDa, 100 to 110 kDa, 57 kDa, and 150 to 250 kDa) were selected. For the purpose of purifying the five types of antigen protein groups using immunoaffinity columns, three types of columns were produced. That is, column A: a healthy subject serum column (NAI, TOM and KOB serum ligands), column B: a column for purifying a clear band (No. 7350, No. 6921 and No. 6870 serum ligands) and column C: a column for purifying a smear-like band (No. 7107, No. 7523 and No. 6980 serum ligands) were produced.

Purification of Antigen Proteins Using Immunoaffinity Columns

For identifying the selected antigen proteins, it is needed to purify the antigen proteins from antigen preparation solutions. Then, antibody columns were produced using the selected sera and the antigen proteins were purified.

Immunoaffinity columns were produced in accordance with the method mentioned below based on Masato OKADA and Kaori MIYAZAKI ed., "Experiment note of proteins (second volume)", Yodosha, pp. 131-136 (1990) and Kiyoshi TAKATSU et al., ed., "Antibody experiment manual for study of proteins", Yodosha, pp. 53-61 (2005).

A periodontal disease patient serum or a healthy subject serum (1.5 ml) (each serum: 500 μl×3 samples) was added with an antibody binding buffer (a 50-mM tartrate buffer, 3 M NaCl, pH 9.0) (2.5 ml) and sodium chloride (0.26 g), and then mixed, thereby preparing an antibody reaction solution.

On the other hand, protein G sepharose (GE Healthcare) was added to an Econo-PACK column (BIO-RAD) and washed with ultrapure water and then with an antibody-binding buffer. The whole of the prepared antibody reaction solution was added to the column, the column was hermetically sealed, and then solution was stirred using a rotator. After stirring, the antibody reaction solution was removed, and then the column was washed with an antibody-binding buffer (a 50-mM tartrate buffer, 3 M NaCl, pH 9.0).

A cross-linker BS3 (PIERCE) (100 mg) was dissolved in a cross-linker solution (0.2 M triethanolamine-HCl, pH 8.0) (6.8 ml), and the resultant solution was dispensed into three columns (a healthy subject serum column and two patient serum columns) and then stirred at room temperature using a rotator.

After the removal of the cross-linker solution from the column, the column was washed with a blocking solution (0.2 M ethanolamine-HCl, pH 8.0). The column was hermetically sealed, and then the blocking solution was added to the column and stirred at room temperature using a rotator. Subsequently, the blocking solution was removed, then the column was washed with an elution solution (0.1 M glycine-HCl, pH 2.8) and then with 50 mM Tris-HCl (pH 7.5), and then the column was added with 50 mM Tris-HCl (pH 7.5) and stored (immunoaffinity columns A, B and C).

Preparation of Antigen Protein Samples

A solution (270 μl) was prepared by adding PBS to an antigen preparation solution of *P. gingivalis* bacteria (strain FDC381 and strain SU63) (Institute of Special Immunity Co. Ltd., 200 μg protein equivalent). Trichloroacetic acid was added to the solution, and the resultant solution was allowed to stand in ice and then centrifuged at a low temperature to remove a supernatant. Ice-cold ethanol was further added to the resultant solution to wash the precipitate, and then the resultant solution was centrifuged again at a low temperature to remove a supernatant. The above-mentioned procedure was repeated three times.

After air-drying the precipitate, PBS (200 μl) containing 0.06% of SDS was added to dissolve the precipitate. Subsequently, the protein solutions for each of the strains were combined. PBS (containing 0.01% of Brij-35 and 0.2% of CHAPS) in the same volume as that of the combined protein solution was added to the combined protein solution to dissolve the precipitate, thereby preparing antigen protein samples for each of the strains.

Quantification of Antigen Proteins

Each of the prepared standards (concentrations: 1000, 500, 250, 125, 62.5 and 31.25 ng/μl) (25 μl), an antigen protein sample diluted with PBS (25 μl) and PBS (25 μl) as a control were added to each well of a 96-well plate, and then a protein working solution (a mixture of Thermo scientific, Reagent A:B=50:1) (200 μl) was added to each well. Subsequently, the reaction solution was stirred with a shaker and then incubated in a constant-temperature-humidity unit at 37° C. for 30 minutes. Subsequently, an absorbance at 577 nm was measured using a plate reader (Intermed, NJ2000). In this manner, the antigen proteins in the samples were quantified.

Purification of Antigen Proteins Using Immunoaffinity Columns

An antigen protein sample (about 133 μg/1.5 ml) was applied onto each of PBS-equilibrated immunoaffinity columns (A, B and C) (the buffer composition for the sample: PBS containing 0.03% SDS, 0.005% Brij-35 and 0.2% CHAPS (Dojin Laboratories). The column was stirred using a rotator at room temperature, a flow-through was collected and stored as a sample. A wash buffer (0.005% Brij-35, 0.1% CHAPS, 20 mM Tris-HCl and 500 mM NaCl, pH 7.5) was added to the column, and then the column was stirred using a rotator at room temperature to wash the column. After stirring, a flow-through was collected and stored as a sample. This procedure was repeated three times.

After the column was washed with ultrapure water, an elution buffer (0.05% trifluoroacetic acid) (5 ml) was added two times, and an eluted protein solution was collected and lyophilized.

SDS-PAGE Electrophoresis

A portion of the antigen protein sample, a flow-through obtained in each step and the eluted protein was separated and then prepared into a sample buffer containing mercaptoethanol at a final concentration of 5%.

The prepared sample was thermally denatured and then subjected to SDS-PAGE electrophoresis (10 μl for CBB staining, 5 μl for antigen-antibody reaction).

A gel that had been subjected to SDS-PAGE electrophoresis was washed with distilled water, then immersed in a CBB staining solution, and stirred at room temperature. Subsequently, the gel was washed with distilled water until bands could be observed clearly.

The gel that had been subjected to SDS-PAGE electrophoresis was also subjected to blotting on a PVDF membrane using an iBlot dry blotting system (Invitrogen).

After transferring onto the PVDF membrane, a layout was cleaved as one set and then immersed in a blocking solution (TBS containing 3% of skim milk and 0.1% of Tween 20).

Antigen-Antibody Reactions Using Sera

With respect to a slit that had been subjected to blocking, the blocking solution was removed therefrom, then a serum reaction solution (a solution prepared by adding 8 μl of a serum to 20 ml of TBS containing 3% of skim milk) was added to the slit, and the resultant product was shaken at room temperature. The sets of sera added are as follows.

Set A (healthy subject sera): NAI, TOM, KOB

Set B (patient sera 1): No. 7350, No. 6921

Set C (patient sera 2): No. 7107, No. 7523, No. 6980

The slit was washed with TBS containing 0.05% of Tween 20, a 5000-fold-diluted horseradish peroxidase-conjugated sheep anti-human secondary antibody reaction solution (a solution prepared by adding a human secondary antibody (CHEMICON) to TBS containing 3% of skim milk) was added thereto, and the resultant product was stirred at room temperature.

Subsequently, the slit was washed with TBS containing 0.05% of Tween 20, the slit was immersed in a color-developing solution (TBS containing 0.61 mg/ml of 4-methoxy-1-naphthol and 0.018% of aqueous hydrogen peroxide), and the development of color in the slit was confirmed, and then the slit was washed with purified water and dried.

Purification of Strain FDC381 Antigen Protein

Figure 2:
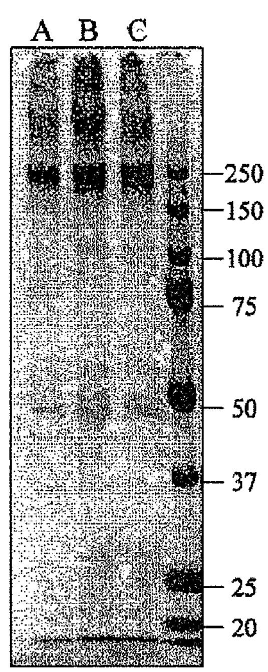
FIG. 2 illustrates a SDS-PAGE electrophoresis pattern of a Porphyromonas gingivalis strain FDC381 antigen protein roughly purified using an antibody column. Lane A: an antigen protein roughly purified from a healthy subject serum column; lane B: an antigen protein roughly purified from a patient serum 1 column, lane C: an antigen protein roughly purified from a patient sera 2.

The SDS-PAGE electrophoresis patterns of the antigen proteins purified from the columns are shown in FIG. 2.

A flow-through obtained after the application of the antigen protein samples onto immunoaffinity columns was confirmed, and any significant difference was not observed between a healthy subject serum column and patient serum columns. However, when purified proteins were observed, proteins purified from the patient serum columns apparently showed stronger signals in CBB staining (FIG. 2, lanes B and C) as compared with a protein purified from the healthy subject serum column (FIG. 2, lane A). Particularly, a band having a size of about 50 kDa showed a significantly strong signal in the patient serum columns. A band having a size larger than 25 kDa also showed a strong signal in the patient sera (FIG. 2, lanes B and C).

Purification of Strain SU63 Antigen Protein

Figure 4:
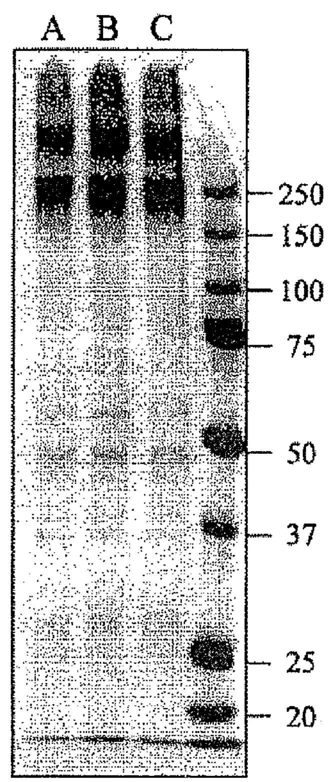
FIG. 4 illustrates an SDS-PAGE electrophoresis pattern of a Porphyromonas gingivalis strain SU63 antigen protein roughly purified using an antibody column. Lane A: an antigen protein roughly purified from a healthy subject serum column, lane B: an antigen protein roughly purified from a patient serum 1 column, lane C: an antigen protein roughly purified from a patient serum 2 column.

The SDS-PAGE electrophoresis patterns of the antigen proteins purified from the columns were shown in FIG. 4.

When proteins purified after the application of the antigen protein samples onto immunoaffinity columns were observed, antigen proteins purified from the patient serum columns apparently showed stronger signals in CBB staining (FIG. 4, lanes B and C) as compared with an antigen protein purified from the healthy subject serum column (FIG. 4, lane A), although it was not so clear than in the case of strain FDC381. A particularly significant difference was observed between a band having a size slightly larger than 25 kDa and a band having a size slightly larger than 50 kDa. A strong signal observed in the purification of strain FDC381 also tended to show a strong signal in the purification of strain SU63 (FIG. 4).

Antigen-Antibody Reactions of Antigen Proteins

Figure 3:
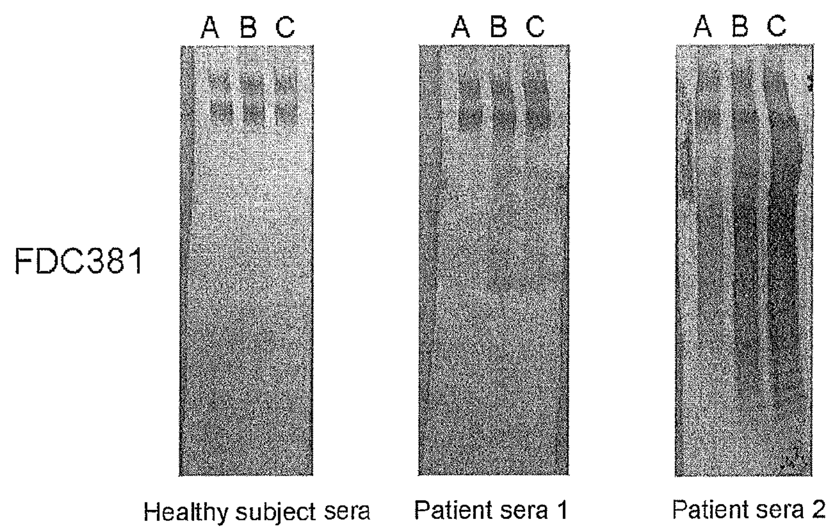
FIG. 3 illustrates antigen-antibody reactions between a roughly purified strain FDC381 antigen protein and sera. Lane A: an antigen protein roughly purified from a healthy subject serum column, lane B: an antigen protein roughly purified from a patient serum 1 column, lane C: an antigen protein roughly purified from a patient serum 2 column.
Figure 5:
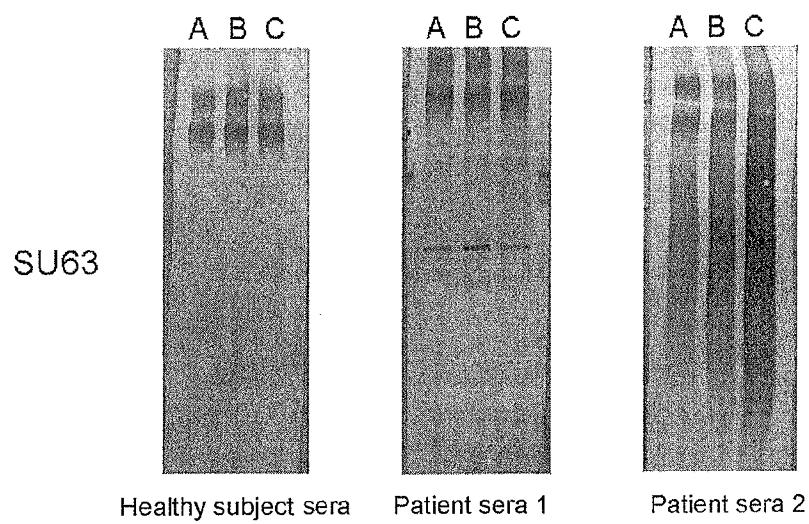
FIG. 5 illustrates antigen-antibody reactions between a roughly purified strain SU63 antigen protein and sera. Lane A: an antigen protein roughly purified from a healthy subject serum column, lane B: an antigen protein roughly purified from a patient serum 1 column, lane C: an antigen protein roughly purified from a patient serum 2 column.

The results of the antigen-antibody reactions of antigen proteins of strain FDC381 and strain SU63 which were subjected to SDS-PAGE electrophoresis are shown in FIG. 3 and FIG. 5, respectively.

Serum set A (healthy subject sera) reacted with proteins each having a high molecular weight but hardly with proteins each having a size of 150 kDa or less among any of the antigen proteins eluted from the healthy subject serum column and the patient serum columns (FIGS. 3 and 5).

On the other hand, serum set B (the patient sera 1; a group of sera used in the production of column B) strongly reacted with the antigen proteins eluted from the patient serum columns (FIGS. 3 and 5, lanes B and C of the "patient sera 1"). Note that stronger signals were observed in the proteins eluted from the patient serum column (column B).

Similar to serum set B, serum set C (the patient sera 2; a group of sera used for the production of column C) also strongly reacted with the proteins eluted from the patient serum columns (FIGS. 3 and 5, lanes B and C of the "patient sera 2"). On the other hand, serum set C relatively reacted also with the proteins eluted from the healthy subject serum column (FIGS. 3 and 5, lane A of the "patient sera 2"). Note that stronger signals were observed in the proteins eluted from the patient serum column (column C).

When the proteins eluted from the immunoaffinity columns were observed, the number of the proteins eluted from the patient serum columns was apparently larger as compared with that of the proteins eluted from the healthy subject serum column. It is considered that this is because many antibodies against *P. gingivalis* bacteria were bound to the protein G sepharose in each of the patient serum columns, and a larger number of the antibodies could be bound to the *P. gingivalis* bacterium antigen proteins during purification process using the same to be purified.

From the above, candidates for the antigen proteins were selected by comparing the proteins purified using the healthy subject serum column with the proteins purified using the patient serum columns.

As a result of the comparison among the purified antigen proteins, it was found that antigen proteins shown in Table 1 as candidates, each of which contained a common antigen (46 kDa, 25 to 37 kDa, and 100 to 110 kDa), were contained in larger amounts in the proteins purified from the patient serum columns than in the proteins purified from the healthy subject serum column. Therefore, it is possible to select as candidates for the antigen proteins that could be used in the test kit by elucidating the entire constitutions of the purified proteins and comparing both proteins. Then, all of the proteins constituting each of the purified proteins were subjected to mass spectrometry and identified.

Mass Spectrometry

In the same manner as mentioned above, a roughly purified antigen protein was separated by subjecting to SDS-PAGE electrophoresis, all of three lanes of each of bands of a CBB-stained eluted protein (column A, B and C) were cleaved in one lump. The cleaved gel was placed in a Falcon tube, ultrapure water (200 μl) was added thereto, and the resultant solution was subjected to mass spectrometry as mentioned below.

Preparation of Samples for Mass Spectrometry

The prepared sample was protein-digested using ProGest (Genomic Solutions) workstation, reduced with dithiothreitol at 60° C., and then cooled to room temperature. Subsequently, the resultant product was alkylated with iodoacetamide. The alkylated product was incubated at 37° C. for 4 hours in the presence of trypsin, and formic acid was added to the solution to terminate the reaction. A supernatant obtained after the termination of the reaction was used as a sample for the analysis.

LC/MS/MS

The prepared sample was subjected to a nano-LC/MS/MS analysis using ThermoFisher LTQ Orbitrap XL.

A hydrolysis product (30 μl) was applied onto an ID C12 column (Jupiter Proteo, Phenomenex) vented column having a size of 5 mm×75 μm. The gradient elution was carried out at 300 nl/min on an ID C12 column having a size of 15 cm×75 μm.

With respect to MS/MS, analysis was carried out using a mass spectrometer that was operated by data-dependent mode, six most abundant ions. The Orbitrap MS scan was carried out at an FWHM resolution of 60000.

The MS/MS data was searched using a Mascot (www.matrixscience.com) local copy.

The parameters for the LC/MS/MS search were set as follows.

Type of search: MS/MS ion search

Classification: whole bacteria or whole organism species

Enzyme: trypsin

Default modification: carbamidemethylation

Variable modification: oxidation, acetylation, pyroglutamylation and deamidation Mass value: monoisotopic Mass of protein: not limited Peptide mass tolerance: ±10 ppm (Orbitrap)

Fragment mass tolerance: ±0.5 dalton (LTQ)

Maximum value of error cutting: 2

Scaffold

A sample was processed in Scaffold algorithm (www.proteomesoftware.com) using a DAT file created by Mascot. LTQ Orbitrap XL data parameter had identified a protein that matches two or more peptides.

The results are shown in FIG. 6.

Strain FDC381

With respect to the analyzed three samples (A to C; A: a healthy subject serum column, B: a patient serum column 1, C: a patient serum column 2), the Mascot search was carried out on the whole bacteria. As a result, 28 types in total of proteins were identified (FIG. 6, left). Among the identified proteins, each of proteins of Nos. 9, 17 and 18 was a part of an IgG antibody. Among the 28 types of proteins, 15 types were identified only in protein groups purified from the patient serum columns (B and C). On the other hand, the other 10 types of proteins were observed also in the protein groups purified from the healthy subject serum column (A), but the number of spectral counts was high in the protein groups purified from the patient serum columns (B and C).

Strain SU63

With respect to the analyzed three samples (A to C), the Mascot search was carried out on the whole bacteria. As a result, 28 types in total of proteins were identified (FIG. 6, right). Among the identified proteins, each of proteins of Nos. 8 and 12 was a part of an IgG antibody. Among the 28 types of proteins, 20 types were identified only in protein groups purified from the patient serum columns (B and C). On the other hand, 5 types of proteins were observed also in the protein groups purified from the healthy subject serum column (A), but the number of spectral counts was high in the protein groups purified from the patient serum columns (B and C). The protein of No. 22 was identified only in the healthy subject serum column (A).

Reviewing the results obtained this time, in both strain FDC381 and strain SU63, the number of types and the amount together were apparently larger in the protein groups eluted from the patient serum columns than those in the protein groups eluted from the healthy subject serum column. This fact suggests that antigen proteins maintained in antibodies in patient sera were purified by an immunoaffinity column method. Among the identified proteins, proteins that have been already reported as antigens were included. From this fact, it is suggested that the proteins produced by the purification employing the immunoaffinity column method in this time also are highly probably antigen proteins.

Selection of Synthesized Proteins

Proteins that have been observed in the two times of the antigen protein identification were organized, and proteins to be actually synthesized were selected.

For the proteins that have been identified, those proteins which had been identified in both strains based on accession numbers were described as the same line, genetic information of the proteins were examined to determine whether or not the function is known and whether or not antigenicity is known, and the proteins were classified (FIG. 7).

With respect to the matter that whether or not the proteins were specific to patients, a case where the spectrum count of a protein that had been identified from the healthy subject column was apparently high was determined "x", a case where the spectrum count of a protein that had been identified from the healthy subject column and the spectrum count of a protein that had been identified from the patient column were almost the same was determined "Δ", and a case where the spectrum count of a protein that had been identified from the patient column was apparently high was determined "o" (primary selection). In addition, for the purpose of determining whether or not proteins were specific to *P. gingivalis* bacteria, proteins having high homology were examined on the basis of nucleotide sequences. A protein having slight homology with other bacterial species was determined "Δ", a protein having high homology with other bacterial species was determined "x", and a protein having low homology and being specific to *P. gingivalis* bacteria was determined "o" (secondary selection).

Proteins that had been identified by the two times of mass spectrometry were organized. As a result, 37 types in total of, proteins were identified as candidate antigen proteins. As a result of the overlapping of amino acid sequences, the primary selection and the secondary selection, proteins that fulfilled all of the requirements were 13 types in total of proteins, i.e., proteins of Nos. 3, 4, 6, 9, 10, 15, 16, 19, 24, 26, 37, 32 and 37.

It was thought to select patient-specific and *P. gingivalis*-bacteria-specific proteins through the primary selection and the secondary selection. However, the selection of candidate proteins in this stage might cause the loss of available antigen proteins. For example, in the case of a protein that is not selected because of its non-patient-specificity, if the protein has a satisfactorily higher antibody titer against patients than that against healthy subjects, the protein is a protein that can be used as a test antigen. Therefore, it was considered that the loss of candidate antigen proteins could be better prevented when antigenicity of actually synthesized proteins was evaluated.

Then, protein synthesis was carried out using, as candidates, 31 types in total of proteins, other than protein Nos. 1, 17, 18, 25, 30 and 31 of which the amino acid sequences were overlapped, among 37 types in total of proteins that had been identified by mass spectrometry.

Protein Synthesis and Evaluation of Antigenicity of Synthesized Proteins

For the purpose of evaluating whether or not the 31 types of candidate proteins actually showed antigenicity, proteins were synthesized and the antigenicity of the synthesized proteins was subsequently evaluated using healthy subject sera and patient sera.

Genetic information on each of the proteins of interest was obtained from a database (antigen protein information), desired genes were amplified from genomic DNA of a *P. gingivalis* bacterium strain using the synthesized primer pairs represented by SEQ ID NOs: 71 to 132 in the Sequence Listing and cloned into plasmid DNA (a pDONR vector) using a Gateway system (Invitrogen).

Subsequently, the pDONR vector DNA into which each of the genes had been cloned was treated with a restriction enzyme and then ligated to a protein expression vector (Cell-Free Sciences Co., Ltd.: a pEu vector) that had been treated with the same restriction enzyme. A ligation product was introduced into a cell of *Escherichia coli* (*E. coli*) by transformation. Subsequently, a clone having the gene introduced thereinto was selected.

Plasmid DNA was collected from the selected clone and then subjected to sequence analysis. With respect to a clone in which any significant mutation was not recognized from the results of the sequence analysis, a large amount of a plasmid was prepared, a protein was synthesized using a wheat germ cell-free protein synthesis system, and the resultant protein was purified using a GST tag.

It was tried to carry out in vitro protein synthesis with respect to all of 31 types of genes. However, with respect No. 33, the cloning into the protein expression vector was not achieved; and with respect to No. 5, the protein synthesis was not achieved or the amount of a synthesized protein was extremely small. Therefore, antigenicity was evaluated on the remaining 29 types of proteins. For the evaluation of antigenicity with respect to the synthesized proteins, dot blot analysis was carried out.

Dot Blotting 29 types of antigen proteins were subjected to dot blotting. The amount of each of the antigen proteins was adjusted to 50 ng, four sets of dot blot were produced for each of the antigen proteins. With respect to the proteins of Nos. 32 and 35, it was impossible to quantify the proteins and therefore a solution of the synthesized protein (4 μl) was subjected to dot blotting. After the dot blotting, the dot blot was immersed in a blocking solution (a TBS solution containing skim milk (3%) and Tween 20 (0.1%)).

As a primary antibody, a portion (8 μl) of a healthy subject serum pool prepared by mixing sera from normal subjects NAI, TOM and KOB (3 μl for each) together, a portion (8 μl) of a patient serum pool 1 prepared by mixing sera from periodontal disease patients Nos. 7350 and 6921 (4 μl for each) together, and a portion (8 μl) of a patient serum pool 2 prepared by mixing sera from periodontal disease patients Nos. 7107, 7523 and 6980 (3 μl for each) together were used. Each of the portions was added to TBS (20 ml) containing 3% of skim milk. The slit of the dot blot was added to each of the three kinds of antibody solutions, thereby carrying out an antigen-antibody reaction.

Subsequently, the slit was washed with TBS containing Tween 20 (0.05%). After washing, a 5000-fold-diluted horseradish peroxidase-conjugated goat anti-human IgG antibody reaction solution (a solution prepared by adding an anti-human secondary antibody (CHEMICON) to TBS containing skim milk (3%)) was added to the resultant mixture and then shaken at room temperature. Subsequently, the slit was washed with TBS containing Tween 20 (0.05%). After washing, the slit was immersed in TBS containing 4-methoxy-1-naphthol (0.61 mg/ml) and hydrogen peroxide (0.018%), the occurrence of development of color was confirmed, and then the slit was washed with purified water and dried.

The layouts of the synthesized proteins that had been subjected to dot blotting and the results of the dot blot analysis are shown in FIG. 8.

As a result of the dot blot analysis, in the reaction with the healthy subject serum pools, development of color on spots was recognized in Nos. 2, 6, 10, 26, 29, 32 and 35. While in the reaction with the patient serum pool 1, development of color on spots was observed in Nos. 2, 3, 4, 6, 9, 10, 11, 13, 19, 21, 22, 24, 26, 28, 32 and 35. In the reaction with the patient serum pool 2, development of color on spots was observed in Nos. 2, 3, 4, 6, 10, 11, 19, 24, 26, 32 and 35.

When confirmed with visual observations, in each of the spots, the development of color in the patient serum pools was stronger than that in the healthy subject serum pools. In the patient serum pools, development of color on spots, which was not observed in the healthy subject serum pools, was confirmed.

Detection of Signal Values

Subsequently, the results of the dot blot analysis were quantified in the following manner.

1. Using ImageQuant LAS4000 (GE Healthcare), an image of the membrane was taken. After adjusting the focus, the image was taken under the following conditions.

Conditions for Image Capture

Exposure Type: Precision

Exposure Time: 1/100 sec.

Sensitivity/Resolution: Standard

2. Using ImageQuant TL (GE Healthcare), the dot signal values in the image taken were determined.

Conditions for Signal Value Capture

In an Array analysis mode, a signal value was digitized in conjunction with the spot size and placement of the dots. As for the setting of background, a part adjacent to the spot was set.

3. After digitizing, the signal values for individual spots were summarized in a table. A signal value that is the largest value among the signal values of spots on which any antigen protein was not arranged (blank), was employed as a reference value, and a signal value that was smaller than the reference value was deemed as a noise. The quantified signal values are shown in FIG. 9.

As a result of the digitization of the signals of the spots, almost the same results as those obtained by the confirmation with visual observations were obtained. Note that No. 28 in patient serum pool 1 had so low signal value as to be determined as a noise. On the other hand, with respect to No. 34, although almost no spot was confirmed with visual observations, a signal value was detected. With respect to No. 19 in the patient serum pool 2, a signal value was so small as to be determined as a noise.

Taken these results together, among the 29 types of synthesized proteins, those proteins reacted only with the patient sera without reacting with the healthy subject sera were 10 types of proteins, i.e., proteins of Nos. 3, 4, 9, 11, 13, 19, 21, 22, 24 and 28. On the other hand, those proteins showed higher color development in the patient sera than in the healthy subject sera were 16 types of proteins, i.e., proteins of Nos. 2, 3, 4, 6, 9, 10, 11, 13, 19, 21, 22, 24, 26, 28, 32 and 35.

These results demonstrated that the proteins of Nos. 2, 3, 4, 6, 9, 10, 11, 13, 19, 21, 22, 24, 26, 28, 32 and 35 were suitable as the antigen proteins to be used in the antibody titer test kit of the present invention.

Stability of Synthesized Proteins

For the purpose of confirming as to whether or not the synthesized antigen proteins could be actually used in the antibody titer test kit, SDS-PAGE was carried out to examine the states of the synthesized proteins.

A sample was prepared so that an antigen protein was contained at a concentration of 50 ng/10 μl sample buffer (+DTT). With respect to the proteins of Nos. 5, 32 and 35, there was no quantified value and therefore a sample was prepared by mixing a solution of the synthesized protein (4 μl) with a sample buffer (+DTT) (6 μl).

Figure 10:
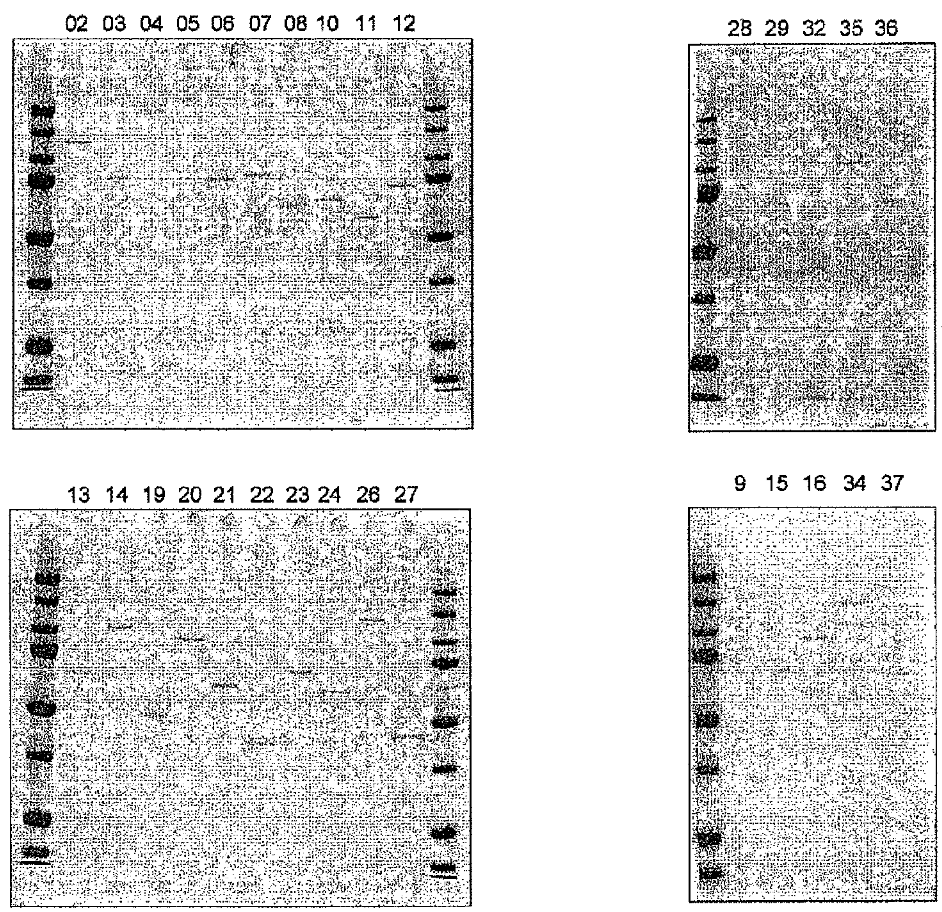
FIG. 10 illustrates SDS-PAGE electrophoresis patterns showing the stability of synthetic antigen proteins.

The prepared sample was thermally denatured, and the sample (10 μl in total) was applied to carry out SDS-PAGE electrophoresis. Subsequently, a gel that had been subjected to electrophoresis was washed with distilled water, then stained with CBB, and then washed with distilled water until bands could be observed clearly. The results are shown in FIG. 10.

With respect to proteins other than the proteins of Nos. 5, 32 and 35, it was confirmed that proteins having desired sizes were synthesized. On the other hand, with respect to the protein of No. 5, no band was observed; and with respect to the proteins of Nos. 32 and 35, multiple bands were observed.

With respect to No. 5, although so far as the synthesis of messenger RNA could be confirmed, the synthesis of a protein could not be confirmed. Therefore, it was assumed that the protein was very instable or was difficult to be synthesized.

On the other hand, the proteins of Nos. 32 and 35 are known as proteases, and therefore it was considered that synthesized proteins also had a protease activity and was self-digested. If some of the antigen proteins have a protease activity, the decomposition of the other antigen proteins contained in the antibody titer test kit of the present invention may occur, and therefore the stability of the proteins may be deteriorated and the proteins cannot be used for the testing.

As mentioned above, it was found that the protein of No. 5 was difficult to be synthesized and therefore could not be used, and the proteins of Nos. 32 and 35 had a protease activity and therefore could not be used without any modification.

Antigen-Antibody Reactions with Patient Sera

As apparent from Table 1, it is considered that proteins which can be utilized as antigens by the antibodies are different among the individual sera. Then, for the purpose of selecting antigen proteins having high reactivity with many patient sera, antigen-antibody reactions of proteins in which antigenicity was observed with varied patient sera were examined.

In this experiment, 16 types of antigen proteins showed stronger color development in the patient sera than in the healthy subject sera were subjected to dot blotting. The amount of a protein subjected to dot blotting was 50 ng. With respect to Nos. 32 and 35, the protein concentration was unknown, and therefore 4 μl of a synthesized protein solution was applied. Each of the antigen proteins was reacted with each of the healthy subject sera to set a reference value.

Detection of Signal Values

1. Using ImageQuant LAS4000 (GE Healthcare), an image of the membrane was taken. After adjusting the focus, the image was taken under the following conditions.

Conditions for Image Capture

Exposure Type: Precision

Exposure Time: 1/100 sec.

Sensitivity/Resolution: Standard

2. Next, using ImageQuant TL (GE Healthcare), the dot signal values in the image taken were determined.

Conditions for Signal Value Capture

In an Array analysis mode, the spot size of the dots was fit, the spots were arranged in the layout of 3 columns×8 rows for the layout of 2 columns×8 rows (2×8), and the signal values were digitized.

3. After the digitization, from the signal value of each spot, a column located at the center was determined as a background that was closed to the spots, and the differences therefrom were organized as the signal value of each spot in a table. A signal value of a spot that could not be confirmed with visual observations was treated as being undetectable.

4. As the healthy subject reference, signal values for NAI, TOM and KOB were determined. Among these values, signal values of spots which could be confirmed with visual observations were compared and the largest signal value among the three samples was employed as a healthy subject serum reference (FIG. 11). As for a spot for which the color development could not be confirmed in any sample, the reference value was set as “0”. A spot which showed a higher signal value than the signal value was marked with a round stamp and organized (FIGS. 12 and 13).

As a result, it was confirmed that the number of color-developed spots was apparently larger in the patient sera as compared with those in healthy subject sera and their signal values were also higher as compared with the developed colors in the healthy subject sera. As expected, there were proteins that could not be used as antigens in some patients.

Here, it was demonstrated that periodontal diseases could be determined in all of the patients by using the antigen protein Nos. 32 or 35, whose reactions with all of the patient antibodies were recognized. With taking the changing antigenicity of periodontal disease-causing bacteria and various immunoresponses of subject to be tested into consideration, the test on periodontal diseases in a wide scope of periodontal disease-causing bacteria and subjects to be tested can be achieved using a properly selected combination of at least two among the selected proteins.

A color-developing signal value reflects an antibody titer against periodontal disease-causing bacteria proteins in a plasma or serum from a patient. Therefore, the degree of progression (severity) of a periodontal disease can be tested on the basis of the signal values obtained. In this case also, the test on a wide scope of periodontal disease-causing bacteria and the degree of progression of periodontal disease based on subjects to be tested can also be achieved using a properly selected one or a combination of at least two among the selected proteins.

Signal Value Comparison Between Healthy Subject Sera and Patient Sera

Antigen proteins which exhibited higher signal values against patient sera as compared with the healthy subject reference were organized, and it was found that the antigen proteins of Nos. 32 and 35 showed higher signal values against all of the sera collected from 23 persons investigated as compared with the reference, and therefore were particularly suitable as antigen proteins to be used in the antibody titer test kit of the present invention (FIGS. 12 and 13). In addition, the antigen proteins of Nos. 2, 3 and 26 showed higher signal values against sera from 19 persons, 16 persons and 12 persons, respectively, among 23 persons investigated as compared with the reference, and therefore it was found that the rates of covering the subjects to be tested were relatively high (FIGS. 12 and 13).

As mentioned above, both the signal values and cover rates of the antigen proteins of Nos. 32 and 35 were high and therefore it was found that these antigen proteins were suitable as antigens to be used in the antibody titer test kit. However, these antigen proteins have a protease activity and therefore cannot be used as the test antigen without modifications.

On the other hand, for using proteins other than Nos. 32 and 35 as antigens for the antibody titer test kit, it is needed to combine at least two of the antigen proteins. For example, it was confirmed that, when the antigen proteins of Nos. 2 and 3 were used in combination, the cover rate could be increased to 100%.

As mentioned above, the antigen proteins of Nos. 32 and 35 had excellent properties. However, the antigen proteins are proteases and therefore cannot be used as test antigens.

Therefore, modified polypeptides in which a protease activity was eliminated while keeping the antigenicity of these antigen proteins, were produced.

The amino acid sequences for the proteins of Nos. 32 and 35 were analyzed using a Genetyx homology search tool, and two cysteine residues of which occurrence had been confirmed in the proteins, were substituted by an alanine residue in the following manner. The amino acid sequences for two modified polypeptides (Nos. 32A and 32B) produced for No. 32 are respectively shown in SEQ ID NOs: 63 and 65, and the polynucleotide sequences encoding the modified polypeptides are respectively shown in SEQ ID NOs: 64 and 66. The amino acid sequences for two modified polypeptides (Nos. 35A and 35B) produced for No. 35 are respectively shown in SEQ ID NOs: 67 and 69, and the polynucleotide sequences encoding the modified polypeptides are respectively shown in SEQ ID NOs: 68 and 70.

Production of Protein Expression Plasmid

Primer Synthesis

The below-mentioned primer pairs represented by the SEQ ID NOs in the Sequence Listing, each of which contains a mutation-introduced site, were synthesized.

Modified polypeptide No. 32A
Forward primer: SEQ ID NO: 133
Reverse primer: SEQ ID NO: 134
Modified polypeptide No. 32B
Forward primer: SEQ ID NO: 135
Reverse primer: SEQ ID NO: 136
Modified polypeptide No. 35A
Forward primer: SEQ ID NO: 137
Reverse primer: SEQ ID NO: 138
Modified polypeptide No. 35B
Forward primer: SEQ ID NO: 139
Reverse primer: SEQ ID NO: 140

Phosphorylation of primers: T4 Polynucleotide Kinase (Toyobo Co., Ltd.)

| Composition of reaction solution for preparation of 20 µl | |
|---|---|
| Synthetic primer (50 µM) | 14 µl |
| 10 × Protruding End Kinase Buffer | 2 µl |
| 10 mM ATP | 2 µl |
| T4 Polynucleotide Kinase (5 to 20 U/µl) | 2 µl |

Reaction Composition

After retaining at 37° C. for 60 min and then at 95° C. for 5 min, 50 µl of DW was added (10 pmol/µl primer DNA).

Inverse PCR: Prime STAR MAX (Takara)

| Composition of reaction solution for reparation of 50 µl | |
|---|---|
| Takara PrimeSTAR MAX Premix (2×) | 25 µl |
| Forward primer (10 pmol/µl) | 1.5 µl |
| Reverse primer (10 pmol/µl) | 1.5 µl |
| Template DNA (plasmid DNA of No. 32 or 35 antigen protein: | |
| 10 ng/µl) | 1 µl |
| Sterilized water | 21 µl |

Reaction Conditions

After treating at 98° C. for 30 sec, a cycle of 98° C. for 10 sec, 55° C. for 5 sec and 72° C. for 50 sec was repeated 30 times.

A PCR product was purified using a QIAGEN kit, and then the purified product was treated with DpnI to decompose Template DNA (plasmid DNA).

The PCR product was purified in the composition shown below using a QIAGEN kit.

| DpnI treatment | |
|---|---|
| Purified PCR product | 30 µl |
| NEB4 | 5 µl |
| BSA | 5 µl |
| DpnI (20 unit/µL) | 0.5 µl |
| Sterilized water | 9.5 µl |
| 37° C., for 1 hour | |

Purification of restriction enzyme treatment product: a DNA product was purified by carrying out PCI treatment.

| Ligation | |
|---|---|
| Purified DNA | 5 µl |
| Ligation Mighty Mix | 5 µl |
| 16° C., for 1 hour | |

A ligation product was introduced into a cell of *Escherichia coli* (*E. coli*) by transformation.

Plasmid DNA in which the introduction of a gene had been confirmed was subjected to sequence analysis.

A plasmid into which a desired mutation had been introduced was prepared in a large amount, and a protein was synthesized using a wheat germ cell-free protein synthesis system and then purified using a GST tag.

Confirmation of Synthesized Proteins

SDS-PAGE

A synthesized protein solution (4 µl) was mixed with a sample buffer (+DTT) (6 µl) to prepare a sample. The prepared sample was thermally denatured, and a total portion of the sample (10 µl) was applied and subjected to SDS-PAGE electrophoresis.

CBB Staining

A gel that had been subjected to SDS-PAGE was washed with distilled water and then immersed in a CBB staining solution, and then the solution was stirred.

The gel was washed with distilled water until bands could be observed clearly.

Dot Blotting

Four types of modified polypeptides produced (Nos. 32A, 32B, 35A and 35B) were subjected to dot blotting. Each of the modified polypeptides to be dot-blotted was applied at a volume of 4 μl at an antigen protein concentration of 12.5 ng/μl so that 50 ng of the antigen protein could be applied. Three sets of dot blotting were carried out. The dot blots were immersed in TBS containing 5% of skim milk overnight to cause blocking, and then reacted with serum solutions as mentioned below at room temperature.

Serum Solutions (Primary Antibody)

A: a solution prepared by mixing a portion (8 μl) of a mixture of sera from NAI, TOM and KOB (3 μl for each) with TBS containing 3% of skim milk (20 ml).

B: a solution prepared by mixing a portion (8 μl) of a mixture of sera of Nos. 7350 and 6921 (4 μl for each) with TBS containing 3% skim milk (20 ml).

C: a solution prepared by mixing a portion (8 μl) of a mixture of sera of Nos. 7107, 7523 and 6980 (3 μl for each) with TBS containing 3% skim milk (20 ml), 140 mL 1×TBS.

Subsequently, the slit was washed with TBS containing Tween 20 (0.05%). After washing, a 5000-fold-diluted horse-radish peroxidase-conjugated goat anti-human IgG antibody reaction solution (a solution prepared by adding anti-human secondary antibody (CHEMICON) to TBS containing skim milk (3%)) (20 ml) was added to the slit and the resultant product was shaken at room temperature. Subsequently, the slit was washed with TBS containing Tween 20 (0.05%). After washing, the slit was immersed in TBS containing 4-methoxy-1-naphthol (0.61 mg/ml) and hydrogen peroxide (0.018%), the occurrence of development of color was confirmed, and then the slit was washed with purified water and dried.

Figure 14:
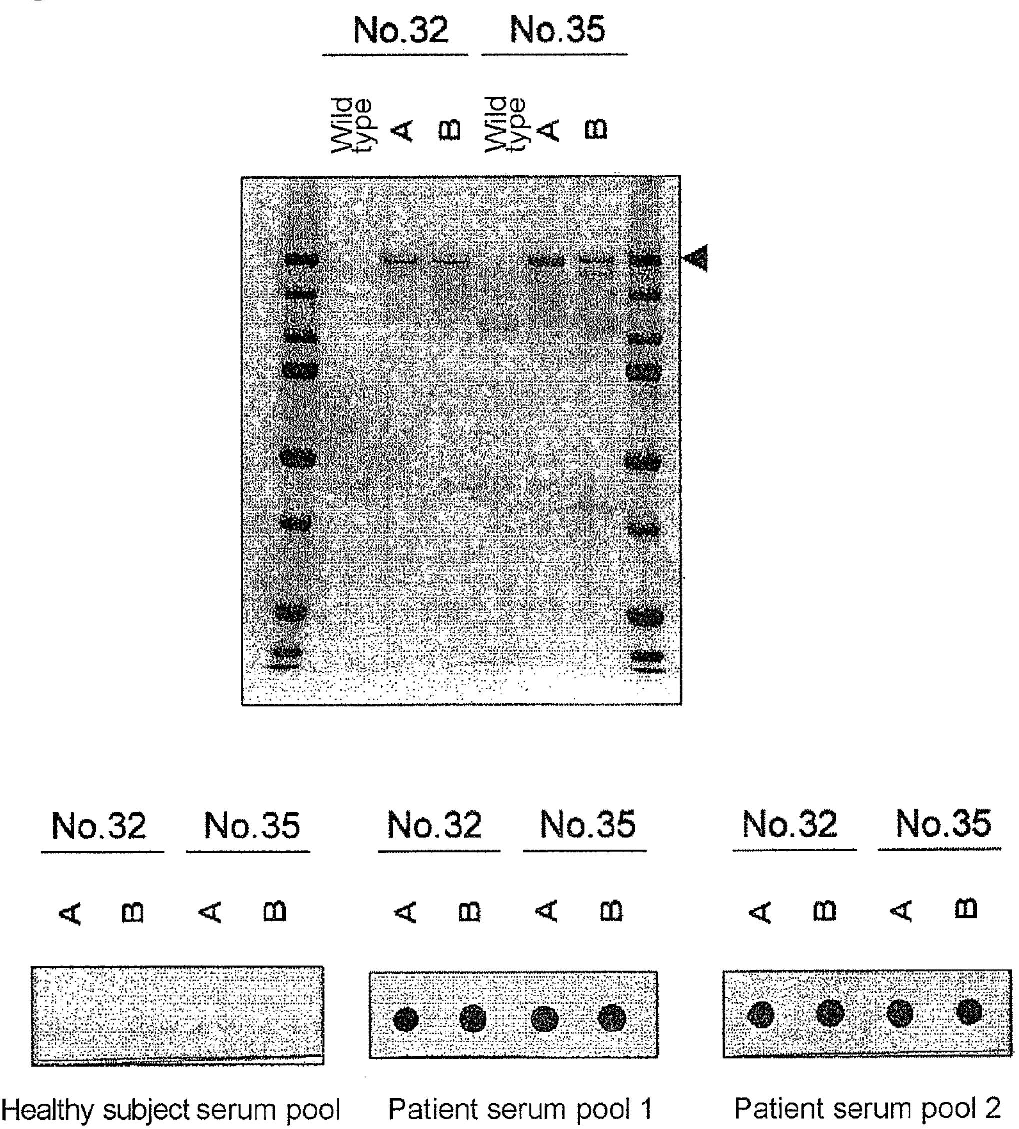
FIG. 14 illustrates the stability and antigenicity of modified polypeptides.

The results are shown in FIG. 14.

With respect to No. 32, the protease activity was inhibited in both of the modified polypeptides. On the other hand, with respect to No. 35, the protease activity was not inhibited completely in the modified polypeptide of No. 35B but the protease activity was inhibited in the modified polypeptide of No. 35A. In addition, the antigenicity was examined, and it was confirmed that antigenicity was maintained in all of the modified polypeptides.

Test Methods

Dot Blot Analysis

In the same manner as the experiment mentioned above, each of 16 types of antigen proteins was dot-blotted against each of sera from 10 healthy subjects and sera from periodontal disease patients (with respect to the antigen proteins of No. 32 and No. 35, produced modified polypeptides of No. 32A and No. 35A were used). The amount of a protein subjected to the dot blotting was 50 ng (with respect to the antigen protein of No. 4, the protein concentration was low and therefore 37 ng was applied, and the volume of a protein solution became insufficient during the test and therefore the blotting was not carried out against serum Nos. H9, H10, P10 and P20).

After the dot blotting, the dots were immersed in a blocking solution (a TBS solution containing skim milk (5%)).

As a primary antibody solution, a solution prepared by mixing each of the healthy subject sera (H1 to H10) or each of the periodontal disease patient sera (P1 to P20) (8 μL) with TBS (20 mL) containing 3% of skim milk was used. The blocked slit was immersed in the solution and an antigen-antibody reaction was carried out at room temperature for 2 hours.

Subsequently, the slit was washed with TBS containing Tween 20 (0.05%). After washing, a 5000-fold-diluted horse-radish peroxidase-conjugated goat anti-human IgG antibody reaction solution (a solution prepared by adding an anti-human secondary antibody (MILLIPORE) to TBS containing skim milk (3%)) (20 mL) was added to the slit and an antigen-antibody reaction was carried out at room temperature for 1 hour.

Figure 15:
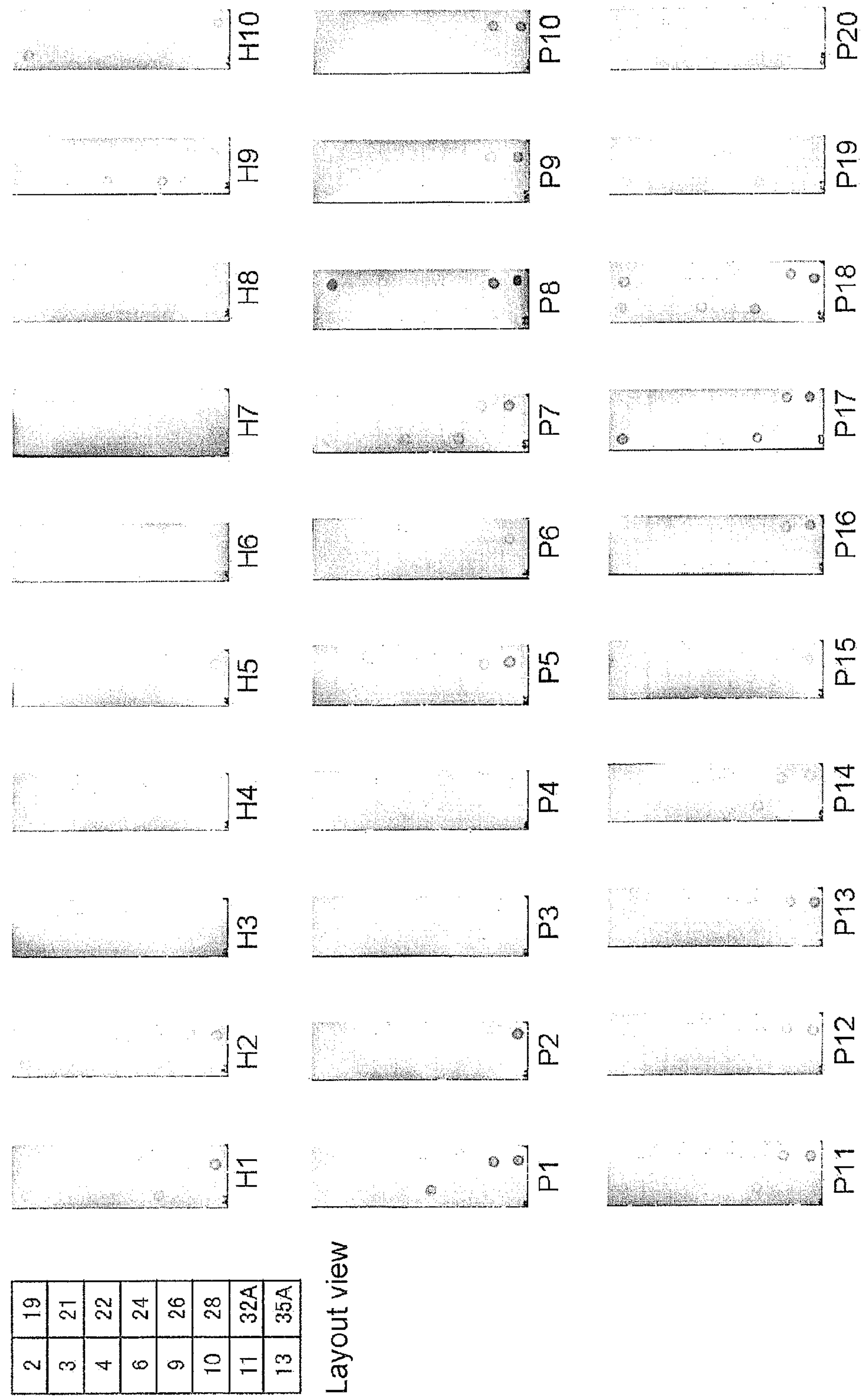
FIG. 15 illustrates antigen-antibody reactions between sera and synthetic antigen proteins.

Subsequently, the slit was washed with TBS containing Tween 20 (0.05%). After washing, the slit was immersed in TBS containing 4-methoxy-1-naphthol (0.61 mg/ml) and hydrogen peroxide (0.018%), the occurrence of development of color was confirmed, and then the slit was washed with purified water and dried. The results are shown in FIG. 15.

Detection of Signal Values

1. Using ImageQuant LAS4000 (GE Healthcare), an image of the membrane was taken. After adjusting the focus, the image was taken under the following conditions.

Conditions for Image Capture

Exposure Type: Precision

Exposure Time: 1/100 sec.

Sensitivity/Resolution: Standard

2. Using ImageQuant TL (GE Healthcare), the dot signal values in the image taken were determined.

Conditions for Signal Value Capture

In an Array analysis mode, a round-shaped cursor was moved so as to surround the whole area of the spots of the dots wherein the spots of the dots were arranged in the layout of 2 columns×8 rows, and the signal values were digitized.

The background was set in a Spot Edge Average mode, so that signal values of the spots could be reflected against the background surrounding the spots.

Analysis of Signal Values

1. With respect to signal values of each serum against individual antigen proteins, signal average values for a healthy subject serum group and a patient serum group were calculated (FIGS. 16 and 17). As a result, it was found that the antigen proteins of Nos. 13, 21, 22 and 28 were not reacted with any of the sera or reacted at a low reaction rate.

Subsequently, a Signal/Noise ratio was determined employing the signal value of the patient serum group as a Signal value and the signal value of the healthy subject serum group as a Noise value. In this determination, when a healthy subject serum group had a signal average value of 0, the calculation of a calculated value was impossible and therefore the healthy subject serum group was determined "Noise: 0" (FIG. 18). As a result, it was demonstrated that, with respect to the antigen proteins of Nos. 2, 6, 10 and 26, the signal average values were high but the S/N ratios were low, and therefore the antigen proteins were not suitable for the test of a periodontal disease in a wide scope of patients having various immunotypes. On the other hand, with respect to the antigen proteins of Nos. 3, 4, 9, 11, 19, 24, 32A and 35A, the S/N ratios were high and therefore it was considered that the antigen proteins had high specificity to the patient sera.

Figure 19:
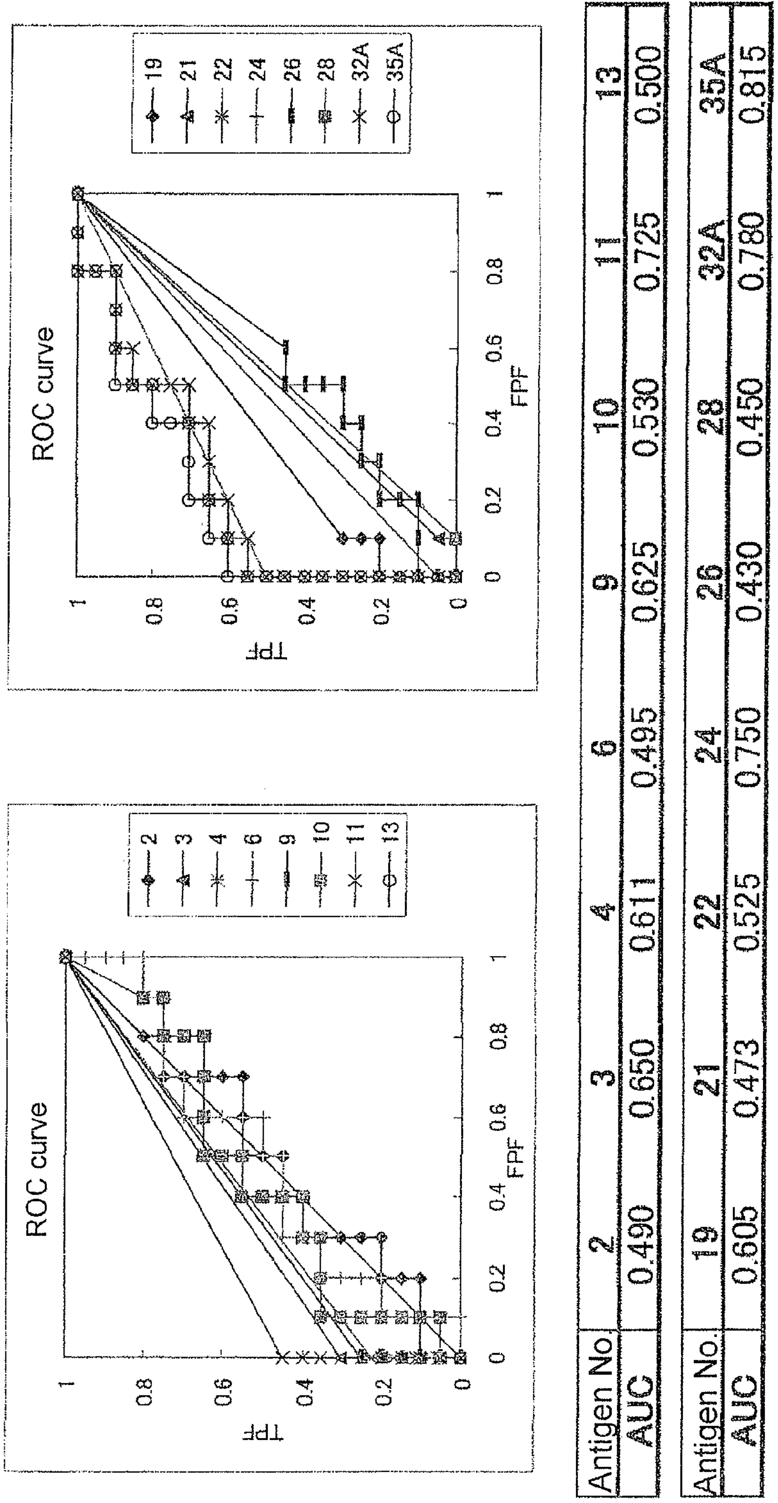
FIG. 19 illustrates ROC curves and AUC values determined for signal values of individual sera against diverse antigen proteins.
Figure 20:
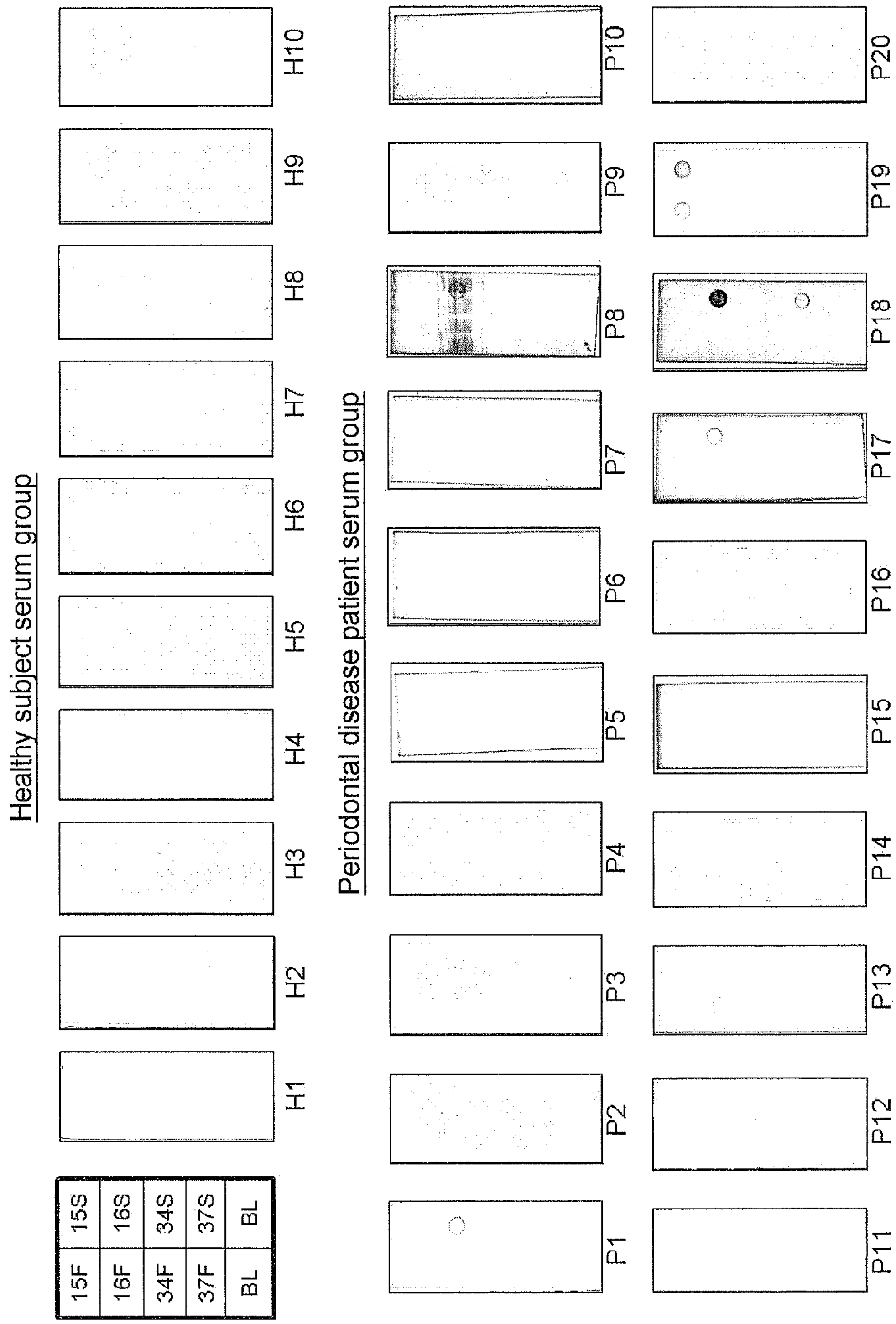
FIG. 20 illustrates the antigen-antibody reactions between sera and diverse antigen proteins (strain SU63).

2. With respect to signal values of each serum against the individual antigen proteins, an ROC (Receiver Operating Characteristic) curve and an area under the ROC curve (Area under the curve, AUC) were determined using statistical software Excel 2010 (FIG. 19).

The ROC curve was a graph showing as to how the positive prevalence (sensitivity) and the false positive prevalence (1-degree of specificity) are changed when a boundary value (a cut-off value) is altered. Given the ideal test, a state in which each of the sensitivity and degree of specificity is 1.0 (i.e., a state in which the value of each of the sensitivity and degree of specificity is positioned at an upper left end point) is the ideal state. Therefore, it is considered that high diagnostic-predictive performance of the test can be achieved when the ROC curve graph is shifted so as to become close to the upper left end. Thus, by measuring the area under the curve ROC, it is possible to determine the predictive-diagnostic performance of the test.

Generally, the predictive/diagnostic capability on the basis of AUC values can be determined as follows.

AUC 0.9 to 1.0: High accuracy

AUC 0.7 to 0.9: Moderate accuracy

AUC 0.5 to 0.7: Low accuracy

From the results shown in FIG. 19, it was found that the antigen proteins of Nos. 3, 4, 9, 11, 19, 24, 32A and 35A had such diagnostic/predictive capability of AUC 0.6 or more.

Production of High-Expression Antigen Proteins

Test Methods

Synthesis of Proteins of Nos. 32N, 32C, 35N and 35C

A desired gene sequence was amplified so that the size of the nucleotide become half of the original sequence on the basis of each of the nucleotide sequences for Nos. 32A and No. 35A using each of the synthesized primer pairs shown in the primer list below.

Production of Protein-Expressing Plasmid

Primer Synthesis

The primer pairs represented by SEQ ID NOs shown in the Sequence Listing were synthesized.

Modified polypeptide No. 32N

Forward primer: SEQ ID NO: 157

Reverse primer: SEQ ID NO: 158

Modified polypeptide No. 32C

Forward primer: SEQ ID NO: 159

Reverse primer: SEQ ID NO: 160

Modified polypeptide No. 35N

Forward primer: SEQ ID NO: 161

Reverse primer: SEQ ID NO: 162

Modified polypeptide No. 35C

Forward primer: SEQ ID NO: 163

Reverse primer: SEQ ID NO: 164

Subsequently, the amplified DNA product was treated with a restriction enzyme and then ligated to a protein expression vector (CellFree Sciences Co., Ltd.; a pEu vector) that had been treated with the same restriction enzyme, so as to be matched in reading frame with each other. A ligation product was introduced into a cell of *Escherichia coli* (*E. coli*) by transformation. Subsequently, a clone having the gene introduced thereinto was selected.

Plasmid DNA was collected from the selected clone and then subjected to sequence analysis. The amino acid sequences for two modified polypeptides (Nos. 32N and 32C) produced for No. 32A are shown in SEQ ID NOs: 141 and 143, and the polynucleotide sequences respectively encoding the modified polypeptides are shown in SEQ ID NOs: 142 and 144. The amino acid sequences for two modified polypeptides (Nos. 35N and 35C) produced for No. 35A are shown in SEQ ID NOs: 145 and 147, and the polynucleotide sequences respectively encoding the modified polypeptides are shown in SEQ ID NOs: 146 and 148.

With respect to a clone in which any significant mutation was not recognized from the results of the sequence analysis, a large amount of a plasmid was prepared, a protein was synthesized using a wheat germ cell-free protein synthesis system, and the resultant protein was purified using a GST tag.

The synthesis of 4 types of proteins, i.e., the N-terminal and the C-terminal of No. 32A and the N-terminal and the C-terminal of No. 35A, were successfully achieved, and these proteins were subjected to dot blot analysis.

As a result, it was demonstrated that these modified peptides could react with the patient serum groups even when the lengths thereof were half of the original sequences thereof, and it was confirmed that the antigenicity of these modified peptides was maintained.

Antigen Proteins Capable of Recognizing *Porphyromonas gingivalis* Strain SU63

Test Methods

Confirmation of Homology Among Strains

The search was carried out on the basis of amino acid sequences for each of the proteins of strain FDC381 using a blastp of BLAST (Basic Local Alignment Search Tool) in NCBI site.

From the results of the search, the homology among proteins in Porphyromonas gingivalis bacterium strains W83, ATCC33277 and TDC60, which have been registered on a database, was confirmed.

Cloning of Gene Derived from Strain SU63 and Synthesis of Proteins

The genetic information on the selected proteins was reviewed from a database, and a desired gene was amplified from genomic DNA derived from *P. gingivalis* bacterium strain SU63 using each of the primer pairs represented by SEQ ID NOs shown in the following Sequence Listing.

Strain Su63: No. 15 antigen protein (No. 15Su)

Forward primer: SEQ ID NO: 165

Reverse primer: SEQ ID NO: 166

Strain Su63: No. 16 antigen protein (No. 16Su)

Forward primer: SEQ ID NO: 167

Reverse primer: SEQ ID NO: 168

Strain Su63: No. 34 antigen protein (No. 34Su)

Forward primer: SEQ ID NO: 169

Reverse primer: SEQ ID NO: 170

Strain Su63: No. 37 antigen protein (No. 37Su)

Forward primer: SEQ ID NO: 171

Reverse primer: SEQ ID NO: 172

Subsequently, the amplified DNA product was treated with a restriction enzyme and then ligated to a protein expression vector (CellFree Sciences Co., Ltd.; a pEu vector) that had been treated with the same restriction enzyme. A ligation product was introduced into a cell of *Escherichia coli* (*E. coli*) by transformation. Subsequently, a clone having the gene introduced thereinto was selected.

Plasmid DNA was collected from the selected clone and then subjected to sequence analysis. The amino acid sequences for the antigen proteins of No. 15Su, No. 16Su, No. 34Su and No. 37Su are respectively shown in SEQ ID NOs: 149, 151, 153 and 155, and the polynucleotide sequences encoding the antigen proteins are respectively shown in SEQ ID NOs: 150, 152, 154 and 156. As a result, it was demonstrated that the sequence for the polynucleotide encoding the antigen protein of No. 15Su was different by one nucleotide from corresponding polynucleotide sequence in strain W83, the sequence for the polynucleotide encoding the antigen protein of No. 16Su had high homology with the corresponding polynucleotide sequences in strains TDC60 and ATCC33277, and the sequence for the polynucleotide encoding the antigen protein of No. 34Su had high homology with the polynucleotide sequence of strain ragA (strain A011/9).

With respect to a clone in which any significant mutation was not recognized from the results of the sequence analysis, a large amount of a plasmid was prepared, a protein was synthesized using a wheat germ cell-free protein synthesis system, and the resultant protein was purified using a GST tag.

As a result, four types of proteins derived from strain SU63, i.e., proteins of Nos. 15, 16, 34 and 37, were successfully synthesized, and the proteins were subjected to dot blot analysis.

Dot Blot Analysis

Eight types of antigen proteins (strain FDC381: Nos. 15, 16, 34 and 37, strain SU63: Nos. 15Su, 16Su, 34Su and 37Su) were dot-blotted. The amount of a protein to be dot-blotted was 50 ng.

After dot blotting, the dot was immersed in a blocking solution (a TBS solution containing skim milk (5%)).

As a primary antibody solution, a solution prepared by mixing each of the healthy subject sera (H1 to H10) or each of the periodontal disease patient sera (P1 to P20) (4 μL) with TBS (10 mL) containing 3% of skim milk was used. The blocked slit was immersed in the solution and an antigen-antibody reaction was carried out at room temperature for 2 hours.

Subsequently, the slit was washed with TBS containing Tween 20 (0.05%). After washing, a 5000-fold-diluted horse-radish peroxidase-conjugated goat anti-human IgG antibody reaction solution (a solution prepared by adding an anti-human secondary antibody (MILLIPORE) to TBS containing skim milk (3%)) (10 mL) was added to the slit and an antigen-antibody reaction was carried out at room temperature for 1 hour.

Subsequently, the slit was washed with TBS containing Tween 20 (0.05%). After washing, the slit was immersed in TBS containing 4-methoxy-1-naphthol (0.61 mg/ml) and hydrogen peroxide (0.018%), the occurrence of development of color was confirmed, and then the slit was washed with purified water and dried. The results are shown in FIGS. 24 and 25.

As apparent from these figures, the antigen protein of No. 15 was an antigen protein from both strains FDC381 and SU63 and showed antigenicity against the patient serum P19. On the other hand, the antigen proteins of No. 16, 34 and 37, either one of the antigen proteins of strain FDC381 and strain SU63, had antigenicity against either one of the healthy subject sera and the patient sera.

Consequently, it was suggested that the antigen proteins of Nos. 16, 34 and 37 enables the discrimination and recognition between the infection with strain FDC381 and the infection with strain SU63.

Results of Test

The homology between strains was examined, and the homology between the proteins from strain FDC381 and the protein on the database is as follows. It was confirmed that the homology between strains was low.

| No. | strain W83 | strain ATCC33277 | strain TDC60 |
|---|---|---|---|
| 15 | 387/387 (100%) | 202/398 (51%) | 213/402 (53%) |
| 16 | 553/553 (100%) | 242/566 (43%) | 243/566 (43%) |
| 34 | 1015/1016 (99%) | 737/1039 (71%) | 719/1022 (70%) |
| 37 | 500/500 (100%) | 249/511 (49%) | 249/511 (49%) |

A sequence analysis was carried out and it was demonstrated that the homology between each protein derived from strain FDC381 and proteins derived from strain SU63 were as follows.

No. 15: 99.7%

No. 16: 41.4%

No. 34: 65.2%

No. 37: 47.3%

Industrial Applicability

The test kit for a plasma or serum antibody titer against a periodontal disease-causing bacterium of the present invention can be suitably used in a test system for a plasma or serum antibody titer against a periodontal disease-causing bacterium which treats a large quantity of samples automatically and at a high speed.

Sequence Listing Free Text

SEQ ID NO: 1 is an amino acid sequence for a conserved hypothetical protein having a zinc-carboxypeptidase domain.

SEQ ID NO: 2 is a nucleotide sequence encoding a conserved hypothetical protein having a zinc-carboxypeptidase domain.

SEQ ID NO: 3 is an amino acid sequence for a hypothetical protein PG1881.

SEQ ID NO: 4 is a nucleotide sequence encoding a hypothetical protein PG1881.

SEQ ID NO: 5 is an amino acid sequence for a hypothetical protein PGN_0291.

SEQ ID NO: 6 is a nucleotide sequence encoding a hypothetical protein PGN_0291.

SEQ ID NO: 7 is an amino acid sequence for a hypothetical protein PG0491.

SEQ ID NO: 8 is a nucleotide sequence encoding a hypothetical protein PG0491.

SEQ ID NO: 9 is an amino acid sequence for a hypothetical protein PGN_1611.

SEQ ID NO: 10 is a nucleotide sequence encoding a hypothetical protein PGN_1611.

SEQ ID NO: 11 is an amino acid sequence for a hypothetical protein PGN_0477.

SEQ ID NO: 12 is a nucleotide sequence encoding a hypothetical protein PGN_0477.

SEQ ID NO: 13 is an amino acid sequence for a hypothetical protein PGN_0860.

SEQ ID NO: 14 is a nucleotide sequence encoding a hypothetical protein PGN_0860.

SEQ ID NO: 15 is an amino acid sequence for a 53 kDa major outer membrane protein.

SEQ ID NO: 16 is a nucleotide sequence encoding a 53 kDa major outer membrane protein.

SEQ ID NO: 17 is an amino acid sequence for a 35 kDa heroin-binding protein.

SEQ ID NO: 18 is a nucleotide sequence encoding a 35 kDa hemin-binding protein.

SEQ ID NO: 19 is an amino acid sequence for a heme-binding protein FetB.

SEQ ID NO: 20 is a nucleotide sequence encoding a heme-binding protein FetB.

SEQ ID NO: 21 is an amino acid sequence for an NAD-dependent glutamate dehydrogenase.

SEQ ID NO: 22 is a nucleotide sequence encoding an NAD-dependent glutamate dehydrogenase.

SEQ ID NO: 23 is an amino acid sequence for a phosphoserine aminotransferase.

SEQ ID NO: 24 is a nucleotide sequence encoding a phosphoserine aminotransferase.

SEQ ID NO: 25 is an amino acid sequence for a TonB-binding receptor Tlr.

SEQ ID NO: 26 is a nucleotide sequence encoding a TonB-binding receptor Tlr.

SEQ ID NO: 27 is an amino acid sequence for fimbrillin (strain FDC381).

SEQ ID NO: 28 is a nucleotide sequence encoding fimbrillin.

SEQ ID NO: 29 is an amino acid sequence for a trace component FimE (strain FDC381).

SEQ ID NO: 30 is a nucleotide sequence encoding a trace component FimE.

SEQ ID NO: 31 is an amino acid sequence for HmuY'.

SEQ ID NO: 32 is a nucleotide sequence encoding HmuY'.

SEQ ID NO: 33 is an amino acid sequence for an M24 family peptidase.

SEQ ID NO: 34 is a nucleotide sequence encoding an M24 family peptidase.

SEQ ID NO: 35 is an amino acid sequence for glyceraldehyde-3-phosphate dehydrogenase type-1.

SEQ ID NO: 36 is a nucleotide sequence encoding glyceraldehyde-3-phosphate dehydrogenase type-1.

SEQ ID NO: 37 is an amino acid sequence for ferritin.

SEQ ID NO: 38 is a nucleotide sequence encoding ferritin.

SEQ ID NO: 39 is an amino acid sequence for a serine hydroxymethyl transferase.

SEQ ID NO: 40 is a nucleotide sequence encoding a serine hydroxymethyl transferase.

SEQ ID NO: 41 is an amino acid sequence for an outer membrane lipoprotein Omp28.

SEQ ID NO: 42 is a nucleotide sequence encoding an outer membrane lipoprotein Omp28.

SEQ ID NO: 43 is an amino acid sequence for a promising lysyl endopeptidase precursor.

SEQ ID NO: 44 is a nucleotide sequence encoding a promising lysyl endopeptidase precursor.

SEQ ID NO: 45 is an amino acid sequence for a quinone family NAD (P) dehydrogenase.

SEQ ID NO: 46 is a nucleotide sequence encoding a quinone family NAD (P) dehydrogenase.

SEQ ID NO: 47 is an amino acid sequence for a DNA-binding protein from a starved cell Dps.

SEQ ID NO: 48 is a nucleotide sequence encoding a DNA-binding protein from a starved cell Dps.

SEQ ID NO: 49 is an amino acid sequence for an immunoresponsive 42 kDa antigen PG33.

SEQ ID NO: 50 is a nucleotide sequence encoding an immunoresponsive 42 kDa antigen PG33.

SEQ ID NO: 51 is an amino acid sequence for Lys-gingipain.

SEQ ID NO: 52 is a nucleotide sequence encoding Lys-gingipain.

SEQ ID NO: 53 is an amino acid sequence for a peptidyl-arginine deiminase.

SEQ ID NO: 54 is a nucleotide sequence encoding a peptidyl-arginine deiminase.

SEQ ID NO: 55 is an amino acid sequence for a ragA protein (strain FDC381).

SEQ ID NO: 56 is a nucleotide sequence encoding a ragA protein.

SEQ ID NO: 57 is an amino acid sequence for an arginine-specific cysteine proteinase RgpA.

SEQ ID NO: 58 is a nucleotide sequence encoding an arginine-specific cysteine proteinase RgpA.

SEQ ID NO: 59 is an amino acid sequence for an outer membrane protein 41 precursor.

SEQ ID NO: 60 is a nucleotide sequence encoding an outer membrane protein 41 precursor.

SEQ ID NO: 61 is an amino acid sequence for a lipoprotein RagB (strain FDC381).

SEQ ID NO: 62 is a nucleotide sequence encoding a lipoprotein RagB.

SEQ ID NO: 63 is an amino acid sequence for a mutation-introduced Lys-gingipain.

SEQ ID NO: 64 is a nucleotide sequence encoding a mutation-introduced Lys-gingipain.

SEQ ID NO: 65 is an amino acid sequence for a mutation-introduced Lys-gingipain.

SEQ ID NO: 66 is a nucleotide sequence encoding a mutation-introduced Lys-gingipain.

SEQ ID NO: 67 is an amino acid sequence for a mutation-introduced arginine-specific cysteine proteinase RgpA.

SEQ ID NO: 68 is a nucleotide sequence encoding a mutation-introduced arginine-specific cysteine proteinase RgpA.

SEQ ID NO: 69 is an amino acid sequence for a mutation-introduced arginine-specific cysteine proteinase RgpA.

SEQ ID NO: 70 is a nucleotide sequence encoding a mutation-introduced arginine-specific cysteine proteinase RgpA.

SEQ ID NO: 71 is a forward primer used in the PCR amplification of a polynucleotide encoding a conserved hypothetical protein having a zinc-carboxypeptidase domain.

SEQ ID NO: 72 is a reverse primer used in the PCR amplification of a polynucleotide encoding a conserved hypothetical protein having a zinc-carboxypeptidase domain.

SEQ ID NO: 73 is a forward primer used in the PCR amplification of a polynucleotide encoding a hypothetical protein PG1881.

SEQ ID NO: 74 is a reverse primer used in the PCR amplification of a polynucleotide encoding a hypothetical protein PG1881.

SEQ ID NO: 75 is a forward primer used in the PCR amplification of a polynucleotide encoding a hypothetical protein PGN_0291.

SEQ ID NO: 76 is a reverse primer used in the PCR amplification of a polynucleotide encoding a hypothetical protein PGN_0291.

SEQ ID NO: 77 is a forward primer used in the PCR amplification of a polynucleotide encoding a hypothetical protein PG0491.

SEQ ID NO: 78 is a reverse primer used in the PCR amplification of a polynucleotide encoding a hypothetical protein PG0491.

SEQ ID NO: 79 is a forward primer used in the PCR amplification of a polynucleotide encoding a hypothetical protein PGN_1611.

SEQ ID NO: 80 is a reverse primer used in the PCR amplification of a polynucleotide encoding a hypothetical protein PGN_1611.

SEQ ID NO: 81 is a forward primer used in the PCR amplification of a polynucleotide encoding a hypothetical protein PGN_0477.

SEQ ID NO: 82 is a reverse primer used in the PCR amplification of a polynucleotide encoding a hypothetical protein PGN_0477.

SEQ ID NO: 83 is a forward primer used in the PCR amplification of a polynucleotide encoding a hypothetical protein PGN_0860.

SEQ ID NO: 84 is a reverse primer used in the PCR amplification of a polynucleotide encoding a hypothetical protein PGN_0860.

SEQ ID NO: 85 is a forward primer used in the PCR amplification of a polynucleotide encoding a 53 kDa major outer membrane protein.

SEQ ID NO: 86 is a reverse primer used in the PCR amplification of a polynucleotide encoding a 53 kDa major outer membrane protein.

SEQ ID NO: 87 is a forward primer used in the PCR amplification of a polynucleotide encoding a 35 kDa hemin-binding protein.

SEQ ID NO: 88 is a reverse primer used in the PCR amplification of a polynucleotide encoding a 35 kDa hemin-binding protein.

SEQ ID NO: 89 is a forward primer used in the PCR amplification of a polynucleotide encoding a heme-binding protein FetB.

SEQ ID NO: 90 is a reverse primer used in the PCR amplification of a polynucleotide encoding a heme-binding protein FetB.

SEQ ID NO: 91 is a forward primer used in the PCR amplification of a polynucleotide encoding an NAD-dependent glutamate dehydrogenase.

SEQ ID NO: 92 is a reverse primer used in the PCR amplification of a polynucleotide encoding an NAD-dependent glutamate dehydrogenase.

SEQ ID NO: 93 is a forward primer used in the PCR amplification of a polynucleotide encoding a phosphoserine aminotransferase.

SEQ ID NO: 94 is a reverse primer used in the PCR amplification of a polynucleotide encoding a phosphoserine aminotransferase.

SEQ ID NO: 95 is a forward primer used in the PCR amplification of a polynucleotide encoding a TonB-binding receptor Tlr.

SEQ ID NO: 96 is a reverse primer used in the PCR amplification of a polynucleotide encoding a TonB-binding receptor Tlr.

SEQ ID NO: 97 is a forward primer used in the PCR amplification of a polynucleotide encoding fimbrillin.

SEQ ID NO: 98 is a reverse primer used in the PCR amplification of a polynucleotide encoding fimbrillin.

SEQ ID NO: 99 is a forward primer used in the PCR amplification of a polynucleotide encoding a trace component FimE.

SEQ ID NO: 100 is a reverse primer used in the PCR amplification of a polynucleotide encoding a trace component FimE.

SEQ ID NO: 101 is a forward primer used in the PCR amplification of a polynucleotide encoding HmuY'.

SEQ ID NO: 102 is a reverse primer used in the PCR amplification of a polynucleotide encoding HmuY'.

SEQ ID NO: 103 is a forward primer used in the PCR amplification of a polynucleotide encoding an M24 family peptidase.

SEQ ID NO: 104 is a reverse primer used in the PCR amplification of a polynucleotide encoding an M24 family peptidase.

SEQ ID NO: 105 is a forward primer used in the PCR amplification of a polynucleotide encoding glyceraldehyde-3-phosphate dehydrogenase type-1.

SEQ ID NO: 106 is a reverse primer used in the PCR amplification of a polynucleotide encoding glyceraldehyde-3-phosphate dehydrogenase type-1.

SEQ ID NO: 107 is a forward primer used in the PCR amplification of a polynucleotide encoding ferritin.

SEQ ID NO: 108 is a reverse primer used in the PCR amplification of a polynucleotide encoding ferritin.

SEQ ID NO: 109 is a forward primer used in the PCR amplification of a polynucleotide encoding a serine hydroxymethyl transferase.

SEQ ID NO: 110 is a reverse primer used in the PCR amplification of a polynucleotide encoding a serine hydroxymethyl transferase.

SEQ ID NO: 111 is a forward primer used in the PCR amplification of a polynucleotide encoding an outer membrane lipoprotein Omp28.

SEQ ID NO: 112 is a reverse primer used in the PCR amplification of a polynucleotide encoding an outer membrane lipoprotein Omp28.

SEQ ID NO: 113 is a forward primer used in the PCR amplification of a polynucleotide encoding a promising lysyl endopeptidase precursor.

SEQ ID NO: 114 is a reverse primer used in the PCR amplification of a polynucleotide encoding a promising lysyl endopeptidase precursor.

SEQ ID NO: 115 is a forward primer used in the PCR amplification of a polynucleotide encoding a quinone family NAD (P) dehydrogenase.

SEQ ID NO: 116 is a reverse primer used in the PCR amplification of a polynucleotide encoding a quinone family NAD (P) dehydrogenase.

SEQ ID NO: 117 is a forward primer used in the PCR amplification of a polynucleotide encoding a DNA-binding protein from a starved cell Dps.

SEQ ID NO: 118 is a reverse primer used in the PCR amplification of a polynucleotide encoding a DNA-binding protein from a starved cell Dps.

SEQ ID NO: 119 is a forward primer used in the PCR amplification of a polynucleotide encoding an immunoresponsive 42 kDa antigen PG33.

SEQ ID NO: 120 is a reverse primer used in the PCR amplification of a polynucleotide encoding an immunoresponsive 42 kDa antigen. PG33.

SEQ ID NO: 121 is a forward primer used in the PCR amplification of a polynucleotide encoding Lys-gingipain.

SEQ ID NO: 122 is a reverse primer used in the PCR amplification of a polynucleotide encoding Lys-gingipain.

SEQ ID NO: 123 is a forward primer used in the PCR amplification of a polynucleotide encoding a peptidyl-arginine deiminase.

SEQ ID NO: 124 is a reverse primer used in the PCR amplification of a polynucleotide encoding a peptidyl-arginine deiminase.

SEQ ID NO: 125 is a forward primer used in the PCR amplification of a polynucleotide encoding a ragA protein.

SEQ ID NO: 126 is a reverse primer used in the PCR amplification of a polynucleotide encoding a ragA protein.

SEQ ID NO: 127 is a forward primer used in the PCR amplification of a polynucleotide encoding an arginine-specific cysteine proteinase RgpA.

SEQ ID NO: 128 is a reverse primer used in the PCR amplification of a polynucleotide encoding an arginine-specific cysteine proteinase RgpA.

SEQ ID NO: 129 is a forward primer used in the PCR amplification of a polynucleotide encoding an outer membrane protein 41 precursor.

SEQ ID NO: 130 is a reverse primer used in the PCR amplification of a polynucleotide encoding an outer membrane protein 41 precursor.

SEQ ID NO: 131 is a forward primer used in the PCR amplification of a polynucleotide encoding a lipoprotein RagB.

SEQ ID NO: 132 is a reverse primer used in the PCR amplification of a polynucleotide encoding a lipoprotein RagB.

SEQ ID NO: 133 is a forward primer used in the PCR amplification of a polynucleotide encoding mutation-introduced Lys-gingipain.

SEQ ID NO: 134 is a reverse primer used in the PCR amplification of a polynucleotide encoding mutation-introduced Lys-gingipain.

SEQ ID NO: 135 is a forward primer used in the PCR amplification of a polynucleotide encoding mutation-introduced Lys-gingipain.

SEQ ID NO: 136 is a reverse primer used in the PCR amplification of a polynucleotide encoding mutation-introduced Lys-gingipain.

SEQ ID NO: 137 is a forward primer used in the PCR amplification of a polynucleotide encoding a mutation-introduced arginine-specific cysteine proteinase RgpA.

SEQ ID NO: 138 is a reverse primer used in the PCR amplification of a polynucleotide encoding a mutation-introduced arginine-specific cysteine proteinase RgpA.

SEQ ID NO: 139 is a forward primer used in the PCR amplification of a polynucleotide encoding a mutation-introduced arginine-specific cysteine proteinase RgpA.

SEQ ID NO: 140 is a reverse primer used in the PCR amplification of a polynucleotide encoding a mutation-introduced arginine-specific cysteine proteinase RgpA.

SEQ ID NO: 141 is an amino acid sequence for about half of the N-terminal side of a mutation-introduced Lys-gingipain.

SEQ ID NO: 142 is a nucleotide sequence encoding about half of the N-terminal side of a mutation-introduced Lys-gingipain.

SEQ ID NO: 143 is an amino acid sequence for about half of the C-terminal side of a mutation-introduced Lys-gingipain.

SEQ ID NO: 144 is a nucleotide sequence encoding about half of the C-terminal side of a mutation-introduced Lys-gingipain.

SEQ ID NO: 145 is an amino acid sequence for about half of the N-terminal side of a mutation-introduced arginine-specific cysteine proteinase RgpA.

SEQ ID NO: 146 is a nucleotide sequence encoding about half of the N-terminal side of a mutation-introduced arginine-specific cysteine proteinase RgpA.

SEQ ID NO: 147 is an amino acid sequence for about half of the C-terminal side of a mutation-introduced arginine-specific cysteine proteinase RgpA.

SEQ ID NO: 148 is a nucleotide sequence encoding about half of the C-terminal side of a mutation-introduced arginine-specific cysteine proteinase RgpA.

SEQ ID NO: 149 is an amino acid sequence for fimbrillin (strain SU63).

SEQ ID NO: 150 is a nucleotide sequence encoding fimbrillin (strain SU63).

SEQ ID NO: 151 is an amino acid sequence for a trace component FimE (strain SU63).

SEQ ID NO: 152 is a nucleotide sequence encoding a trace component FimE (strain SU63).

SEQ ID NO: 153 is an amino acid sequence for a ragA protein (strain SU63).

SEQ ID NO: 154 is a nucleotide sequence encoding a ragA (strain SU63).

SEQ ID NO: 155 is an amino acid sequence for a lipoprotein RagB (strain SU63).

SEQ ID NO: 156 is a nucleotide sequence encoding a lipoprotein RagB (strain SU63).

SEQ ID NO: 157 is a forward primer used in the PCR amplification of a polynucleotide encoding about half of the N-terminal side of a mutation-introduced Lys-gingipain.

SEQ ID NO: 158 is a reverse primer used in the PCR amplification of a polynucleotide encoding about half of the N-terminal side of a mutation-introduced Lys-gingipain.

SEQ ID NO: 159 is a forward primer used in the PCR amplification of a polynucleotide encoding about half of the C-terminal side of a mutation-introduced Lys-gingipain.

SEQ ID NO: 160 is a reverse primer used in the PCR amplification of a polynucleotide encoding about half of the C-terminal side of a mutation-introduced Lys-gingipain.

SEQ ID NO: 161 is a forward primer used in the PCR amplification of a polynucleotide encoding about half of the N-terminal side of a mutation-introduced arginine-specific cysteine proteinase RgpA.

SEQ ID NO: 162 is a reverse primer used in the PCR amplification of a polynucleotide encoding about half of the N-terminal side of a mutation-introduced arginine-specific cysteine proteinase RgpA.

SEQ ID NO: 163 is a forward primer used in the PCR amplification of a polynucleotide encoding about half of the C-terminal side of a mutation-introduced arginine-specific cysteine proteinase RgpA.

SEQ ID NO: 164 is a reverse primer used in the PCR amplification of a polynucleotide encoding about half of the C-terminal side of a mutation-introduced arginine-specific cysteine proteinase RgpA.

SEQ ID NO: 165 is a forward primer used in the PCR amplification of a polynucleotide encoding fimbrillin of strain SU63.

SEQ ID NO: 166 is a reverse primer used in the PCR amplification of a polynucleotide encoding fimbrillin of strain SU63.

SEQ ID NO: 167 is a forward primer used in the PCR amplification of a polynucleotide encoding a trace component FimE of strain SU63.

SEQ ID NO: 168 is a reverse primer used in the PCR amplification of a polynucleotide encoding a trace component FimE of strain SU63.

SEQ ID NO: 169 is a forward primer used in the PCR amplification of a polynucleotide encoding a ragA protein of strain SU63.

SEQ ID NO: 170 is a reverse primer used in the PCR amplification of a polynucleotide encoding a ragA protein of strain SU63.

SEQ ID NO: 171 is a forward primer used in the PCR amplification of a polynucleotide encoding a lipoprotein RagB of strain SU63.

SEQ ID NO: 172 is a reverse primer used in the PCR amplification of a polynucleotide encoding a lipoprotein RagB of strain SU63.

[Sequence Listing]

What is claimed is:

1. A test kit for a plasma or serum antibody titer against a periodontal disease-causing bacterium, comprising a modified polypeptide consisting of the amino acid sequence set forth in SEQ ID NO: 145.

2. The test kit for a plasma or serum antibody titer against a periodontal disease-causing bacterium according to claim 1, wherein the modified polypeptide is encoded by the nucleotide sequence consisting of SEQ ID NO: 146.

3. A method for measuring an antibody titer against a periodontal disease-causing bacterium in a blood sample, comprising bringing the blood sample into contact with a modified polypeptide, said method being characterized in that the modified polypeptide is a modified polypeptide consisting of the amino acid sequence SEQ ID NO: 145.

4. The method according to claim 3, wherein the modified polypeptide encoded by polynucleotide sequence consisting of SEQ ID NO: 146.

* * * * *